(12) United States Patent
Schnatbaum et al.

(10) Patent No.: US 8,071,810 B2
(45) Date of Patent: Dec. 6, 2011

(54) C5A RECEPTOR ANTAGONISTS

(75) Inventors: Karsten Schnatbaum, Berlin (DE);
Dirk Scharn, Berlin (DE); Elsa Locardi, Berlin (DE); Thomas Polakowski, Berlin (DE); Uwe Richter, Berlin (DE); Ulrich Reineke, Berlin (DE); Gerd Hummel, Berlin (DE)

(73) Assignee: Jerini AG, Berlin (DE)

( * ) Notice: Subject to any disclaimer, the term of this patent is extended or adjusted under 35 U.S.C. 154(b) by 852 days.

(21) Appl. No.: 11/915,892

(22) PCT Filed: May 30, 2006

(86) PCT No.: PCT/EP2006/005141
§ 371 (c)(1),
(2), (4) Date: Nov. 29, 2007

(87) PCT Pub. No.: WO2006/128670
PCT Pub. Date: Dec. 7, 2006

(65) Prior Publication Data
US 2008/0220003 A1      Sep. 11, 2008

(30) Foreign Application Priority Data

May 30, 2005   (EP) .................................... 05011620

(51) Int. Cl.
*C07C 275/00* (2006.01)
*C07C 273/00* (2006.01)
(52) U.S. Cl. .......................................... 564/50; 564/47
(58) Field of Classification Search ............... 564/50, 564/47
See application file for complete search history.

(56) References Cited

U.S. PATENT DOCUMENTS 7,105,567 B2 *   9/2006   Ishibuchi et al. ............. 514/466

FOREIGN PATENT DOCUMENTS

| EP | 1 308 438 A | 5/2003 |
|---|---|---|
| EP | 1308438 A1 * | 5/2003 |
| EP | 1 318 140 A | 6/2003 |
| WO | WO 03/082826 A | 10/2003 |

OTHER PUBLICATIONS

Finch et al., "Low-Molecular-Weight Peptidic and Cyclic Antagonists of the Receptor for the Complement Factor C5a", J. Med. Chem., 1999, 42, 1965-1974.

* cited by examiner

*Primary Examiner* — Nizal Chandrakumar
(74) *Attorney, Agent, or Firm* — Morse, Barnes-Brown & Pendleton, P.C.; Lisa M. Treannie, Esq.

(57) ABSTRACT

The present invention is related to a compound, preferably a C5a receptor antagonist, having the following structure, R1, R2, R3, R4, R5, R6, R7, R8, R9, R10, R11, R12, R13, R14, R15, R16, R17, R18, R19, R20, R21 and R22 are individually and independently selected from the group comprising H, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl, arylalkyl, substituted arylalkyl, heteroarylalkyl, substituted heteroarylalkyl, alkoxyl, substituted alkoxyl, aryloxy, substituted aryloxy, arylalkyloxy, substituted arylalkyloxy, acyloxy, substituted acyloxy, halogen, hydroxyl, nitro, cyano, acyl, substituted acyl, mercapto, alkylthio, substituted alkylthio, amino, substituted amino, alkylamino, substituted alkylamino, bisalkyl amino, substituted bisalkyl amino, cyclic amino, substituted cyclic amino, carbamoyl (—$CONH_2$), substituted carbamoyl, carboxyl, carbamate, alkoxycarbonyl, substituted alkoxycarbonyl, acylamino, substituted acylamino, sulfamoyl (—$SO_2NH_2$), substituted sulfamoyl, haloalkyl, haloalkyloxy, —C(O)H, trialkylsilyl and azido.

18 Claims, 6 Drawing Sheets

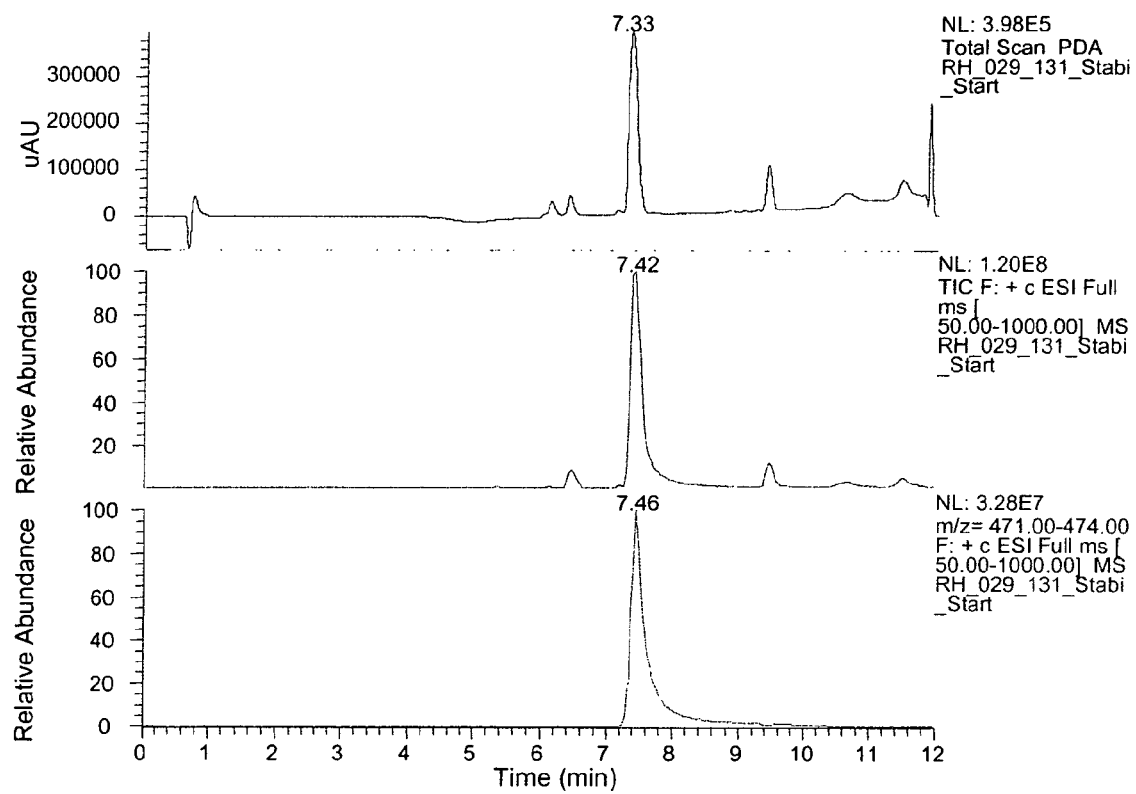

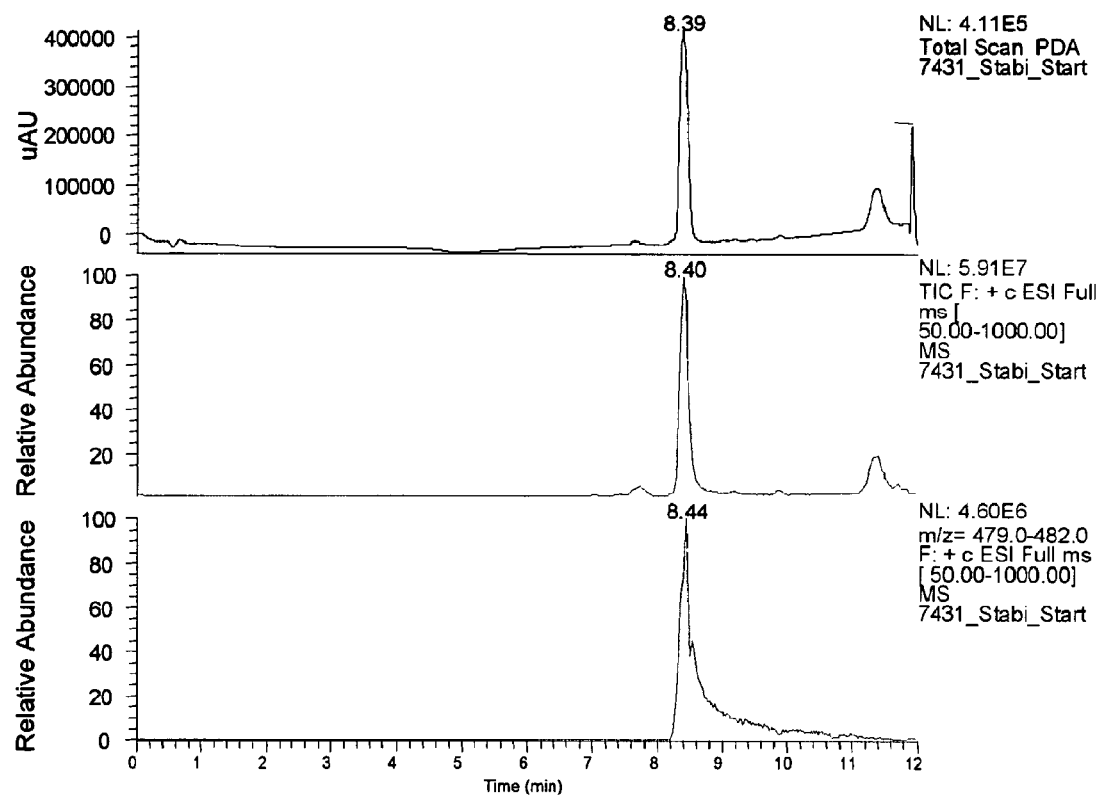
13

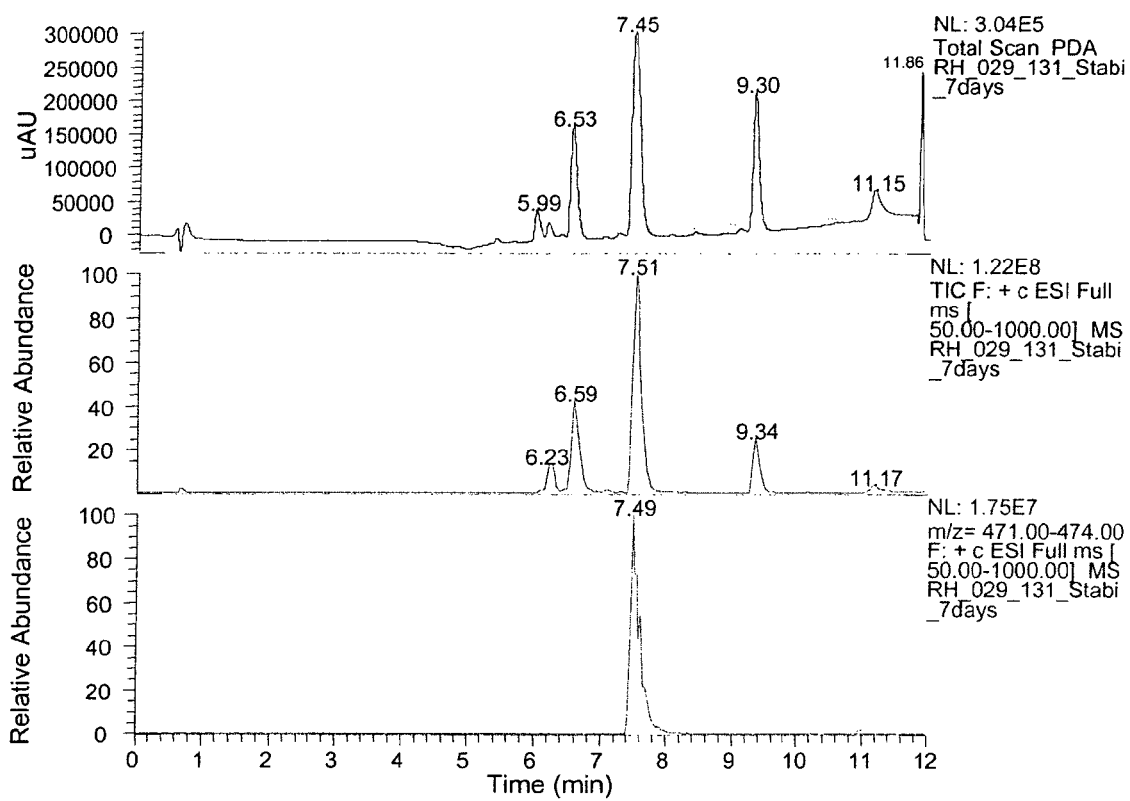

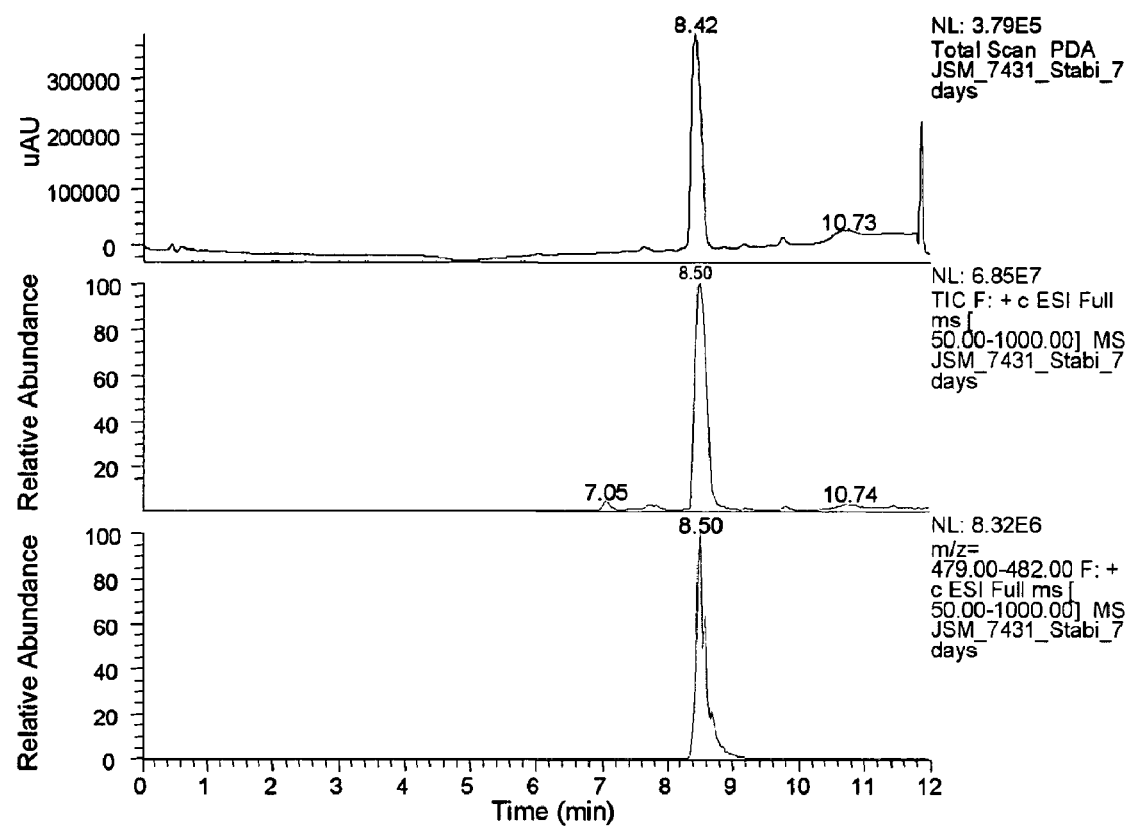

C5A RECEPTOR ANTAGONISTS

CROSS REFERENCE TO RELATED APPLICATION

This application is a 35 U.S.C. 371 National Phase Entry Application from PCT/EP2006/005141, filed May 30, 2006, which claims the benefit of European Patent Application No. 05011620.1 filed on May 30, 2005, the disclosure of which is incorporated herein in its entirety by reference.

The present invention is related to antagonists of the C5a receptor and the use thereof.

Besides the adaptive immune system another—in terms of evolutionary development much older—system for the defence against infection exists. This system is called complement system and consists of more than 30 soluble and membrane bound proteins. The complement system can be activated without or together with the adaptive immune system to eliminate, e.g., pathogenic bacteria. An uncontrolled activation or inadequate regulation of the complement system is related to a number of inflammatory diseases like septic shock, reperfusion injury, rheumatoid arthritis, transplant rejection, acute respiratory distress syndrome (ARDS), systemic lupus erythematosis (SLE), and glomerulonephritis. Numerous overviews over the relation between the complement system and diseases are published (e.g. Kirschfink 1997 Immunopharmacology 38: 51-62; Markides 1998 Pharmacological Reviews 50: 59-87, Walport 2001 The New England Journal of Medicine 344: 1140-1144, Walport 2001 The New England Journal of Medicine 344: 1058-66).

Activation of the complement system takes place via three different pathways. They are called classical, alternative, and mannose-binding lectin (MBL) way. All pathways proceed via the sequential processing and thus activation of pro-forms of proteases. As each activated protease can cleave and therefore activate the next pro-form, an amplification of the initial reaction is obtained. This is similar to the clotting cascade. An overview over the complement system is given by Sim and Laich (2000 Biochemical Society Transactions 28: 545-550).

Some of the most important proteins that are generated upon complement activation are C3a, C3b, C5a, and C5b. These proteins will be discussed in detail.

C3b is an essential part of a central protease of the complement cascade, the C5 convertase. C3b is part of the C5 convertase from both, the classical and alternative pathway of complement activation. The MLB pathway is proceeding via the convertases of the classical pathway, too.

The C5 convertase is responsible for the progress of the complement cascade and catalyses the cleavage of C5. Additionally, C3b is covalently attached to the surface of, e.g., bacteria which are thus more prone to phagocytosis by macrophages. Similar processes are described for immune complex clearance.

C3a is the smaller fragment that is produced in addition to C3b upon cleavage of C3. C3a is a comparatively weak chemokine and belongs to the anaphylatoxins.

C5b is formed upon cleavage of C5. This cleavage product is the starting point for the formation of the membrane attack complex (MAC). The MAC forms a pore which perforates both plasma membranes of bacteria and endogenous cells. Due to the pore formation the perforated cells can be lysed.

C5a is the 74 amino acid N-terminal cleavage product of the α-chain of plasma protein C5 and is released by the activity of the C5 convertase. C5a is bound by its receptor which is referred to as C5a receptor C5aR1 or CD88, with high affinity and triggers a number of pro-inflammatory effects. It is one of the most potent chemokines and belongs as C3a to the anaphylatoxins. The C5aR can be found on many cells. This receptor is particularly found on neutrophils, macrophages, smooth muscle cells, and endothelial cells.

C5a release is thought to be directly or indirectly responsible for many acute and chronic diseases as well as symptoms thereof. Examples for acute diseases and symptoms are septic shock, SIRS (systemic/severe inflammatory response syndrome), MOF (multi organ failure) oder ARDS (acute respiratory distress syndrome). An example for a chronic disease is rheumatoid arthritis. Several systemic diseases cause local manifestations which can be treated with a C5a receptor antagonist.

Finally, C5a and its receptor are interesting targets also for infections and diseases associated therewith, i.e. inflammatory diseases as for instance mycarditis.

Due to the involvement of C5a and its receptor in several diseases and symptoms thereof, in the prior art several strategies were developed for the treatment of these.

C5a receptor antagonists, as reported in detail below, can be used for an intracorporal therapy as well as for an extracorporal treatment of blood and organs. For instance, for the treatment of dialysis patients or other patients observing thereby unwanted side effects, one should evaluate the possibility that e.g. the complement system might be activated at the artificial surfaces. Furthermore, such a treatment can be used to treat reperfusion injuries that can occur in patients undergoing revascularization or other treatments to increase or renew blood circulation, such as e.g. PTCA or thrombolysis, as well as in patients undergoing surgery during which the blood circulation is entirely or partially interrupted as e.g. during aneurysm surgery. An option is the extracorporal treatment of organs before being transplanted.

The C5a receptor (C5aR) is a particularly interesting target for the development of a drug for the treatment of C5a induced diseases and symptoms. This is especially the case due to the finding that mice lacking the receptor do not show an unusual phenotype (Hopken et al. 1996 Nature 383: 86-89). Thus it appears that blocking the C5a receptor probably does not have any negative effect. Merely, a higher sensitivity versus pseudomonad infection was observed in mice lacking the receptor. This means that the complement cascade with its useful functions for defense against pathogens (MAC formation) and immune complex clearance can still proceed in an unhindered manner even when the receptor is totally inactivated. Nevertheless, these animals are protected against ischemia reperfusion injury. For this reason, the inhibition of the C5a receptor appears more favorable than e.g. an inhibition of the complement system at the level of the cleavage of C5 or above.

Up to now several methods for the development of C5a receptor antagonists were used. Among them recombinant proteins, peptides and also few small molecules are known in the literature.

Examples for C5aR inhibitors based on the use of recombinant proteins are CGS 32359 (Ciba-Geigy, Pellas et al. 1998 Journal of Immunology 160: 5616-5621), ΔpIII-A8 (Heller et al. 1999 Journal of Immunology 163: 985-994) and antibodies, which can be of recombinant or non-recombinant origin (Huber-Lang et al. 2001 Faseb Journal 15: 568-570). These C5aR antagonists are proteins and therefore expensive in production. They have comparatively high affinities and specificities but have the drawback of pronounced immunogenicity. In addition proteins can be effectively administered only by costly procedures such as, e.g., i.v. or s.c. injection.

Peptidic antagonists were developed following different strategies. For example the C-terminal sequence information of C5a was used for the development of peptidic C5aR antagonists. Peptides as therapeutically useable antagonists of the C5aR are advantageous over protein therapeutics because of lower production costs and reduced immunogenicity. Many peptidic antagonists are described in the literature. Examples for these peptidic C5aR antagonists or partial agonists are found in the following patents and patent applications: U.S. Pat. No. 4,692,511, U.S. Pat. No. 5,663,148, WO 9009162, WO 9211858, WO 9212168, WO 9221361, WO 9407518, WO 9407815, WO 9525957, WO 9606629, WO 9900406 and WO 9913899, WO 03033528, EP01498422 and WO05010030. However, disadvantages of peptides are often poor oral bioavailability or higher synthetic effort which is very disadvantageous especially for very long peptides composed of more than ten amino acids. Furthermore, peptidic bonds in peptides composed of proteinogenic amino acids can be cleaved e.g. via proteases in biological fluids.

For the therapy of chronic diseases the use of orally bioavailable so called small molecules is particularly advisable. This term usually refers to compounds with a molecular weight up to 1000 g/mol, preferably up to 500 g/mol, which have only few peptidic structural features, as e.g. peptide bonds. Examples of small molecule developments are amongst others L-156602 (Merck; Tsuji et al. 1992 Bioscience Biotechnologie and Biochemistry 56: 2034-2036), TAN-2474 (Takeda; JP10182648), RPR120033 (Rhone-Poulenc, Wong et al. 1999 IDrugs 2: 686), W-54011 (Mitsubishi Pharma, Sumichika et al. 2002 Journal of Biological Chemistry 277: 49403) and NGD 2000-1 (Neurogen, Shaw and Hutchison, 220th ACS National Meeting, Washington, D.C., August 2000). The development of these inhibitors is described in numerous patents and patent applications, as for instance in the following: WO0214265, WO0222556, WO0249993, WO03082829, WO03082828, WO03082826, WO03084524, WO04018460, US2004/0048913, U.S. Pat. No. 6,723,743, US2004/0082577, WO04043925, US2004/0116424, US2004/0158067, U.S. Pat. No. 6,777,422, UA2004/0204446, WO03082829, WO05007087, U.S. Pat. No. 6,858,637, U.S. Pat. No. 6,069,172, WO179189, WO02068377, WO03029187, WO02068377 and WO04043925.

Small molecules known up to now, which interact with the C5a receptor either as antagonist or agonist, are described in detail in the following section.

The first small molecule C5a receptor antagonist was developed by Merck Sharp and Dohme in the early 1990s. Successively, positively charged molecules as e.g. compounds 1 and 2 were identified (Merck, Lanza et al. 1992 J. Med. Chem. 35: 252). These compounds showed moderate binding activities of 3.3 and 12 µg/ml (=8.9 and 35.5 µM, respectively). However, also undesired side effects were observed (compound 7 inhibited the fMLF-induced neutrophil activation) and no further development or data were described. Instead, Merck identified another series of C5a binding molecules (Merck, Laszlo et al. 1997 Bioorg. Med. Chem. Lett. 7: 213) through screening of an in-house library. The molecules with the highest affinity for the C5a receptor were compounds 3 and 4. However, both compounds are agonists and the attempt to eliminate the agonistic activity, via modifications of the structure, failed. Other lead series as, e.g., benzodiazepine (L-747 981, Flanagan et al. 210th ACS National Meeting, Chicago, Ill., Aug. 20-24, 1995) or tetrahydroimidazopyridine (L-164 712, Kim et al. 210th ACS National Meeting, Chicago, Ill., Aug. 20-24, 1995) were also not successful in this respect. During the last years no development was announced by the company Merck in the area of C5a receptor antagonists.

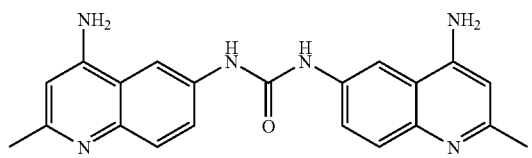

1

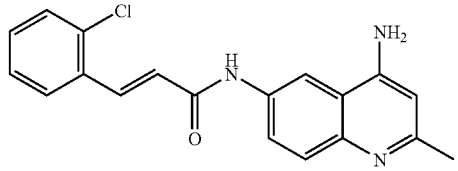

2

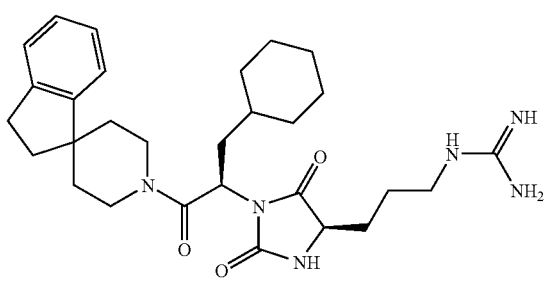

3

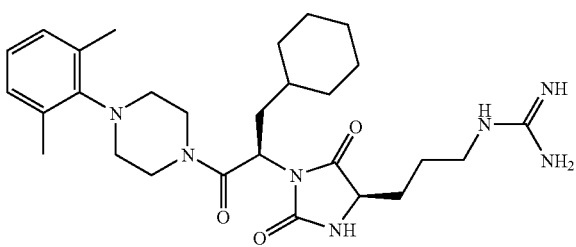

4

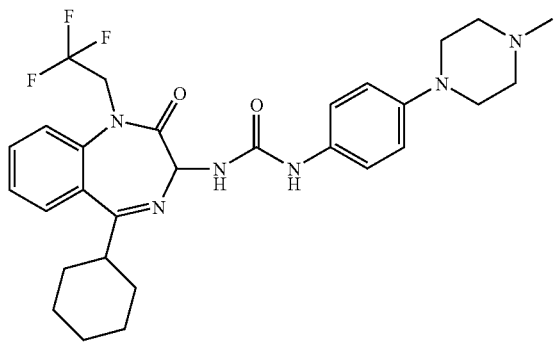

L-747 981

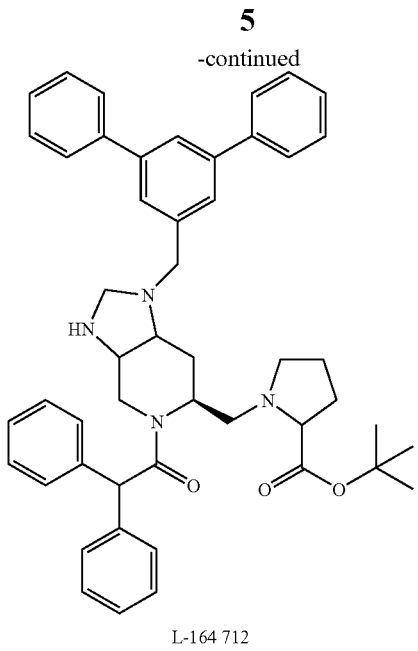

L-164 712

The company Rhône-Poulenc-Rorer identified and optimized C5a receptor antagonists as well, but no further development was reported (Astles et al. 1997 Bioorg. Med. Chem. Lett. 7: 907). A reason for that could be that even the most active compound 5 (RPR121154 and RPR120033) shows only a moderate activity of 0.8 μM. The compound contains a guanidino moiety, which often has a negative influence on oral bioavailability (Reiner et al. 1992 Bioorg. Med. Chem. Lett. 12: 120). In addition it was described that the compound shows cytotoxicity (Sumichika et al. 2002 J. Biol. Chem. 277: 49403).

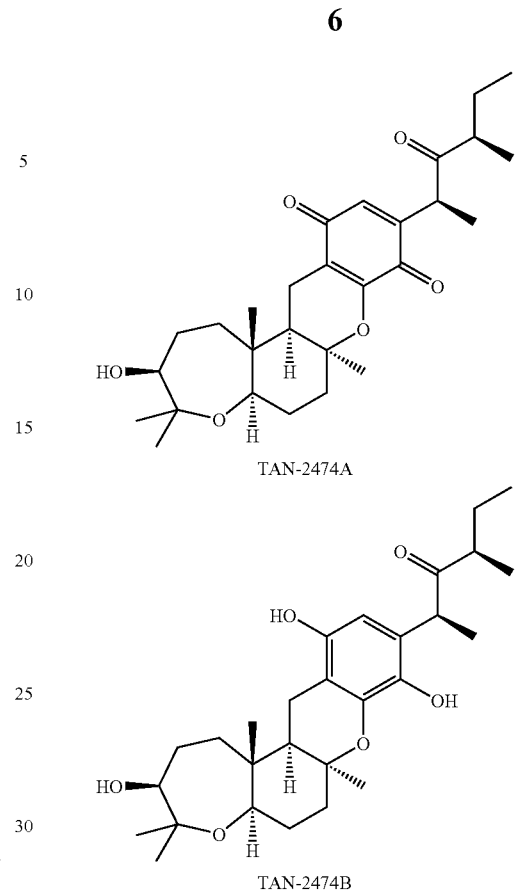

TAN-2474A

TAN-2474B

Further small molecules, whose interaction with the C5a receptor was described, are compounds from the company DOMPÉ S.P.A., as e.g. the compound 6 (U.S. Pat. No. 6,069,172, WO0179189, WO02068377 or WO03029187). However, the compound shows only poor activity (24 μM) in a chemotaxis assay.

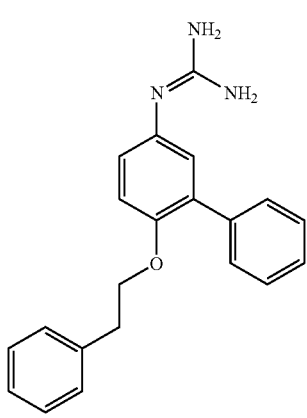

5

6

The company Takeda also described compounds which interact with the C5a receptor (e.g. TAN2474A and TAN2474B). However, the compounds feature potentially reactive ketone- and quinone- or dihydroquinone-groups. Further development of these compounds was not communicated.

In the last years, the company Neurogen filed a series of patent applications with respect to C5a receptor antagonists, which disclose structures as the compounds 1-4 described e.g. in WO0249993, WO03082829, WO03082828, WO03082826, WO03084524, WO04018460, US2004/0048913, U.S. Pat. No. 6,723,743, US2004/0082577, WO04043925, US2004/0116424, US2004/0158067, U.S. Pat. No. 6,777,422, UA2004/0204446, WO03082829, WO05007087 and U.S. Pat. No. 6,858,637. The biological properties were specified only for a few compounds. To these belong 9 and 10, whose activity, in an assay concerning the inhibition of C5a induced calcium mobilization, was described to be 24 and 465 nM, respectively. However, further analysis of the compounds in a functional assay of C5a induced enzyme release by stablye transfected rat-basophil cells expressing the human C5a receptor (Example 28), shows that 9 and 10 have only a minor activity of 7152 nM or >4760 nM. Compound 8 which is claimed in the patent WO03082826, shows only very low activity (1917 nM) in an enzyme release assay.

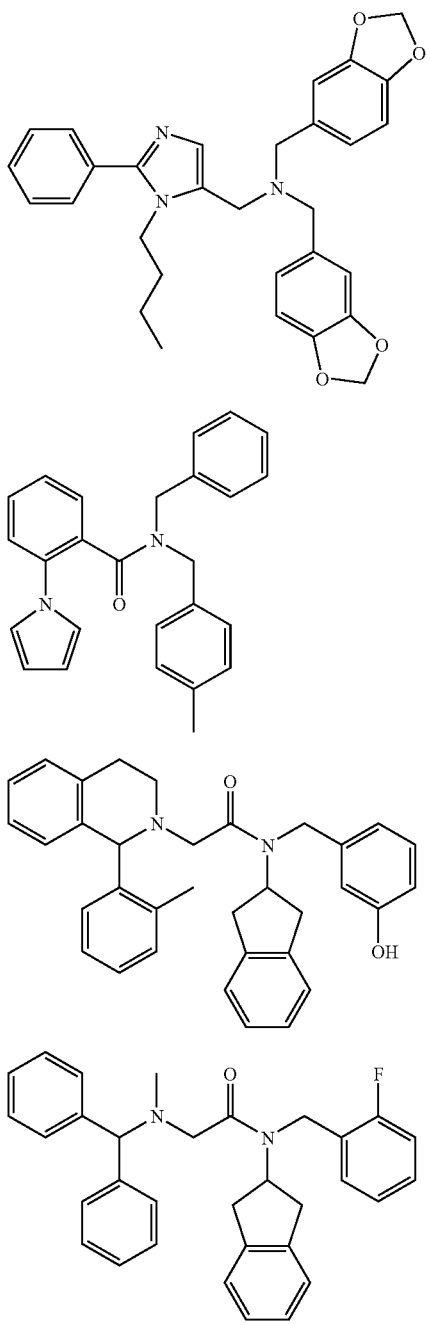

The company Mitsubishi Pharma Corporation filed patent applications with two principally different scaffolds, which can be represented by 11 and 12 (W-54011). The compound 11 not only has got a poor activity (Example 28) but also the disadvantage of a poor shelf life (Example 25). For W-54011 a very high biologic activity was described: an $IC_{50}$ value of 3.1, 2.7 and 1.6 nM for the rhC5a-induced calcium mobilization, chemotaxis and ROS release was respectively measured (Sumichika et al. 2002 J. Biol. Chem. 277: 49403). Sumichika described the compound as being more active in a binding assay than the peptide mimetic PMX53 (a hexamer, cyclic peptide with the formula Ac-F[OPchaWR]) and even more active than an anti C5a receptor monoclonal antibody (Sumichika 2004 Curr. Opin. Invest. Drugs 5: 505). In an enzyme release assay according to Example 28W-54011 shows an IC50 value of 90 nM which is notedly bigger than the $IC_{50}$ value given in the previously described assay. Despite this still satisfactory activity, the compound has other disadvantages: the solubility in PBS-buffered aqueous solution is only 0.4 µM and the chemical synthesis requires an enantioselective step or an enantiomer separation, if there is the need to administer only one enantiomer. In the last years no further development or data concerning the compound W-54011 were published.

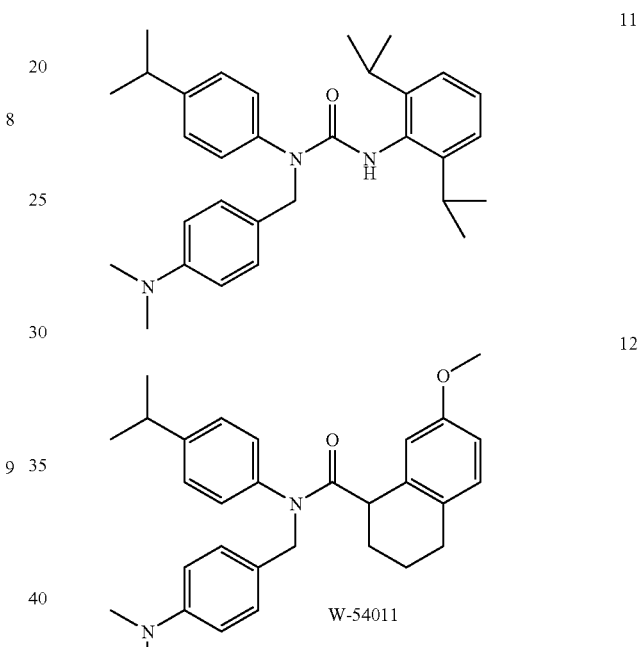

Finally, it can be concluded that all small molecule inhibitors known until now, as reported in the prior art, show at least one of these disadvantages: poor specificity, agonistic activity, poor affinity, poor solubility in water, poor shelf life, chemical reactivity, poor metabolic stability or inhibition of P450 enzymes. Clinical studies were carried out solely with one of the small molecule C5a-inhibitors (NGD 2000-1 of the company Neurogen; Shaw and Hutchison, 220th ACS National Meeting, Washington, D.C., August 2000). Therein, the efficacy of the C5a inhibitor was proven for the indication rheumatoid arthritis (ACR improvement), however the properties of the substance (e.g. cytochrome inhibition) were not adequate for a higher dosage in human in a way to reach a clinically relevant therapeutic efficacy (press release of the company Neurogen, www.neurogen.com, 16.06.2004). It is therefore desirable that new improved C5a receptor antagonists are developed, which are suitable for oral administration.

The problem underlying the present application is the provision of C5aR antagonists. Another problem underlying the present invention is the provision of drugs that can be used for the treatment of diseases in which the C5a receptor and/or C5a are involved in a causal, indirect or symptomatic manner.

The problem underlying the present application is solved in a general manner by means of a compound having a molecular weight less than 700, an aromatic or heteroaromatic moiety, where the compound shows an antagonistic activity towards the C5a receptor of <5000 nM ($IC_{50}$) and an agonistic activity towards the C5a receptor of <10% at 1 μM.

According to the present invention the problem is solved by a compound, preferably a C5a receptor antagonist, having the following structure (I):

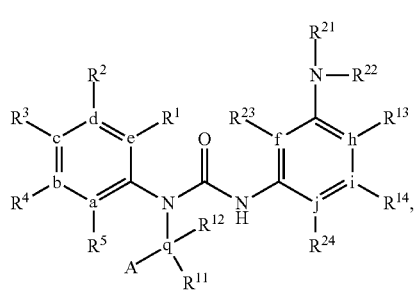
(I)

whereby
A is selected from the group comprising H, alkyl, substituted alkyl, cycloalkyl, substituted cycloalkyl, heterocyclyl, substituted heterocyclyl, arylalkyl, substituted arylalkyl, aryl, substituted aryl, heteroaryl, substituted heteroaryl, cyclic amino, and substituted cyclic amino,
a, b, c, d, e, f, h, i and j individually and independently are selected from the group comprising C and N,
R1, R2, R3, R4, R5, R11, R12, R13, R14, R21 and R22 are individually and independently selected from the group comprising H, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl, arylalkyl, substituted arylalkyl, heteroarylalkyl, substituted heteroarylalkyl, alkoxyl, substituted alkoxyl, aryloxy, substituted aryloxy, arylalkyloxy, substituted arylalkyloxy, acyloxy, substituted acyloxy, halogen, hydroxyl, nitro, cyano, acyl, substituted acyl, mercapto, alkylthio, substituted alkylthio, amino, substituted amino, alkylamino, substituted alkylamino, dialkylamino, substituted dialkylamino, cyclic amino, substituted cyclic amino, carbamoyl (—CONH$_2$), substituted carbamoyl, carboxyl, carbamate, alkoxycarbonyl, substituted alkoxycarbonyl, acylamino, substituted acylamino, sulfamoyl (—SO$_2$NH$_2$), substituted sulfamoyl, haloalkyl, haloalkyloxy, —C(O)H, trialkylsilyl and azido,
whereby 2 groups can form an aliphatic or an aromatic ring with each other, whereby the groups are selected from the group comprising A, R1, R2, R3, R4, R5, R1, R12, R13, R14, R21, R22, R23 and R24, whereby such a formation of a ring can occur 0, 1, 2 or 3-times within one molecule,
and in the case that one of the atoms a, b, c, d, e, f, h, i and/or j is N, the group R1, R2, R3, R4, R5, R13, R14, R23, R24 which is adjacent to N is missing or is selected from the group comprising O, alkyl and substituted alkyl,
whereby R23 and R24 are individually and independently selected from the group comprising alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl, alkoxyl, substituted alkoxyl, aryloxy, substituted aryloxy, acyloxy, substituted acyloxy, halogen, hydroxyl, nitro, cyano, acyl, substituted acyl, mercapto, alkylthio, substituted alkylthio, amino, substituted amino, alkylamino, substituted alkylamino, dialkylamino, substituted dialkylamino, cyclic amino, substituted cyclic amino, carbamoyl (—CONH$_2$), substituted carbamoyl, carboxyl, carbamate, alkoxycarbonyl, substituted alkoxycarbonyl, acylamino, substituted acylamino, sulfamoyl (—SO$_2$NH$_2$), substituted sulfamoyl, haloalkyl, haloalkyloxy, —C(O)H, trialkylsilyl and azido,
whereby q is selected from the group comprising C and N, or q is a bond in which if q is N then R11 is missing, and if q is a bond, then R11 and R12 are missing.

In one embodiment the compound has the following structure (II):

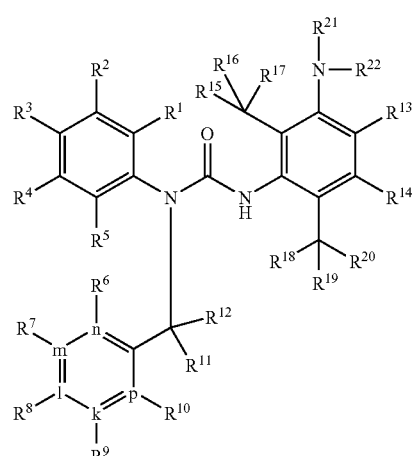
(II)

whereby R1, R2, R3, R4, R5, R6, R7, R8, R9, R10, R15, R16, R17, R18, R19 and R20 are individually and independently selected from the group comprising H, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl, arylalkyl, substituted arylalkyl, heteroarylalkyl, substituted heteroarylalkyl, alkoxyl, substituted alkoxyl, aryloxy, substituted aryloxy, arylalkyloxy, substituted arylalkyloxy, acyloxy, substituted acyloxy, halogen, hydroxyl, nitro, cyano, acyl, substituted acyl, mercapto, alkylthio, substituted alkylthio, amino, substituted amino, alkylamino, substituted alkylamino, dialkylamino, substituted dialkylamino, cyclic amino, substituted cyclic amino, carbamoyl (—CONH$_2$), substituted carbamoyl, carboxyl, carbamate, alkoxycarbonyl, substituted alkoxycarbonyl, acylamino, substituted acylamino, sulfamoyl (—SO$_2$NH$_2$), substituted sulfamoyl, haloalkyl, haloalkyloxy, —C(O)H, trialkylsilyl and azido; and k, l, m, n and p are individually and independently selected from the group comprising C and N, —R23 is represented by the following group

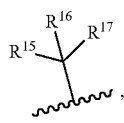

—R24 is represented by the following group

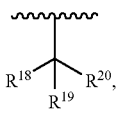

-A is represented by the following group

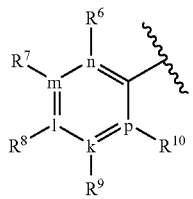

and q is C.

In one embodiment, that is a preferred embodiment of the preceding embodiment, the compound has the following structure (III)

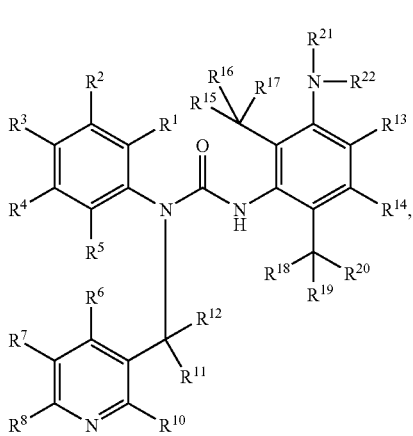

(III)

whereby R1, R2, R3, R4, R5, R6, R7, R8, R10, R15, R16, R17, R18, R19 and R20 are individually and independently selected from the group comprising H, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl, arylalkyl, substituted arylalkyl, heteroarylalkyl, substituted heteroarylalkyl, alkoxyl, substituted alkoxyl, aryloxy, substituted aryloxy, arylalkyloxy, substituted arylalkyloxy, acyloxy, substituted acyloxy, halogen, hydroxyl, nitro, cyano, acyl, substituted acyl, mercapto, alkylthio, substituted alkylthio, amino, substituted amino, alkylamino, substituted alkylamino, dialkylamino, substituted dialkylamino, cyclic amino, substituted cyclic amino, carbamoyl (—CONH$_2$), substituted carbamoyl, carboxyl, carbamate, alkoxycarbonyl, substituted alkoxycarbonyl, acylamino, substituted acylamino, sulfamoyl (—SO$_2$NH$_2$), substituted sulfamoyl, haloalkyl, haloalkyloxy, —C(O)H, trialkylsilyl and azido, —R23 is represented by the following group

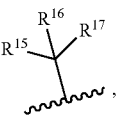

—R24 is represented by the following group

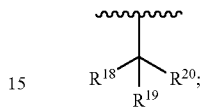

and -A is represented by the following group

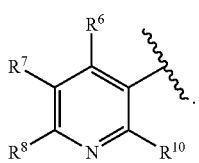

In one embodiment, that is a preferred embodiment of the first embodiment, the compound has the following structure (IIIB)

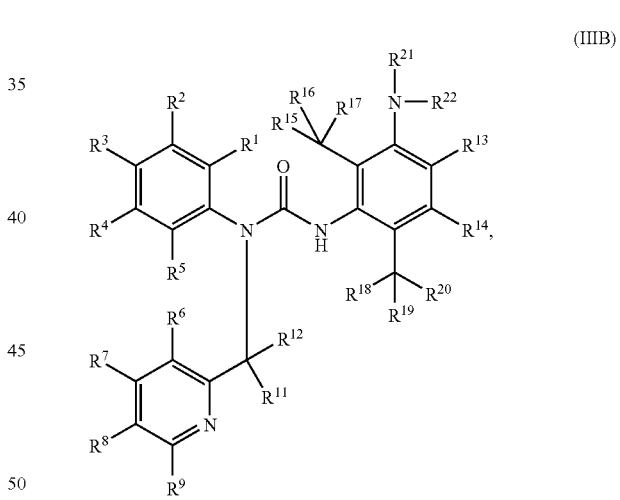

(IIIB)

whereby R1, R2, R3, R4, R5, R6, R7, R8, R9, R15, R16, R17, R18, R19 and R20 individually and independently are selected from the group comprising H, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl, arylalkyl, substituted arylalkyl, heteroarylalkyl, substituted heteroarylalkyl, alkoxyl, substituted alkoxyl, aryloxy, substituted aryloxy, arylalkyloxy, substituted arylalkyloxy, acyloxy, substituted acyloxy, halogen, hydroxyl, nitro, cyano, acyl, substituted acyl, mercapto, alkylthio, substituted alkylthio, amino, substituted amino, alkylamino, substituted alkylamino, dialkylamino, substituted dialkylamino, cyclic amino, substituted cyclic amino, carbamoyl (—CONH$_2$), substituted carbamoyl, carboxyl, carbamate, alkoxycarbonyl, substituted alkoxycarbonyl, acylamino, substituted acylamino, sulfamoyl (—SO$_2$NH$_2$), substituted sulfamoyl, haloalkyl, haloalkyloxy, —C(O)H, trialkylsilyl and azido, —R23 is represented by the following group

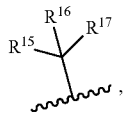

—R24 is represented by the following group

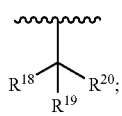

and -A is represented by the following group

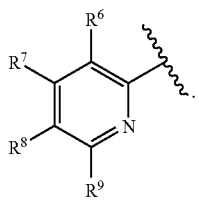

In one embodiment, that is a preferred embodiment of the first embodiment, the compound has the following structure (IIIC)

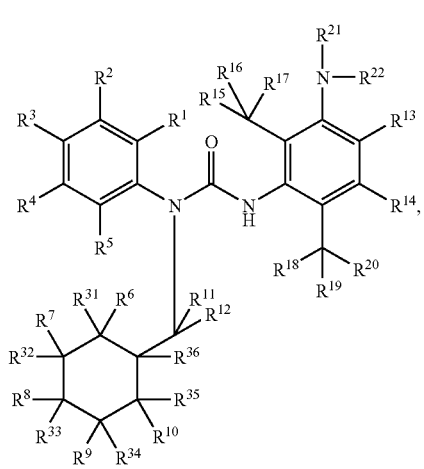

(IIIC)

whereby R1, R2, R3, R4, R5, R6, R7, R8, R9, R10, R11, R12, R13, R14, R15, R16, R17, R18, R19, R20, R31, R32, R33, R34, R35 and R36 are individually and independently selected from the group comprising H, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl, arylalkyl, substituted arylalkyl, heteroarylalkyl, substituted heteroarylalkyl, alkoxyl, substituted alkoxyl, aryloxy, substituted aryloxy, arylalkyloxy, substituted arylalkyloxy, acyloxy, substituted acyloxy, halogen, hydroxyl, nitro, cyano, acyl, substituted acyl, mercapto, alkylthio, substituted alkylthio, amino, substituted amino, alkylamino, substituted alkylamino, dialkylamino, substituted dialkylamino, cyclic amino, substituted cyclic amino, carbamoyl (—CONH$_2$), substituted carbamoyl, carboxyl, carbamate, alkoxycarbonyl, substituted alkoxycarbonyl, acylamino, substituted acylamino, sulfamoyl (—SO$_2$NH$_2$), substituted sulfamoyl, haloalkyl, haloalkyloxy, —C(O)H, trialkylsilyl and azido, —R23 is represented by the following group

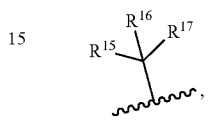

—R24 is represented by the following group

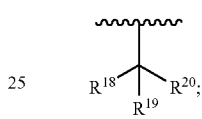

and -A is represented by the following group

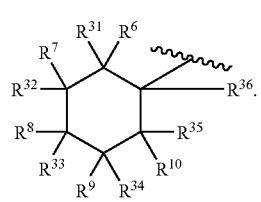

In one embodiment, that is the preferred second embodiment, the compound has the following structure (IV) and ist preferably a C5a receptor antagonist:

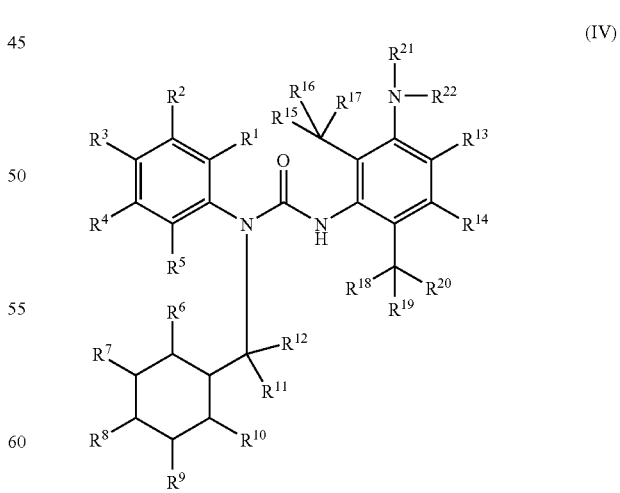

(IV)

For reasons of convenience, the above described compounds constitute an aspect of the present invention, although the following recitation of further aspects starts with an aspect which is referred to as the first aspect. It will be acknowledged by the ones skilled in the art that the compounds of the above aspect can, in principle, be used in connection with any further aspect of the present invention, including, but not limited to, the use of said compounds for the manufacture of a medicament which is to be used in accordance with the present invention.

In a first aspect which is also a first embodiment thereof, the problem underlying the present invention is solved by a compound, preferably a C5a receptor antagonist, having the following structure (IV):

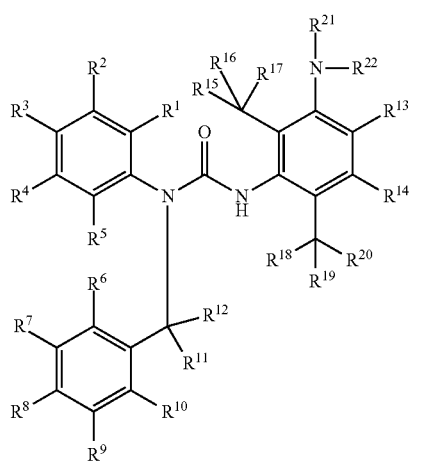
(IV)

whereby R1, R2, R3, R4, R5, R6, R7, R8, R9, R10, R11, R12, R13, R14, R15, R16, R17, R18, R19, R20, R21 and R22 are individually and independently selected from the group comprising H, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl, arylalkyl, substituted arylalkyl, heteroarylalkyl, substituted heteroarylalkyl, alkoxyl, substituted alkoxyl, aryloxy, substituted aryloxy, arylalkyloxy, substituted arylalkyloxy, acyloxy, substituted acyloxy, halogen, hydroxyl, nitro, cyano, acyl, substituted acyl, mercapto, alkylthio, substituted alkylthio, amino, substituted amino, alkylamino, substituted alkylamino, bisalkyl amino, substituted bisalkyl amino, cyclic amino, substituted cyclic amino, carbamoyl (—CONH$_2$), substituted carbamoyl, carboxyl, carbamate, alkoxycarbonyl, substituted alkoxycarbonyl, acylamino, substituted acylamino, sulfamoyl (—SO$_2$NH$_2$), substituted sulfamoyl, haloalkyl, haloalkyloxy, —C(O)H, trialkylsilyl and azido.

In a second embodiment of the first aspect R1, R2, R3, R4 and R5 are individually and independently selected from the group comprising H, alkyl, substituted alkyl, alkynyl, cycloalkyl, alkoxyl, substituted alkoxyl, acyloxy, halogen, nitro, cyano, acyl, alkylthio, substituted alkylthio, amino, substituted amino, alkylamino, substituted alkylamino, bisalkyl amino, cyclic amino, carbamoyl (—CONH$_2$), acylamino, and substituted acylamino, or this moiety

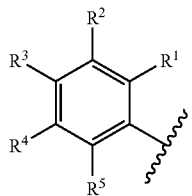

is substituted by a moiety which is selected from the group comprising

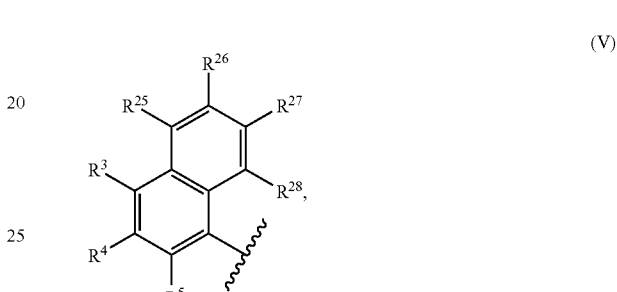
(V)

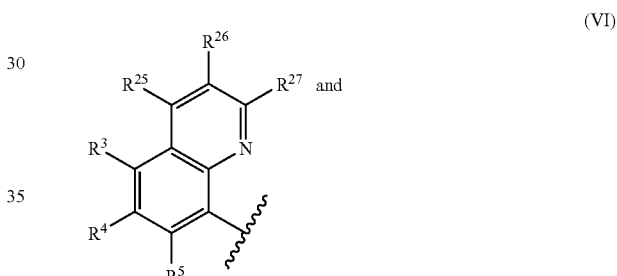
(VI)

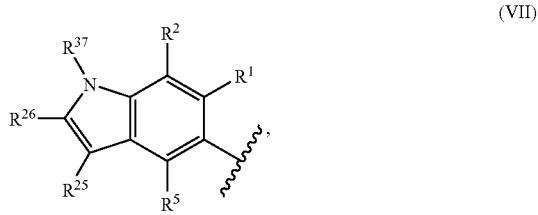
(VII)

whereby R1, R2, R3, R4 and R5 are individually and independently defined as described above, whereby R25, R26, R27 and R28 are selected individually and independently from the group comprising H, alkyl, substituted alkyl, alkynyl, cycloalkyl, alkoxyl, substituted alkoxyl, acyloxy, halogen, nitro, cyano, acyl, alkylthio, substituted alkylthio, amino, substituted amino, alkylamino, substituted alkylamino, bisalkyl amino, cyclic amino, carbamoyl (—CONH$_2$), acylamino, and substituted acylamino, and R37 is selected from the group which comprises H, alkyl and substituted alkyl.

In a third embodiment of the first aspect R1, R2, R4 and R5 are individually and independently selected from the group comprising H, alkyl, alkoxyl and halogen, R3 is selected from the group comprising H, alkyl, substituted alkyl, alkynyl, cycloalkyl, alkoxyl, acyl, alkylthio, substituted alkylthio, alkylamino and substituted alkylamino, or this moiety

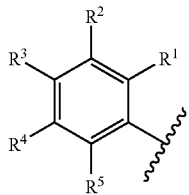

is substituted by a moiety which is selected from the group comprising

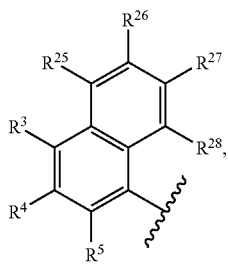
(V)

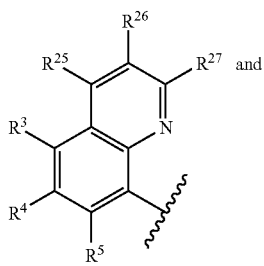
(VI)

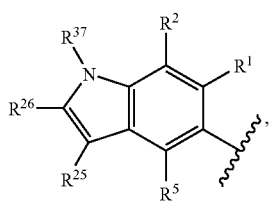
(VII)

whereby R1, R2, R4, R5 and R3 are individually and independently defined as described above, whereby R25, R26, R27 and R28 are individually and independently selected from the group comprising H, alkyl, alkoxyl and halogen, and R37 is selected from the group comprising H, alkyl and substituted alkyl.

In a fourth embodiment of the first aspect R1, R2, R4 and R5 are individually and independently selected from the group comprising H, Me, OMe, F, Cl and Br, R3 is selected from the group which comprises Et-, iPr—, CF$_3$CH$_2$—, cyclopropyl, HCC—, MeO—, MeS—, CF$_3$S—, MeNH—, and CF$_3$NH—, or this moiety

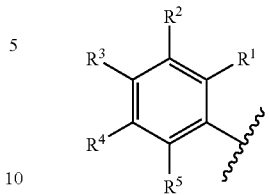

is substituted by a moiety which is selected from the group comprising

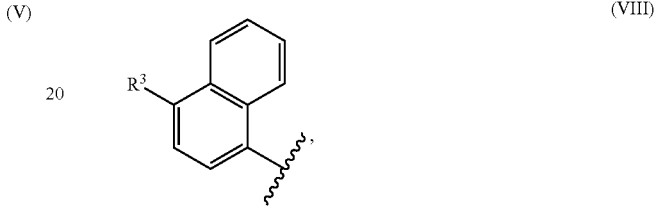
(VIII)

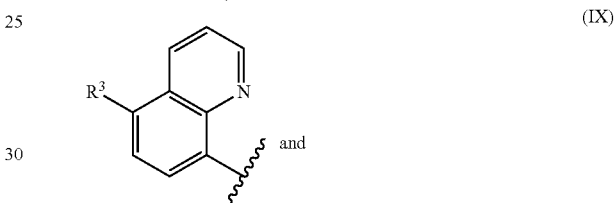
(IX)

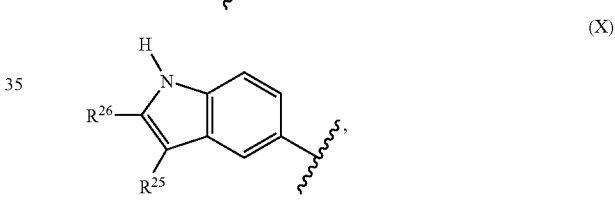
(X)

whereby R3 is defined as described above, whereby R25 and R26 are individually and independently selected from the group comprising H, Me, OMe, F, Cl, Br and CF$_3$.

In a fifth embodiment of the first aspect R6, R7, R8, R9 and R10 are individually and independently selected from the group comprising H, alkyl, substituted alkyl, heterocyclyl, substituted heterocyclyl, aryl, substituted aryl, heteroaryl, substituted heteroaryl, alkoxyl, substituted alkoxyl, acyloxy, halogen, nitro, cyano, acyl, alkylthio, substituted alkylthio, amino, substituted amino, alkylamino, substituted alkylamino, bisalkyl amino, substituted bisalkyl amino, cyclic amino, carbamoyl (—CONH$_2$) and acylamino, or this moiety

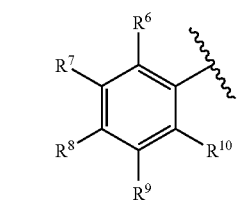

is substituted by the following moiety

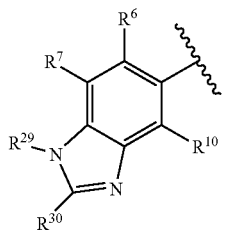
(XI)

whereby R6, R7 and R10 are individually and independently defined as described above,
whereby R29 and R30 are individually and independently selected from the group comprising H, alkyl, substituted alkyl, heterocyclyl, substituted heterocyclyl, aryl, substituted aryl, heteroaryl, substituted heteroaryl, alkoxyl, substituted alkoxyl, acyloxy, halogen, nitro, cyano, acyl, alkylthio, substituted alkylthio, amino, substituted amino, alkylamino, substituted alkylamino, bisalkyl amino, substituted bisalkyl amino, cyclic amino, carbamoyl (—CONH$_2$), and acylamino.

In a sixth embodiment of the first aspect which is also an embodiment of the fifth embodiment R6, R7, R9 and R10 are individually and independently selected from the group comprising H, alkyl, substituted alkyl, heterocyclyl, substituted heterocyclyl, aryl, heteroaryl, alkoxyl, substituted alkoxyl, halogen, alkylthio, substituted alkylthio, amino, substituted amino and cyclic amino,
R8 is selected from the group comprising H, alkyl, substituted alkyl, heterocyclyl, substituted heterocyclyl, aryl, heteroaryl, substituted heteroaryl, alkoxyl, substituted alkoxyl, halogen, alkylthio, substituted alkylthio, amino, substituted amino, alkylamino, substituted alkylamino, bisalkyl amino, substituted bisalkyl amino and cyclic amino,
or this moiety

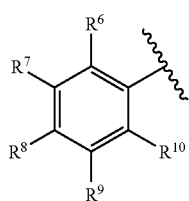
(XI)

is substituted by the following moiety

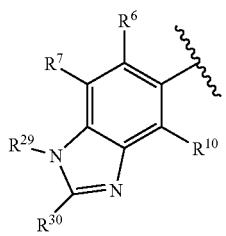
(XI)

whereby R6, R7 and R10 are individually and independently defined as described above,
whereby R29 and R30 are individually and independently selected from the group comprising H, alkyl, substituted alkyl, heterocyclyl, substituted heterocyclyl, aryl, heteroaryl, alkoxyl, substituted alkoxyl, halogen, alkylthio, substituted alkylthio, amino, substituted amino and cyclic amino.

In a seventh embodiment of the first aspect which is also an embodiment of the fifth embodiment R6, R7, R9 and R10 are individually and independently selected from the group comprising H—, Me-, —CF$_3$, —OMe, —OCF$_3$, —F, —Cl, —Br and —SCF$_3$,
R8 is selected from the group comprising H—, Me-, —CF$_3$, —OMe, —F, —Cl, —Br, —SMe, —NMe$_2$ and —NHMe,
or this moiety

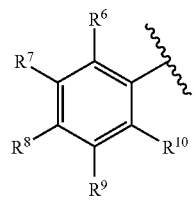

is substituted by the following moiety

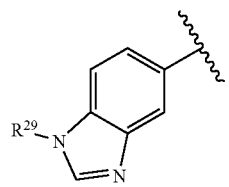
(XII)

whereby R29 is selected from the group comprising H—, Me-, —CH$_2$F, CHF$_2$, and —CF$_3$.

In an eight embodiment of the first aspect which is also an embodiment of the first embodiment R11 and R12 are individually and independently selected from the group comprising H, alkyl, substituted alkyl and halogen,
or
R11 and R12 taken together form a cycloalkyl ring,
or this moiety

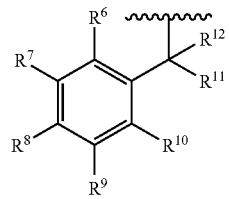

is substituted by the following moiety

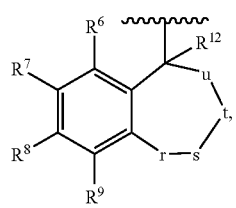
(XV)

whereby R12 is selected from the group comprising H, alkyl, substituted alkyl, and halogen, whereby r, s, t and u are individually and independently selected from the group comprising —CH$_2$—, —O—, —N-alkyl- and —NH—, or whereby r, s, t, and u individually and independently optionally represent a chemical bond.

In a ninth embodiment of the first aspect which is also an embodiment of the eight embodiment R11 and R12 are individually and independently selected from the group comprising —H, -Me, -Et, —CF$_3$, and —F,
or this moiety

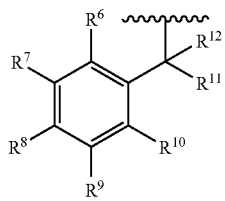

is substituted by the following moiety

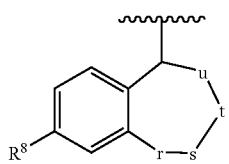
(XVI)

, whereby r, s, t and u are individually and independently selected from the group comprising —CH$_2$— and —O—, or whereby r, s, t, and u individually and independently optionally represent a chemical bond.

In a tenth embodiment of the first aspect which is also an embodiment of the first embodiment this moiety

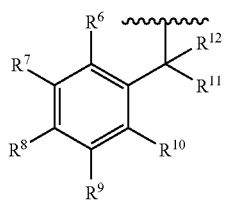

is substituted by the following moiety

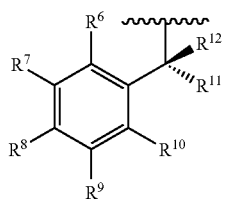

whereby R11 is H,
whereby R12 is selected from the group comprising H, alkyl, substituted alkyl and halogen.

In an eleventh embodiment of the first aspect which is also an embodiment of the tenth embodiment R11 is H, and R12 is selected from the group comprising —H, -Me, -Et, —CF$_3$ and —F.

In a twelfth embodiment of the first aspect which is also an embodiment of the first embodiment R13 and R14 are selected individually and independently from the group comprising H, alkyl, substituted alkyl, alkoxyl, substituted alkoxyl, halogen, cyano, alkylthio, amino and substituted ammo.

In a thirteenth embodiment of the first aspect which is also an embodiment of the twelfth embodiment R13 and R14 are individually and independently selected from the group comprising —H, -Me, —CF$_3$, —OMe, —F, —Cl and —Br.

In a fourteenth embodiment of the first aspect which is also an embodiment of the first embodiment R15, R16, R17, R18, R19 and R20 are individually and independently selected from the group comprising H, alkyl, substituted alkyl, alkoxyl, substituted alkoxyl, acyloxy, halogen, alkylthio, substituted alkylthio, amino, substituted amino and carbamoyl (—CONH$_2$), or two or three of the substituents from the group comprising R15, R16 and R17 and/or from the group comprising R18, R19, and R20, form together alkynyl, substituted alkynyl, cycloalkyl, substituted cycloalkyl, heterocyclyl, aryl, heteroaryl or keto.

In a fifteenth embodiment of the first aspect which is also an embodiment of the fourteenth embodiment R15, R16, R17, R18, R19 and R20 are individually and independently selected from the group comprising —H, -Me, —CF$_3$, and —F.

In a sixteenth embodiment of the first aspect which is also an embodiment of the first embodiment R21 and R22 are individually and independently selected from the group comprising H, alkyl, substituted alkyl, acyl, substituted acyl, alkylthio and substituted alkylthio,
or this moiety

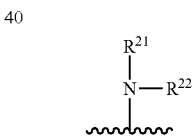

is substituted by a substituent which is selected from the group comprising nitro, nitroso (NO) and azido.

In a seventeenth embodiment of the first aspect which is also an embodiment of the sixteenth embodiment R21 and R22 are individually and independently selected from the group comprising —H, -Me and —CF$_3$,
or this moiety

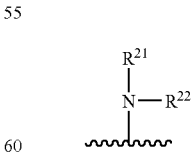

is substituted by nitroso (NO).

In a second aspect which is also a first embodiment thereof, the problem underlying the present invention is solved by a compound, whereby the compound has one of the following structures

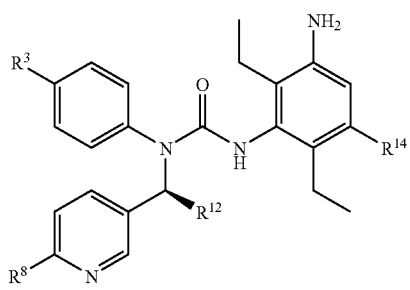

(XVIII)

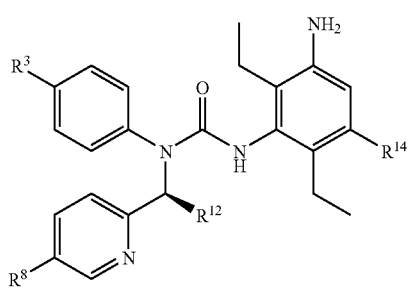

(XIX)

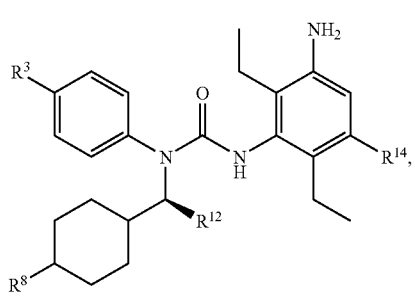

(XX)

and whereby
R3 is selected from the group comprising Et-, iPr—, CF$_3$CH$_2$—, cyclopropyl, HCC—, MeO—, MeS—, CF$_3$S—, MeNH— and CF$_3$NH—,
R8 is selected from the group comprising H—, Me-, —CF$_3$, —OMe, —F, —Cl, —Br, —SMe, —NMe$_2$ and —NHMe,
R12 is selected from the group comprising H— and Me-, und
R14 is selected from the group comprising H— and —Cl.

In an eighteenth embodiment of the first aspect which is also an embodiment of the first embodiment the compound has the following structure

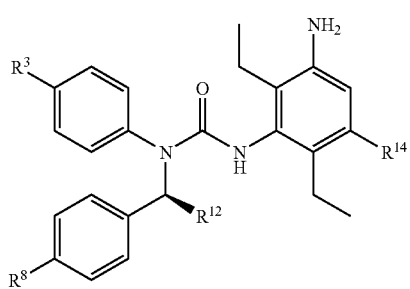

(XI)

and whereby
R3 is selected from the group comprising Et-, iPr—, CF$_3$CH$_2$—, cyclopropyl, HCC—, MeO—, MeS—, CF$_3$S—, MeNH— and CF$_3$NH—,
R8 is selected from the group comprising H—, Me-, —CF$_3$, —OMe, —F, —Cl, —Br, —SMe, —NMe$_2$, and —NHMe,
R12 is selected from the group comprising H— and Me-, and
R14 is selected from the group comprising H— and —Cl.

In a nineteenth embodiment of the first aspect which is also an embodiment of the first embodiment the compound has one of the following structures:

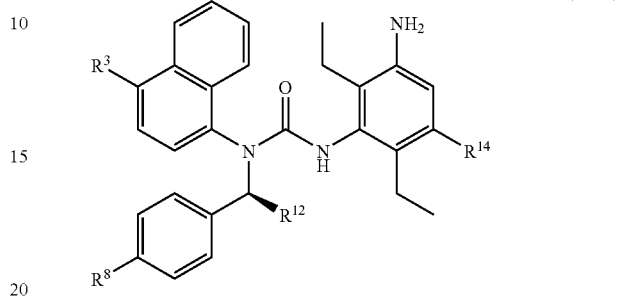

(XXII)

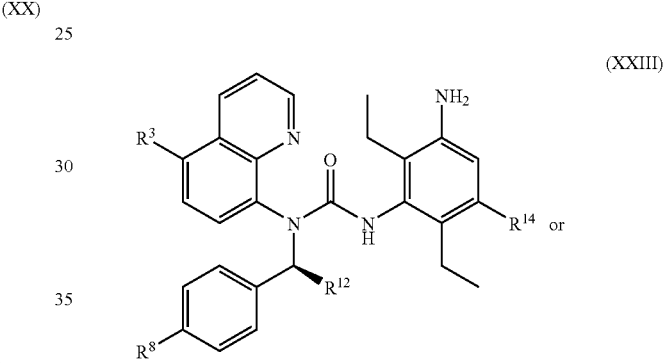

(XXIII)

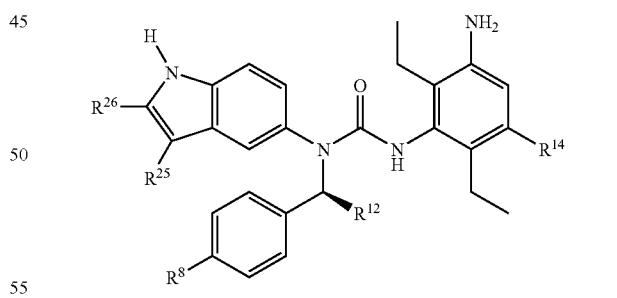

(XXIV)

and whereby
R3, R25 and R26 are individually and independently selected from the group comprising H—, Et-, iPr—, CF$_3$CH$_2$—, cyclopropyl, HCC—, MeO—, MeS—, CF$_3$S—, MeNH—, CF$_3$NH— and,
R8 is selected from the group comprising H—, Me-, —CF$_3$, —OMe, —F, —Cl, —Br, —SMe, —NMe$_2$ and —NHMe,
R12 is selected from the group comprising H— and Me-, and
R14 is selected from the group comprising H— and —Cl.

In a twentieth embodiment of the first aspect which is also an embodiment of the first embodiment the compound has one of the following structures:

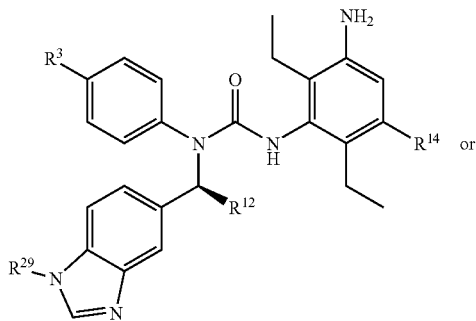

(XXV)

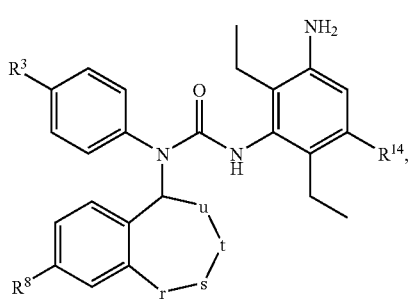

(XXVI)

and whereby R3 is selected from the group comprising Et-, iPr—, CF$_3$CH$_2$—, cyclopropyl, HCC—, MeO—, MeS—, CF$_3$S—, MeNH— and CF$_3$NH—,
R8 is selected from the group comprising H—, Me-, —CF$_3$, —OMe, —F, —Cl, —Br, —SMe, —NMe$_2$ and —NHMe,
R29 is selected from the group comprising H—, Me-, —CH$_2$F, CHF$_2$ and —CF$_3$.
R14 is selected from the group comprising H— and —Cl,
R12 is selected from the group comprising H— and Me-, and r, s, t and u are individually and independently selected from the group comprising —CH$_2$— and —O—, or whereby r, s, t and u individually and independently optionally represent a chemical bond.

In a twenty-first embodiment of the first aspect, which is also a second embodiment of the second aspect, which is an embodiment of any embodiments of the first and of the second aspect the compound is selected from the group comprising 3-(3-Amino-2,6-diisopropyl-phenyl)-1-(4-isopropyl-phenyl)-1-(4-methoxy-benzyl)-urea
3-(3-Amino-2,6-diethyl-phenyl)-1-(4-isopropyl-phenyl)-1-(4-methoxy-benzyl)-urea
2-{2,4-Diethyl-3-[3-(4-isopropyl-phenyl)-3-(4-methoxy-benzyl)-ureido]-phenylamino}-acetamide
{2,4-Diethyl-3-[3-(4-isopropyl-phenyl)-3-(4-methoxy-benzyl)-ureido]-phenylamino}-acetic acid-methyl-ester
3-(3-Amino-5-chloro-2,6-diethyl-phenyl)-1-(4-isopropyl-phenyl)-1-(4-methoxy-benzyl)-urea
3-(3-Amino-5-chloro-2,6-diethyl-phenyl)-1-(4-ethyl-phenyl)-1-(4-methoxy-benzyl)-urea
3-(3-Amino-5-chloro-2,6-diethyl-phenyl)-1-(4-isopropyl-phenyl)-1-(4-trifluoromethoxy-benzyl)-urea
3-(3-Amino-5-chloro-2,6-diethyl-phenyl)-1-(4-isopropyl-phenyl)-1-(4-methyl-benzyl)-urea
3-(3-Amino-5-chloro-2,6-diethyl-phenyl)-1-(4-ethyl-benzyl)-1-(4-isopropyl-phenyl)-urea
3-{3-Chloro-2,6-diethyl-5-[(furan-2-ylmethyl)-amino]-phenyl}-1-(4-isopropyl-phenyl)-1-(4-methoxy-benzyl)-urea
2-{5-Chloro-2,4-diethyl-3-[3-(4-isopropyl-phenyl)-3-(4-methoxy-benzyl)-ureido]-phenylamino}-N,N-dimethyl-acetamide
3-{3-Chloro-2,6-diethyl-5-[(1-methyl-1H-imidazol-2-ylmethyl)-amino]-phenyl}-1-(4-isopropyl-phenyl)-1-(4-methoxy-benzyl)-urea
3-(3-Amino-2,6-diethyl-phenyl)-1-(4-isopropyl-phenyl)-1-(4-methyl-benzyl)-urea
(R)-3-(3-Amino-5-chloro-2,6-diethyl-phenyl)-1-(4-isopropyl-phenyl)-1-(1,2,3,4-tetrahydro-naphthalen-1-yl)-urea
(S)-3-(3-Amino-5-chloro-2,6-diethyl-phenyl)-1-(4-isopropyl-phenyl)-1-(1,2,3,4-tetrahydro-naphthalen-1-yl)-urea
3-(3-Amino-5-chloro-2,6-diethyl-phenyl)-1-benzyl-1-(4-isopropyl-phenyl)-urea
3-(3-Amino-5-chloro-2,6-diethyl-phenyl)-1-indan-5-yl-1-(4-methoxy-benzyl)-urea
2-{5-Chloro-2,4-diethyl-3-[3-(4-isopropyl-phenyl)-3-(4-methoxy-benzyl)-ureido]-phenylamino}-acetamide
3-(3-Amino-5-chloro-2,6-diethyl-phenyl)-1-(4-isopropyl-phenyl)-1-(6-methoxy-pyridin-3-ylmethyl)-urea
3-(3-Amino-2,6-diethyl-phenyl)-1-(4-isopropyl-phenyl)-1-(6-methoxy-pyridin-3-ylmethyl)-urea
3-(3-Amino-5-chloro-2,6-diethyl-phenyl)-1-(4-isopropyl-phenyl)-1-(4-trifluoromethyl-benzyl)-urea
3-(3-Amino-2,6-diethyl-phenyl)-1-(4-isopropyl-phenyl)-1-(4-trifluoromethyl-benzyl)-urea
3-(3-Amino-2,6-diethyl-phenyl)-1-(4-isopropyl-phenyl)-1-phenethyl-urea
3-(3-Amino-5-chloro-2,6-diethyl-phenyl)-1-(4-isopropyl-phenyl)-1-(2-p-tolyl-ethyl)-urea
3-(3-Amino-5-chloro-2,6-diethyl-phenyl)-1-(4-ethyl-phenyl)-1-(4-methyl-benzyl)-urea
3-(3-Amino-2,6-diethyl-phenyl)-1-(4-ethyl-phenyl)-1-(4-methyl-benzyl)-urea
{5-Chloro-2,4-diethyl-3-[3-(4-isopropyl-phenyl)-3-(4-methoxy-benzyl)-ureido]-phenylamino}-acetic-acid-methyl-ester
(R)-3-(3-Amino-5-chloro-2,6-diethyl-phenyl)-1-(4-isopropyl-phenyl)-1-[1-(4-methoxy-phenyl)-ethyl]-urea
(R)-3-(3-Amino-5-chloro-2,6-diethyl-phenyl)-1-(4-isopropyl-phenyl)-1-(1-p-tolyl-ethyl)-urea
3-(3-Amino-5-chloro-2,6-diethyl-phenyl)-1-(2-fluoro-4-methoxy-benzyl)-1-(4-isopropyl-phenyl)-urea
3-(3-Amino-2,6-diethyl-phenyl)-1-(2-fluoro-4-methoxy-benzyl)-1-(4-isopropyl-phenyl)-urea
3-(3-Amino-5-chloro-2,6-diethyl-phenyl)-1-cyclohexylmethyl-1-(4-isopropyl-phenyl)-urea
3-(3-Amino-2,6-diethyl-phenyl)-1-cyclohexylmethyl-1-(4-isopropyl-phenyl)-urea
3-(3-Amino-5-chloro-2,6-diethyl-phenyl)-1-(4-isopropyl-phenyl)-1-(2-methoxy-benzyl)-urea
3-(3-Amino-2,6-diethyl-phenyl)-1-(4-isopropyl-phenyl)-1-(2-methoxy-benzyl)-urea
3-(3-Amino-5-chloro-2,6-diethyl-phenyl)-1-(4-isopropyl-phenyl)-1-(4-methanesulfonyl-benzyl)-urea
3-(3-Amino-5-chloro-2,6-diethyl-phenyl)-1-(2,3-dihydro-benzofuran-5-ylmethyl)-1-(4-isopropyl-phenyl)-urea
(S)-3-(3-Amino-5-chloro-2,6-diethyl-phenyl)-1-(4-isopropyl-phenyl)-1-[1-(4-methoxy-phenyl)-ethyl]-urea
3-(3-Amino-2,6-diethyl-phenyl)-1-(2,3-dihydro-benzofuran-5-ylmethyl)-1-(4-isopropyl-phenyl)-urea
(R)-3-(3-Amino-2,6-diethyl-phenyl)-1-(4-isopropyl-phenyl)-1-(1-p-tolyl-ethyl)-urea (S)-3-(3-Amino-2,6-diethyl-phenyl)-1-(4-isopropyl-phenyl)-1-(1-p-tolyl-ethyl)-urea
(R)-3-(3-Amino-2,6-diethyl-phenyl)-1-(4-isopropyl-phenyl)-1-[1-(4-methoxy-phenyl)-ethyl]-urea
(S)-3-(3-Amino-2,6-diethyl-phenyl)-1-(4-isopropyl-phenyl)-1-[1-(4-methoxy-phenyl)-ethyl]-urea
3-(3-Amino-5-chloro-2,6-diethyl-phenyl)-1-(4-chloro-benzyl)-1-(4-isopropyl-phenyl)-urea
(S)-3-(3-Amino-5-chloro-2,6-diethyl-phenyl)-1-(4-isopropyl-phenyl)-1-(1-p-tolyl-ethyl)-urea
3-(3-Amino-5-chloro-2,6-diethyl-phenyl)-1-(4-isopropyl-phenyl)-1-pyridin-3-ylmethyl-urea
3-(3-Amino-5-chloro-2,6-diethyl-phenyl)-1-(4-isopropyl-phenyl)-1-(5-methyl-pyrazin-2-ylmethyl)-urea
3-(3-Amino-5-chloro-2,6-diethyl-phenyl)-1-(4-isopropyl-phenyl)-1-(6-methyl-pyridin-3-ylmethyl)-urea
3-(3-Amino-5-chloro-2,6-diethyl-phenyl)-1-(2,4-dimethoxy-pyrimidin-5-ylmethyl)-1-(4-isopropyl-phenyl)-urea
(S)-3-(3-Amino-5-chloro-2,6-diethyl-phenyl)-1-[1-(4-chloro-phenyl)-ethyl]-1-(4-isopropyl-phenyl)-urea
(S)-3-(3-Amino-5-chloro-2,6-dimethyl-phenyl)-1-(4-isopropyl-phenyl)-1-(1-p-tolyl-ethyl)-urea
(S)-3-(3-Amino-5-chloro-2,6-diethyl-phenyl)-1-[1-(4-chloro-phenyl)-ethyl]-1-(4-ethyl-phenyl)-urea
(S)-3-(3-Amino-5-chloro-2,6-diethyl-phenyl)-1-[1-(4-fluoro-phenyl)-ethyl]-1-(4-isopropyl-phenyl)-urea
(S)-3-(3-Amino-5-chloro-2,6-diethyl-phenyl)-1-(4-ethyl-phenyl)-1-[1-(4-fluoro-phenyl)-ethyl]-urea
(S)-3-(3-Amino-5-chloro-2,6-diethyl-phenyl)-1-[1-(4-chloro-phenyl)-ethyl]-1-(4-methylsulfanyl-phenyl)-urea
3-(3-Amino-5-chloro-2,6-diethyl-phenyl)-1-indan-1-yl-1-(4-isopropyl-phenyl)-urea
3-(3-Amino-5-chloro-2,6-diethyl-phenyl)-1-(4-ethynyl-phenyl)-1-(4-methoxy-benzyl)-urea
(S)-3-(3-Amino-5-chloro-2,6-diethyl-phenyl)-1-(4-chloro-phenyl)-1-[1-(4-chloro-phenyl)-ethyl]-urea
3-(3-Amino-5-chloro-2,6-diethyl-phenyl)-1-(4-isopropyl-phenyl)-1-(6-trifluoromethyl-pyridin-3-ylmethyl)-urea
3-(3-Amino-5-chloro-2,6-diethyl-phenyl)-1-(5-chloro-indan-1-yl)-1-(4-isopropyl-phenyl)-urea
3-(3-Amino-5-chloro-2,6-diethyl-phenyl)-1-chroman-4-yl-1-(4-isopropyl-phenyl)-urea
3-(3-Amino-2,6-diethyl-phenyl)-1-indan-1-yl-1-(4-isopropyl-phenyl)-urea
3-(3-Amino-5-chloro-2,6-diethyl-phenyl)-1-(4-ethyl-phenyl)-1-(1-ethyl-1H-pyrazol-4-ylmethyl)-urea
(S)-3-(3-Amino-5-chloro-2,6-diethyl-phenyl)-1-[1-(4-chloro-phenyl)-ethyl]-1-(4-methoxy-phenyl)-urea
3-(3-Amino-5-chloro-2,6-diethyl-phenyl)-1-(4-chloro-benzyl)-1-(4-trifluoromethylsulfanyl-phenyl)-urea
(S)-3-(3-Amino-5-chloro-2,6-diethyl-phenyl)-1-[1-(4-chloro-phenyl)-ethyl]-1-(3-fluoro-4-methoxy-phenyl)-urea
(S)-3-(3-Amino-5-chloro-2,6-diethyl-phenyl)-1-[1-(4-chloro-phenyl)-ethyl]-1-(4-methanesulfinyl-phenyl)-urea
3-(3-Amino-5-chloro-2,6-diethyl-phenyl)-1-(4-ethyl-phenyl)-1-(4-fluoro-benzyl)-urea
(S)-3-(3-Amino-5-chloro-2,6-diethyl-phenyl)-1-[1-(4-chloro-phenyl)-ethyl]-1-(4-ethyl-3-fluoro-phenyl)-urea
3-(3-Amino-5-chloro-2,6-diethyl-phenyl)-1-(4-chloro-benzyl)-1-(4-ethyl-phenyl)-urea
3-(3-Amino-5-chloro-2,6-diethyl-phenyl)-1-(4-bromo-benzyl)-1-(4-ethyl-phenyl)-urea
3-(3-Amino-5-chloro-2,6-diethyl-phenyl)-1-(6-chloro-pyridin-3-ylmethyl)-1-(4-isopropyl-phenyl)-urea
3-(3-Amino-5-chloro-2,6-diethyl-phenyl)-1-(4-isopropyl-phenyl)-1-thiochroman-4-yl-urea
(S)-3-(3-Amino-5-chloro-2,6-diethyl-phenyl)-1-[1-(4-chloro-phenyl)-ethyl]-1-(2-fluoro-4-methoxy-phenyl)-urea
3-(3-Amino-5-chloro-2,6-diethyl-phenyl)-1-(4-chloro-benzyl)-1-[4-(2,2,2-trifluoro-ethyl)-phenyl]-urea
3-(3-Amino-5-chloro-2,6-diethyl-phenyl)-1-(5-chloro-indan-1-yl)-1-(4-ethyl-phenyl)-urea
3-(3-Amino-5-chloro-2,6-diethyl-phenyl)-1-(5-chloro-pyridin-2-ylmethyl)-1-(4-isopropyl-phenyl)-urea
3-(3-Amino-5-chloro-2,6-diethyl-phenyl)-1-(4-ethyl-phenyl)-1-(6-methyl-pyridin-3-ylmethyl)-urea
3-(3-Amino-2,6-diethyl-phenyl)-1-(4-ethyl-phenyl)-1-(6-methyl-pyridin-3-ylmethyl)-urea
3-(3-Amino-5-chloro-2,6-diethyl-phenyl)-1-(4-chloro-benzyl)-1-naphthalen-1-yl-urea
(S)-3-(3-Amino-5-chloro-2,6-diethyl-phenyl)-1-[1-(4-chloro-phenyl)-ethyl]-1-(2-hydroxymethyl-4-methoxy-phenyl)-urea
3-(3-Amino-5-chloro-2,6-diethyl-phenyl)-1-(4-ethyl-phenyl)-1-(4-pyrazol-1-yl-benzyl)-urea
(S)-3-(3-Amino-6-tert-butyl-2-methyl-phenyl)-1-[1-(4-chloro-phenyl)-ethyl]-1-(4-ethyl-phenyl)-urea
3-(3-Amino-5-chloro-2,6-diethyl-phenyl)-1-(4-ethyl-phenyl)-1-(2-nitro-1-phenyl-ethyl)-urea
3-(3-Amino-5-chloro-2,6-diethyl-phenyl)-1-(4-cyano-benzyl)-1-(4-ethyl-phenyl)-urea
3-(3-Amino-5-chloro-2,6-diethyl-phenyl)-1-(4-chloro-benzyl)-1-(3,4-dimethoxy-phenyl)-urea
3-(3-Amino-5-chloro-2,6-diethyl-phenyl)-1-(4-chloro-benzyl)-1-(4-methoxy-naphthalen-1-yl)-urea
1-(4-Amino-benzyl)-3-(3-amino-5-chloro-2,6-diethyl-phenyl)-1-(4-ethyl-phenyl)-urea
3-(3-Amino-5-chloro-2,6-diethyl-phenyl)-1-(4-chloro-benzyl)-1-(4-difluoromethoxy-phenyl)-urea
3-(3-Amino-5-chloro-2,6-diethyl-phenyl)-1-(4-ethyl-phenyl)-1-(1-methyl-1H-benzoimidazol-5-ylmethyl)-urea
3-(3-Amino-2,6-diethyl-phenyl)-1-(4-chloro-benzyl)-1-(4-methylamino-phenyl)-urea
3-(3-Amino-5-chloro-2,6-diethyl-phenyl)-1-(4-chloro-benzyl)-1-(4-methylamino-phenyl)-urea
3-(3-Amino-5-chloro-2,6-diethyl-phenyl)-1-(2-dimethylamino-pyrimidin-5-ylmethyl)-1-(4-ethyl-phenyl)-urea
3-(3-Amino-5-chloro-2,6-diethyl-phenyl)-1-(4-ethyl-phenyl)-1-[1-(1-methyl-1H-benzoimidazol-5-yl)-ethyl]-urea
3-(3-Amino-5-chloro-2,6-diethyl-phenyl)-1-(4-ethyl-phenyl)-1-[1-(6-methyl-pyridin-3-yl)-ethyl]-urea
3-(3-Amino-5-chloro-2,6-diethyl-phenyl)-1-(2-fluoro-4-methoxy-phenyl)-1-(6-methyl-pyridin-3-ylmethyl)-urea
3-(3-Amino-5-chloro-2,6-diethyl-phenyl)-1-(4-chloro-benzyl)-1-(5-methoxy-quinolin-8-yl)-urea
3-(3-Amino-5-chloro-2,6-diethyl-phenyl)-1-(6-methyl-pyridin-3-ylmethyl)-1-[4-(2,2,2-trifluoro-ethyl)-phenyl]-urea
3-(3-Amino-5-chloro-2,6-diethyl-phenyl)-1-(4-chloro-benzyl)-1-(4-dimethylamino-phenyl)-urea
3-(3-Amino-5-chloro-2,6-diethyl-phenyl)-1-benzyl-1-(4-dimethylamino-phenyl)-urea
3-(3-Amino-5-chloro-2,6-diethyl-phenyl)-1-benzyl-1-(4-methylamino-phenyl)-urea
3-(3-Amino-5-chloro-2,6-diethyl-phenyl)-1-(4-chloro-benzyl)-1-(8-methoxy-2,3-dimethyl-chinoxalin-5-yl)-urea
(S)-3-(3-Amino-5-chloro-2,6-diethyl-phenyl)-1-[1-(4-chloro-phenyl)-ethyl]-1-(4-methylamino-phenyl)-urea
3-(3-Amino-5-chloro-2,6-diethyl-phenyl)-1-(4-methylamino-phenyl)-1-(1-phenyl-ethyl)-urea (S)-3-(3-Chloro-2,6-diethyl-5-nitroso-phenyl)-1-[1-(4-chloro-phenyl)-ethyl]-1-(4-methylamino-phenyl)-urea 3-(3-Amino-5-chloro-2,6-diethyl-phenyl)-1-(4-methoxy-naphthalen-1-yl)-1-(6-methyl-pyridin-3-ylmethyl)-urea 3-(3-Amino-5-chloro-2,6-diethyl-phenyl)-1-(4-chloro-benzyl)-1-(4-ethylamino-phenyl)-urea 3-(3-Amino-5-chloro-2,6-diethyl-phenyl)-1-[4-(2-amino-ethyl)-benzyl]-1-(4-ethyl-phenyl)-urea 3-(3-Amino-5-chloro-2,6-diethyl-phenyl)-1-(4-methylamino-phenyl)-1-[1-(1-methyl-1H-benzoimidazol-5-yl)-ethyl]-urea 3-(3-Amino-5-chloro-2,6-diethyl-phenyl)-1-(4-chloro-benzyl)-1-(4-methylamino-naphthalen-1-yl)-urea N-{4-[3-(3-Amino-5-chloro-2,6-diethyl-phenyl)-1-(4-chloro-benzyl)-ureido]-phenyl}-acetamide (S)-3-(3-Amino-5-chloro-2,6-diethyl-phenyl)-1-[1-(4-chloro-phenyl)-ethyl]-1-(1H-indol-5-yl)-urea 3-(3-Amino-5-chloro-2,6-diethyl-phenyl)-1-[1-(4-chloro-phenyl)-ethyl]-1-[4-(2,2,2-trifluoro-ethyl)-phenyl]-urea In a twenty-second embodiment of the first aspect which is also an embodiment of the twenty-first embodiment the compound is selected from the group comprising 3-(3-Amino-2,6-diisopropyl-phenyl)-1-(4-isopropyl-phenyl)-1-(4-methoxy-benzyl)-urea 3-(3-Amino-2,6-diethyl-phenyl)-1-(4-isopropyl-phenyl)-1-(4-methoxy-benzyl)-urea 3-(3-Amino-5-chloro-2,6-diethyl-phenyl)-1-(4-isopropyl-phenyl)-1-(4-methoxy-benzyl)-urea 3-(3-Amino-5-chloro-2,6-diethyl-phenyl)-1-(4-ethyl-phenyl)-1-(4-methoxy-benzyl)-urea 3-(3-Amino-5-chloro-2,6-diethyl-phenyl)-1-(4-isopropyl-phenyl)-1-(4-methyl-benzyl)-urea 3-(3-Amino-5-chloro-2,6-diethyl-phenyl)-1-(4-ethyl-benzyl)-1-(4-isopropyl-phenyl)-urea 3-(3-Amino-2,6-diethyl-phenyl)-1-(4-isopropyl-phenyl)-1-(4-methyl-benzyl)-urea (R)-3-(3-Amino-5-chloro-2,6-diethyl-phenyl)-1-(4-isopropyl-phenyl)-1-(1,2,3,4-tetrahydro-naphthalen-1-yl)-urea (S)-3-(3-Amino-5-chloro-2,6-diethyl-phenyl)-1-(4-isopropyl-phenyl)-1-(1,2,3,4-tetrahydro-naphthalen-1-yl)-urea 3-(3-Amino-5-chloro-2,6-diethyl-phenyl)-1-benzyl-1-(4-isopropyl-phenyl)-urea 3-(3-Amino-5-chloro-2,6-diethyl-phenyl)-1-(4-isopropyl-phenyl)-1-(6-methoxy-pyridin-3-ylmethyl)-urea 3-(3-Amino-5-chloro-2,6-diethyl-phenyl)-1-(4-isopropyl-phenyl)-1-(4-trifluoromethyl-benzyl)-urea 3-(3-Amino-2,6-diethyl-phenyl)-1-(4-isopropyl-phenyl)-1-(4-trifluoromethyl-benzyl)-urea 3-(3-Amino-5-chloro-2,6-diethyl-phenyl)-1-(4-isopropyl-phenyl)-1-(2-p-tolyl-ethyl)-urea 3-(3-Amino-5-chloro-2,6-diethyl-phenyl)-1-(4-ethyl-phenyl)-1-(4-methyl-benzyl)-urea 3-(3-Amino-2,6-diethyl-phenyl)-1-(4-ethyl-phenyl)-1-(4-methyl-benzyl)-urea (R)-3-(3-Amino-5-chloro-2,6-diethyl-phenyl)-1-(4-isopropyl-phenyl)-1-[1-(4-methoxy-phenyl)-ethyl]-urea (R)-3-(3-Amino-5-chloro-2,6-diethyl-phenyl)-1-(4-isopropyl-phenyl)-1-(1-p-tolyl-ethyl)-urea 3-(3-Amino-5-chloro-2,6-diethyl-phenyl)-1-(2-fluoro-4-methoxy-benzyl)-1-(4-isopropyl-phenyl)-urea 3-(3-Amino-2,6-diethyl-phenyl)-1-(2-fluoro-4-methoxy-benzyl)-1-(4-isopropyl-phenyl)-urea 3-(3-Amino-2,6-diethyl-phenyl)-1-cyclohexylmethyl-1-(4-isopropyl-phenyl)-urea 3-(3-Amino-5-chloro-2,6-diethyl-phenyl)-1-(4-isopropyl-phenyl)-1-(2-methoxy-benzyl)-urea 3-(3-Amino-5-chloro-2,6-diethyl-phenyl)-1-(2,3-dihydro-benzofuran-5-ylmethyl)-1-(4-isopropyl-phenyl)-urea (S)-3-(3-Amino-5-chloro-2,6-diethyl-phenyl)-1-(4-isopropyl-phenyl)-1-[1-(4-methoxy-phenyl)-ethyl]-urea 3-(3-Amino-2,6-diethyl-phenyl)-1-(2,3-dihydro-benzofuran-5-ylmethyl)-1-(4-isopropyl-phenyl)-urea (S)-3-(3-Amino-2,6-diethyl-phenyl)-1-(4-isopropyl-phenyl)-1-(1-p-tolyl-ethyl)-urea (S)-3-(3-Amino-2,6-diethyl-phenyl)-1-(4-isopropyl-phenyl)-1-[1-(4-methoxy-phenyl)-ethyl]-urea 3-(3-Amino-5-chloro-2,6-diethyl-phenyl)-1-(4-chloro-benzyl)-1-(4-isopropyl-phenyl)-urea (S)-3-(3-Amino-5-chloro-2,6-diethyl-phenyl)-1-(4-isopropyl-phenyl)-1-(1-p-tolyl-ethyl)-urea 3-(3-Amino-5-chloro-2,6-diethyl-phenyl)-1-(4-isopropyl-phenyl)-1-pyridin-3-ylmethyl-urea 3-(3-Amino-5-chloro-2,6-diethyl-phenyl)-1-(4-isopropyl-phenyl)-1-(5-methyl-pyrazin-2-ylmethyl)-urea 3-(3-Amino-5-chloro-2,6-diethyl-phenyl)-1-(4-isopropyl-phenyl)-1-(6-methyl-pyridin-3-ylmethyl)-urea 3-(3-Amino-5-chloro-2,6-diethyl-phenyl)-1-(2,4-dimethoxy-pyrimidin-5-ylmethyl)-1-(4-isopropyl-phenyl)-urea (S)-3-(3-Amino-5-chloro-2,6-diethyl-phenyl)-1-[1-(4-chloro-phenyl)-ethyl]-1-(4-isopropyl-phenyl)-urea (S)-3-(3-Amino-5-chloro-2,6-dimethyl-phenyl)-1-(4-isopropyl-phenyl)-1-(1-p-tolyl-ethyl)-urea (S)-3-(3-Amino-5-chloro-2,6-diethyl-phenyl)-1-[1-(4-chloro-phenyl)-ethyl]-1-(4-ethyl-phenyl)-urea (S)-3-(3-Amino-5-chloro-2,6-diethyl-phenyl)-1-[1-(4-fluoro-phenyl)-ethyl]-1-(4-isopropyl-phenyl)-urea (S)-3-(3-Amino-5-chloro-2,6-diethyl-phenyl)-1-(4-ethyl-phenyl)-1-[1-(4-fluoro-phenyl)-ethyl]-urea (S)-3-(3-Amino-5-chloro-2,6-diethyl-phenyl)-1-[1-(4-chloro-phenyl)-ethyl]-1-(4-methylsulfanyl-phenyl)-urea 3-(3-Amino-5-chloro-2,6-diethyl-phenyl)-1-indan-1-yl-1-(4-isopropyl-phenyl)-urea 3-(3-Amino-5-chloro-2,6-diethyl-phenyl)-1-(4-ethynyl-phenyl)-1-(4-methoxy-benzyl)-urea (S)-3-(3-Amino-5-chloro-2,6-diethyl-phenyl)-1-(4-chloro-phenyl)-1-[1-(4-chloro-phenyl)-ethyl]-urea 3-(3-Amino-5-chloro-2,6-diethyl-phenyl)-1-(4-isopropyl-phenyl)-1-(6-trifluoromethyl-pyridin-3-ylmethyl)-urea 3-(3-Amino-5-chloro-2,6-diethyl-phenyl)-1-(5-chloro-indan-1-yl)-1-(4-isopropyl-phenyl)-urea 3-(3-Amino-5-chloro-2,6-diethyl-phenyl)-1-chroman-4-yl-1-(4-isopropyl-phenyl)-urea 3-(3-Amino-2,6-diethyl-phenyl)-1-indan-1-yl-1-(4-isopropyl-phenyl)-urea 3-(3-Amino-5-chloro-2,6-diethyl-phenyl)-1-(4-ethyl-phenyl)-1-(1-ethyl-1H-pyrazol-4-ylmethyl)-urea (S)-3-(3-Amino-5-chloro-2,6-diethyl-phenyl)-1-[1-(4-chloro-phenyl)-ethyl]-1-(4-methoxy-phenyl)-urea 3-(3-Amino-5-chloro-2,6-diethyl-phenyl)-1-(4-chloro-benzyl)-1-(4-trifluoromethylsulfanyl-phenyl)-urea (S)-3-(3-Amino-5-chloro-2,6-diethyl-phenyl)-1-[1-(4-chloro-phenyl)-ethyl]-1-(3-fluoro-4-methoxy-phenyl)-urea (S)-3-(3-Amino-5-chloro-2,6-diethyl-phenyl)-1-[1-(4-chloro-phenyl)-ethyl]-1-(4-methanesulfinyl-phenyl)-urea 3-(3-Amino-5-chloro-2,6-diethyl-phenyl)-1-(4-ethyl-phenyl)-1-(4-fluoro-benzyl)-urea (S)-3-(3-Amino-5-chloro-2,6-diethyl-phenyl)-1-[1-(4-chloro-phenyl)-ethyl]-1-(4-ethyl-3-fluoro-phenyl)-urea 3-(3-Amino-5-chloro-2,6-diethyl-phenyl)-1-(4-chloro-benzyl)-1-(4-ethyl-phenyl)-urea 3-(3-Amino-5-chloro-2,6-diethyl-phenyl)-1-(4-bromo-benzyl)-1-(4-ethyl-phenyl)-urea
3-(3-Amino-5-chloro-2,6-diethyl-phenyl)-1-(6-chloro-pyridin-3-ylmethyl)-1-(4-isopropyl-phenyl)-urea
(S)-3-(3-Amino-5-chloro-2,6-diethyl-phenyl)-1-[1-(4-chloro-phenyl)-ethyl]-1-(2-fluoro-4-methoxy-phenyl)-urea
3-(3-Amino-5-chloro-2,6-diethyl-phenyl)-1-(4-chloro-benzyl)-1-[4-(2,2,2-trifluoro-ethyl)-phenyl]-urea
3-(3-Amino-5-chloro-2,6-diethyl-phenyl)-1-(5-chloro-indan-1-yl)-1-(4-ethyl-phenyl)-urea
3-(3-Amino-5-chloro-2,6-diethyl-phenyl)-1-(5-chloro-pyridin-2-ylmethyl)-1-(4-isopropyl-phenyl)-urea
3-(3-Amino-5-chloro-2,6-diethyl-phenyl)-1-(4-ethyl-phenyl)-1-(6-methyl-pyridin-3-ylmethyl)-urea
3-(3-Amino-2,6-diethyl-phenyl)-1-(4-ethyl-phenyl)-1-(6-methyl-pyridin-3-ylmethyl)-urea
3-(3-Amino-5-chloro-2,6-diethyl-phenyl)-1-(4-chloro-benzyl)-1-naphthalen-1-yl-urea
(S)-3-(3-Amino-6-tert-butyl-2-methyl-phenyl)-1-[1-(4-chloro-phenyl)-ethyl]-1-(4-ethyl-phenyl)-urea
3-(3-Amino-5-chloro-2,6-diethyl-phenyl)-1-(4-cyano-benzyl)-1-(4-ethyl-phenyl)-urea
3-(3-Amino-5-chloro-2,6-diethyl-phenyl)-1-(4-chloro-benzyl)-1-(3,4-dimethoxy-phenyl)-urea
3-(3-Amino-5-chloro-2,6-diethyl-phenyl)-1-(4-chloro-benzyl)-1-(4-methoxy-naphthalen-1-yl)-urea
3-(3-Amino-5-chloro-2,6-diethyl-phenyl)-1-(4-chloro-benzyl)-1-(4-difluoromethoxy-phenyl)-urea
3-(3-Amino-5-chloro-2,6-diethyl-phenyl)-1-(4-ethyl-phenyl)-1-(1-methyl-1H-benzoimidazol-5-ylmethyl)-urea
3-(3-Amino-2,6-diethyl-phenyl)-1-(4-chloro-benzyl)-1-(4-methylamino-phenyl)-urea
3-(3-Amino-5-chloro-2,6-diethyl-phenyl)-1-(4-chloro-benzyl)-1-(4-methylamino-phenyl)-urea
3-(3-Amino-5-chloro-2,6-diethyl-phenyl)-1-(4-ethyl-phenyl)-1-[1-(1-methyl-1H-benzoimidazol-5-yl)-ethyl]-urea
3-(3-Amino-5-chloro-2,6-diethyl-phenyl)-1-(4-ethyl-phenyl)-1-[1-(6-methyl-pyridin-3-yl)-ethyl]-urea
3-(3-Amino-5-chloro-2,6-diethyl-phenyl)-1-(2-fluoro-4-methoxy-phenyl)-1-(6-methyl-pyridin-3-ylmethyl)-urea
3-(3-Amino-5-chloro-2,6-diethyl-phenyl)-1-(4-chloro-benzyl)-1-(5-methoxy-quinolin-8-yl)-urea
3-(3-Amino-5-chloro-2,6-diethyl-phenyl)-1-(6-methyl-pyridin-3-ylmethyl)-1-[4-(2,2,2-trifluoro-ethyl)-phenyl]-urea
3-(3-Amino-5-chloro-2,6-diethyl-phenyl)-1-(4-chloro-benzyl)-1-(4-dimethylamino-phenyl)-urea
3-(3-Amino-5-chloro-2,6-diethyl-phenyl)-1-benzyl-1-(4-methylamino-phenyl)-urea
(S)-3-(3-Amino-5-chloro-2,6-diethyl-phenyl)-1-[1-(4-chloro-phenyl)-ethyl]-1-(4-methylamino-phenyl)-urea
3-(3-Amino-5-chloro-2,6-diethyl-phenyl)-1-(4-methylamino-phenyl)-1-(1-phenyl-ethyl)-urea
(S)-3-(3-Chloro-2,6-diethyl-5-nitroso-phenyl)-1-[1-(4-chloro-phenyl)-ethyl]-1-(4-methylamino-phenyl)-urea
3-(3-Amino-5-chloro-2,6-diethyl-phenyl)-1-(4-methoxy-naphthalen-1-yl)-1-(6-methyl-pyridin-3-ylmethyl)-urea
3-(3-Amino-5-chloro-2,6-diethyl-phenyl)-1-(4-chloro-benzyl)-1-(4-ethylamino-phenyl)-urea
3-(3-Amino-5-chloro-2,6-diethyl-phenyl)-1-[4-(2-amino-ethyl)-benzyl]-1-(4-ethyl-phenyl)-urea
3-(3-Amino-5-chloro-2,6-diethyl-phenyl)-1-(4-methylamino-phenyl)-1-[1-(1-methyl-1H-benzoimidazol-5-yl)-ethyl]-urea
N-{4-[3-(3-Amino-5-chloro-2,6-diethyl-phenyl)-1-(4-chloro-benzyl)-ureido]-phenyl}-acetamide
(S)-3-(3-Amino-5-chloro-2,6-diethyl-phenyl)-1-[1-(4-chloro-phenyl)-ethyl]-1-(1H-indol-5-yl)-urea
3-(3-Amino-5-chloro-2,6-diethyl-phenyl)-1-[1-(4-chloro-phenyl)-ethyl]-1-[4-(2,2,2-trifluoro-ethyl)-phenyl]-urea In a third aspect which is also a first embodiment thereof, the problem underlying the present invention is solved by a pharmaceutical composition comprising at least one compound according to any of the various embodiments of the first or second aspect, and a pharmaceutically acceptable carrier.

In a fourth aspect which is also a first embodiment thereof, the problem underlying the present invention is solved by the use of at least one compound according to any of the various embodiments of the first or second aspect for the manufacture of a medicament.

In a second embodiment of the fourth aspect which is also an embodiment of the first embodiment of the fourth aspect, the medicament is for the prevention and/or treatment of a disease in connection with which the complement system is activated and/or in connection with which the inhibition of the complement system causes an abatement of the symptoms.

In a third embodiment of the fourth aspect which is also an embodiment of the first embodiment of the fourth aspect, the medicament is for the prevention and/or treatment of a disease in connection with which the inhibition of the activation of the C5a receptor alone and/or in combination with other therapeutics causes an abatement of the symptoms.

In a fourth embodiment of the fourth aspect which is also an embodiment of the first, second or third embodiment of the fourth aspect, the disease and/or the symptoms are selected from the group comprising autoimmune diseases, acute and chronic inflammatory diseases, trauma, local inflammations, shock and burn injuries.

In a fifth embodiment of the fourth aspect which is also an embodiment of the first, second or third embodiment of the fourth aspect, the disease is a serious burn injury.

In a sixth embodiment of the fourth aspect which is also an embodiment of the first, second or third embodiment of the fourth aspect, the disease is a consequential damage caused by burn injury, whereby the consequential damage comprises organ breakdown, shock, SIRS (severe/systemic inflammatory response syndrome), sepsis, edema formation, intricacies during the removal of skin by surgery and fibrosis of skin or organs.

In a seventh embodiment of the fourth aspect which is also an embodiment of the first to fourth embodiment of the fourth aspect, the disease is selected from the group comprising septic shock, hemorrhagic shock, SIRS (systemic/severe inflammatory response syndrom), MOF (multi organ failure), acute respiratory insufficiency (ARDS), stroke (apoplexia), myocardial infarction, reperfusion injury and acute injuries of the central nervous system.

In an eighth embodiment of the fourth aspect which is an embodiment of the seventh embodiment of the fourth aspect, the reperfusion injury occurs at one or multiple organs, organ systems or body parts, which are selected from the group comprising liver, kidney, intestine, lung, heart, spleen, urinary bladder, stomach, muscles, skin, extremities, brain and pancreas.

In a ninth embodiment of the fourth aspect which is an embodiment of the seventh and of the eighth embodiment of the fourth aspect, acute consequences and/or chronic consequences of a reperfusion injury are treated, whereby preferably acute consequences are acute organ failure or the formation of necrotic areas, and preferably chronic consequences are changes like the dilatative/dilated cardiomyopathy or fibrosis, preferably fibrosis caused by a trauma, fibrosis caused by a myocardial infarction or by transplantation, whereby the consequences are preferably a limited organ function.

In a tenth embodiment of the fourth aspect which is an embodiment of the ninth embodiment of the fourth aspect, the reperfusion injury occurs after myocardial infarction.

In an eleventh embodiment of the fourth aspect which is an embodiment of the ninth embodiment of the fourth aspect, the reperfusion injury occurs at the kidney.

In a twelfth embodiment of the fourth aspect which is an embodiment of the ninth embodiment of the fourth aspect, the reperfusion injury occurs after or during an aneurysm surgery.

In a thirteenth embodiment of the fourth aspect which is an embodiment of the first to the fourth embodiment of the fourth aspect, the disease is selected from the group comprising asthma, myocarditis, inflammatory bowel disease (IBD; morbus crohn and colitis ulcerosa), inflammatory diseases of the eye, glomerulonephritis, inflammatory vascular diseases, and local manifestations of systemic diseases.

In a fourteenth embodiment of the fourth aspect which is an embodiment of the thirteenth embodiment of the fourth aspect, the inflammatory disease of the eye is selected from the group comprising uveitis, age related macular degeneration (AMD), diabetic retinopathy, diabetic macular edema, ocular pemphigoid, keratoconjunctivitis, Stevens-Johnson syndrome and Graves opthalmophaty.

In a fifteenth embodiment of the fourth aspect which is an embodiment of the fourteenth embodiment of the fourth aspect, the inflammatory disease of the eye is age related macular degeneration.

In a sixteenth embodiment of the fourth aspect which is an embodiment of the fourteenth embodiment of the fourth aspect, the disease is a local manifestation of systemic diseases, whereby the systemic disease is selected from the group comprising rheumatism, SLE and type I and type II diabetes.

In a seventeenth embodiment of the fourth aspect which is an embodiment of the fourteenth or sixteenth embodiment of the fourth aspect, the manifestation is selected from the group comprising manifestations at the eye, at or in the brain, at the vessels, at the heart, at the lung, at the kidney, at the liver, at the gastrointestinal tract, at the spleen, at the skin, at bones, at the lymphatic system and manifestations in the blood.

In an eighteenth embodiment of the fourth aspect which is an embodiment of the fourth embodiment of the fourth aspect, the chronic inflammatory disease is an autoimmune disease, whereby the autoimmune disease preferably is selected from the group comprising alopecia greata, autoimmune hemolytic anemia (AIHA) cold type (cold agglutinin disease), autoimmune hemolytic anemia (AIHA) warm type, Addison's anemia (Morbus Biermer), Antiphospholipid-syndrome (APS), Arteriitis temporalis, artheriosclerosis, autoimmune adrenalitis (autoimmune adrenal-glands atrophie, Addison's disease), chronic fatigue syndrome (CFIDS), chronic inflammatory, demyelinising polyneuropathie, Churg-Strauss syndrome, Cogan-syndrome, colitis ulcerosa, CREST syndrome, diabetes mellitus type I, Dermatitis Herpetiformis During, dermatomyositis, fibromoyalgitis chronic autoimmune gastritis, Goodpasture's syndrome (anti-GBM mediated glomerulonephritis), Guillain-Barré-syndrome (GBS; Polyradikuloneuritis), Hashimoto Thyroiditis, autoimmune Hepatitis, idiopatc pulmonary fibrosis, autoimmune thrombozytopenic purpura (Morbus Werlhof), autoimmune infertility, autoimmune internal ear deafness (AIED), juvenile rheumathoid arthritis, autoimmune cardiomyopathie, Lambert-Eaton syndrome, lichen sclerosis, discoid lupus erythematodes, lyme disease, Sharp syndrome, Morbus Basedow (Graves Disease), Morbus Behçet, Morbus Bechterew (Spondylitis ankylosans), Morbus Ménière, Morbus Reiter, multiple sclerosis (MS, Encephalomyelitis), myasthenia gravis, sympatic ophthalmia, scarred pemphigoid, bulloes pemphigoid, Pemphigus vulgaris, Polyarteriitis nodosa, Polychondritis (Panchondritis), polyglandular autoimmune-(PGA)-syndrome, Polymyalgia rheumatica, Polymoysitis, primary billiary cirrhosis (primary autoimmune-cholangitis), psoriasis, rheumathoid fever, rheumatic arthritis, sarkoidosis (Morbus Boeck, Besnier-Boeck-Schaumann disease), Sjörgensen-syndrome, scleroremia, celiac disease, Stiff-Man-syndrome (Moersch-Woltmann-syndrome), systemic lupus erythematodes, Takayasu Arteriitis (aortic arch syndrome), transient gluten intolerance, Urticaria, autoimmune uveitis, vasculitides and vitiligo.

In a nineteenth embodiment of the fourth aspect which is an embodiment of the thirteenth embodiment of the fourth aspect, the inflammatory disease of the vessel is selected from the group comprising vasculitis, vascular leakage and atherosclerosis.

In a twentieth embodiment of the fourth aspect which is an embodiment of the nineteenth embodiment of the fourth aspect, the vasculitis is selected from the group comprising primary vasculitis and secondary vasculitis.

In a twenty-first embodiment of the fourth aspect which is an embodiment of the twentieth embodiment of the fourth aspect, the primary vasculitis is selected from the group comprising the vasculitides, Morbus Wegener, Churg-Strauss-syndrome and microscopic polyangiitis.

In a twenty-second embodiment of the fourth aspect which is an embodiment of the twentieth embodiment of the fourth aspect, the secondary vasculitits is selected from the group comprising vasculitides caused by medicaments or by other diseases.

In a twenty-third embodiment of the fourth aspect which is an embodiment of the twenty-second embodiment of the fourth aspect, the other diseases are selected from the group comprising AIDS, hepatitis B, hepatitis C and cytomegalie virus infection.

In a twenty-fourth embodiment of the fourth aspect which is an embodiment of the eighteenth embodiment of the fourth aspect, the urticaria is selected from the group comprising spontaneous and physical urticaria and special forms of the urticaria.

In a twenty-fifth embodiment of the fourth aspect which is an embodiment of the twenty-fourth embodiment of the fourth aspect, the physical urticaria is selected from the group comprising urticaria factitia, cold urticaria, heat urticaria, pressure urticaria and light urticaria.

In a twenty-sixth embodiment of the fourth aspect which is an embodiment of the twenty-fourth embodiment of the fourth aspect, the spontaneous urticaria is selected from the group comprising acute urticaria and chronic urticaria.

In a twenty-seventh embodiment of the fourth aspect which is an embodiment of the twenty-fourth embodiment of the fourth aspect, the spontaneous urticaria is characterized by autoantibodies against IgE or the IgE receptor, which can be detected.

In a twenty-eighth embodiment of the fourth aspect which is an embodiment of the twenty-fourth embodiment of the fourth aspect, the special forms of the urticaria are cholinergic urticaria, adrenergic urticaria, contact urticaria and urticaria that is caused by water (aquagenic urticaria).

In a twenty-ninth embodiment of the fourth aspect which is an embodiment of the first to third embodiment of the fourth aspect, the medicament is used for the prevention and/or support of surgeries.

In a thirtieth embodiment of the fourth aspect which is an embodiment of the twenty-nineth embodiment of the fourth aspect, the medicament or the compound is used for the support and/or for the prevention and/or for the aftercare of a surgery, whereby the surgery is selected from the group comprising CABG, PCTA, PTA, MidCAB, OPCAB, thrombolysis, organ transplantation, aneurysma surgery and vascular obliteration (clamping), whereby, preferably, one aspect is to cease or prevent neurocognitive dysfunctions which possibly follow extracorporal circulation (e.g. heart-lung machine).

In a thirty-first embodiment of the fourth aspect which is an embodiment of the first to third embodiment of the fourth aspect, the medicamental support is used for thrombolytic treatment.

In a thirty-second embodiment of the fourth aspect which is an embodiment of the first to third embodiment of the fourth aspect, the medicament is applied in connection with a dialysis treatment, before, during or after the treatment.

In a thirty-third embodiment of the fourth aspect which is an embodiment of the first to third embodiment of the fourth aspect, the medicament is used for the prevention of damages to a transplanted organ and/or an organ that will be transplanted.

In a thirty-fourth embodiment of the fourth aspect which is an embodiment of the first to third embodiment of the fourth aspect, the medicament is used for the conservation or as a support for the conservation of organs that are designated to be transplanted.

In a thirty-fifth embodiment of the fourth aspect which is an embodiment of the first to third embodiment of the fourth aspect, the medicament is used for the prophylaxis or treatment of a rejection reaction of a transplanted organ.

In a thirty-sixth embodiment of the fourth aspect which is an embodiment of the thirty-third to thirty-fifth embodiment of the fourth aspect, the transplanted or designated to be transplanted organ is selected from the group comprising kidney, liver, lung, heart, skin, horny skin, pancreas and intestine.

In a thirty-seventh embodiment of the fourth aspect which is an embodiment of the thirty-third to thirty-sixth embodiment of the fourth aspect, the organ is for self donation, preferably self-donation of skin for the treatment of burn injuries, or blood.

In a thirty-eighth embodiment of the fourth aspect which is an embodiment of the first to third embodiment of the fourth aspect the medicament is used for the prophylaxis of fibrotic events, preferably treatment or prevention or reduction of scar tissue formation.

In a thirty-ninth embodiment of the fourth aspect which is an embodiment of the thirty-eighth embodiment of the fourth aspect, the fibrotic event can occur in one or several of the organs selected from the group comprising liver, lung, kidney, skin, heart and other organs.

In a fortieth embodiment of the fourth aspect which is an embodiment of the first to third embodiment of the fourth aspect, the medicament is used for the prophylaxis or treatment of the IgA nephropathy.

In a fifth aspect which is also a first embodiment thereof, the problem underlying the present invention is solved by the use of a compound according to any of the first and the second aspect for the cosmetic treatment of a human or animal body.

In a forty-first embodiment of the fourth aspect which is an embodiment of the thirteenth embodiment of the fourth aspect, the inflammatory bowel disease is selected from the group comprising Morbus Crohn or ulcerative colitis.

In a forty-second embodiment of the fourth aspect which is an embodiment of the first to third embodiment of the fourth aspect, the disease is caused by intracellular parasites or viruses.

In a forty-third embodiment of the fourth aspect which is an embodiment of the forty-second embodiment of the fourth aspect, the intracellular parasites are selected from the group comprising leishmania, rickettsiae, chlamydia, coxiella, plasmodia, brucella, mycobacteria, listeria, toxoplasmics and trypanosomes.

In a forty-fourth embodiment of the fourth aspect which is an embodiment of the third embodiment of the fourth aspect, the disease is prevented and/or treated with a medicament as defined in any embodiment of the fourth aspect in combination with one or several anti-inflammatory and/or one or several immunosuppressive therapeutics.

In a forty-fifth embodiment of the fourth aspect which is also an embodiment of the third embodiment of the fourth aspect, the disease is prevented and/or treated with a medicament as defined in any embodiment of the fourth aspect in combination with one or several immunosuppressive therapeutics.

In a forty-sixth embodiment of the fourth aspect which is an embodiment of the forty-fifth embodiment of the fourth aspect, the combination is comprised of a medicament as defined in any embodiment of the fourth embodiment and a medicament selected from the group comprising calcineurin inhibitors, or a medicament comprising one or several substances selected from the group comprising Cyclosporine A, Methotrexate, Azathioprine, FK506 (Tacrolimus), Rapamycine, Leflunomide, Mycophenolatmofetile, Brequinar, Mizoribine, Thalidomide and Deoxyspergualine.

In a forty-seventh embodiment of the fourth aspect which is an embodiment of the third embodiment of the fourth aspect, the disease is prevented and/or treated with a medicament as defined in any embodiment of the fourth aspect, in combination with one or several antihistamines.

In a forty-eighth embodiment of the fourth aspect which is an embodiment of the forthy-seventh embodiment of the fourth aspect, the antihistamine is selected from the group comprising Meclozine, Clemastine, Dimetindene, Bamipine, Ketotifene, Cetirizine, Lovecetirizine, Loratidine, Desloratidine, Azelastine, Mizolastine, Levocabastine, Terfenadine, Fexofenadine and Ebastine.

In a forty-ninth embodiment of the fourth aspect which is an embodiment of the third embodiment of the fourth aspect, the disease is prevented and/or treated with a medicament as defined in any embodiment of the fourth aspect, in combination with one or several glucocorticoids.

In a fiftieth embodiment of the fourth aspect which is an embodiment of the forty-ninth embodiment of the fourth aspect, the glucocorticoid is selected from the group comprising Betamethasone, Effervescent, Budesonide, Cortisone, Dexamethasone, Elixir, Hydrocortisone, Methylprednisolone, Prednisolone, Prednisone and Triamcinolone.

In a fifty-first embodiment of the fourth aspect which is an embodiment of the third embodiment of the fourth aspect, the disease is prevented and/or treated with a medicament as defined in any embodiment of the fourth aspect, in combination with one or several antibiotics.

In a fifty-second embodiment of the fourth aspect which is an embodiment of the fifty-first embodiment of the fourth aspect, the antibiotic is selected from the group comprising aminoglycosides, β-lactam antibiotics, glycopeptide antibiotics, gyrase inhibitors, Lincosamide, makrolide antibiotics, nitroimidazol derivates, polypeptide antibiotics, sulfonamides, Trimethoprime and Tetracycline.

In a fifty-third embodiment of the fourth aspect which is an embodiment of the third embodiment of the fourth aspect, the disease is prevented and/or treated with a medicament as defined in any embodiment of the fourth aspect, in combination with one or several anti-inflammatory agents and more preferably anti-inflammatory biologicals.

In a fifty-fourth embodiment of the fourth aspect which is an embodiment of the fifty-third embodiment of the fourth aspect, the anti-inflammatory agent is selected from the group comprising IL-10, Erlizumab, TolerMab, Rituximab, Gomiliximab, Basiliximab, Daclizumab, HuMax-TAC, Visilizumab, HuMaxCD4, Clenoliximab, MAX 16H5, TNX 100, Toralizumab, Alemtuzumab, CY 1788, Galiximab, Pexelizumab, Eculizumab, ETI 104, FG 3019, Bertilimumab, 249417 (anti-Faktor IX), Abciximab, YM 337, Omalizumab, Talizumab, Fontolizumab, J695 (anti-IL12), HuMax IL-15, Mepolizumab, Elsilimomab, HuDREG, Adalimumab, Infliximab, Certolizumab, Afelimomab, CytoFab, AME 527, Vapaliximab, Avastin, Vitaxin, Belimumab, MLN 1202, Volociximab, F200 (anti-α5β1), Efalizumab, m60.11 (anti-CD11b), Etanercept, Onerecept, Natalizumab and Siplizumab.

In a fifty-fifth embodiment of the fourth aspect which is an embodiment of the third embodiment of the fourth aspect, the disease is prevented and/or treated with a medicament as defined in any embodiment of the fourth aspect in combination with photodynamic therapy, preferably photodynamic therapy with Visodyne.

In a fifty-sixth embodiment of the fourth aspect which is an embodiment of the third embodiment of the fourth aspect, the disease is AMD (age related macular degeneration) and AMD is prevented and/or treated with a medicament as defined in any of the third and the fourth aspects in combination with a medicament which is selected from the group comprising Visodyne, VEGF inhibitors and α5β1 inhibitors.

In an fifty-seventh embodiment of the fourth aspect which is an embodiment of the third embodiment of the fourth aspect, the disease is prevented and/or treated with a medicament as defined in any embodiment of the fourth aspect, in combination with a medicament selected from the group comprising acetylsalicylic acid, Ibuprofen, Diclofenac and Naproxen.

In a fifty-eighth embodiment of the fourth aspect which is an embodiment of the third embodiment of the fourth aspect, the disease is prevented and/or treated with a medicament as defined in any embodiment of the fourth aspect, in combination with a medicament which is selected from the group comprising antagonists of the bradykinine receptor 1 and antagonists of the bradykinine receptor 2.

In a fifty-ninth embodiment of the fourth aspect which is an embodiment of the fifty-eighth embodiment of the fourth aspect, the prevention and/or treatment is for the treatment and/or prevention of acute inflammatory diseases, whereby the disease is selected from the group comprising sepsis, severe burn injury, reperfusion injury, myocardial infarction, organ rejection and hemorrhagic shock.

In a sixtieth embodiment of the fourth aspect which is an embodiment of the fifty-ninth embodiment of the fourth aspect, the prevention and/or treatment is for the treatment and/or prevention of chronic autoimmune diseases and/or the treatment and/or prevention of infectious diseases.

In a sixth aspect which is also a first embodiment thereof, the problem underlying the present invention is solved by a combination of an antagonist of the bradykinine receptor 2 and a C5a receptor antagonist for the therapy of severe burn injury.

As used herein the term medicament according to the third or fourth aspect is a medicament which is or can be manufactured in accordance with the present disclosure using the compounds according to the invention or as defined in connection with any aspect of the present invention.

In connection with the present invention, the following terms and expressions are preferably used in an interchangeable manner, namely medicament, formulation, medication and pharmaceutical composition; invention-based compounds, compound based on the present invention, compounds of this invention, compounds of the present invention, and compounds in accordance with this/the present invention. It will also be acknowledged by the ones skilled in the art that what is disclosed herein in connection with the one of these terms to be used and understood, respectively, in an interchangeable manner, is also disclosed for such other terms or any terms obviously used in an interchangeable manner.

The present invention is based on the surprising finding that the bi- and/or tri-substituted urea compounds disclosed in the present invention which exhibit at least one aromatic substituent at each of either N-atoms of the urea compounds, are potent antagonists of the C5a receptor.

Furthermore, it was also surprisingly found that the advantageous properties arise in particular from the presence of the NR21R22 group at one of the two aromatic substituents of the urea derivatives disclosed in the present invention. This NR21R22 group in addition distinguishes the present compounds from the compounds claimed in the international patent applications WO0214265 and WO0222556 of the company Mitsubishi Pharma. In preferred embodiments of the present invention, the NR21R22 group refers to an amino group.

Besides the high potency as C5a receptor antagonists, the described compounds possess a set of other favorable properties, e.g. higher specificity compared to the prior art, lower agonistic activity, higher affinity, higher solubility in water, longer shelf life, lower chemical reactivity, higher microsomal stability, or lower inhibition of P450 enzymes. In particular, this is also true for the compounds claimed in the international patent applications WO0214265 and WO0222556.

Without wishing to be bound by any theory in the following the present inventors assume that the NR21R22 group at the aromatic substituent is responsible for or involved in the improvement of a set of properties featured by the compounds in accordance with the present invention. This group can improve the solubility of the compounds in water, since it can favourably interact with water molecules. Due to the ability to form H-bonds, this group can also favour the binding to biological receptors, which could for instance explain the higher antagonistic activity. Due to a higher hydrophilic content, this group can improve the receptor specificity or decrease the cytochrome inhibition, since hydrophobic substances often tend to undergo unspecific binding and lead to high interaction with cytochromes.

Another aspect of the present invention is that some preferred compounds carry a stereo or chiral centre. Preferably, the stereo centre is in alpha position to one aromatic ring and more preferably the stereo centre possesses the (s)-configuration.

The (S)-configuration is accomplished for instance when the residue

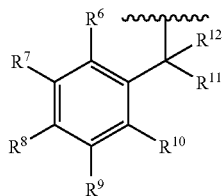

is replaced by the residue

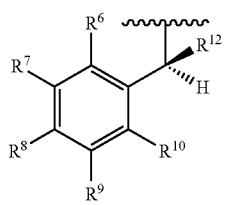

and R12 is selected from the group consisting of alkyl, substituted alkyl and halogen.

Choosing the ideal stereo centre for instance can positively influence the antagonistic activity of a compound.

Despite the positive properties of several compounds carrying a stereo centre, also compounds without a stereo centre show very favorable properties. When a stereo centre exists, this is preferably in the (s)-configuration.

Another aspect of the present invention is that several compounds possess an H-donor (hydrogen bond donor) at the R3 position in structure (IV). In so far, the present invention in particular also relates to those compounds that are included in the herein disclosed general formulas containing an H-donor at one position which corresponds to the R3 position in structure (IV).

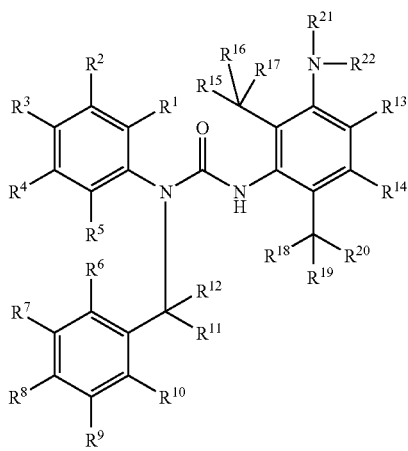

(IV)

Despite the positive properties of several compounds carrying an H-donor at the R3 position, also compounds without an H-donor at the mentioned position show very favorable properties.

The positive characteristics of the compounds disclosed in the present invention can be unequivocally accomplished by means of further structural features of the compounds. In fact, a higher chemical stability compared to compounds according to the prior art can be achieved by choosing suitable substituents. In Example 25, such an example is described: A compound according to the prior art, which has a very short shelf life, is converted into a more stable compound disclosed in the present invention, via the introduction of 5 different groups.

The compounds which are disclosed in the present invention were tested for their $IC_{50}$ values in a functional assay system (Köhl 1997 The Anaphylatoxins. In: Dodds, A. W., Sim, R. B. (Eds.), Complement: A Practical Approach. Oxford: 135). Preferably, all compounds are regarded to have noteworthy inhibitory activity in the sense of the present invention, that have an $IC_{50}$ value of less than 200 nM in a functional assay system as described in Example 31.

Particularly preferred examples for compounds according to the present invention are reported below and in Table 1 (in each case the $IC_{50}$ value is given for the inhibition of C5a induced enzyme release according to Example 31):

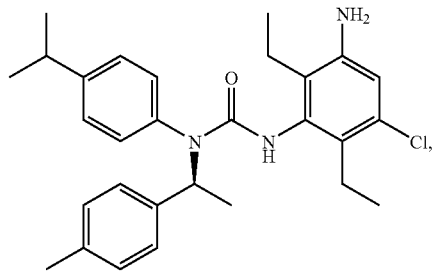

73

(S)-3-(3-Amino-5-chlor-2,6-diethyl-phenyl)-1-(4-isopropyl-phenyl)-1-(1-p-tolyl-ethyl)-urea; 32 nM

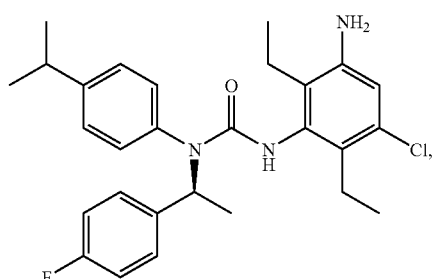

81

(S)-3-(3-Amino-5-chlor-2,6-diethyl-phenyl)-1-[1-(4-fluorphenyl)-ethyl]-1-(4-isopropyl-phenyl)-urea; 38 nM

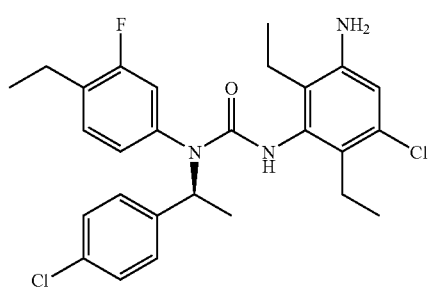

(S)-3-(3-Amino-5-chlor-2,6-diethyl-phenyl)-1-[1-(4-chlor-phenyl)-ethyl]-1-(4-ethyl-3-fluor-phenyl)-urea; 35 nM

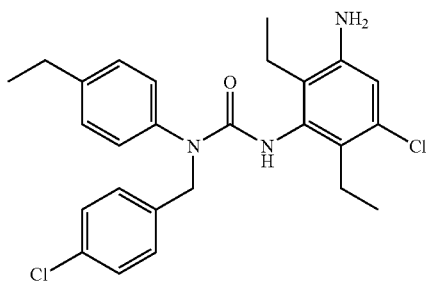

3-(3-Amino-5-chlor-2,6-diethyl-phenyl)-1-(4-chlor-benzyl)-1-(4-ethyl-phenyl)-urea; 86 nM

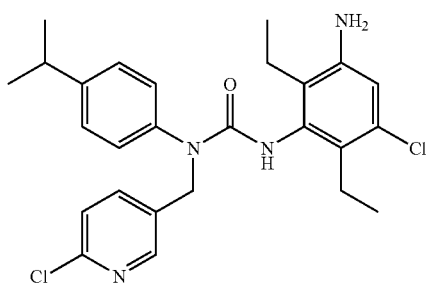

3-(3-Amino-5-chlor-2,6-diethyl-phenyl)-1-(6-chlor-pyridin-3-ylmethyl)-1-(4-isopropyl-phenyl)-urea; 62 nM

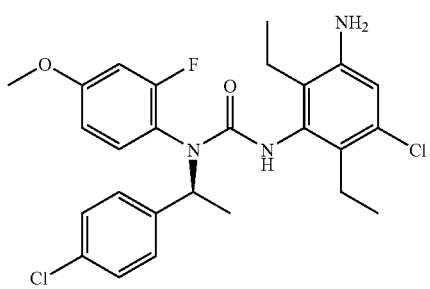

(S)-3-(3-Amino-5-chlor-2,6-diethyl-phenyl)-1-[1-(4-chlor-phenyl)-ethyl]-1-(2-fluor-4-methoxy-phenyl)-urea; 31 nM

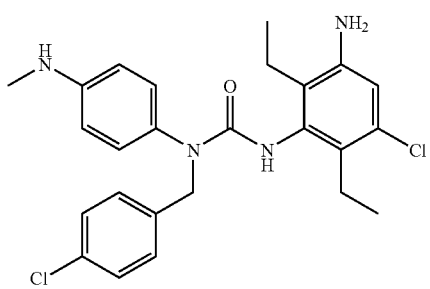

3-(3-Amino-5-chlor-2,6-diethyl-phenyl)-1-(4-chlor-benzyl)-1-(4-methylamino-phenyl)-urea 19 nM

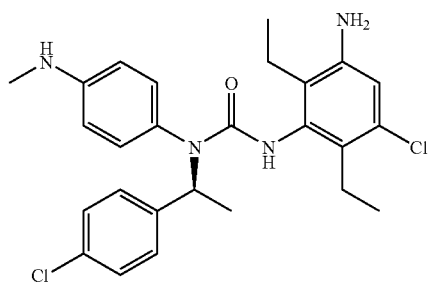

(S)-3-(3-Amino-5-chlor-2,6-diethyl-phenyl)-1-[1-(4-chlor-phenyl)-ethyl]-1-(4-methylamino-phenyl)-urea; 3 nM

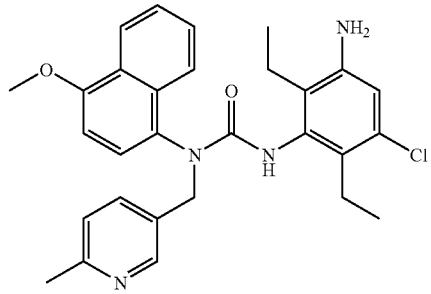

3-(3-Amino-5-chlor-2,6-diethyl-phenyl)-1-(4-methoxy-naphthalin-1-yl)-1-(6-methyl-pyridin-3-ylmethyl)-urea; 55 nM It is obvious that several compounds disclosed in the present invention show a noteworthy higher inhibitory activity if compared to compound W-54011 (89 nM) which is a compound of the prior art.

In a preferred embodiment the compounds disclosed in this invention do not posses any agonistic activity in a cellular assay up to a concentration of at least 7100 nM as shown in Example 32. An antagonist according to the present invention, as preferably used herein, shows no agonistic activity if the antagonist, up to a concentration of at least 7100 nM, preferably reaches less than 5% of the maximum C5a-induced glucosamidase release. Particularly preferred is the release of up to 1% of the maximum C5a-induced enzyme released at a concentration of a compound according to the present invention of 7100 nM in such an assay. Example 32 shows by way of example results from measurements with selected compounds according to the present invention using a method for determining C5aR agonistic activities. None of the investigated compounds is an agonist.

In the following some terms are set forth, the meaning of which is to be used for embodiments of the present invention, in particular those which are set forth herein in more detail. Although these terms are occasionally referred to as definitions, the meaning of the various terms is not necessarily limited thereto.

The term "contains" means, in preferred embodiments, that the respective structural element is included, but the structure is not limited to it.

The term "substituted" means, in preferred embodiments, that one or several hydrogen atoms of a group or a compound is/are replaced by a different atom, group of atoms, molecule or group of molecules or a moiety or moieties. In connection therewith, such an atom, group of atoms, molecules and group of molecules or a moiety or moieties itself/themselves is/are referred to as substituents or substitutions. A prerequisite for any substitution is that the normal valence of the respective atom is not exceeded, and that the substitution results in a stable compound. By the substitution of two hydrogen atoms a carbonyl group (C=O) can be generated. Carbonyl groups are preferably not present in aromatic moieties.

Substituents or substitutions can preferably be selected individually or in any combination from the group comprising hydroxyl, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl, arylalkyl, substituted arylalkyl, heteroarylalkyl, substituted heteroarylalkyl, alkoxyl, substituted alkokyl, aryloxy, substituted aryloxy, arylalkyloxy, substituted arylalkyloxy, acyloxy, substituted acyloxy, halogen, hydroxyl, nitro, cyano, acyl, substituted acyl, mercapto, alkylthio, substituted alkylthio, amino, substituted amino, alkylamino, substituted alkylamino, dialkylamino, substituted dialkylamino, cyclic amino, substituted cyclic amino, carbamoyl (—$CONH_2$), substituted carbamoyl, carboxyl, carbamat, alkoxycarbonyl, substituted alkoxycarbonyl, acylamino, substituted acylamino, sulfamoyl (—$SO_2NH_2$), substituted sulfamoyl, haloalkyl, haloalkyloxy, —C(O)H, trialkylsilyl and azido. Each substituent itself can be substituted further by one or several further substituents. This applies particularly to alkyl, cycloalkyl, heterocyclyl, aryl, heteroaryl and aryloxy. Furthermore any definitions set forth herein apply also to substituents.

The term "alkyl" refers, in an embodiment of the present invention, to a saturated aliphatic radical consisting of from one to ten carbon atoms or a mono- or polyunsaturated aliphatic hydrocarbon radical containing from two to twelve carbon atoms and at least one double and triple bound. The term "alkyl" includes both branched and unbranched alkyl groups. Unbranched alkyl groups having from one to eight carbon atoms are preferred. Unbranched alkyl groups having from one to six carbon atoms and branched alkyl groups having from three to six carbon atoms are particularly preferred. It should be understood that the term "alkyl" comprises any analogs which can be put together from combination terms of the prefix "alk" or "alkyl".

In a preferred embodiment, the abbreviation Me stands for a methyl group or radical, the abbreviation Et for an ethyl group or radical and the abbreviation Pr for a propyl group or propyl radical.

For example, the term "alkoxy" or "alkylthio" refers to an alkyl group which is linked by an oxygen or sulfur atom. "Alkanoyl" refers to an alkyl group which is linked by a carbonyl group (C=O).

The term "cycloalkyl" refers, in an embodiment of the present invention, to the cyclic derivatives of an alkyl group as defined above, which is optionally unsaturated and/or substituted. Saturated cycloalkyl groups are preferred, particularly those having from three to eight carbon atoms. Particularly preferred are cycloalkyl groups having three to six carbon atoms.

The term "aryl" refers, in an embodiment of the present invention, to an aromatic group having from 6 to 14 carbon atoms, whereby "substituted aryl" refers to aryl groups bearing one or more substituents.

Each of the above defined groups "alkyl", "cycloalkyl", and "aryl" comprise the respective halogenated derivatives, whereby the halogenated derivatives may comprise one or several halogen atoms. The halogenated derivatives comprise any halogen radical as defined in the following.

The term "halo" refers, in an embodiment of the present invention, to a halogen radical selected from fluoro, chloro, bromo, and iodo. Preferred halo groups are fluoro, chloro and bromo.

The term "heteroaryl" refers, in an embodiment of the present invention, to a stable 5- to 8-membered, preferably 5- or 6-membered monocyclic or 8- to 11-membered bicyclic aromatic heterocyclicradical, whereby each heterocycle may consist of carbon atoms and from 1 to 4 heteroatoms selected from the group consisting of nitrogen, oxygen, and sulfur. The heterocycle may be linked by any atom of the cycle creating a stable structure. Within the present invention preferred heteroaryl radicals are, for example, furanyl, thienyl, pyrrolyl, oxazolyl, thiazolyl, imidazolyl, pyrazolyl, isoxazolyl, oxadiazolyl, triazolyl, tetrazolyl, thiadiazolyl, pyridinyl, pyridazinyl, pyrimidinyl, pyrazinyl, indolizinyl, indolyl, isoindolyl, benzofuranyl, benzothienyl, indazolyl, benzimidazolyl, benzthiazolyl, benzoxazolyl, purinyl, quinolizinyl, quinolinyl, isoquinolinyl, cinnolinyl, phthalazinyl, quinazolinyl, quinoxalinyl, naphthridinyl, pteridinyl, carbazolyl, acridinyl, phenazinyl, phenothiazinyl and phenoxazinyl.

The term "heterocyclyl" refers, in an embodiment of the present invention, to a stable 5- to 8-membered, preferably 5- or 6-membered monocyclic or 8- to 11-membered bicyclic heterocyclic radical which may be either saturated or unsaturated, but is not aromatic. Each heterocycle consists of carbon atoms and from 1 to 4 heteroatoms selected from the group consisting of nitrogen, oxygen and sulfur. The heterocycle may be linked by any atom of the cycle, which results in a stable structure. Preferred heterocyclic radicals within the present invention include, for example, pyrrolinyl, pyrrolidinyl, pyrazolinyl, pyrazolidinyl, piperidinyl, morpholinyl, thiomorpholinyl, pyranyl, thiopyranyl, piperazinyl, indolinyl, azetidinyl, tetrahydropyranyl, tetrahydrothiopyranyl, tetrahydrofuranyl, hexahydropyrimidinyl, hexahydropyridazinyl, 2,5-dioxo-hexahydro-pyrimidin-4-yl, 2,6-dioxopiperidin-4-yl, 2-oxo-hexahydro-pyrimidin-4-yl, 2,6-dioxohexahydro-pyrimidin-4-yl, 3,6-dioxo-piperazin-2-yl, 1,4,5,6-tetrahydropyrimidin-2-ylamine, dihydro-oxazolyl, 1,2-thiazinanyl-1,1-dioxide, 1,2,6-thiadiazinanyl-1,1-dioxide, isothiazolidinyl-1,1-dioxide and imidazolidinyl-2,4-dione.

When the terms "heterocyclyl", "heteroaryl" and "aryl" are used together with other expressions and terms, the above definitions are further applicable. For example, "aroyl" refers to a phenyl or naphthyl group linked to a carbonyl group (C=O).

Each aryl or heteroaryl compound also includes its partially or fully hydrogenated derivatives. For example, quinolinyl may also include decahydroquinolinyl and tetrahydroquinolinyl. Naphthyl may also include the hydrogenated derivatives such as tetrahydronaphthyl.

Within the present invention the terms "nitrogen" or "N" and "sulfur" or "S" include any oxidized derivative of nitrogen like nitrones, N-oxides or of sulfur like sulfoxides, sulfones and the quaternized forms of any basic nitrogen like HCl— or other salts known to the one skilled in the art.

The term "bond", as preferably used herein together with substituents, refers preferably to single bond, unless otherwise specified.

Radicals can be any of mono-, di-, tri-, and tetra-radicals. Because of this it is possible that the meaning of various terms slightly changes. For example, a di-radical described as "propyl", inevitably means "propyplene" (e.g. —(CH$_2$)$_3$—).

Any wording which specifies the limits of a range such as, e.g., "from 1 to 5" means any integer from 1 to 5, i.e. 1, 2, 3, 4 and 5. In other words, any range that is defined by two integers comprises both the two integers defining said limits of the definition and any integer comprised in said range.

The present invention also comprises all isotopes of atoms of the described compounds. Isotopes are atoms having the same atomic number but different mass numbers. For example, tritium and deuterium are isotopes of hydrogen. Examples for carbon isotopes are $^{11}$C, $^{13}$C and $^{14}$C.

As used herein in connection with the definition of the groups, the term "and respective derivatives thereof" refers to the fact that all derivatives of the individual compounds, groups of compounds, parts of molecules, moieties, radicals or chemical groups as recited in the respective group, can each be present as derivatives. It is generally within the scope of the present invention that by using specific group definition the use of the correspondent derivatives is also implied.

As used herein the term "individually and independently (from each other)" or "in each case individually and independently" refers to the fact that the two or more substituents mentioned can be designed as described in the respective paragraph. The wording "individually and independently" shall only avoid unnecessary repetitions and discloses that any of the mentioned substituents can exhibit the described arrangement, whereby the arrangement for each substituent is made individually or is individually present and is not affected by the selection of one or several of the other substituents. It is within the scope of the present invention to claim any combination, including any subcombination, of the collectively defined residues or substitutions with each other and/or among each other.

It is generally within the scope of the present invention that the substituents described for the individual compounds according to the present invention, in particular for the generic structures, are also applicable to all of the generic formulas with the corresponding substituents, if not indicated to the contrary.

Any compound disclosed in the present invention containing one or more asymmetric carbon atom can occur as racemic mixture or mixture of enantiomers, individual enantiomers, diastereoisomeric mixture, individual diastereoisomers or in each case a mixture of them. All such isomeric forms of the compounds are covered in the present invention. Each stereogenic carbon atom can be in the (S)- or (R)-configuration or in a mixture of both configurations.

It is within the scope of the present invention that the compounds of this invention are pharmaceutically active compounds. Such pharmaceutically active compounds could arise from the compounds of this invention through metabolism and any form of breakdown or degradation. Relevant reactions are known to the ones skilled in the field (Yan et al. 2001 Curr. Top. Med. Chem. 1:403; Fura et al. 2004 J. Med. Chem. 47:4339; Lin et al. 1997 Pharmacological Reviews 49:403, and references cited therein). Furthermore, it is within the scope of the present invention that these precursors are converted to the compounds referred to herein. These precursors can, for example, be so-called pro-drugs. Relevant, generally applicable concepts for producing pro-drugs from the compounds of this invention are know in the field (Anand et al. 2002 Expert Opin. Biol. Ther. 2:607; Majumdar et al. 2004 Adv. Drug Deliv. Rev. 56:1437; Wang et al. 1999 Curr. Pharm. Des. 5:265; Shan et al. 1997 J. Pharm. Sci. 86:765, and references cited therein).

The present invention is also related to formulations and compositions, respectively, in particular pharmaceutical formulations and compositions, which contain at least one of the compounds according to the invention. Frequently pharmaceutically active compounds or drugs are combined with other pharmaceutically acceptable ingredients or excipients, in order to ensure an improved efficacy like improved transport, shelf-life, release behaviour over time and the like. A variety of such appropriate formulations are known to the one skilled in the art. Ingredients of such formulations are, among others, inert diluents, calcium carbonate, sodium carbonate, lactose, calcium phosphate, sodium phosphate, starch, alginate, gelatine, magnesium stearate and talcum. Certain ingredients can be added, in order to allow for a retarded release of the pharmaceutically active compounds. Respective examples are glycerol monostearate and glycerol distearate. For oral application in particular hard gelatine capsules are used, whereby the pharmaceutically active ingredient is admixed with calcium carbonate, calcium phosphate or kaolin. For soft gelatine capsules the pharmaceutically active compounds are admixed, e.g., with oils (peanut oil, liquid paraffin, olive oil). For the application in aqueous solutions the pharmaceutically active ingredients can be admixed in particular with the following components: carboxymethyl cellulose, methyl cellulose, hydropropylmethyl cellulose, sodium alginate, polyvinylpyrrolidone, lecithin, polymer products of alkylene oxides and fatty acids as for example polyoxyethylenestearate, heptadecaethyleneoxycetanol, polyoxyethylenesorbitol monooleate and polyoxyethylenesorbitane monooleate. For the purpose of preservation different additives may be used. Respective examples are ethyl or n-propyl-p-hydroxybenzoate.

Particular formulations are used to permit specific forms of application. The compounds of this invention can be provided as pharmaceutically acceptable salts or solvate. Depending on the individual disease to be treated, the compounds of this invention could be administered systemically or locally, preferably systemically with systemic diseases, and locally with local diseases, (e.g. alopecia greata) and formulated accordingly. Examples of procedures for formulation and administration are described in "Remington's Pharmaceutical Sciences", 1990, 18$^{th}$ edition, Mack Publishing Co., Easton, Pa. The administration of a compound based on the presented invention can be achieved in various ways, including, but not limited to oral, buccal, subcutaneous, intravenous, intranasal, transdermal, intraperitonial, intramuscular, intrapulmonary, vaginal, rectal, intraocular, periocular, intraorbital, intracapsular, intasynovial, intracisternal or topical, to mention just a few.

For nasal application the compounds would be used pure or mixed with the usual additives for this method such as stabilisers or inert dilution agents, and delivered through the usual methods, such as aqueous, alcohol or oil suspensions or aqueous, alcohol or oil solutions in suitable forms of administration. Chelate forming substances such as ethylene diamine-N,N,N',N'-tetra-acetic acid, citric acid, tartaric acid or their salts can be added to aqueous intranasal preparations. The application of nasal solutions can be achieved using dosage sprays or as nose drops with viscosity increasing components, nose gels or nose creams.

Nebulizers or pressurized gas capsules using inert carrier gases can be used for inhalation applications.

A preparation for topical application can be available as an aqueous or oil solution, lotion, emulsion or gel, ointment or cream, or if possible in spray form, whereby if required the adhesion can be improved by addition of a polymer.

A suitable dosage range for topical and inhalation applications of the discovery-based compounds are solutions with 0.01 to 5 mg/ml. Solutions with 0.01 to 50 mg/kg are suitable for systemic applications.

For injection purposes the compounds of this invention can be formulated as aqueous solutions with or without dissolving aids, preferably in physiologically compatible buffers such as Hank's solution, Ringer solution or physiological saline buffer. For transmuscular administration penetrance agents are used that help the invention-based compounds to overcome penetrance barriers. Such penetrance agents are known in state-of-the-art techniques.

The use of pharmaceutically acceptable carriers for formulating the compounds based on the present invention in dosage form or with pharmaceutical preparations or compositions that are particularly suitable for systemic administration is within the scope of the present invention. A suitable choice of carrier and a suitable production procedure, will allow the preparations of the present invention, particularly if as a solution, to be administered parenterally, for example by intravenous injection. The compounds of this invention can easily be formulated in a dosage form by using pharmaceutically acceptable carriers, which are well known in current techniques, and which are suitable for oral administration. Such carriers allow the compounds from the presented invention to be formulated as tablets, pills, capsules, lozenges, fluids, gels, syrups, pastes, suspensions, etc., for oral consumption by a patient under treatment.

In addition, suspensions of the active compound can be produced as suitable oil-based injection suspensions. Suitable lipophile solvents or vesicles surround fatty oils such as sesame or castor oil, or synthetic fatty acid esters such as ethyloleate, triglycerides or liposomes. Aqueous injection suspensions can contain compounds that increase the viscosity of the suspension, such as carboxymethyl cellulose, sorbitol, dextran, etc. As an option, the suspension can also contain suitable stabilisers or agents that increase the solubility of the compound, to permit production of highly concentrated solutions.

Pharmaceutical preparations or compositions that contain a compound based on the present invention for oral applications can be obtained by combining the active compound(s) with solid binding substances. As an option the resulting mixture can be ground and prepared as granules according to the suitability of the added substance as required to produce tablets or the contents of sugar coated pills.

Suitable binding agents are, in particular, additives such as sugar, including lactose, saccharose, manitol, sorbitol and similar substances; cellulose preparations such as corn, wheat, rice and potato starch, gelatine, gum extract, methyl cellulose, hydroxypropylmethyl cellulose, sodium carboxymethyl cellulose, polyvinyl pyrrolidon (PVP), etc., as well as mixtures of two or more of these. If desired, expanding substances can be added such as cross-linked polyvinyl pyrrolidon, alginic acid or a salt of this such as sodium alginate and similar compounds.

The content of coated pills that contain a pharmaceutical preparation or a compound of the present invention are coated with suitable substances. For this purpose, concentrated sugar solutions can be used that can as an option contain: gum arabic, talcum powder, polyvinyl pyrrolidon, carbopol gel, polyethylene glycol, titanium dioxide, suitable organic solvents or solvent mixtures and similar substances. Colouring or pigments can be added to the tablet or coated pill surface to serve as identification or indicate various combinations or different dosages of the active compound.

Pharmaceutical preparations that contain a compound of the present invention and that can be used orally mainly include push-fit capsules that are made from gelatine, as well as soft capsules made of gelatine and a softening agent such as glycerine or sorbitol. The push-fit capsules can contain the active agent in a mixture with a volume additive such as lactose, binding substance such as starch and/or spreading substance such as talcum powder or magnesium stearate and optionally stabilizers. With soft capsules the active compound can be suspended or dissolved in a suitable liquid such as oils, liquid paraffin or liquid polyethylene glycols. In addition, stabilizers can be added.

Therapy with a medication of this invention can be achieved with <100 mg/kg, <50 mg/kg, <10 mg/kg, <1 mg/kg or <0.1 mg/kg.

In one embodiment of this invention the pharmaceutical preparation or compositions of the present invention comprises at least one compound of the present invention in a form that is suitable for administration to a patient. Preferably, a compound of the presented invention is generally and in particular available in an aqueous form in a pharmaceutical preparation based on the presented invention, for example in a pharmaceutically acceptable salt, which within the framework of the presented invention can either be an acidic or basic addition salt, that is also generally described as a pharmaceutically acceptable salt here. "Acidic addition salt" in particular "pharmaceutically acceptable acidic addition salt" describes those salts that retain the biological efficacy of the free base and are not biologically, medically or in any other way undesirable. These salts are primarily formed with inorganic salts such as hydrogen chloride, hydrogen bromide, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid and the like. "Base addition salts" and more particularly "pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium, and magnesium salts. Salts derived from pharmaceutically acceptable organic non-toxic bases include salts of primary, secondary, and tertiary amines, substituted amines including naturally occurring substituted amines, cyclic amines and basic ion exchange resins. Preferred amines to form salts are isopropylamine, trimethylamine, diethylamine, dicyclohexylamine, triethylamine, tripropylamine, and ethanolamine.

A "patient" for the purpose of the present invention, i.e. a living being who is administered a compound of the presented invention or a pharmaceutical preparation of the present invention includes humans as well as animals and other organisms. This means the field of application for the compounds of the presented invention and their pharmaceutical preparation covers the area of human and also veterinary medicine as well as diagnostics and diagnostic procedures and staging procedures for both of these fields. Veterinary medical applications cover, but are not limited to, monkeys, dogs, cattle, cats, pigs, donkeys, horses, farm animals as well as house pets, as well as reptiles such as tortoises, snakes and iguanas, birds such as finches and members of the parrot family, lagomorphs such as rabbits, rodents such as rats, mice, guinea pigs, hamsters, amphibians, fish and arthropods. Patients can also be zoo animals. Preferably, the patient is a mammal and more preferably the patient is human.

In a further aspect the present invention applies to a method or procedure for the treatment and/or therapy of diseases, whereby the method of administration to a patient covers at least one of the invention-based compounds or a compound of the presented invention. A compound and/or preparation will preferably be administered in an amount and/or form that is suitable for preventing, alleviating or treating the disease or associated symptoms. Furthermore, this is preferably to be administered to a patient who is in need for such treatment or prevention.

Diseases that are preferably associated in conjunction with the various aspects of the present invention are preferably those involved directly, i.e. causal, indirectly, or symptomatically with the C5a or C5a receptor. Preferred are also inflammatory diseases associated with an activation of the complete system.

Without wishing to be bound to specific details in the following, the presenting inventors are currently focusing on two fundamental pathogenic mechanisms of C5a. The first mechanism involves processes that are triggered directly by the effect of C5a on cells that express the C5a receptor. Cell types that express the receptor include the following: astrocytes, microglia, neurons, granulocytes (neutrophiles, basophiles, eosinophiles), mast cells, endothelial cells, epithelial cells, macrophages, T cells, dentritic cells, hepatic cells, cells of the kidney (e.g. glomeruli and the tubolointerstitium), the lungs and the smooth muscles. The direct action of C5a is very diverse and depends on the observed cell type. Examples of direct action are chemotaxis and degranulation of granulocytes. Degranulation, in turn, subsequently leads to the indirect effect of damaging surrounding tissues (e.g. by matrix metalloproteases, oxygen radicals, elastase, etc.). A further direct effect is the delay of apoptosis in neutrophiles by C5a (Perianayagam et al. 2004 European Journal of Clinical Investigations 34: 50) or the production of Plasminogen Activator Inhibitor-1 in mast cells and basophiles (Wojita 2002 Blood 100: 517). The second fundamental pathogenic mechanism include processes that are induced indirectly via C5a. This includes influencing the adaptive immune defence by C5a and changes in the cytokine pattern, which can be observed by the effect of C5a on cytokine secreting cells (Jauneau et al. 2003 FEBS Letters 537: 17). These effects are also induced by cells that do not belong to the inherited immune system: the C5a receptor is also found on T cells (Nataf et al. 1999 Journal of Immunology 162: 4018), B cells or antigen presenting cells (APCs). The altered cytokine pattern can lead to different differentiation of T cells into Th1 or Th2 cells primarily through a dosage-dependent change in release of IL-12 (Hawlisch et al. 2004 Molecular Immunology 41: 123). Further important cytokines that influence T cell differentiation are, for example, IL-2, IL-4, IL-5, IL-10, IL-23 and IL-27. Similar results are also known from genetically modified mouse strains lacking the C5 gene. These animals produce significantly less IL-12 than the corresponding control strains.

The cytokine pattern altered by C5a can also result in the immune system being less effective in combating intracellular parasites (e.g. viruses, leishmania, rickettsia, chlamydia, coxiella, plasmodia, brucella, mycobacteria, listeria, toxoplasma, trypanosomes). Hawlisch et al. (2005 Immunity 22: 415) showed that mice that do not express the C5a receptor are significantly more resistant to leishmania infection than the corresponding control animals expressing the functional receptor. This means it is possible that diseases caused by intracellular parasites or viruses can be treated or treatment can be supported by using a C5a receptor antagonist according to this invention for therapy or supportive therapy.

The impact of influencing the cytokine pattern is not limited to changing the balance between Th1 and Th2 cells. However, for many diseases it has been shown that changes in this balance are decisive for their pathogenesis (Bamias et al. 2001 Current Opinion Investigational Drugs 11: 1279; Lucey et al. 1996 Clinical Microbiology Reviews 9: 532).

Finally, numerous processes are indirectly influenced by C5a. Here, of course, organs and cells that express very little or no C5a receptors can also be affected.

It is often not possible to separate the two pathogenic mechanisms such that any disease can clearly be ascribed to one of the two processes. One can however assume that the first pathogenic mechanism is more important in acute inflammatory reactions, while the second pathogenic mechanism plays a role in chronic and immune or autoimmune diseases. But the dividing line is diffuse, as shown, for example, by acute sepsis, where in animal models a C5a blockade (knock-out animals, antibodies or antagonists) can relieve disturbances in chemotaxis and the oxidative burst of neutrophiles, as well as positively influence the cytokine pattern (cytokine storm) (Huber-Lang et al. 2002 FASEB Journal 16: 1567; Ward 2004 Nature Review Immunology 4: 133; Riedenmann et al. 2003 Immunity 19: 193, Riedenmann et al. 2003 Nature Medicine 9: 517; Czermak et al. 1999 Nature Medicine 5: 788, Huber-Lang et al. 2001 FASEB Journal 15: 568, Huber-Lang et al. 2001 Journal of Immunology 166: 1193).

The source of C5a is of secondary importance. It is possible that C5a is released through activation of the complement system (e.g. the classical, alternative or MBL pathways) or directly from certain cells (e.g. phagocytotic cells) (Huber-Lang 2002 American Journal of Pathology 161: 1849).

Examples for acute indications, or indications that can proceed with acute phases, associated with C5a, and therefore that could be treated with a compound of this invention or medication of this invention are asthma (Köhl 2001 Molecular Immunology 38: 51), inflammatory bowel disease (Crohn's disease, Colitis ulcerosa) (Woodruff et al. 2003 Journal of Immunology 171: 5514), sepsis or septic shock (Huber-Lang et al. 2001 Faseb Journal 15: 568), severe burn injuries (Piccolo et al. 1999 Experimental and Molecular Pathology 66: 220) and the acute consequences of severe burn injuries (organ failure, shock, sepsis, SIRS), multiple sclerosis (Mullerladner et al. 1996 Journal of Neurological Science 144: 135) and reperfusion damage to different organs such as the heart (heart attack), spleen, bladder, pancreas, stomach, lungs, liver, kidneys, extremities, brain, (stroke), muscles or intestines (Riley et al. 2000 Journal of Thoriacic and Cardiovascular Surgery 120: 350).

Based on the two pathogenic mechanisms described also all inflammatory or immuno-inflammatory diseases could be treated or undergo preventative treatment using the compounds of the present invention. Köhl (2001 Molecular Immunology 38: 51) provides an overview of the inflammatory diseases associated with C5a.

Immune complex associated diseases (Heller et al. 1999 Journal of Immunology 163: 985) are similarly diseases that could be treated with the C5a receptor antagonists of the present invention. An example of an immune complex associated or immune complex induced disease is glomerulonephritis.

Accordingly, diseases caused by infections, such as myocarditis, also belong to those diseases that could be treated with one of the compounds or medications of the present invention. Similarly, a therapeutic procedure with a C5a receptor antagonist is possible with several diseases of the eye, such as uveitis, age-related macular degradation, diabetic retinopathy, diabetic macular oedema, ocular pemphigoid, keratoconjunctivitis, Stevens-Johnson syndrome and Graves' opthalmopathy.

It could be shown in an animal model of age-related macular degradation (AMD) that the pro-inflammatory part of the disease is induced by C5a, among other things (Ambati et al. 2003 Nature Medicine 9: 1390). Therefore, this indication is also a candidate for therapy with one of the compounds of this invention.

In accordance with the novel approach to influence T cell populations and other cell types, respectively, which are affected by an altered cytokine pattern, by a C5a receptor antagonist according to the present invention, it is possible, for example, to also influence primarily T cell induced immune responses. Such an application opens up the possibility of treating a large spectrum of difficult to treat immune or autoimmune diseases with the compounds and medications, respectively, according to the present invention. In particular, the group of autoimmune diseases includes, but is not limited to, the following diseases: Alopecia greata, cold agglutinin immunohemolytic anemia (cold agglutinin disease), warm antibody immunohemolytic anemia, pernicious anemia (Biermer's disease, Addison's anemia), antiphospholipid antibody syndrom (APS), arteriitis temporalis, atherosclerosis, autoimmune adrenalitis (autoimmune adrenal cortex athrophy, Addison's disease), chronic fatigue/immune dysfunction syndrome (CFIDS), chronic-inflammatory demyelinating polyneuropathy, Churg-Strauss syndrome, Cogan's syndrome, ulcerative colitis, CREST syndrome, diabetes mellitus type I, dermatitis herpetiformis, dermatomyositis, fibromyalgia, chronic autoimmune gastritis, Goodpasture syndrome (anti-GBM antibody related glomerulonephritis), Guillain-Barré syndrome (GBS; Polyradiculoneuropathy), Hashimoto thyroiditis, autoimmune hepatitis, idiopathic pulmonary fibrosis, immunothrombocytopenice purpura (Werlhof's disease), autoimmune infertility, autoimmune inner ear deafness (AIED), juvenile rheumatoid arthritis, autoimmune cardiomyopathy, Lambert-Eaton syndrome, Lichen sclerosis, Lupus erythematosus (particularly the dicoide form), Lyme arthritis (Lyme's disease), collagenosis, Basedow's disease (Graves' disease), Behçet disease, Bechterev's disease (ankylosing spndylitis), Crohn's disease, Ménière's disease, Reiter's disease, multiple sclerosis (MS, encephalomyelitis), myasthenia gravis (myasthenia), sympathic ophtalmia, scaring pemphigoid, bullous pemphigoid, pemphigus vulgaris, polyarteriitis nodosa, polychondritis (panchondritis), polyglandular autoimmune (PGA) syndrome, polymyalgia rheumatica, polymoysitis, primary biliary cirrhosis (primary autoimmune cholangitis), psoriasis, rheumatic fever, rheumatoid arthritis, sarcoidosis (Besnier-Boeck-Schaumann's disease), Sjörgen's syndrome, scleroderma, sprue/celiac disease, stiff-man syndrome (Moersch-Woltmann syndrome), systemic lupus erythematosus, Takayasu arteritis (aortic arch syndrome), transient gluten intolerance, urticaria, autoimmune uveitis, vasculitis and vitiligo (white spot disease).

Vasculites have to be considered as a form of immune or autoimmune diseases. In more detail: They are a group of different inflammatory diseases of the vessels. Primary and secondary vasculites are sub-groups of the vasculites. Primary vasculites are triggered by autoantibodies found in patients. One primarily preferred group of vasculites which can be treated with the compounds according to the invention is the group of vasculites which are triggered by cytoplasmatic anti-neutrophile antibodies (ANCA). To this group belongs e.g. Wegener's disease (Wegener's granulomatosis), Churg-Strauss syndrome and microscopic polyangiitis. Secondary vasculites are e.g. drug-induced vasculites and vasculites which are induced through diseases like AIDS, hepatitis B or C, or cytomegaly-virus infection.

In the course of the primary disease forms, leukoplastic vasculitis and/or tissue infiltration with eosinophils which is also called Churg-Strauss syndrome can occur. The diseases are characterized by e.g. a deposit of immune complexes and an activation of the complement system. Additionally the autoantibodies against the neutrophils activate them, leading to the production and release of reactive oxygen. This leads additionally to a damage of e.g. endothelial cells. Neutrophils and other leukocytes carry the C5a receptor and can be activated by binding of C5a.

Without therapy Wegner's disease can be rapidly fatal. Mostly patients die because of acute lung or renal failure. The current treatment includes unspecific suppression of the excessive immune response with drugs like cyclophosphamide, glucocorticoids, methotrexate, mycophenolate mofetil, azathioprine or leflunomide. These therapies are associated with numerous side effects like increased infections and decrease in white blood cell counts. Therefore, a more targeted and safer therapy for this indication is needed and can be provided by treatment with compounds according to the present invention.

The term urticaria covers a whole range of different forms of blister rashes. They are divided into spontaneous (acute and chronic urticaria) and physical urticaria (urticaria factitia, urticaria e frigore, urticaria e calore, urticaria mechanica, urticaria solaris) (Zuberbier et al. 2001 Journal of Investigative Dermatology Symposium Proceedings 6: 123). In addition, there are particular forms of urticaria such as cholinergic urticaria, adrenergic urticaria, contact urticaria and urticaria caused by water.

Particularly for chronic urticaria it has been shown experimentally that the complement system and particularly C5a participate in the release of histamine in the course of the disease (Kaplan et al. 2004 Current Reviews of Allergy and Clinical Immunology 114: 465). A therapy for urticaria with C5a inhibitors would seem a highly appropriate a novel approach.

A further aspect of the indirect action of C5a is, for example, fibrosis. The chemotaxis of neutrophiles and other leucocytes to the location of an inflammation induced by C5a can in part resulting from this infiltration lead to increased fibrosis there. However, C5a can also act directly on cells from the affected organs resulting in increased fibrotic events. C5a inhibition reduces the degree of fibrosis in a number of organs and diseases. Examples of this are liver fibrosis, lung fibrosis, fibrosis in the kidneys, skin and other organs. Fibrotic events also occur with myocardial infarction and can play a decisive role in reduced ejection performance of the heart following healing of the infarction. Similarly, reduced, or loss of function of kidneys and other organs following transplantation can be traced back to fibrosis and other factors. Therefore the C5a receptor antagonists of this invention could be used to prevent or reduce fibrotic events.

Based on the pathogenic mechanisms described, there are further applications for the compounds according to the present invention which are also referred to herein as invention-based compounds: for support and follow-up treatment of patients receiving organ transplants such as kidneys, liver, lung, heart, skin (particularly self donors with burn injuries), cornea, pancreas or intestine. This can act positively on the acute rejection reaction (by reducing reperfusion damage) and the chronic rejection reaction (by modulating the cytokine pattern). C5a plays a direct or indirect role in each of these processes. Therefore, transplantation is a potential application area for C5a receptor antagonists of this invention.

Another option is the use of a substance or compound of this invention, or at least a preparation derived from one of these, for conserving organs to be transplanted. In one embodiment a C5a receptor antagonist should be used to pre-treat the donor, and treat the organ and/or the recipient. Preferably, the compound of this invention would be used, more preferably the same compound of this invention would be used at all stages of the procedure. A combined treatment of the organ, donor and/or recipient also seems to be appropriate. Such organs could be, for example, kidneys, liver, lung, heart, skin (particularly self donors with burn injuries), cornea, pancreas or intestine.

In principle every surgical event represents a trauma that according to its severity could well be treated with a C5a receptor antagonist of the present invention. Examples here are CABG, PTCA, PTA, MidCAB, OPCAB, thrombolysis, organ transplantation, aneurysmal operations and vascular occlusion (clamping). One additional aspect is reducing or preventing possible neurocognitive dysfunction or local and/or systemic reperfusion damage resulting from extra-corporal circulation (e.g. heart-lung machine or dialysis). In particular, this could be used as a prophylactic approach by treating the patient before surgery or reperfusion.

Several systemic diseases result in local manifestations that could be treated with a C5a receptor antagonist. Examples here are the local manifestations of rheumatism, SLE and type I and II diabetes, which can affect the eyes, brain, blood vessels, heart, lungs, kidneys, liver, gastrointestinal tract, spleen, skin, bones, lymphatic system and the blood.

In addition, C5a receptor antagonists could be usefully used to prevent or treat haemorrhagic shock if large amounts of fluid have to be administered to stabilize the circulatory system. The condition of haemorrhagic shock is comparable with systemic ischaemia. If the circulation is restabilized by the infusion of liquid, this results in a situation comparable to reperfusion damage.

A therapy with a medicament or medication of the present invention can be carried out alone or with other therapeutic agents. Here, anti-inflammatory and immunosuppressive therapeutic agents are particularly well-suited. Here, the term combination therapy is preferably used to mean the combination of two or more therapeutically active compounds. The combination can be carried out on several levels and includes, but is not limited to, the following examples. The combination can be a pharmaceutical formulation including two or at least two of several therapeutically active compounds. A further embodiment can comprise two or at least two of several therapeutically active compounds that are contained in two or more different pharmaceutical formulations, but the formulations are contained in one package, usually accompanied by instructions, which describe the temporal relationship in applying, administering or taking these formulations. Finally, in terms of a preferred finalized form, a combination can also comprise two or at least two of several therapeutically active compounds in different formulations and in different packaging. Preferably, at least one of the packages should contain instructions describing the temporal relationship in applying, administering or taking these formulations. In the context of combination therapies as preferably described here, it is within the framework of the presented invention that the term for various formulations also includes those embodiments containing different formulations, and the differences in the formulations depend ultimately on the therapeutically active compound contained in the formulation.

There are currently already therapeutic procedures for most of the disease whose pathogenic mechanism can be treated with an C5a receptor antagonist of this invention. In many cases, however, these procedures are unsatisfactory and/or the side-effects of the administered medications are high. It is therefore desirable to improve the therapeutic effect of an existing therapy or one under development, or to reduce the dosage of therapeutic agents with side-effects, through combinations with an invention-based C5a receptor antagonist. Described below are several existing therapies and the medications or drugs used, which within the framework of the present invention could be used in conjunction with the compounds and/or medications of this invention.

In connection with the indication transplantation immunosuppressive therapeutic agents are used in particular to prevent chronic transplant rejection. The mechanism of action of current immunosuppressive agents is quite different from the mechanism of action of the compounds of this invention. Therefore one might expect an additive or synergistic effect of the two therapy approaches. A combination comprising current immunosuppressive agents and the compounds of this invention is therefore very appropriate. Examples of current immunosuppressive agents are calcineurin inhibitors or other substances such as cyclosporin A, methotrexate, azathioprine, FK506 (tacrolimus), rapamycin, leflunomide, mycophenolatemofetil, brequinar, mizoribin and deoxyspergulin. These immunosuppressive agents are also used for other indications. A combination comprising the compounds of this invention and immunosuppressive agents is therefore relevant for other indications such as: Alopecia greata, cold agglutinin immunohemolytic anemia (cold agglutinin disease), warm antibody immunohemolytic anemia, pernicious anemia (Biermer's disease, Addison's anemia), antiphospholipid antibody syndrom (APS), arteriitis temporalis, atherosclerosis, autoimmune adrenalitis (autoimmune adrenal cortex athrophy, Addison's disease), chronic fatigue/immune dysfunction syndrome (CFIDS), chronic-inflammatory demyelinating polyneuropathy, Churg-Strauss syndrome, Cogan's syndrome, ulcerative colitis, CREST syndrome, diabetes mellitus type I, dermatitis herpetiformis, dermatomyositis, fibromyalgia, chronic autoimmune gastritis, Goodpasture syndrome (anti-GBM antibody related glomerulonephritis), Guillain-Barré syndrome (GBS; Polyradiculoneuropathy), Hashimoto thyroiditis, autoimmune hepatitis, idiopathic pulmonary fibrosis, immunothrombocytopenice purpura (Werlhof's disease), autoimmune infertility, autoimmune inner ear deafness (AIED), juvenile rheumatoid arthritis, autoimmune cardiomyopathy, Lambert-Eaton syndrome, Lichen sclerosis, Lupus erythematosus (particularly the dicoide form), Lyme arthritis (Lyme's disease), collagenosis, Basedow's disease (Graves' disease), Behçet disease, Bechterev's disease (ankylosing spndylitis), Crohn's disease, Ménière's disease, Reiter's disease, multiple sclerosis (MS, encephalomyelitis), myasthenia gravis (myasthenia), sympathic ophtalmia, scaring pemphigoid, bullous pemphigoid, pemphigus vulgaris, polyarteriitis nodosa, polychondritis (panchondritis), polyglandular autoimmune (PGA) syndrome, polymyalgia rheumatica, polymoysitis, primary biliary cirrhosis (primary autoimmune cholangitis), psoriasis, rheumatic fever, rheumatoid arthritis, sarcoidosis (Besnier-Boeck-Schaumann's disease), Sjörgen's syndrome, scleroderma, sprue/celiac disease, stiff-man syndrome (Moersch-Woltmann syndrome), systemic lupus erythematosus, Takayasu arteritis (aortic arch syndrome), transient gluten intolerance, urticaria, autoimmune uveitis, vasculitis and vitiligo (white spot disease).

Urticaria is primarily treated with anti-histamine agents. It is known, for example, that with chronic urticaria C5a plays a vital role in the activation of mast cells via autoantibodies that bind to the IgE-receptor or the Fc region of IgE. Therefore, a combination of anti-histamine and the therapeutic agents of this invention is relevant and also promises relief from the disease symptoms in patients who respond poorly or not all to anti-histamine agents.

Glucocorticoids (e.g. prednisolon) are used in a large number of different indications. These substances can be used particularly for diseases involving inflammatory or autoimmune responses. Examples of diseases where combination therapy with glucocorticoids and C5a receptor antagonists are relevant are: rheumatoid arthritis, systemic lupus erythematosus, ulcerative colitis, Crohn's disease, COPD, uveitis, keratoconjunctivitis, asthma, Bechterew's disease, multiple sclerosis, Wegener's disease and many other immune and autoimmune diseases.

Bacterial and other infections can overload the human immune system and/or a systemic infection can set in motion a massive activation of the defence mechanisms, which can lead to adverse reactions in those affected. The most prominent example is septic shock, which can be triggered by, for example, a systemic bacterial infection or the release of sufficient amounts of LPS, for example, from local infection foci. An important reason for the adverse systemic effects of an infection lies in the release of C5a. Therefore, antimicrobial therapies with antibiotics offer a particular opportunity for combination with C5a receptor antagonists. Examples of antibiotic classes suited to combination therapies are amynoglycosides, β-lactam antibiotics, glycopeptide antibiotics, gyrase inhibitors, lincosamides, macrolide antibiotics, nitroimidazole derivatives, polypeptide antibiotics, sulfonamides, trimethoprim and tetracycline.

Anti-inflammatory therapeutic antibodies or other anti-inflammatory proteins, nucleic acids and their derivatives, as well as peptides and small molecules that, for example, inhibit the action or effects of pro-inflammatory molecules, or support the action of anti-inflammatory molecules (e.g. IL-10), are preferably well-suited for a combination therapy with the C5a receptor antagonists of this invention. Most of the substances listed here can be grouped in the class of biologicals and are substances that mostly show a very specific mechanism.

Often it is useful to modify several pathways within a biological system in order to achieve a better effect. Therefore, it is particularly advantageous to combine C5a receptor antagonists of this invention with inhibitors of pro-inflammatory molecules.

Examples of pro-inflammatory molecules whose action could be inhibited in combination with invention-based C5a receptor antagonists in order to achieve a better therapeutic effect include: IL-1, IL-5, IL-6, IL-8, IL-10, IL-12, IL-13, IL-15, IL-16, IL-17, IL-18, TNFα, α4β7, α5β1, BlyS, cadherin, CCR2, CD11a, CD11b, CD125, CD130, CD16, CD18, CD2, CD20, CD22, CD23, CD25, CD28, CD3, CD30, CD4, CD40, CD40L, CD44, CD45R, CD54, CD62E, CD62L, CD8, CD80, CD95, CEP, gastrin-R, complement C1 or C1-esterase, complement factor 5, complement factor D, complement MBL, complement receptor 1, CRTH2 receptor, CTGF, E- and P-selectin, eotaxin, factor IX, FGF-20, Fg1-2, GM-CSFr, GP IIb/IIIa receptor, HMG1, IgE, thymocytes, IFNγ, IFNr, IP-10, MCP-1, M-CSF receptor, MIF, MMP9, PDGF-D, P-selectin, TGFβ1, tissue factor, TrkA (tyrosine kinase receptor), VAP-1, VCAM-1, VEGF, VLA1 and vWF. Inhibition of the pro-inflammatory molecules from the list can be achieved, for example, by antibodies, soluble receptors or other natural or artificial inactivating binding partners, aptameres, Spiegelmers, RNAi, antisense molecules or small molecules.

Besides drusen formation, neogenesis of blood vessels is an important disease characteristic in AMD. Amongst other factors, the in growth of blood vessels leads to a loss of eyesight in patients. Currently, AMD patients are treated with photodynamic therapy. In addition, antibodies against VEGF and integrin α5β1 are being developed for AMD therapy. A combination of these therapy approaches with an C5a receptor antagonist of this invention is therefore preferred.

Generally anti-inflammatory or pain relieving therapeutic agents such as acetylsalicylic acid, ibuprofen, diclofenac, naproxen, are also well-suited for use in a combination therapy with C5a receptor antagonists of this invention. Those affected by rheumatic diseases represent an example of a patient collective that would profit from such a kind of combination treatment.

Like the components of the complement cascade, the components of the kinin cascade and the blood clotting system are located in blood plasma. In addition to the complement system, the kinin system is also activated by artificial surfaces or other triggers such as burns or sepis. This suggests a close connection between the complement cascade, the kinin cascade and the blood clotting system. A close connection between the three pathways is also suggested by the fact that the C1-esterase inhibitor (C1Inh, a naturally existing protein) not only inhibits the complement system but also the kinin system and the intrinsic pathway of blood clotting. Therefore, it is primarily preferred to combine antagonists of the end products of the kinin system, such as bradykinin, desArg-bradykinin, kalidin and desArg-kalidin, with C5a inhibitors of this invention. An example of one of such antagonists that seems suitable for combination is icatibant (a $BR_2$ antagonist). Similarly well-suited is the combination with inhibitors of the kinin cascade or blood clotting system. Examples for indications where a combination of two or three inhibitors from the kinin, clotting and complement cascades would be particularly relevant are, for example, reperfusion damage (heart, lungs, liver, kidneys, intestine, brain or skin), severe burns and septic shock. Most preferred is the combination of bradykinin-receptor antagonists with C5a receptor antagonists. The combination of therapeutic agents that inhibit the kinin cascade or inhibitors of the kinin receptors $BR_1$ and $BR_2$, such as icatibant, with the compounds of this invention would be highly preferred. The influence of bradykinin on the inherited immune response has been shown (Aliberti et al. 2003 Journal of Immunology 170: 5349), and it is apparent that particularly $BR_2$ antagonists are suited for a combination therapy with compounds of this invention in order to specifically act on the inherited immune response through two targets. A new aspect of this invention is thus influencing the inherited immune response with a combination therapy comprising C5a receptor antagonists and $BR_2$ antagonists. It was shown that bradykinin receptors also play an important role in connection with intracellular parasites (*Trypanosoma cruzi*, Scharfstein et al. 2003 FASEB Journal 17: 73). A combination of a C5a inhibitor and a bradykinin antagonist is also relevant for these indications.

Further possible targets for combination therapy with a C5a receptor antagonist are p38 MAP kinase, phosphodiesterase 4 (PDE-4), the NO system (NO synthase) and IL-1β converting enzyme (caspase-1).

The combination of a C5a receptor antagonist with an other medicament refers not only to the C5a receptor antagonists of this invention but also to the a C5a receptor antagonists that come under the claims of the application WO2005/010030, which are included here through disclosure by reference. Particularly relevant here are the compounds with the following structure:

$$X1-X2-X3-X4-X5-X6-X7-X8 \quad (C5a)$$

whereas

X1 is a radical with a mass of around 1-300, and whereas X1 is preferentially chosen from the group comprising R5-, R5-CO—, R5-N(R6)-CO—, R5-O—CO—, R5-SO$_2$—, R5-N(R6)-SO$_2$—, R5-N(R6)-, R5-N(R6)-CS—, R5-N(R6)-C(NH)—, R5-CS—, R5-P(O)OH—, R5-B(OH)—, R5-CH=N—O—CH$_2$—CO—, whereas R5 and R6 are chosen individually and independently from each other from the group comprising H, F, hydroxy, alkyl, substituted alkyl, cycloalkyl, substituted cycloalkyl, heterocyclyl, substituted heterocyclyl, arylalkyl, substituted arylalkyl, aryl, substituted aryl, heteroaryl, substituted heteroaryl, acyl, substituted acyl, alkoxy, alkoxyalkyl, substituted alkoxyalkyl, aryloxyalkyl and substituted aryloxyalkyl, X2 is a radical that mimics the biological binding characteristics of a phenylalanine unit, X4 is individually and independently a spacer, whereas the spacer is preferentially chosen from the group comprising amino acids, amino acid analogues, and amino acid derivatives, X5 is a radical that mimics the biological binding characteristics of a cyclohexylalanine unit, X6 is a radical that mimics the biological binding characteristics of a tryptophan unit, X7 is a radical that mimics the biological binding characteristics of a norleucine or phenylalanine unit, X8 is a radical whereby the presence of the radical is optional in structure I, and if present, is chosen from the group comprising: H, NH$_2$, OH, NH—OH, amino, substituted amino, alcoxy, substituted alcoxy, hydrazino, substituted hydrazino, aminooxy, substituted aminooxy, alkyl, substituted alkyl, cycloalkyl, substituted cycloalkyl, heterocyclyl, substituted heterocyclyl, heteroaryl, substituted heteroaryl, arylalkyl, substituted arylalkyl, aryl, substituted aryl, amino acids, amino acid derivatives and amino acid analogues;

X3 shows the following structure:

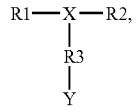

(C5aIV)

whereas

X is C(R4) or N,

R1 is optionally present and if present, is a radical, selected from the group comprising >N—R1B, >C(R1B)(R1C) and >O, wherein R1B and R1C are independently selected from the group, comprising H, alkyl, substituted alkyl, cycloalkyl, substituted cycloalkyl, heterocyclyl, substituted heterocyclyl, aryl, substituted aryl, heteroaryl, substituted heteroaryl, arylalkyl, substituted arylalkyl, cycloalkylalkyl and substituted cycloalkylalkyl;

R2 is optionally present and if present, is a radical, selected from the group, comprising C=O, C=S, SO$_2$, PO(OH), B(OH), CH$_2$, CH$_2$CO, CHF and CF$_2$; R4 is a radical selected from the group comprising H, F, CH$_3$, CF$_3$, alkyl and substituted alkyl;

structure (IV) is preferable connected to the molecule parts X2 and X4 via R1 and R2;

R3 is a radical selected from the group comprising H, alkyl, substituted alkyl, cycloalkyl, substituted cycloalkyl, cycloalkylalkyl, substituted cycloalkylalkyl, heterocyclyl, substituted heterocyclyl, heterocyclylalkyl, substituted heterocyclylalkyl, aryl, substituted aryl, arylalkyl, substituted arylalkyl, heteroaryl, substituted heteroaryl, heteroarylalkyl, substituted heteroarylalkyl, acyl, substituted acyl, alkoxyalkyl, substituted alkoxyalkyl, aryloxyalkyl, substituted aryloxyalkyl, sulfhydrylalkyl, substituted sulfhydrylalkyl, hydroxyalkyl, substituted hydroxyalkyl, carboxyalkyl, substituted carboxyalkyl, carboxamidoalkyl, substituted carboxamidoalkyl, carboxyhydrazinoalkyl, ureidoalkyl aminoalkyl, substituted aminoalkyl, guanidinoalkyl and substituted guanidinoalkyl;

Y is optionally present and if present, is a radical selected from the group comprising H, —N(YB1)-CO—YB2, —N(YB1)-CO—N(YB2)(YB3), —N(YB1)-C(N—YB2)-N(YB3)(YB4), —N(YB1)(YB2), —N(YB1)-SO$_2$—YB2, O—YB1, S—YB1, —CO—YB1, —CO—N(YB1)(YB2) and —C=N—O—YB1, whereby YB1, YB2, YB3 and YB4 individually and independently are selected from the group comprising H, CN, NO$_2$, alkyl, substituted alkyl, cycloalkyl, substituted cycloalkyl, heterocyclyl, substituted heterocyclyl, aryl, substituted aryl, heteroaryl, substituted heteroaryl, arylalkyl, substituted arylalkyl, cycloalkylalkyl and substituted cycloalkylalkyl.

Most preferable are C5a receptor antagonists with the following structure:

$$X1-X2-X3-X4-X5-X6-X7-X8$$

whereby:

X1 is a radical having a molecular weight of approx. 1-300. Preferably X1 is selected from the group, comprising R5-, R5-CO—, R5-N(R6)-CO—, R5-O—CO—, R5-SO$_2$—, R5-N(R6)-SO$_2$—, R5-N(R6)-, R5-N(R6)-CS—, R5-N(R6)-C(NH)—, R5-CS—, R5-P(O)OH—, R5-B(OH)—, R5-CH=N—O—CH$_2$—CO— whereby R5 and R6 are individually and independently selected from the group comprising H, F, hydroxy, alkyl, substituted alkyl, cycloalkyl, substituted cycloalkyl, heterocyclyl, substituted heterocyclyl, aryl alkyl, substituted aryl alkyl, aryl, substituted aryl, heteroaryl, substituted heteroaryl, acyl, substituted acyl, alkoxy, alkoxyalkyl, substituted alkoxyalkyl, aryloxyalkyl and substituted aryloxyalkyl, X2 is an amino acid derivative of an amino acid, which is selected from the group comprising phenylalanine, 2-fluoro-phenylalanine, 3-fluoro-phenylalanine, 4-fluoro-phenylalanine, 2-chlorophenylalanine, 3-chlorophenylalanine, 4-chlorophenylalanine, 1-naphtylalanine, 2-thienylalanine, 3-thienylalanine, 3.3 diphenylalanine, tyrosine, tryptophane, histidine and derivatives thereof;

or X2 and X1 are together equivalent to PhCH$_2$CH$_2$CO— or PhCH$_2$—;

X3 and X4 are used as defined above in connection with the structure (C5a);

X5 is an amino acid derivative of an amino acid is, which is selected from the group comprising D-cyclohexylalanine, D-cyclohexylglycine, D-homo-cyclohexylalanine, octahydroindole-2-carboxylic acid, 2-methyl-D-phenylalanine and derivatives thereof;

X6 is an amino acid derivative of an amino acid, which is selected from the group, comprising tryptophane, phenylalanine, tyrosine, histidine, 1-naphtylalanine, benzothienylalanine, 2-aminoindane-2-carboxylic acid, 2-thienylalanine, 3-thienylalanine, 2-fluoro-phenylalanine, 3-fluoro-phenylalanine, 4-fluoro-phenylalanine, 2-chlorophenylalanine, 3-chlorophenylalanine, 4-chlorophenylalanine and derivatives thereof;

X7 is an amino acid derivative of an amino acid, which is selected from the group, comprising norvaline, norleucine, homo leucine, leucine, isoleucine, valine, cysteine, cysteine (Me), cysteine (Et), cysteine (Pr), methionine, allylglycine, propargylglycine, cyclohexylglycine, cyclohexyl alanine, phenylalanine, tyrosine, tryptophane, histidine, 1-naphtylalanine, 2-thienylalanine, 3-thienylalanine and derivatives thereof.

X8 is a radical optionally included in this kind of compound (structure I) and if included, is selected from the group, comprising H, $NH_2$, OH, NH—OH, amino, substituted amino, alkoxy, substituted alkoxy, hydrazino, substituted hydrazino, aminooxy, substituted aminooxy, alkyl, substituted alkyl, cycloalkyl, substituted cycloalkyl, heterocyclyl, substituted heterocyclyl, heteroaryl, substituted heteroaryl, arylalkyl, substituted arylalkyl, aryl, substituted aryl, aminoacid, amino acid derivative and amino acid analogue.

Amino acid derivatives, as preferably used herein, represent compounds, which result from amino acids by modifying the N and/or C-termus. Non-limiting examples are the conversion of the carboxyl group to salts, esters, acylhydrazides, hydroxamic acids or amides, and the conversion of the amino group to amides, ureas, thioureas, thioamides, sulfonamides, phosphoric acid amides, boric acid amides or alkyl amines. Parts of compounds, which result from modifications of amino acids at the C and/or N-terminus, can also be referred to as amino acid units. Furthermore, amino acids derivatives can also represent amino acids derivatized at their side chains. If amino acid derivative represents such an amino acid, whereby the side chain is modified one or several times, it is usually specifically indicated herein. A preferred derivatisation of the side chain may be made in particular at positions, at which the side chain carries a functional group. Preferred functional groups are, for example, an amino group, a carboxyl group, a thiol group or an alcohol group.

Amino acid analogues are compounds, which result from amino acids by replacing the amino and/or carboxyl group by other groups which can mimic them. Non-limiting examples are the incorporation of thioamides, ureas, thioureas, acylhydrazides, esters, alkyl amines, sulfonamides, phosphoric acid amides, ketones, alcohols, boronic acid amides, benzodiazepines and other aromatic or non-aromatic heterocycles (for a review see M. A. Estiarte, D. H. Rich in Burgers Medicinal Chemistry, $6^{th}$ edition, volume 1, part 4, John Wiley & Sons, New York, 2002).

The biological binding characteristics of an amino acid unit as described herein are preferable those binding characteristics shown by the respective amino acid during the interaction with a biological molecule. Biological molecules are especially molecules exerting a biological function. Non-limiting examples of such biological molecules are protein- or peptide-based receptors.

Groups or units, which mimic or imitate the biological binding characteristics of an amino acid, are defined as groups, which can interact in a way identical or similar to the amino acid itself with a receptor or interacting partner, preferably a biological receptor or a biological interaction partner. For the selection of such groups it is preferred to take into consideration those which are the most wide-spread ones in terms of most preferred interactions of the respective amino acids with biological receptors. For example, the oxygen atom of a carbonyl group of an amino acid can function as hydrogen bond acceptor, whereas the NH proton can act as hydrogen bond donor. Additionally, amino acids can interact with receptors via their side chains. Phenylalanine and tryptophane can establish both hydrophobic interactions via the methylene side chain or the aromatic groups and π-π-interactions via the aromatic groups. Additionally, the indole group of the tryptophane can serve as a hydrogen bond donor via its NH group. Cyclohexylalanine and norleucine can, in principle, establish hydrophobic interactions with biological receptors via their alkyl and/or cycloalkyl side chains. Not only the complete side chain of an amino acid, but also parts of the side chain can establish important interactions.

If a group or a unit, which is to mimic or imitate the biological binding characteristics of an amino acid or shall exhibit this characteristic, is capable of establishing at least one of the above-mentioned interactions of the respective amino acid, then this group or unit can mimic its biological binding characteristics.

As used herein, in connection with group definitions, the term "and respective derivatives thereof" refers to the fact that all derivatives of the individual compounds, groups of compounds, parts of molecules, radicals or chemical groups can be present as derivatives.

Most preferable C5a receptor antagonists are the following compounds: Ac-Phe-[Orn-Pro-cha-Trp-Phe], Ac-Phe-[Orn-Hyp-cha-Trp-Phe], $HOCH_2(CHOH)_4$—C=N—O—$CH_2$—CO-Phe-[Orn-Pro-cha-Trp-Nle], X-Phe-[Orn-Pro-cha-Trp-Nle]; X=2-acetamido-1-methyl-glucuronyl, Ac-Phe-[Orn-Hyp($COCH_2OCH_2CH_2OCH_2CH_2OCH_3$)-cha-Trp-Nle], Ac-Phe-[Orn-Hyp(CONH—$CH_2CH(OH)$—$CH_2OH$)-cha-Trp-Nle], Ac-Phe-[Orn-Pro-cha-Trp-Ecr], Ac-Phe-[Orn-Pro-cha-Trp-Nle], Ac-Phe-[Orn-Pro-cha-Trp-Met], Ac-Phe-[Orn-Pro-cha-Trp-Nva], Ac-Phe-[Orn-Pro-cha-Trp-Hle], Ac-Phe-[Orn-Pro-cha-Trp-Eaf], Ac-Phe-[Orn-Pro-cha-Trp-Ebd], Ac-Phe-[Orn-Pro-cha-Trp-Eag], Ac-Phe-[Orn-Pro-cha-Trp-Pmf], Ac-Phe-[Orn-Pro-cha-Trp-2Ni], Ac-Phe-[Orn-Pro-cha-Trp-Thi], Ph-$CH_2$—$CH_2$—CO-[Orn-Pro-cha-Trp-Nle], H-Phe-[Orn-Pro-cha-Trp-Nle], Ac-Lys-Phe-[Orn-Pro-cha-Trp-Nle], H-Phe-[Orn-Ser-cha-Trp-Nle], Ac-Phe-Orn-Pro-cha-Trp-Phe-$NH_2$, Ac-Phe-Orn-Aze-cha-Bta-Phe-$NH_2$, Ac-Phe-Orn-Pro-cha-Bta-2Ni-$NH_2$, Ac-Phe-Orn-Pro-cha-Bta-Cha-$NH_2$, Ac-Phe-Orn-Pip-cha-Trp-Phe-$NH_2$, Ph-$CH_2$-[Orn-Pro-cha-Trp-Nle], Ph-$CH_2$-[Orn-Pro-cha-Trp-Phe], Ac-Phe-[Orn-Pro-cha-Trp-1Ni], Ph-CH(OH)—$CH_2$—CO-[Orn-Pro-cha-Trp-Nle], Ac-Phe-Orn-Pro-cha-Trp-Phe-$NH_2$, Ac-Phe-Orn-Pro-cha-Bta-Phe-$NH_2$, Ac-Phe-Orn-Pro-cha-Trp-2Ni-$NH_2$, Ac-Phe-Orn-Pro-cha-Trp-Cha-$NH_2$, Ac-Thi-Orn-Aze-cha-Bta-Phe-$NH_2$, Ac-Thi-Orn-Pip-cha-Bta-Phe-$NH_2$, Ac-Phe-Orn-Pro-cha-Trp-Eap-$NH_2$, $Me_2$-Phe-Orn-Pro-cha-Trp-Phe-$NH_2$, $Ph_2$-CH—$CH_2$—CO-Orn-Pro-cha-Trp-Phe-$NH_2$, Ac-Ebw-Orn-Pro-cha-Trp-Phe-$NH_2$, Ac-Phe-Orn-Pro-cha-Trp-NH—$CH_2$—$CH_2$-Ph, Ac-Phe-Orn-Aze-cha-Bta-NH—$CH_2$—$CH_2$-Ph, H-Phe-Orn-Pro-cha-Trp-Phe-$NH_2$, H-Me-Phe-Orn-Pro-cha-Trp-Phe-$NH_2$, Bu-NH—CO-Phe-Orn-Pro-cha-Trp-Phe-$NH_2$, Ac-Thi-Orn-Pro-cha-Trp-Phe-$NH_2$, Ac-Ebw-Orn-Pro-cha-Trp-Phe-$NH_2$, Ac-Phe-Orn-Ala-cha-Trp-Phe-$NH_2$, Ac-Phe-Orn-Pro-cha-Trp-Thi-$NH_2$, Ac-Phe-Orn-Aze-cha-Pcf-Phe-$NH_2$, Ac-Phe-Orn(Ac)-Pro-cha-Trp-Phe-$NH_2$, Ac-Phe-Orn-Aze-cha-Trp-Phe-$NH_2$, Ac-Phe-Trp-Pro-cha-Trp-Phe-$NH_2$, Ph-NH—CO-Phe-Orn-Pro-cha-Trp-Phe-$NH_2$, Bu-O—CO-Phe-Orn-Pro-cha-Trp-Phe-$NH_2$, Ac-Phe-Lys-Pro-cha-Trp-Phe-$NH_2$, Ac-Phe-Arg-Pro-cha-Trp-Phe-$NH_2$, Ac-Phe-Gln-Pro-cha-Trp-Phe-$NH_2$, Ac-Phe-Orn-Pip-cha-Trp-Phe-$NH_2$, Ac-Phe-Orn-Hyp-cha-Trp-Phe-$NH_2$, Ac-Phe-Orn-Pro-cha-Trp-1Ni-$NH_2$, Ac-Phe-Orn-Aze-cha-Bta-Phe-NH-Me, $CH_3$—$SO_2$-Phe-Orn-Aze-cha-Bta-Phe-$NH_2$, Ac-Phe-Orn-Aze-cha-Pff-Phe-$NH_2$, Ac-Phe-Orn-Aze-cha-Mcf-Phe-$NH_2$, Ac-Phe-Orn(Ac)-Aze-cha-Bta-Phe-$NH_2$, Ac-Ebw-Orn-Pro-cha-Tip- Phe-NH₂, Ac-Phe-Trp-Pro-cha-Trp-Phe-NH₂, Ac-Phe-Arg-Pro-cha-Trp-Phe-NH₂, Ac-Phe-Orn-Pip-cha-Trp-Phe-NH₂, 3PP-Orn-Aze-cha-Bta-Phe-NH₂, Ac-Phe-Orn-Tic-cha-Trp-Phe-NH₂, Ac-Phe-Orn-Ser-cha-Trp-Phe-NH₂, Ac-Phe-Orn-Pro-chg-Trp-Phe-NH₂, Ac-Phe-Orn-Pro-hch-Trp-Phe-NH₂, Ac-Phe-Orn-Pro-cha-Trp-Phg-NH₂, Ac-Phe-Bta-Aze-cha-Bta-Phe-NH₂, Ac-Phe-Trp-Pro-cha-Bta-Phe-NH₂, Ac-Phe-Orn-Pip-cha-Trp-Phe-OH, Ac-Phe-Orn-Tic-cha-Trp-Phe-OH, Ac-Phe-Orn-Ser-cha-Trp-Phe-OH, Ac-Phe-Orn-Pro-chg-Trp-Phe-OH, Ac-Phe-Eec-Pro-cha-Bta-Phe-NH₂, Ac-Phe-Nle-Pro-cha-Bta-Phe-NH₂, Ac-Phe-Har-Pro-cha-Bta-Phe-NH₂, Ac-Phe-Arg-Pro-cha-Bta-Phe-NH₂, Ac-Phe-Cys(Acm)-Pro-cha-Bta-Phe-NH₂, Ac-Phe-Mpa-Pro-cha-Bta-Phe-NH₂, Ac-Eby-Orn-Pro-cha-Bta-Phe-NH₂, Ac-Phg-Orn-Pro-cha-Bta-Phe-NH₂, Ac-Phe-Paf-Pro-cha-Bta-Phe-NH₂, H₂N—CO-Phe-Orn-Pro-cha-Bta-Phe-NH₂, Me-O—CO-Phe-Orn-Pro-cha-Bta-Phe-NH₂, (—CO—CH₂—NH—CO—)-Phe-Orn-Pro-cha-Bta-Phe-NH₂, Ac-Phe-Orn-Pro-hch-Trp-Phe-OH, (—CO—CH₂—CH₂—CO—)-Phe-Orn-Pro-cha-Bta-Phe-NH₂, tBu-CO-Phe-Orn-Pro-cha-Bta-Phe-NH₂, Ac-Lys-Phe-Orn-Aze-cha-Bta-Phe-NH₂, Ac-Gly-Phe-Orn-Aze-cha-Bta-Phe-NH₂, Ac-Arg-Phe-Orn-Aze-cha-Bta-Phe-NH₂, Ac-His-Phe-Orn-Aze-cha-Bta-Phe-NH₂, Ac-Ser-Phe-Orn-Aze-cha-Bta-Phe-NH₂, Ac-Guf-Phe-Orn-Aze-cha-Bta-Phe-NH₂, Ac-Dab-Phe-Orn-Aze-cha-Bta-Phe-NH₂, FH₂C—CO-Phe-Orn-Pro-cha-Bta-Phe-NH₂, Ac-Phe-Orn(Et₂)-Pro-cha-Trp-Phe-NH₂, Ac-Phe-[Orn-Hyp-cha-Tip-Nle], 3PP-[Orn-Hyp-cha-Trp-Nle], Ac-Phe-[Orn-Pro-cha-Trp-Tyr], Ac-Phe-[Orn-Pro-omf-Trp-Nle], Ac-Phe-Orn-Pro-hle-Bta-Phe-NH₂, Ac-Phe-Arg(CH₂—CH₂)-Pro-cha-Bta-Phe-NH₂, Ac-Ala-Phe-Orn-Aze-cha-Bta-Phe-NH₂, Ac-Arg-Phe-Orn-Aze-cha-Bta-Phe-NH₂, Ac-Cit-Phe-Orn-Aze-cha-Bta-Phe-NH₂, Ac-Gly-Phe-Orn-Aze-cha-Bta-Phe-NH₂, Ac-Gly-Phe-Orn-Aze-chg-Bta-Phe-NH₂, Ac-Gly-Phe-Orn-Aze-hch-Bta-Phe-NH₂, Ac-Gly-Thi-Orn-Aze-cha-Bta-Phe-NH₂, Ac-His-Phe-Orn-Aze-cha-Bta-Phe-NH₂, Ac-Hyp-Phe-Orn-Aze-cha-Bta-Phe-NH₂, Ac-Lys-Phe-Orn-Aze-cha-Bta-Phe-NH₂, Ac-Mff-Orn-Pro-cha-Bta-Phe-NH₂, Ac-Mff-Orn-Pro-hle-Bta-Phe-NH₂, Ac-Mff-Orn-Pro-hle-Mcf-Mff-NH₂, Ac-Mmy-Orn-Pro-hle-Pff-Phe-NH₂, Ac-NMF-Orn-Pro-cha-Bta-Phe-NH₂, Ac-Off-Orn-Pro-cha-Bta-Phe-NH₂, Ac-Off-Orn-Pro-hle-Bta-Phe-NH₂, Ac-Orn-Phe-Orn-Aze-cha-Bta-Phe-NH₂, Ac-Pff-Orn-Pro-cha-Bta-Phe-NH₂, Ac-Pff-Orn-Pro-hle-Bta-Phe-NH₂, Ac-Pff-Orn-Pro-hle-Mcf-Pff-NH₂, Ac-Phe-[Cys-Pro-cha-Bta-Phe-Cys]-NH₂, Ac-Phe-[Orn-Asn-cha-Trp-Nle], Ac-Phe-[Orn-Aze-cha-Trp-Nle], Ac-Phe-[Orn-Chy-cha-Trp-Nle], Ac-Phe-[Orn-HyA-cha-Trp-Phe], Ac-Phe-[Orn-Hyp-hle-Bta-Phe], Ac-Phe-[Orn-Hyp-hle-Mcf-Phe], Ac-Phe-[Orn-Hyp-hle-Pff-Nle], Ac-Phe-[Orn-Hyp-hle-Pff-Phe], Ac-Phe-[Orn-Hyp-hle-Trp-Phe], Ac-Phe-[Orn-Hyp-Mmf-Trp-Nle], Ac-Phe-[Orn-Hyp-Mmf-Trp-Phe], Ac-Phe-[Orn-NMD-cha-Trp-Nle], Ac-Phe-[Orn-Pip-hle-Bta-Phe], Ac-Phe-[Orn-Pro-cha-Pff-Nle], Ac-Phe-[Orn-Pro-cha-Pff-Phe], Ac-Phe-[Orn-Pro-cha-Trp-1Ni], Ac-Phe-[Orn-Pro-cha-Trp-Cha], Ac-Phe-[Orn-Pro-cha-Trp-Chg], Ac-Phe-[Orn-Pro-cha-Trp-Ecr], Ac-Phe-[Orn-Pro-cha-Trp-Leu], Ac-Phe-[Orn-Pro-cha-Trp-nle], Ac-Phe-[Orn-Pro-cha-Trp-Phe], Ac-Phe-[Orn-Pro-hle-Bta-Nle], Ac-Phe-[Orn-Pro-hle-Bta-Phe], Ac-Phe-[Orn-Pro-hle-Pff-Phe], Ac-Phe-[Orn-Pro-hle-Trp-Nle], Ac-Phe-[Orn-Ser-cha-Trp-Nle], Ac-Phe-[Orn-Ser-cha-Trp-Nle], Ac-Phe-[Orn-Ser-hle-Trp-Nle], Ac-Phe-[Orn-Thr-cha-Trp-Nle], Ac-Phe-[Orn-Tic-cha-Trp-Nle], Ac-Phe-[Orn-Tic-cha-Trp-Nle], Ac-Phe-Ala-Pro-cha-Bta-Phe-NH₂, Ac-Phe-Arg-Pro-hle-Bta-Phe-NH₂, Ac-Phe-Arg-Pro-hle-Mcf-Phe-NH₂, Ac-Phe-Cit-Hyp-hle-Bta-Phe-NH₂, Ac-Phe-Cit-Pro-cha-Bta-Phe-NH₂, Ac-Phe-Cit-Pro-hle-Bta-Phe-NH₂, Ac-Phe-Cit-Ser-hle-Bta-Phe-NH₂, Ac-Phe-Dab-Aze-cha-Bta-Phe-NH₂, Ac-Phe-Dab-Aze-hle-Bta-Phe-NH₂, Ac-Phe-Dab-Pro-cha-Bta-Phe-NH₂, Ac-Phe-Dap-Pro-cha-Bta-Phe-NH₂, Ac-Phe-Ech-Pro-cha-Bta-Phe-NH₂, Ac-Phe-Eep-Pro-cha-Bta-Phe-NH₂, Ac-Phe-Fcn-Aze-cha-Bta-Phe-NH₂, Ac-Phe-Fcn-Pro-cha-Bta-Phe-NH₂, Ac-Phe-Fco-Pro-cha-Bta-Phe-NH₂, Ac-Phe-Fco-Pro-cha-Bta-Phe-NH₂, Ac-Phe-Fcp-Aze-cha-Bta-Phe-NH₂, Ac-Phe-Ffa-Aze-cha-Bta-Phe-NH₂, Ac-Phe-Ffa-Pro-cha-Bta-Phe-NH₂, Ac-Phe-Ffa-Pro-hle-Bta-Phe-NH₂, Ac-Phe-G23-Pro-cha-Bta-Phe-NH₂, Ac-Phe-Guf-Pro-cha-Bta-Phe-NH₂, Ac-Phe-Har-Aze-cha-Bta-Phe-NH₂, Ac-Phe-His-Pro-cha-Bta-Phe-NH₂, Ac-Phe-L22-Pro-cha-Bta-Phe-NH₂, Ac-Phe-OrA-Pro-cha-Bta-Phe-NH₂, Ac-Phe-OrE-Pro-cha-Bta-Phe-NH₂, Ac-Phe-Orn-Aze-hle-Bta-Phe-NH₂, Ac-Phe-Orn-Chy-cha-Bta-Phe-NH₂, Ac-Phe-Orn-Chy-hle-Pff-Phe-NH₂, Ac-Phe-Orn-G24-cha-Bta-Phe-NH₂, Ac-Phe-Orn-G25-cha-Bta-Phe-NH₂, Ac-Phe-Orn-G26-cha-Bta-Phe-NH₂, Ac-Phe-Orn-G27-cha-Bta-Phe-NH₂, Ac-Phe-Orn-G30-cha-Bta-Phe-NH₂, Ac-Phe-Orn-G31-cha-Bta-Phe-NH₂, Ac-Phe-Orn-Hse-cha-Bta-Phe-NH₂, Ac-Phe-Orn-Hyp-hle-Bta-Phe-NH₂, Ac-Phe-Orn-Hyp-hle-Pff-Phe-NH₂, Ac-Phe-Orn-NMA-cha-Bta-Phe-NH₂, Ac-Phe-Orn-NMS-cha-Bta-Phe-NH₂, Ac-Phe-Orn-Pro-cha-1 Ni-Phe-NH₂, Ac-Phe-Orn-Pro-cha-Bta-1Ni-NH₂, Ac-Phe-Orn-Pro-cha-Bta-Bhf-NH₂, Ac-Phe-Orn-Pro-cha-Bta-Dff-NH₂, Ac-Phe-Orn-Pro-cha-Bta-Eaa-NH₂, Ac-Phe-Orn-Pro-cha-Bta-L19, Ac-Phe-Orn-Pro-cha-Bta-Mcf-NH₂, Ac-Phe-Orn-Pro-cha-Bta-Mff-NH₂, Ac-Phe-Orn-Pro-cha-Bta-NH—CH(CH₂OH)—CH₂-Ph, Ac-Phe-Orn-Pro-Cha-Bta-NH—NBn-CO—NH₂, Ac-Phe-Orn-Pro-cha-Bta-Opa-NH₂, Ac-Phe-Orn-Pro-cha-Bta-Pcf-NH₂, Ac-Phe-Orn-Pro-cha-Bta-Pmf-NH₂, Ac-Phe-Orn-Pro-cha-Bta-Thi-NH₂, Ac-Phe-Orn-Pro-cha-Otf-Phe-NH₂, Ac-Phe-Orn-Pro-ctb-Bta-Phe-NH₂, Ac-Phe-Orn-Pro-ctb-Eaa-Phe-NH₂, Ac-Phe-Orn-Pro-ctb-Mcf-Phe-NH₂, Ac-Phe-Orn-Pro-ctb-Pff-Phe-NH₂, Ac-Phe-Orn-Pro-hch-Trp-Phe-OH, Ac-Phe-Orn-Pro-hle-1Ni-Phe-NH₂, Ac-Phe-Orn-Pro-hle-6FW-Phe-NH₂, Ac-Phe-Orn-Pro-hle-Bta-1Ni-NH₂, Ac-Phe-Orn-Pro-hle-Bta-2Ni-NH₂, Ac-Phe-Orn-Pro-hle-Bta-5Ff-NH₂, Ac-Phe-Orn-Pro-hle-Bta-Aic-NH₂, Ac-Phe-Orn-Pro-hle-Bta-Cha-NH₂, Ac-Phe-Orn-Pro-hle-Bta-Chg-NH₂, Ac-Phe-Orn-Pro-hle-Bta-Eaa-NH₂, Ac-Phe-Orn-Pro-hle-Bta-Egy-NH₂, Ac-Phe-Orn-Pro-hle-Bta-Pcf-NH₂, Ac-Phe-Orn-Pro-hle-Bta-Pff-NH₂, Ac-Phe-Orn-Pro-hle-Bta-Phe-NH₂, Ac-Phe-Orn-Pro-hle-Bta-phe-OH, Ac-Phe-Orn-Pro-hle-Bta-Tyr-NH₂, Ac-Phe-Orn-Pro-hle-Dff-Phe-NH₂, Ac-Phe-Orn-Pro-hle-Eaa-Phe-NH₂, Ac-Phe-Orn-Pro-hle-Egc-Phe-NH₂, Ac-Phe-Orn-Pro-hle-Egy-Phe-NH₂, Ac-Phe-Orn-Pro-hle-Egz-Phe-NH₂, Ac-Phe-Orn-Pro-hle-Mcf-2Ni-NH₂, Ac-Phe-Orn-Pro-hle-Mcf-Cha-NH₂, Ac-Phe-Orn-Pro-hle-Mcf-Pff-NH₂, Ac-Phe-Orn-Pro-hle-Mcf-Phe-NH₂, Ac-Phe-Orn-Pro-hle-Mff-Phe-NH₂, Ac-Phe-Orn-Pro-hle-Mmy-Phe-NH₂, Ac-Phe-Orn-Pro-hle-Ocf-Phe-NH₂, Ac-Phe-Orn-Pro-hle-Off-Phe-NH₂, Ac-Phe-Orn-Pro-hle-Otf-Phe-NH₂, Ac-Phe-Orn-Pro-hle-Pff-2Ni-NH₂, Ac-Phe-Orn-Pro-hle-Pff-Cha-NH₂, Ac-Phe-Orn-Pro-hle-Pff-Eaa-NH₂, Ac-Phe-Orn-Pro-hle-Pff-Mmy-NH₂, Ac-Phe-Orn-Pro-hle-Pff-Pff-NH₂, Ac-Phe-Orn-Pro-hle-Pff-Phe-NH₂, Ac-Phe-Orn-Pro-hle-Phe-Phe-NH₂, Ac-Phe-Orn-Pro-hle-Tff-Phe-NH₂, Ac-Phe-Orn-Pro-hle-Trp-Phe-NH₂, Ac-Phe-Orn-Pro-Ile-Trp-Phe-NH₂, Ac-Phe-Orn-Pro-omf-Bta-Phe-NH₂, Ac-Phe-Orn-Ser-cha-Bta-Phe-NH₂, Ac-Ser-Phe-Orn-Aze-cha-Bta-Phe-NH₂, Ac-Thi-[Orn-Pro-hle-Bta-Phe], Ac-Thi-Orn-Pro-cha-Bta-Phe-NH₂, Ac-Thi-Orn-Pro-cha-Bta-Thi-NH₂, Ac-Thr-Phe-Orn-Aze-cha-Bta-Phe-NH₂, Bzl-[Orn-Pro-cha-Bta-Nle], CH₃CH₂CO-Phe-Orn-Pro-cha-Bta-Phe-NH₂, Def-[Orn-Ser-hle-Trp-Nle], Eby-Phe-[Orn-Hyp-cha-Trp-Phe], Eth-Phe-

[Orn-Pro-hle-Pff-Nle], FAc-Phe-Fib-Aze-cha-Bta-Phe-NH$_2$, FAc-Phe-Orn-Aze-cha-Bta-Phe-NH$_2$, FAc-Phe-Orn-Pro-cha-Bta-Phe-NH$_2$, Fai-Phe-[Orn-Hyp-cha-Trp-Phe], Faz-Orn-Pro-cha-Bta-Phe-NH$_2$, Fbi-Phe-[Orn-Pro-cha-Trp-Nle], Fbn-Phe-[Orn-Hyp-cha-Trp-Phe], Fbn-Phe-[Orn-Pro-cha-Trp-Nle], Fbn-Phe-[Orn-Pro-cha-Trp-Nle], Fbn-Phe-Cit-Pro-hle-Bta-Phe-NH$_2$, Fbo-Phe-[Orn-Pro-cha-Trp-Nle], Fbp-[Orn-Pro-cha-Trp-Nle], Fci-[Phe-Orn-Hyp-cha-Trp-Phe], Fck-[Phe-Orn-Pro-cha-Trp-Nle], Fck-Phe-[Orn-Pro-cha-Trp-Nle], Fha-Phe-[Orn-Hyp-cha-Trp-Phe], Fhb-[Phe-Orn-Hyp-cha-Trp-Phe], Fhi-Phe-[Orn-Hyp-cha-Trp-Phe], Fhu-Phe-[Orn-Pro-hle-Pff-Nle], Fhu-Phe-Orn-Pro-cha-Bta-Phe-NH$_2$, Fid-Phe-Orn-Pro-cha-Bta-Phe-NH$_2$, H-Amf-[Orn-Aze-hle-Pff-Nle], H-Bal-Phe-[Orn-Hyp-hle-Trp-Nle], H-Bal-Phe-[Orn-Pro-hle-Pff-Nle], H-Eby-[Orn-Hyp-hle-Trp-Nle], H-Gly-Phe-Orn-Pro-cha-Bta-Phe-NH$_2$, H-Nip-Phe-Cit-Pro-hle-Bta-Phe-NH$_2$, Hoo-Phe-[Orn-Hyp-hle-Pff-Nle], Hoo-Phe-Cit-Pro-hle-Pff-Phe-NH$_2$, Hoo-Phe-Orn-Hyp-hle-Pff-Phe-NH$_2$, Hoo-Phe-Orn-Pro-hle-Bta-Phe-NH$_2$, Hoo-Phe-Orn-Pro-hle-Mcf-Phe-NH$_2$, Hoo-Phe-Orn-Pro-hle-Pff-Phe-NH$_2$, H-Phe-[Lys-Hyp-hle-Pff-Nle], H-Phe-[Orn-Hym-hle-Mcf-Nle], H-Phe-[Orn-Hym-hle-Pff-Phe], H-Phe-[Orn-Hyp-cha-Trp-Nle], H-Phe-[Orn-Hyp-cha-Trp-Phe], H-Phe-[Orn-Hyp-ctb-Pff-Nle], H-Phe-[Orn-Hyp-ctb-Trp-Nle], H-Phe-[Orn-Hyp-ctb-Trp-Phe], H-Phe-[Orn-Hyp-hle-Mcf-Leu], H-Phe-[Orn-Hyp-hle-Pff-Chg], H-Phe-[Orn-Hyp-hle-Pff-Hle], H-Phe-[Orn-Hyp-hle-Pff-Leu], H-Phe-[Orn-Hyp-hle-Pff-Nle], H-Phe-[Orn-Hyp-hie-Pff-Phe], H-Phe-[Orn-Hyp-hle-Trp-Hle], H-Phe-[Orn-Hyp-hle-Trp-Leu], H-Phe-[Orn-Hyp-hle-Trp-Nle], H-Phe-[Orn-Hyp-hle-Trp-Nva], H-Phe-[Orn-Hyp-hle-Trp-Phe], H-Phe-[Orn-NMS-cha-Trp-Nle], H-Phe-[Orn-NMS-hle-Pff-Phe], H-Phe-[Orn-Pro-cha-Pff-Nle], H-Phe-[Orn-Pro-cha-Pff-Phe], H-Phe-[Orn-Pro-cha-Trp-Nle], H-Phe-[Orn-Pro-hle-Mcf-Phe], H-Phe-[Orn-Pro-hle-Ocf-Phe], H-Phe-[Orn-Pro-hle-Pff-Me], H-Phe-[Orn-Pro-hle-Pff-Phe], H-Phe-[Orn-Pro-hle-Trp-Nle], H-Phe-[Orn-Ser-cha-Trp-Nle], H-Phe-[Orn-Ser-cha-Trp-Phe], H-Phe-[Orn-Ser-hle-Eaa-Nle], H-Phe-[Orn-Ser-hle-Mcf-Leu], H-Phe-[Orn-Ser-hle-Ocf-Nle], H-Phe-[Orn-Ser-hle-Pff-Leu], H-Phe-[Orn-Ser-hle-Pff-Nle], H-Phe-[Orn-Ser-hle-Pff-Phe], H-Phe-[Orn-Ser-hle-Trp-Nle], H-Phe-Cit-Pro-hle-Bta-Phe-NH$_2$, Ohf-[Orn-Hyp-hle-Trp-Nle], Tmg-Phe-[Orn-Hyp-cha-Trp-Phe].

A further group of compounds and/or derived drugs thereof have an effect on integrins, in particular alpha5beta1-integrins, and are therefore integrin antagonists, in particular alpha5beta1-antagonists. These integrin antagonists can be used together with the C5aR-antagonists and/or derived drugs thereof for the prevention and/or treatment of diseases.

There are at least three major classes of reagents developed as integrin anatagonists, especially alpha5beta1 integrin antagonists. These include antibodies such as monoclonal antibodies, polyclonal antibodies, and antibody fragments (Kim et al., 2000, Am. J. Path., 156, 1345), natural peptides e.g. venom derived "disintegrin" peptides (Marcinkiewicz et al., 1999, Biochemistry, 38, 13302), synthetic peptides (e.g. Koivunen et. al, 1994, JBC, 124, 373, U.S. Pat. No. 6,001, 965) and non-peptidic small molecules such as spiro compounds (WO97/33887) or benzyl compounds (WO95/32710).

Additional small molecules, which can act as integrin-, in particular as alpha5beta1-integrin-antagonists have the following structure:

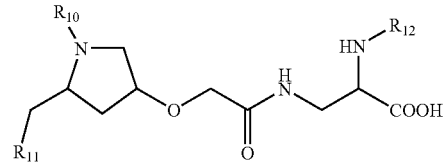

VIII where $R_{10}$ represents —CO—$R_{13}$ or —CO—O—$R_{13}$,
where $R_{11}$ represents a substituted pyridine-2-ylamine,
where $R_{12}$ represents —CO—$R_{13}$ or —SO$_2$—$R_{13}$ and
where $R_{13}$ represents a radical, which is selected from the group, comprising alkyl, substituted alkyl, cycloalkyl, aryl, substituted aryl, heteroaryl and substituted heteroaryl.

A further group of compounds and/or derived drugs thereof have an effect on kinins, in particular bradykinin, and are therefore kinin- or bradykinin-antagonists. These kinin antagonists can be used together with the C5aR-antagonists and/or derived drugs thereof for the prevention and/or treatment of diseases.

Bradykinin antagonists can be selected from the group comprising B1-inhibitors having the following preferred structures:
Ac-Lys-Arg-Pro-Pro-Gly-Phe-Ser-D-beta-NaI-Ile
Ac-Lys-Arg-Pro-Pro-Gly-N-MePhe-Ser-D-beta-NaI-Ile
AcLys-Lys-Arg-Pro-Pro-Gly-NMePhe-Ser-D-betaNaI-Ile
(Gobeil et al. 1999 Hypertension 33: 823)
Ac-Orn-Arg-Oic-Pro-Gly-NMePhe-Ser-D-betaNaI-Phe
(Gabra and Sirois 2003 Peptides 24: 1131)
Lys-Lys-Arg-Pro-Hyp-Gly-Igl-Ser-DIgl-Oic
Lys-Lys-Arg-Pro-Hyp-Gly-CpG-Ser-DTic-CpG
CpG=cyclopentylglycine
(Stewart et al. 1996 Immunopharmacology 33: 51)
2-[1-(3,4-Dichloro-benzenesulfonyl)-3-oxo-1,2,3,4-tetrahydro-quinoxalin-2-yl]-N-{2-[4-(4,5-dihydro-1H-imidazol-2-yl)-phenyl]-ethyl}-acetamide,
N-{2-[4-(4,5-Dihydro-1H-imidazol-2-yl)-phenyl]-ethyl}-2-[1-(naphthalene-2-sulfonyl)-3-oxo-1,2,3,4-tetrahydro-quinoxalin-2-yl]-acetamide,
3-(3,4-Dichloro-phenyl)-N-{1-[4-(4,5-dihydro-1H-imidazol-2-yl)-benzyl]-2-oxo-2-pyrrolidin-1-yl-ethyl}-3-(naphthalene-2-sulfonylamino)-propionamide,
4'-(1-{3-[(2,2-Difluoro-cyclopropanecarbonyl)-amino]-4-methyl-pyridin-2-ylamino}-ethyl)-5-methyl-biphenyl-2-carboxylic acid methyl ester,
N-(4-Chloro-2-{1-[3'-fluoro-2'-(3-methyl-[1,2,4]oxadiazol-5-yl)-biphenyl-4-yl]-ethylamino}-pyridin-3-yl)-3,3,3-trifluoro-propionamide,
(Hess et al. 2004 J. Pharmacol. Exp. Ther. 310: 488)
3-Benzo[1,3]dioxol-5-yl-N-[2-[4-(2,6-dimethyl-piperidin-1-ylmethyl)-phenyl]-1-(isopropyl-methyl-carbamoyl)-ethyl]-3-(6-methoxy-naphthalene-2-sulfonylamino)-propionamide, (Gougat et al. 2004 Pharmacol. Exp. Ther. 309: 661)
{2-(2,2-Diphenyl-ethylamino)-5-[4-(4-isopropyl-piperazine-1-carbonyl)-piperidine-1-sulfonyl]-phenyl}-morpholin-4-yl-methanone,
{2-(2,2-Diphenyl-ethylamino)-5-[4-(4-methyl-piperazine-1-carbonyl)-piperidine-1-sulfonyl]-phenyl}-morpholin-4-yl-methanone,
(Ritchie et al. 2004 J. Med. Chem. 47: 4642)
Bradykinin antagonists can also be selected from the group comprising B2-inhibitors having the following preferred structures:

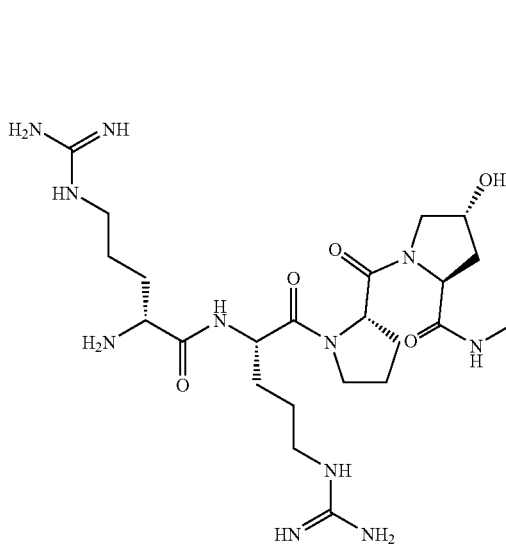
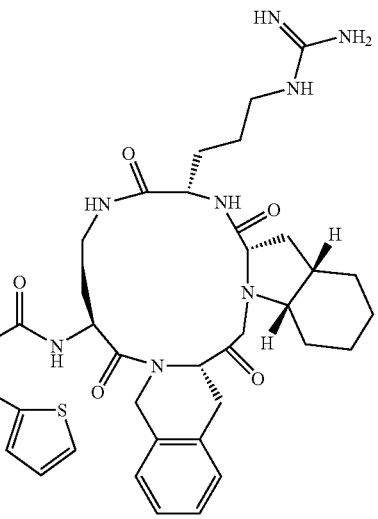

(Meini et al. 1999 J. Pharmacol. Exp. Ther. 289: 1250)
D-Arg-Arg-Pro-Hyp-Gly-Igl-Ser-D-F5f-Igl-Arg (B-10056)
Arg⁰-Arg¹-Pro²-Hyp³-Gly⁴-Igl⁵-Ser⁶-D-Igl⁷-Oic⁸-Arg⁹
(B-9430)
(Stewart et al. 1999 Immunopharmacology 43: 155)
[D-Arg-Arg-Pro-Hyp-Gly-Phe-Cys-D-Phe-Leu-Arg]₂BSH
BSH=bis-succinimidohexane (CP-0127 Bradycor)

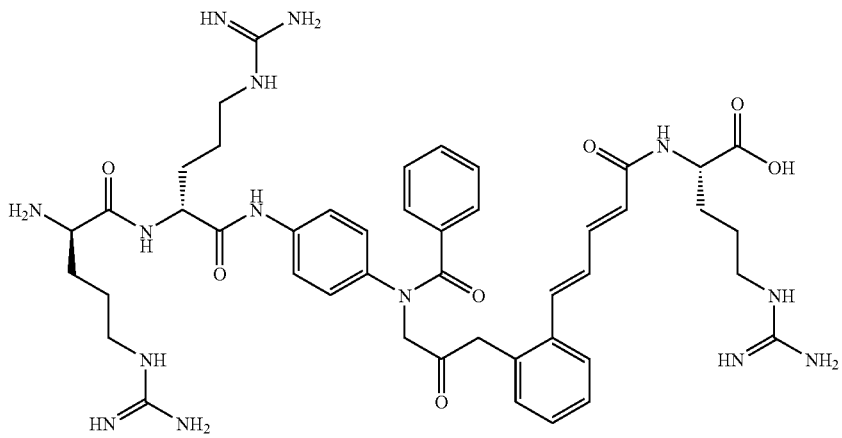

FR 167344; which is 4-{2-[({[3-(3-bromo-2-methyl-imidazo [1,2-a]pyridin-8-yloxymethyl)-2,4-dichloro-phenyl]-methyl-carbamoyl}-methyl)-carbamoyl]-vinyl}-N,N-dimethyl-benzamide, FR 173657 or FK3657 which is 3-(6-acetylamino-pyridin-3-yl)-N-({[2,4-dichloro-3-(2-methyl-quinolin-8-yloxymethyl)-phenyl]-methyl-carbamoyl}-methyl)-acrylamide LF-160687 or Anatibant which is 1-[2,4-dichloro-3-(2,4-dimethyl-quinolin-8-yloxymethyl)-benzenesulfonyl]-pyrrolidine-2-carboxylic acid [3-(4-carbamimidoyl-benzoylamino)-propyl]-amide,

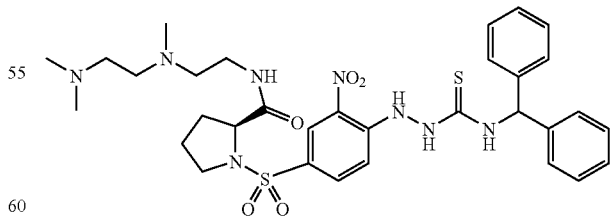

Bradizide
(Heitsch 2002 Curr Med Chem 9: 91)
LF-160335; which is 4-(4-{1-[2,4-dichloro-3-(2,4-dimethyl-quinolin-8-yloxymethyl)-benzenesulfonyl]-pyrrolidine-2-carbonyl}-piperazine-1-carbonyl)-benzamidine (Prmeau, et al. 1998 Br. J. Pharmacol. 125: 365)
2-[5-(4-Cyano-benzoyl)-1-methyl-1H-pyrrol-2-yl]-N-[2,4-dichloro-3-(2-methyl-quinolin-8-yloxymethyl)-phenyl]-N-methyl-acetamide,
(R., C. In *Medicinal Chemistry—28th National Symposium (Part II)—Overnight Report*; IDdb meeting Report: San Diego, 2002)

Additional compounds, which can act as kinin receptor antagonists, preferable as bradykinin antagonists, and therefore can be used together with C5aR-antagonists according to the present invention, are having the following formula (BI):

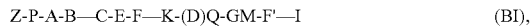

Z-P-A-B—C-E-F—K-(D)Q-GM-F'—I    (BI), whereby

Z is $a_1$) hydrogen, ($C_1$-$C_8$)-alkyl, ($C_1$-$C_8$)-alkanoyl, ($C_1$-$C_8$)-alkoxycarbonyl, ($C_3$-$C_8$)-cycloalkyl, ($C_4$-$C_9$) cycloalkanoyl or ($C_1$-$C_8$)-alkylsulfonyl, whereby 1, 2 or 3 hydrogen atoms are optionally and independently substituted by 1, 2 or 3 identical or different radicals, selected from the group comprising carboxyl, NHR (1), [($C_1$-$C_4$)-alkyl]NR(1) or [($C_6$-$C_{10}$)-aryl-($C_1$-$C_4$)-alkyl]NR(1), whereby R(1) is equivalent to hydrogen or a urethane protective group, ($C_1$-$C_4$)-alkyl, ($C_1$-$C_8$)-alkylamino, ($C_6$-$C_{10}$)-aryl-($C_1$-$C_4$)-alkylamino, hydroxyl, ($C_1$-$C_4$)-alkoxy, halogen, di-($C_1$-$C_8$)-alkylamino, di-[($C_6$-$C_{10}$)-aryl-($C_1$-$C_4$)]-alkylamino, carbamoyl, phthalimido, 1,8-naphthalimido, sulfamoyl, ($C_1$-$C_4$) alkoxycarbonyl, ($C_6$-$C_{14}$)-aryl and ($C_6$-$C_{14}$)-aryl-($C_1$-$C_5$)-alkyl, or whereby 1 hydrogen atom is optionally replaced in each case by a radical, selected from the group comprising ($C_3$-$C_8$)-cycloalkyl, ($C_1$-$C_6$)-alkylsulfonyl, ($C_1$-$C_6$)-alkylsulfinyl, ($C_6$-$C_{14}$)-aryl-($C_1$-$C_4$)-alkylsulfonyl, ($C_6$-$C_{14}$)-aryl-($C_1$-$C_4$)-alkylsulfinyl, ($C_6$-$C_{14}$)-aryl, ($C_6$-$C_{14}$)-aryloxy, ($C_3$-$C_{13}$)-heteroaryl and ($C_3$-$C_{13}$)-heteroaryloxy, and 1 or 2 hydrogen atoms are replaced by 1 or 2 identical or different radicals, selected from the group comprising carboxyl, amino, ($C_1$-$C_8$)-alkylamino, hydroxyl, ($C_1$-$C_4$)-alkoxy, halogen, di-($C_1$-$C_8$)-alkylamino, carbamoyl, sulfamoyl, ($C_1$-$C_4$)-alkoxycarbonyl, ($C_6$-$C_{14}$)-aryl and ($C_6$-$C_{14}$)-aryl-($C_1$-$C_5$)-alkyl;

$a_2$) ($C_6$-$C_{14}$)-aryl, ($C_7$-$C_{15}$)-aroyl, ($C_6$-$C_{14}$)-arylsulfonyl, ($C_3$-$C_{13}$)-heteroaryl or ($C_3$-$C_{13}$)-heteroaroyl; or $a_3$) carbamoyl, which optionally can be substituted at the nitrogen atom with ($C_1$-$C_8$)-alkyl, ($C_6$-$C_{14}$)-aryl or ($C_6$-$C_{14}$)-aryl-($C_1$-$C_5$)-alkyl;

whereby in the radicals defined under $a_1$), $a_2$) and $a_3$), the aryl-, heteroaryl-, aroyl-, aryl sulphonyl and heteroaroyl groups can be optionally substituted by 1, 2, 3 or 4 radicals which are individually and independently selected from the group comprising carboxyl, amino, nitro, ($C_1$-$C_8$)-alkylamino, hydroxyl, ($C_1$-$C_6$)-alkyl, ($C_1$-$C_6$)-alkoxy, ($C_6$-$C_{14}$)-aryl, ($C_7$-$C_{15}$)-aroyl, halogen, cyano, di-($C_1$-$C_8$)-alkylamino, carbamoyl, sulfamoyl and ($C_1$-$C_6$)-alkoxycarbonyl;

P is a chemical bond or a radical of the structure BII,

—NR(2)-(U)—CO—    (BII)

whereby

R(2) is hydrogen, methyl or an urethane protective group,
U is ($C_3$-$C_8$)-cycloalkylidene, ($C_6$-$C_{14}$)-arylidene, ($C_3$-$C_{13}$)-heteroarylidene, ($C_6$-$C_{14}$)-aryl-($C_1$-$C_6$)-alkylidene, which optionally in each case can be independently substituted, or is [CHR(3)]$_n$, whereby n is a number within the range from 1 to 8, preferably from 1 to 6, R(3) is individually and independently selected from the group comprising hydrogen, ($C_1$-$C_6$)-alkyl, ($C_3$-$C_8$)-cycloalkyl, ($C_6$-$C_{14}$)-aryl, ($C_3$-$C_{13}$)-heteroaryl, which are, with the exception of hydrogen, optionally monosubstituted with amino, substituted amino, amidino, substituted amidino, hydroxyl, carboxyl guanidino, substituted guanidino, ureido, substituted ureido, mercapto, methylmercapto, phenyl, 4-chlorphenyl, 4-fluorphenyl, 4-nitrophenyl, 4-methoxyphenyl, 4-hydroxyphenyl, phthalimido, 1,8-naphthalimido, 4-imidazolyl, 3-indolyl, 2-thienyl, 3-thienyl, 2-pyridyl, 3-pyridyl or cyclohexyl, whereby substituted amino preferably is —N(A')-Z, substituted amidino preferably is —(NH=)C—NH—Z, and substituted guanidino preferably is N(A')-C[=N(A')]-NH—Z is and substituted ureido preferably is —CO—N(A')-Z, whereby A' is independently from each other hydrogen or Z, whereby Z is defined as under $a_1$) or $a_2$);

or whereby R(2) and R(3), together with the attached atoms, is forming a mono-, bi or tricyclic ring system containing from 2 to 15 carbon atoms;

A is defined as P;
B is a basic amino acid having L- or D-configuration, which is optionally substituted at the side chain;
C is a compound with formula BIIIa or BIIIb G'-G'-Gly    (BIII a)

G'-NH—(CH$_2$)$_p$—CO    (BIII b)

whereby p is a number within the range of 2 to 8, and
G' is independently a radical with formula BIV

—NR(4)-CHR(5)-CO—    (BIV)

whereby

R(4) and R(5), together with the attached atoms, is forming a mono-, bi or tricyclic ring system containing from 2 to 15 carbon atoms;

E is a radical of a neutral, acidic or basic, aliphatic or alicyclic aliphatic amino acid;

F is independently a radical of a neutral, acidic or basic, aliphatic or aromatic amino acid, which can be substituted at the side chain, or is a chemical bond;

(D)Q is D-TIC, D-Phe, D-Oic, D-Thi or D-NaI, which optionally can be substituted by halogen, methyl or methoxy or a radical of the formula (BV)

(BV)

whereby

X is oxygen, sulfur or a chemical bond;
R is hydrogen, ($C_1$-$C_8$)-alkyl, ($C_3$-$C_8$)-cycloalkyl, ($C_6$-$C_{14}$)-aryl, ($C_6$-$C_{14}$)-aryl-($C_1$-$C_4$)-alkyl, whereby the alicyclic system can be optionally substituted by halogen, methyl or methoxy;
G is defined as for G' above or is a chemical bond;
F' is defined as for F, is a radical —NH—(CH$_2$)$_q$ with q=2 to 8, or, if G is not a chemical bond, is a chemical bond;

I is —OH, —NH$_2$ oder NHC$_2$H$_5$;
K is the radical —NH—(CH$_2$)$_x$—CO, whereby x=1-4, or is a chemical bond, and
M is defined as for F,
or a physiologically acceptable salt thereof.
Preferably the peptide is a peptide having the formula BI, whereby
Z is hydrogen or is defined as a$_1$), a$_2$) or a$_3$) above,
P is a chemical bond or a radical of the formula BII

—NR(2)-(U)—CO— (BII)

whereby U is CHR(3) and
R(3) is defined as above,
R(2) is H or CH$_3$,
A is a chemical bond.
Most preferably the peptide is a peptide as described above, particularly most preferably it is a peptide according to the last description,
whereby
Z is hydrogen or is defined as above under a$_1$), a$_2$) or a$_3$),
P is a chemical bond of the formula BII

—NR(2)-(U)—CO— (BII)

whereby
U is CHR(3) and
R(3) is individually and independently selected from the group comprising hydrogen, (C$_1$-C$_6$)-alkyl, (C$_3$-C$_8$)-cycloalkyl, (C$_6$-C$_{14}$)-aryl, (C$_3$-C$_{13}$)-heteroaryl, which are with the exception of hydrogen optionally monosubstituted by amino, substituted amino, hydroxyl, carboxyl, carbamoyl, guanidino, substituted guanidino, ureido, mercapto, methylmercapto, phenyl, 4-chlorophenyl 4-fluorophenyl, 4-nitrophenyl, 4-methoxyphenyl, 4-hydroxyphenyl, phthalimido, 4-imidazolyl, 3-indolyl, 2-thienyl, 3-thienyl, 2-pyridyl, 3-pyridyl or cyclohexyl,
or whereby R(2) and R(3), together with the attached atoms, is forming a mono-, bi or tricyclic ring system containing from 2 to 15 carbon atoms;
R(2) is H or CH$_3$;
A is a chemical bond;
(D)Q is D-Tic or a physiologically acceptable salt thereof.
Most preferably the peptide is a peptid as described above descriptions, whereby it is selected from the group:
H-D-Arg-Arg-Pro-Hyp-Gly-Thi-Ser-D-Tic-Oic-Arg-OH (HOE 140)
para-guanidobenzoyl-Arg-Pro-Hyp-Gly-Thi-Ser-D-Tic-Oic-Arg-OH
H-D-Arg-Arg-Pro-Hyp-Gly-Phe-Ser-D-HypE(transpropyl)-Oic-Arg-OH
H-D-Arg-Arg-Pro-Hyp-Gly-Cpg-Ser-D-Cpg-Cpg-Arg-OH
H-D-Arg-Arg-Pro-Pro-Gly-Thi-Ser-D-Tic-Oic-Arg-OH
H-Arg(Tos)-Pro-Hyp-Gly-Thi-Ser-D-Tic-Oic-Arg-OH
H-Arg(Tos)-Pro-Hyp-Gly-Phe-Ser-D-Tic-Oic-Arg-OH
H-D-Arg-Arg-Pro-Hyp-Gly-Phe-Ser-D-Tic-Oic-Arg-OH
Fmoc-D-Arg-Arg-Pro-Hyp-Gly-Thi-Ser-D-Tic-Oic-Arg-OH
Fmoc-Aoc-D-Arg-Arg-Pro-Hyp-Gly-Thi-Ser-D-Tic-Oic-Arg-OH
Fmoc-ε-aminocaproyl-D-Arg-Arg-Pro-Hyp-Gly-Thi-Ser-D-Tic-Oic-Arg-OH
benzoyl-D-Arg-Arg-Pro-Hyp-Gly-Thi-Ser-D-Tic-Oic-Arg-OH
cyclohexylcarbonyl-D-Arg-Arg-Pro-Hyp-Gly-Thi-Ser-D-Tic-Oic-Arg-OH
Fmoc-Aeg(Fmoc)-D-Arg-Arg-Pro-Hyp-Gly-Thi-Ser-D-Tic-Oic-Arg-OH
Fmoc-Aeg(Fmoc)-Arg-Pro-Hyp-Gly-Thi-Ser-D-Tic-Oic-Arg-OH
indol-3-yl-acetyl-D-Arg-Arg-Pro-Hyp-Gly-Thi-Ser-D-Tic-Oic-Arg-OH
dibenzylacetyl-D-Arg-Arg-Pro-Hyp-Gly-Thi-Ser-D-Tic-Oic-Arg-OH
or a physically acceptable salt thereof.
Most preferably the peptide is a peptid as described above descriptions, whereby it is selected from the group:
H-D-Arg-Arg-Pro-Hyp-Gly-Thi-Ser-D-Tic-Oic-Arg-OH (HOE 140)
para-guanidobenzoyl-Arg-Pro-Hyp-Gly-Thi-Ser-D-Tic-Oic-Arg-OH; or a physically acceptable salt of it.
Most preferably the peptide is a peptid as described above descriptions, whereby it is selected from the group:
H-D-Arg-Arg-Pro-Hyp-Gly-Thi-Ser-D-Tic-Oic-Arg-OH (HOE 140)

It will be understood by the ones skilled in the art that different diseases can be assigned to different generic terms, as used herein. This assignment does not present any limitation; in fact the respective disease can be treated or prevented alone by the compounds of the present invention. It is also understood by the specialist in the field that the diseases indicated in parentheses herein are synonymously used or are special forms of the indicated disease.

DESCRIPTION OF FIGURES

In the following the invention will be described in more detail using the additional figures and examples. From these further features, embodiments and advantages may be taken.

FIG. 1A) is a chromatogram thereof after purification by HPLC (solution in MeCN/H$_2$O/TFA), FIG. 1 B) is a chromatogram thereof after lyophilization (0 days storage as solid), and FIG. 1 C) is a chromatogram thereof after 7 days of storage as solid.

EXAMPLES

Example 1

Materials and Methods

Figure 1:
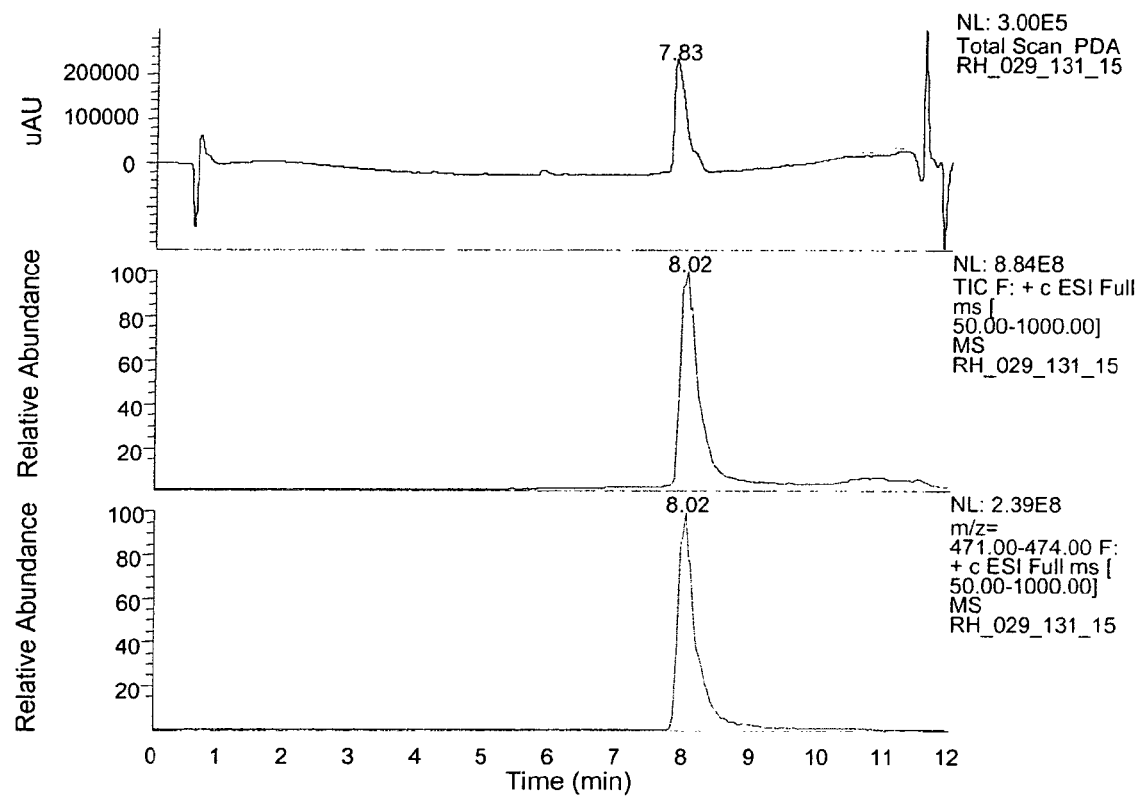
FIG. 1: shows RP HPLC chromatograms of 11 and 13 using different storage conditions, whereby.

The materials and methods as well as general methods are further illustrated by the following examples:
Solvents:
Solvents were used in the specified quality without further purification.
Acetonitrile (Gradient grade, J. T. Baker); dichloromethane (for synthesis, Merck Eurolab); diethylether (for synthesis, Merck Eurolab); N,N-dimethylformamide (LAB, Merck Eurolab); dioxane (for synthesis, Aldrich); methanol (for synthesis, Merck Eurolab).
Water: Milli-Q Plus, Millipore, demineralized.
Chemicals:
Chemicals were synthesized according to or in analogy to literature procedures or purchased from Advanced ChemTech (Bamberg, Deutschland), Sigma-Aldrich-Fluka (Deisenhofen, Germany), Bachem (Heidelberg, Germany), J. T. Baker (Phillipsburg, USA), Lancaster (Mühlheim/Main, Germany), Merck Eurolab (Darmstadt, Germany), Neosystem (Strasbourg, France), Novabiochem (Bad Soden, Germany, from 2003 Merck Biosciences, Darmstadt, Germany) and Acros (Geel, Belgium, distribution company Fisher Scientific GmbH, Schwerte, Germany), Peptech (Cambridge, Mass., USA), Synthetech (Albany, Oreg., USA), Pharmacore (High Point, N.C., USA) and Anaspec (San Jose, Calif., USA) or other companies and used in the assigned quality without further purification.

Commercially not available unnatural amino acids or carboxylic acids used for N-terminal modification were prepared according to standard procedures. For example, Fmoc-cis-Hyp-OH was obtained by reaction of h-cis-Hyp-OH with Fmoc-OSu [Paquet et al. 1982 Canadian Journal of Chemistry 60: 976-980A]. Fmoc-Phe(4-STrt-Amidino)-OH was obtained by a known procedure [Pearson et al. 1996 Journal of Medicinal Chemistry 39:1372]. Sidechain modified cysteine derivatives were prepared by alkylation of Fmoc-cysteine-OH with alkyl halides.

If not stated differently, concentrations are given as percent by volume.

RP-HPLC-MS Analyses:

For analytic chromatography a Hewlett Packard 1100-system (degasser G1322A, quaternary pump G1311A, automatic sample changer G1313A, column heater G 1316A, variable UV detector G1314A) together with an ESI-MS (Finnigan LCQ ion trap mass spectrometer) was used. The system was controlled by "navigator ver. 1,1 sp1" software (Finnigan). As impact gas in the ion trap helium was used. For chromatographic separation a RP-18-column (Vydac 218 TP5215, 2.1×150 mm, 5 µm, C18, 300 A with a pre column (Merck)) was used at 30° C. and a flow of 0.3 ml/min using a linear gradient for all chromatograms (5-95% B for 25 min, linear, A: 0.05% TFA in water and B: 0.05% TFA in $CH_3CN$). UV detection was done at λ=220 nm. The retention times ($R_t$) are indicated in the decimal system (e.g. 1.9 min=1 min 54 s) and are referring to detection in the mass spectrometer. The dead time between injection and UV detection (HPLC) was 1.65 min, and between UV detection and mass detection 0.21 min. The accuracy of the mass spectrometer was approx.±0.2 amu.

HPLC/MS analyses were performed by injection of 5 µl, using a linear gradient from 95:5 to 5:95 in 9.5 min (A: 0.05% TFA in water and B: 0.05% TFA in acetonitrile). RP columns were from Phenomenex (Type Luna C-18, 3 µm, 50×2.00 mm, flow 0.3 ml, HPLC at room temperature); Mass spectrometer: ThermoFinnigan Advantage and/or LCQ Classic (both ion traps), ESI ionization, helium served as impact gas in the ion trap. Excalibur vers. 1.3 and/or. 1.2 was used as software. Retention times ($R_t$) are indicated in the decimal system (e.g. 1.9 min=1 min 54 s).

Preparative HPLC:

Preparative HPLC separations were done using Vydac R18-RP columns with the following gradient solvents: 0.05% TFA in $H_2O$ and B: 0.05% TFA in $CH_3CN$

TABLE 1

| Abbreviations: | |
|---|---|
| Ac | Acetyl |
| CABG | coronary artery bypass grafting |
| d | Doublet |
| DCM | dichloromethane |
| DIPEA | N,N-diisopropylethylamine |
| DMF | N,N-dimethylformamide |
| DMEM | dulbecco's modified eagle medium |
| DMSO | Dimethylsulfoxide |

TABLE 1-continued

| Abbreviations: | |
|---|---|
| eq. | Equivalent |
| FIG. | Figure |
| fMLF | formylmethionine-leucine-phenylalanine |
| GP | general procedure |
| h | Hour(s) |
| HEPES | N-2-2-hydroxyethyl-1-piperazin-N'-2-ethanolsulfonic acid |
| HOBt | 1-hydroxybenzotriazole |
| HPLC | High-pressure liquid chromatography |
| m | Multiplet |
| Me | Methyl |
| MidCAB | minimal invasive direct coronary artery bypass |
| min | Minute |
| ml | millilitre |
| NMP | N-methylpyrrolidone |
| NMR | Nuclear magnetic resonance |
| OPCAB | off pump coronary artery bypass |
| Ph | Phenyl |
| PTCA | percutaneous transluminal coronary angioplasty |
| PTA | percutaneous transluminal angioplasty |
| q | Quartet |
| RT | room temperature |
| s | Singulet |
| $^tBu$ | tert-butyl |
| THF | Tetrahydrofuran |
| TFA | trifluoroacetic acid |
| t | Triplet |
| WSCxHCl | 1-ethyl-3-(3'-dimethylaminopropyl)carbodiimid-hydrochloride |

Example 2

General Procedures for the Synthesis of Compounds

GP-1: Synthesis of Secondary Amines

GP-1a: Synthesis of Secondary Amines by Reductive Amination of Aldehydes or Ketones with $NaBH_3CN$ or $NaBH_4$ and titanium-(IV)-isopropylate.

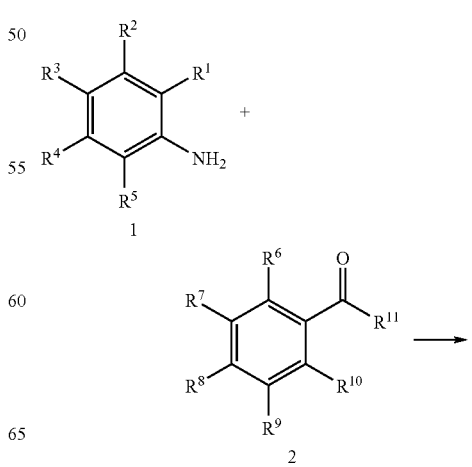

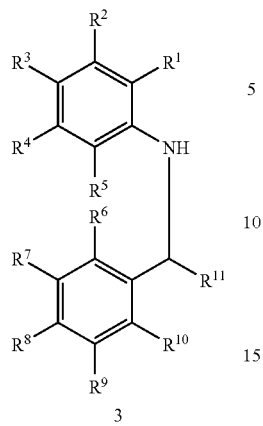

The carbonyl compound 2 is dissolved in THF. 1.1 eq. titanium-(IV)-isopropylate is added followed by 1.0 eq. of amine 1. After stirring for one-day at RT 3.0 eq. of sodium-cyanoborhydride or sodium borohydride dissolved in ethanol are slowly added. Stirring is continued for 2 to 5 hours, and then the solvent is removed at the evaporator. After addition of approx. 20-80 ml 2N NaOH solution and approx. 20-80 ml dichloromethane, the white precipitate is removed by centrifugation. The aqueous phase is extracted three times with dichloromethane. The combined organic phases are dried over magnesium sulfate and the solvent is removed under vacuum. The desired secondary amine 3 was obtained, which was used either directly for further reactions or purified by flash chromatography or HPLC.

The primary amine 2 is dissolved in dichloroethane. 1.0 eq. copper-(II)-acetate and optionally 1.0 eq. 2.6 lutidine are added followed by boronic acid 1. After stirring for one day at RT, the solvent is removed at the evaporator. After addition of approx. 20-80 ml 2N NaOH solution and approx. 20-80 ml dichloromethane, the white precipitate is removed by centrifugation. The aqueous phase is extracted three times with dichloromethane. The combined organic phases are dried over magnesium sulfate and the solvent is removed under vacuum. The desired secondary amine 3 was obtained, which was used either directly for further reactions or purified by flash chromatography or HPLC.

GP-1c: Synthesis of Secondary Amines by Alkylation of Primary Amines with Alkyl Halides GP-1b: Synthesis of Secondary Amines by Reaction of a Boronic Acid with a Primary Amine

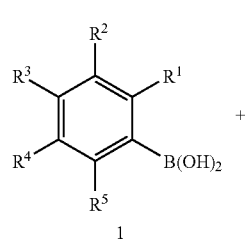

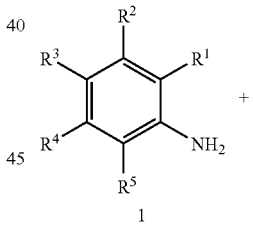

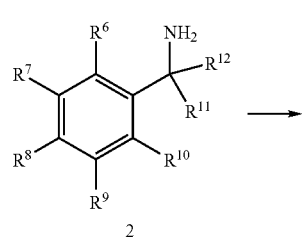

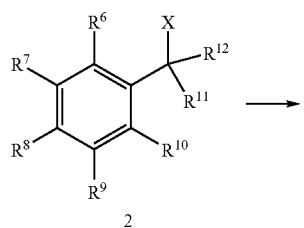

-continued

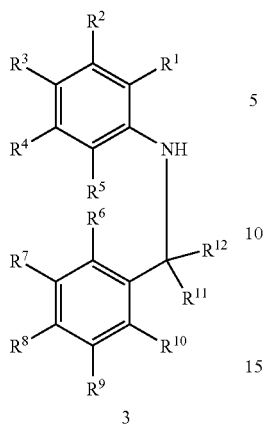

3

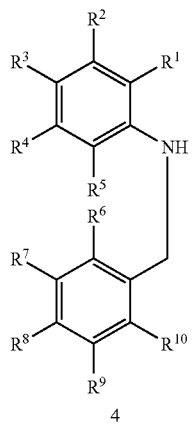

4

Amine 1 is dissolved in THF. A solution of 0.8 to 1.2 eq. of the alkyl halide 2 is slowly added followed by a small amount of potassium carbonate. After one day stirring at 60° C. the solvent is removed at the evaporator. After addition of approx. 20-80 ml 2N NaOH solution and approx. 20-80 ml dichloromethane, the white precipitate is removed by centrifugation. The aqueous phase is extracted three times with dichloromethane. The combined organic phases are dried over magnesium sulfate and the solvent is removed under vacuum. The desired amide 3 was obtained, which was used either directly for the following reduction to the amine 4 or was purified by flash chromatography or HPLC.

GP-1d: Synthesis of Secondary Amines Via Synthesis and Reduction of Carboxamides.

The carboxylic acid 2 is dissolved in dry dichloromethane. 1.5 eq. WSC×HCl and 2.0 eq. N-ethylmorpholine is added. After addition of 1.3 eq. of amine 1, the solution is stirred for 2 to 16 h at RT. After addition of approx. 20-80 ml 2N NaOH solution and approx. 20-80 ml dichloromethane, the white precipitate is removed by centrifugation. The aqueous phase is extracted three times with dichloromethane. The combined organic phases are dried over magnesium sulfate and the solvent is removed under vacuum. The desired secondary amine 3 was obtained, which was used either directly for further reactions or purified by flash chromatography or HPLC.

For the synthesis of secondary amine 4, amide 3 is dissolved under argon atmosphere in THF. 3 to 5 eq. of lithium aluminiumhydride in THF are added and stirring is continued for 1 to 4 days at 55° C. The reaction mixture is cooled in an ice bath and first isopropanol, then methanol and finally water is slowly added. The solvent is removed at the evaporator. After addition of approx. 20-80 ml 2N NaOH solution and approx. 20-80 ml dichloromethane, the white precipitate is removed by centrifugation. The aqueous phase is extracted three times with dichloromethane. The combined organic phases are dried over magnesium sulfate and the solvent is removed under vacuum. The desired amine 4 was obtained, which was used either directly for further reactions or purified by flash chromatography or HPLC.

GP-2: Conversion of Secondary Amines into Ureas

GP-2A: Conversion of Primary Amines into the Corresponding Carbonylchlorides or Isocyanates Followed by Reaction with Secondary Amines to Ureas.

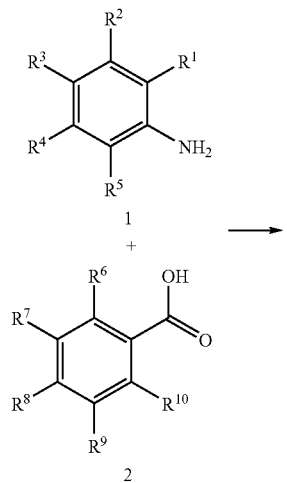

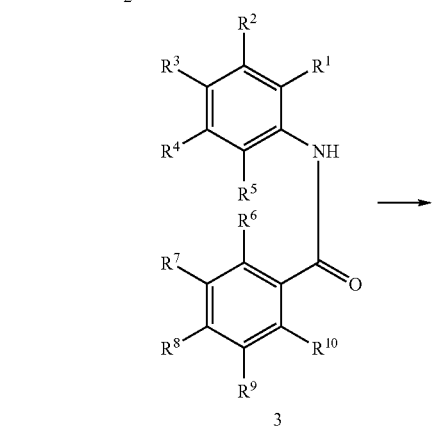

3

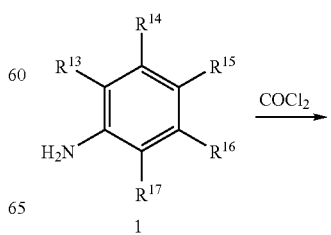

1

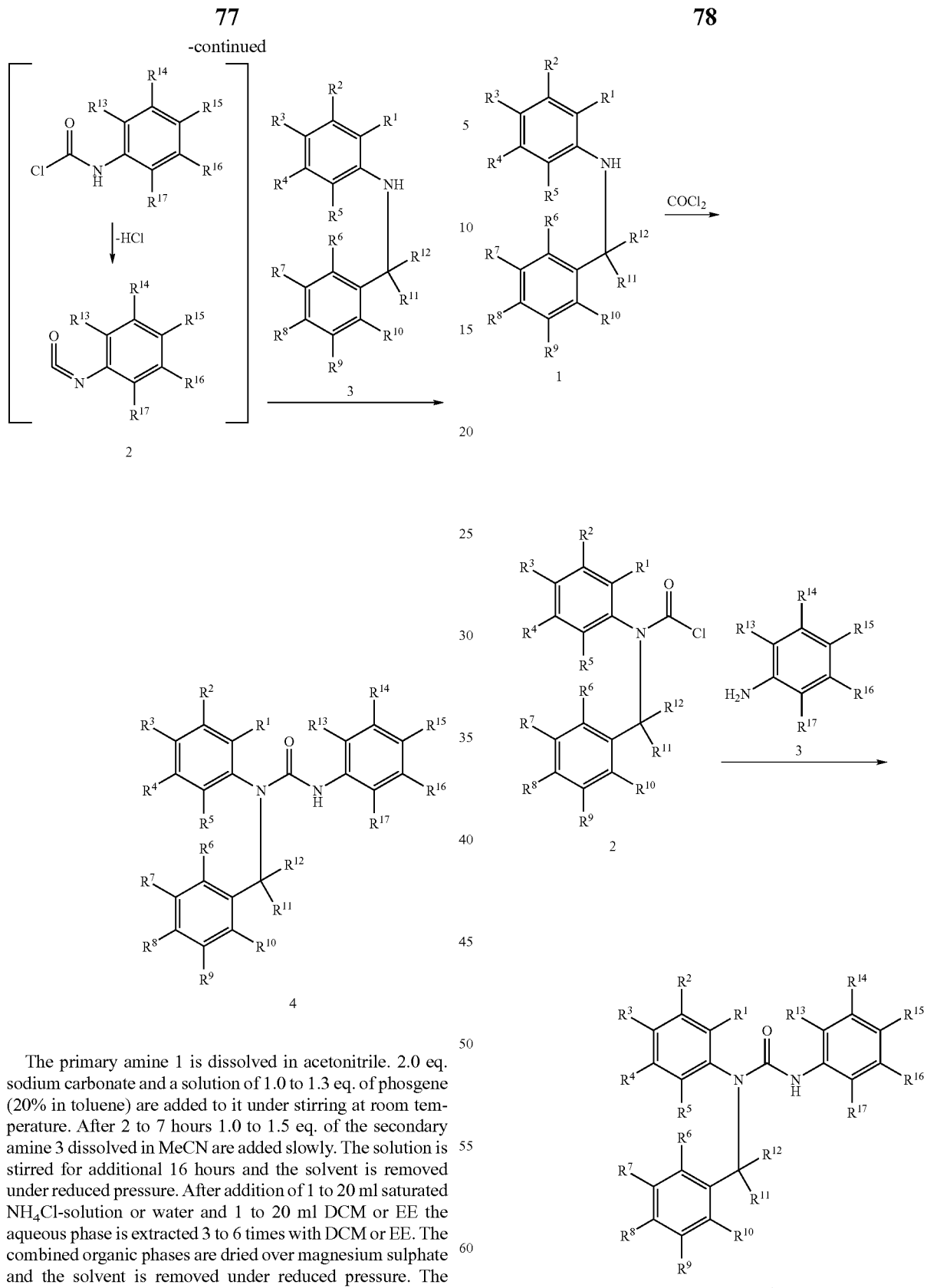

The primary amine 1 is dissolved in acetonitrile. 2.0 eq. sodium carbonate and a solution of 1.0 to 1.3 eq. of phosgene (20% in toluene) are added to it under stirring at room temperature. After 2 to 7 hours 1.0 to 1.5 eq. of the secondary amine 3 dissolved in MeCN are added slowly. The solution is stirred for additional 16 hours and the solvent is removed under reduced pressure. After addition of 1 to 20 ml saturated NH$_4$Cl-solution or water and 1 to 20 ml DCM or EE the aqueous phase is extracted 3 to 6 times with DCM or EE. The combined organic phases are dried over magnesium sulphate and the solvent is removed under reduced pressure. The obtained urea 4 is either subjected to further reactions or purified by flash chromatography or HPLC.

GP-2B: Transformation of Secondary Amines to the Corresponding Carbonyl Chloroide and Subsequent Reaction with Primary Amines Yielding Urea Derivative The synthesis pathway for GP-2B is the same as for GP-1A, only the primary and secondary amines are exchanged.

GP-3: Reduction of Nitro Compounds to Amines

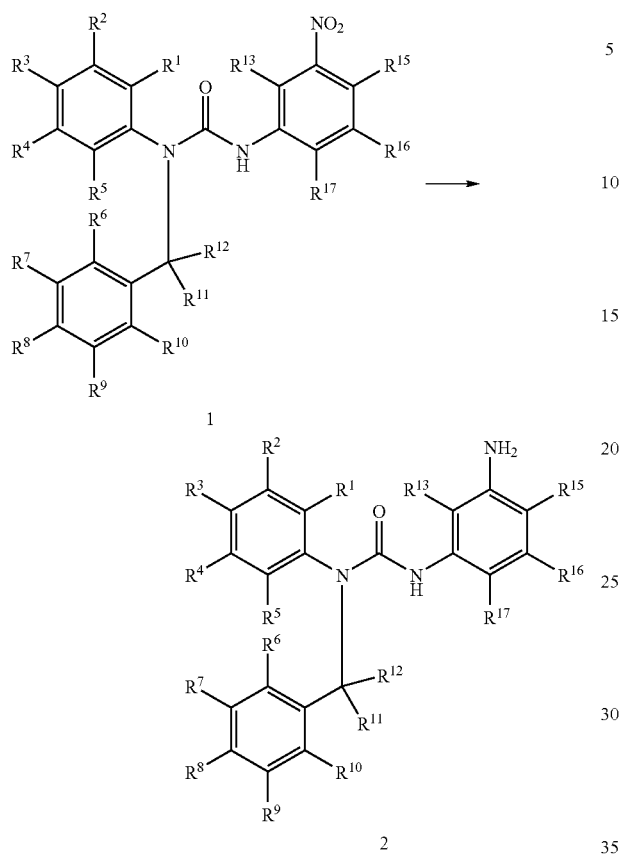

The shown structure is only one example. Likewise other aromatic or non-aromatic nitro compounds can be transformed into the corresponding amines.

GP-3A: Reduction of Nitro Compound to Amines with Hydrogen and Pd/C

The nitro compound 1 is dissolved in MeOH. Some spatula amounts of Pd/C are added and H$_2$-atmosphere is applied. After 10 to 60 minutes of stirring at room temperature the reaction mixture is filtered and the solvent is removed under reduced pressure. The obtained amine 2 is either subjected to further reactions or purified by flash chromatography or HPLC.

GP-3B: Reduction of Nitro Compound to Amines with Stannous (II) Chloroide

The nitro compound 1 is dissolved in EE and 2 to 4 eq. of stannous (II) chloroide-dihydrate is added. The reaction mixture is heated to 80° C. for 1 to 6 hours until HPLC-MS or TLC control shows completeness of the reduction. The solvent is removed under reduced pressure and ca. 1 to 50 ml 2N NaOH-solution and ca. 1 to 50 ml DCM is added. The aqueous layer is extracted 3 to 6 times with DCM. The combined organic layers are dried over magnesium sulphate and the solvent is removed under reduced pressure. The obtained amine 2 is either subjected to further reactions or purified by flash chromatography or HPLC.

GP-3C: Reduction of Nitro Compound to Amines with Iron Powder

The nitro compound 1 is dissolved in EE and some spatula amounts of iron powder are added. The reaction mixture is stirred for 1 to 6 hours until HPLC-MS or TLC control shows completeness of the reduction. Alternatively the reaction can be carried out in EtOH: sat. aqueous NH$_4$Cl solution 10:1 at 60° C. The iron powder is filtered off and the solvent is removed under reduced pressure, ca. 1 to 50 ml 2N NaOH-solution or H$_2$O is added and the aqueous layer is extracted 2 to 3 times with DCM. The combined organic layers are dried over magnesium sulphate and the solvent is removed under reduced pressure. The obtained amine 2 is either subjected to further reactions or purified by flash chromatography or HPLC.

Example 3

Synthesis of 3-Chloro-2,6-diethyl-5-nitro-phenylamine (2)

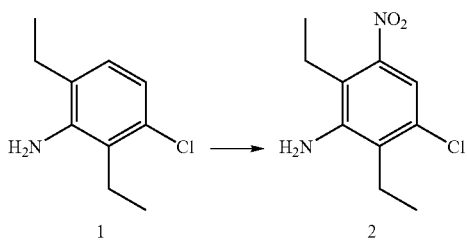

1.83 ml (10.9 mmol) 3-Chloro-2,6-diethyl-phenylamine (1) is dissolved on an ice-bath at 0° C. in 8 ml conc. H$_2$SO$_4$. 562 µl (12.0 mmol; 1.1 eq.) 90% ige HNO$_3$ is added and the reaction mixture is stirred for 2.5 hours at 0° C. The reaction mixture is pored on ca. 200 ml ice and the obtained solution is extracted 8 times with 50 to 100 ml EE each. The combined organic layers are dried over magnesium sulphate and the solvent is removed under reduced pressure yielding 2.1 g of crude product. After purification by flash chromatography 1.24 g (5.42 mmol; 50%) of 2 could be obtained.

Example 4

Synthesis of 106

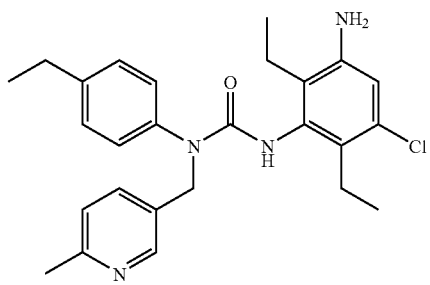

Step 1:

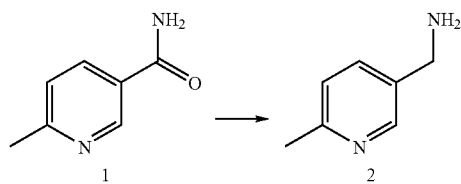

3.00 g (22.0 mmol) 6-methylnicotinamide is dissolved in 10 ml THF under argon-atmosphere and 34 ml (34 mmol; 1.5 eq.) 1 M lithium aluminum hydride in THF are added. After 45 min additional lithium aluminum hydride (1.22 g; 1.5 eq.) in 40 ml THF is added. The reaction mixture is heated to 60° C. for 24 h under stirring. The reaction mixture is carefully quenched under stirring with isopropyl alcohol, methanol and finally water at 0° C. The solvent is removed under vacuum. After addition of 100 ml 2N NaOH solution and 100 ml DCM the white precipitate is centrifuged off and the aqueous layer is extracted 4 times with 60 ml DCM. The combined organic layers are dried over magnesium sulphate and the solvent is removed under reduced pressure yielding 1.57 g (12.9 mmol; 58%) of the amine 2 which is used without further purification for subsequent reaction steps.

Step 2:

Step 3:

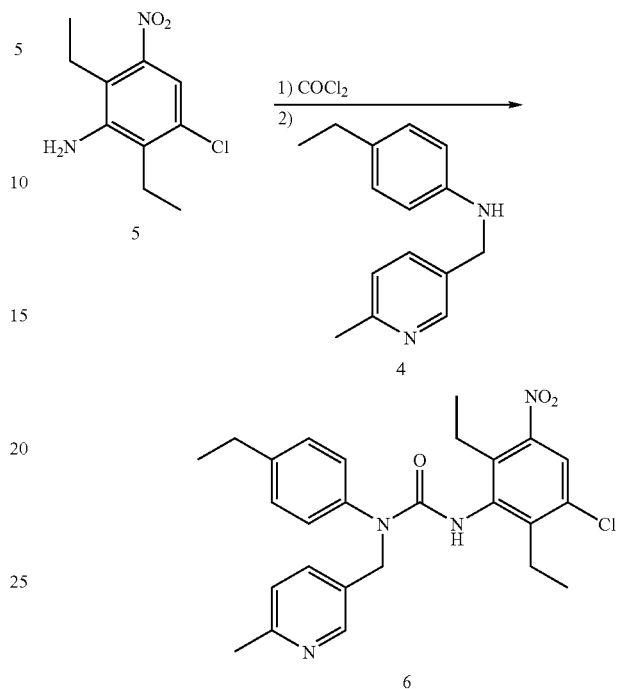

61.3 mg (0.267 mmol) 3-chloro-2,6-diethyl-5-nitro-phenylamine (5) is reacted according to GP-2A with 60.4 mg (0.267 mmol; 1.0 eq.) (4-ethyl-phenyl)-(6-methyl-pyridin-3-ylmethyl)-amine (4). The obtained crude product is used without further purification for subsequent reaction steps.

Step 4:

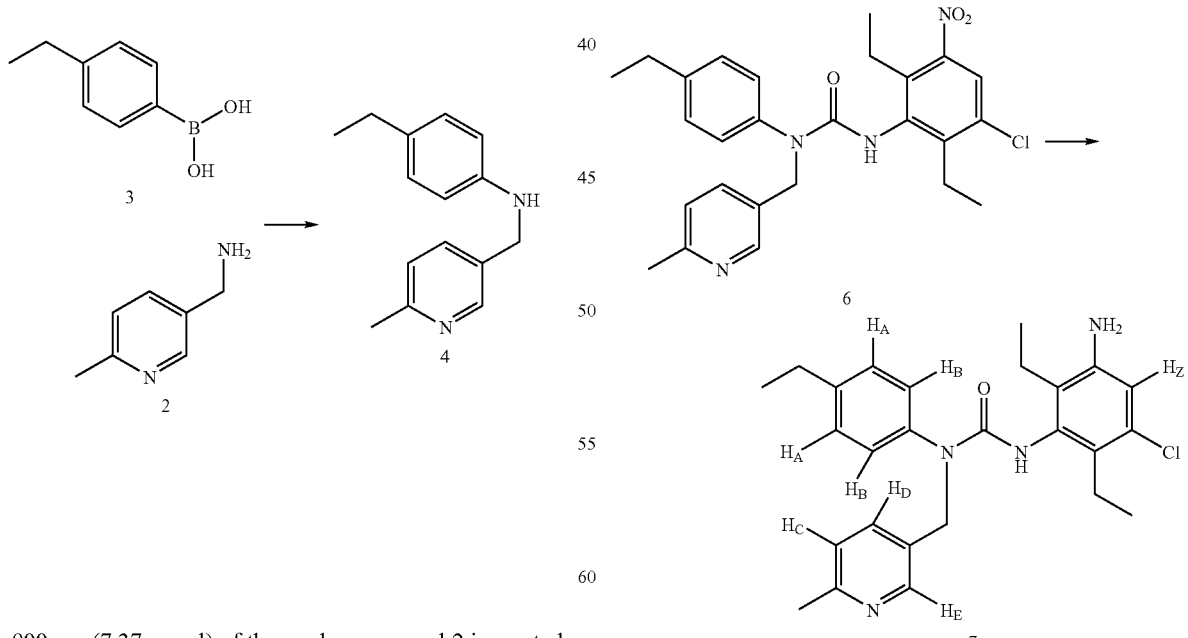

900 mg (7.37 mmol) of the crude compound 2 is reacted according to GP-1B with 4-ethylphenylboronic acid (3) without lutidine yielding 788 mg of crude product. After purification by flash chromatography 60.4 mg (0.27 mmol; 4%) of 4 could be obtained.

The nitro compound 6 obtained in step 3 is reduced according to GP-3A and the product is purified by HPLC yielding 32.64 mg (0.072 mmol; 27%, 2 steps) of compound 7.

$^1$H NMR (CD$_3$OD): δ (ppm)=1.06 (m, 6H, 2×CH$_3$CH$_2$), 1.24 (t, 3H, CH$_3$CH$_2$), 2.50-2.73 (3q, 3×CH$_2$CH$_3$), 2.76 (s, 3H, CH$_3$—Ar), 5.01 (s, 2H, N—CH$_2$), 6.99 (s, 1H, H$_x$), 7.26, 7.37 (2d, 4H, 2×H$_A$, 2×H$_B$), 7.87 (d, 1H, H$_C$), 8.37 (dd, 1H, HD), 8.54 (d, 1H, HE).

Example 5

Synthesis of 53

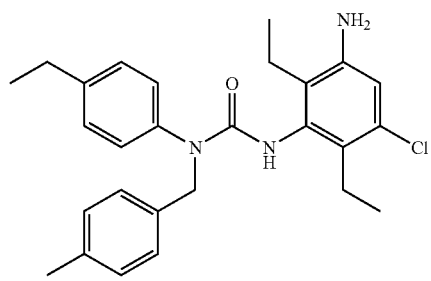

Step 1:

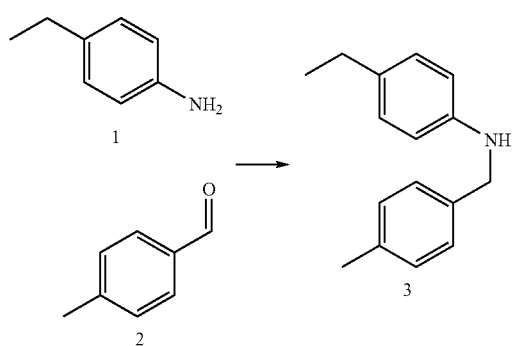

1.50 g (12.34 mmol) 4-ethylaniline (1) is reacted according to GP-1A with 4-methyl-benzaldehyde (2). The obtained 2.32 g (10.3 mmol; 83%) crude product 3 is used without further purification for subsequent reaction steps.

Step 2:

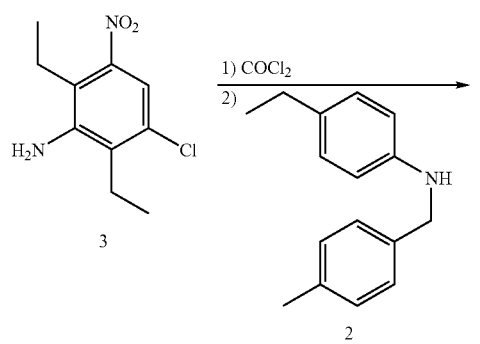

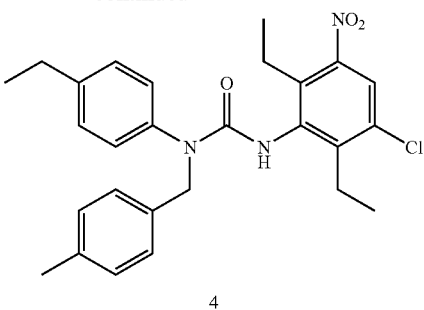

70 mg (0.306 mmol) 3-chloro-2,6-diethyl-5-nitro-phenylamine (3) is reacted with 105 mg (0.459 mmol; 1.5 eq.) (4-ethyl-phenyl)-(4-methyl-benzyl)-amine (2) according to GP-2A. The obtained crude product is used without further purification for subsequent reaction steps.

Step 3:

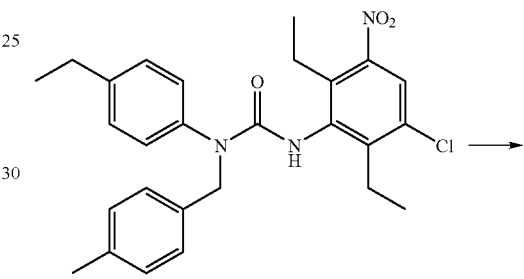

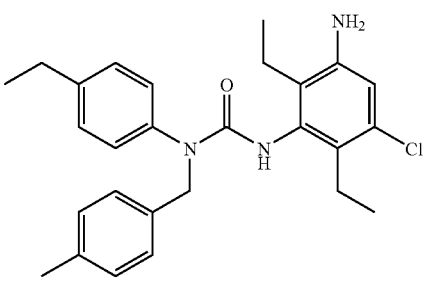

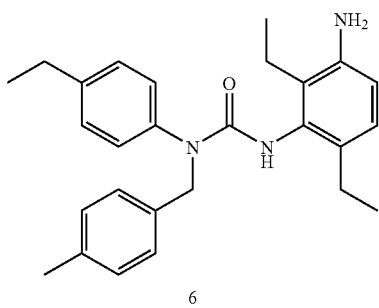

The nitro compound 4 obtained in step 2 is reduced according to GP-3A and the obtained product purified by HPLC yielding 5.1 mg of compound 5 and 7.0 mg of the dechlorinated compound 6 after reduction.

Example 6

Synthesis of 77

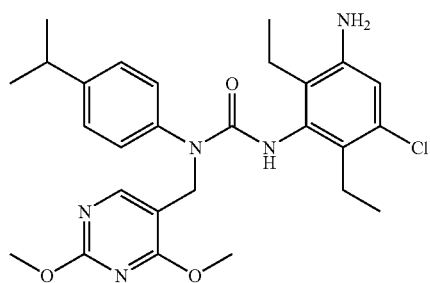

Step 1:

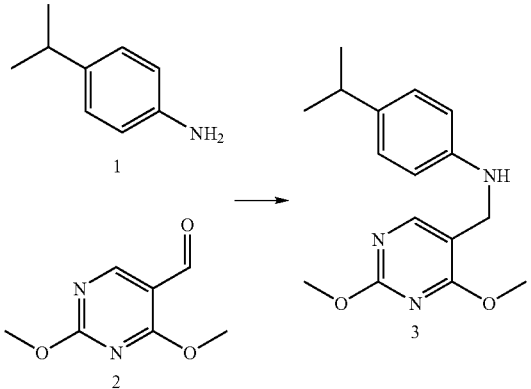

160.9 mg (1.19 mmol) 4-isopropylaniline (1) is reacted with 2,4-dimethoxy-pyrimidin-5-carbaldehyde (2) according to GP-1A. The obtained 318 mg (1.11 mmol; 93%) crude product 3 is used without further purification for subsequent reaction steps.

Step 2:

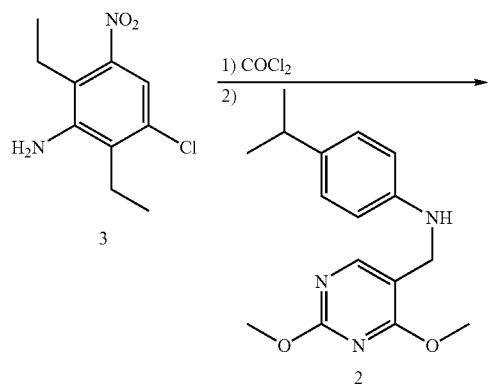

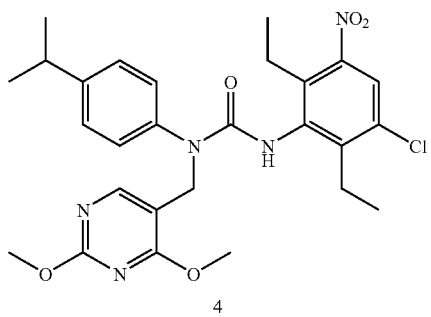

90 mg (0.395 mmol) 3-chloro-2,6-diethyl-5-nitro-phenylamine (3) is reacted with 168.5 mg (0.586 mmol; 1.5 eq.) (2,4-dimethoxy-pyrimidin-5-ylmethyl)-(4-ethyl-phenyl)-amine (2) according to GP-2A. The obtained crude product is used without further purification for subsequent reaction steps.

Step 3:

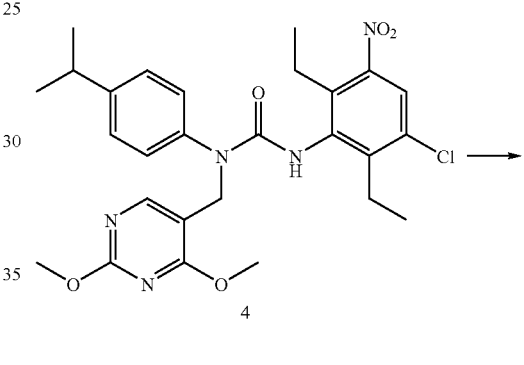

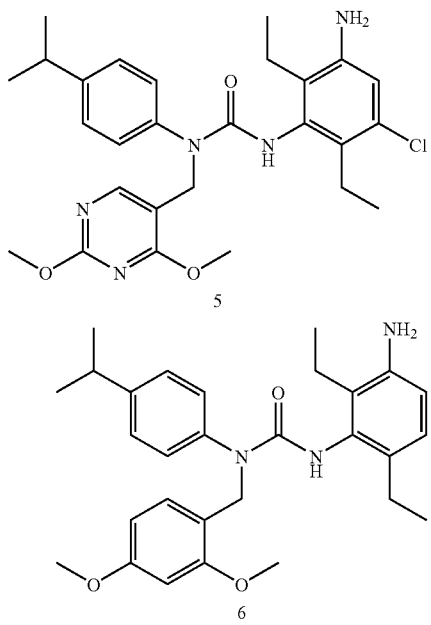

The nitro compound 4 obtained in step 2 is reduced according to GP-3A and the product is purified by HPLC yielding 72.5 mg of compound 5 and 2.8 mg of the dechlorinated compound 6 after reduction.

Example 7

Synthesis of 111

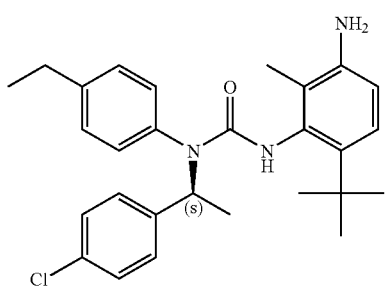

Step 1:

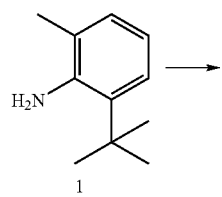

700 mg (4.29 mmol) 6-tert-butyl-o-toluidine (1) is dissolved on an ice-bath at 0° C. in 8 ml conc. H₂SO₄. To it 221.6 µl (4.72 mmol; 1.1 eq.) conc. HNO₃ is added and the reaction mixture is stirred for 3 h at 0° C. The reaction mixture is pored on ca. 75 ml ice and the obtained solution is extracted 5 times with EE. The combined organic layers are dried over magnesium sulphate and the solvent is removed under reduced pressure yielding 844 mg (4.06 mmol; 95%) of a mixture of compounds 2 and 3 as crude product. After purification of 200 mg by HPLC 72 mg (0.35 mmol; 34%) 2 and 36 mg (0.17 mmol; 17%) 3 could be obtained.

Step 2:

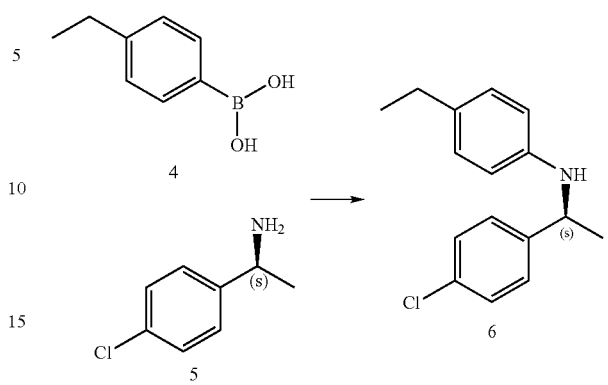

2.25 ml (16.1 mmol) (S)-4-chloro-alpha-methylbenzylamine (5) is reacted with 1.88 ml (16.1 mmol; 1.0 eq.) lutidine and 3.62 g (24.2 mmol; 1.5 eq.) 4-ethylphenylboronic acid (4) according to GP-1B. After purification by flash chromatography (hexane/EE 12:1) 1.96 g (7.54 mmol; 47%) of amine 6 is obtained.

Step 3:

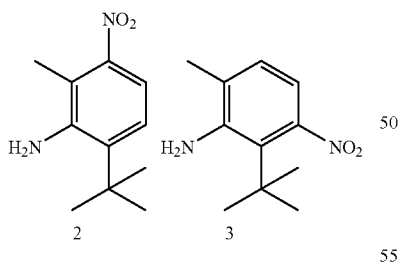

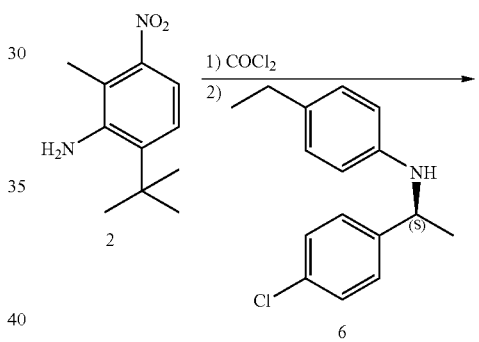

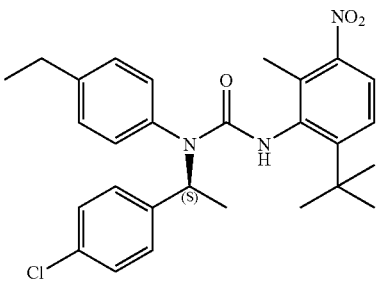

72 mg (0.35 mmol) 6-tert-butyl-2-methyl-3-nitro-phenylamine (2) is reacted with 81 mg (0.31 mmol; 0.9 eq.) (S)-[1-(4-chlorophenyl)-ethyl]-(4-ethyl-phenyl)-amine (6) according to GP-2A. The obtained crude product is used without further purification for subsequent reaction steps.

Step 4:

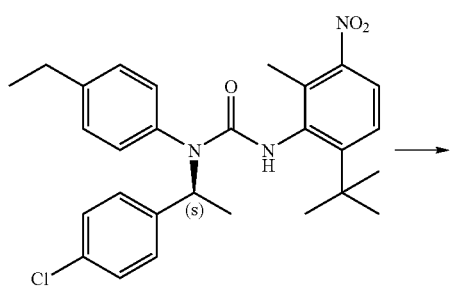

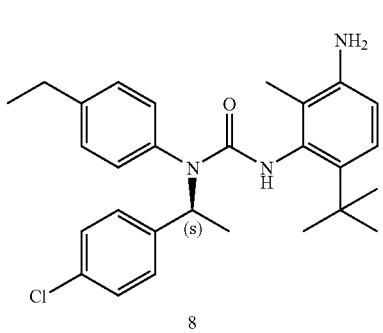

The nitro compound 7 obtained in step 3 is reduced according to GP-3B and the obtained product is purified by HPLC yielding 13.4 mg of compound 8.

Example 8

Synthesis of 112

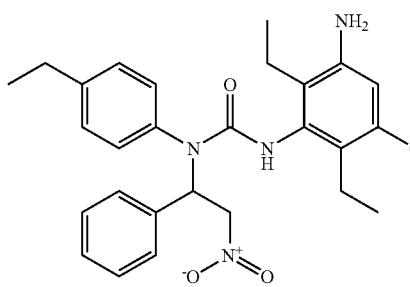

Step 1:

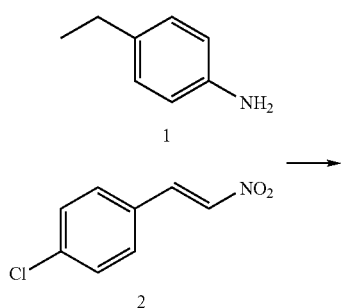

250 mg (1.36 mmol) 1-(4-chlorophenyl)-2-nitroethene (2) and 136 µl (1.09 mmol; 0.8 eq.) 4-ethylaniline (1) are dissolved in 2 ml acetonitrile. The reaction mixture is stirred for two days at 45° C. and concentrated in vacuum. The obtained crude product is used without further purification for subsequent reaction steps.

Step 2:

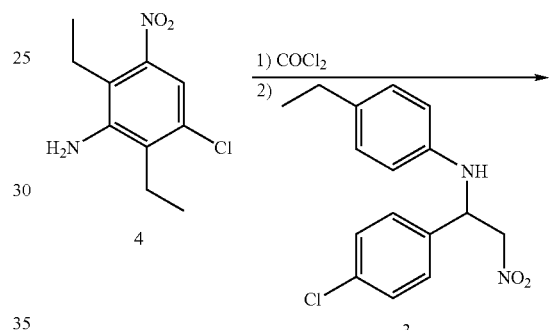

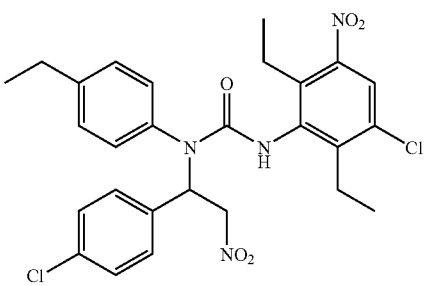

75 mg (0.328 mmol) 3-chloro-2,6-diethyl-5-nitro-phenylamine (4) is reacted with 130 mg (0.43 mmol; 1.3 eq.) [1-(4-chlorophenyl)-2-nitroethyl]-(4-ethylphenyl)-amine (3) (obtained as crude product in step 1) according to GP-2A. Purification by HPLC yielded 22 mg (0.039 mmol; 12%) 5.

Step 3:

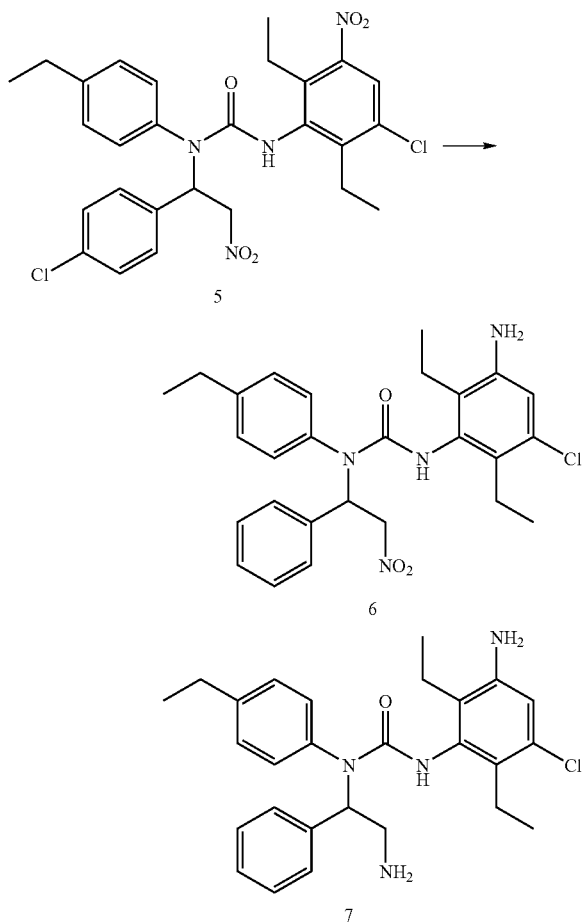

12.7 mg (0.0227 mmol) of the dinitro compound 5 is reduced according to GP-3A and the crude product purified by HPLC yielding 1.41 mg (0.0030 mmol; 13%) of the diamine 7 and 1.56 mg (0.0032 mmol; 14%) of compound 6.

Example 9

Synthesis of 118

Step 1:

150 mg (0.77 mmol) ethyl-3-amino-4-(methyl amino)benzoate (1) is dissolved in 10 ml formic acid. The solution is stirred at 60° C. for one day. Removal of the solvent under reduced pressure yielded 235 mg of the crude product which is used without further purification for subsequent reactions.

Step 2:

235 mg of the ester 2 obtained in step 1 is dissolved in a mixture of 20 ml 1N LiOH and 8 ml dioxane. The solution is stirred for 4 h at room temperature and 11 ml of a 2N HCl-solution is added until pH 7 is reached. The dioxane is removed under reduced pressure. After freeze drying of the aqueous layer 530 mg of the desired compound 3 is obtained as a crude product which is used without further purification for subsequent reactions.

Step 3:

The crude product from step 2 (theor. amount: 0.77 mmol) is suspended in 14 ml DMF and 1038 mg (5.4 mmol; 7.0 eq.) WSC×HCl, 802 mg (3.0 mmol; 3.9 eq.) HOBt and 300 µl (2.4 mmol; 3.1 eq.) 4-ethylaniline are added. After one day of stirring the DMF is removed under reduced pressure. 50 ml of a 2N NaOH-solution is added and the aqueous layer is extracted 5 times with DCM. The combined organic layers are dried over magnesium sulphate and the solvent is removed under reduced pressure yielding 1.04 g of the crude product as a brown oil. The oil is dissolved in 50 ml DCM and extracted 5 times with 30 ml of a 1M HCl-solution. The aqueous layer is adjusted to pH 14 with app. 30 ml of a 1 M NaOH-solution and extracted 5 times with 50 ml DCM. The combined organic layers are dried over magnesium sulphate and the solvent is removed under reduced pressure which is used without further purification for subsequent reactions.

Step 4:

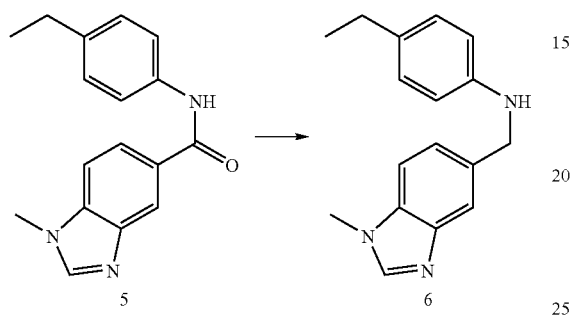

The crude product from step 3 (theor. amount: 0.77 mmol) is reacted according to GP-1D at room temperature for one day. After purification by flash chromatography 57.4 mg (0.22 mmol; 29% over 4 steps) of amine 6 is obtained.

Step 5:

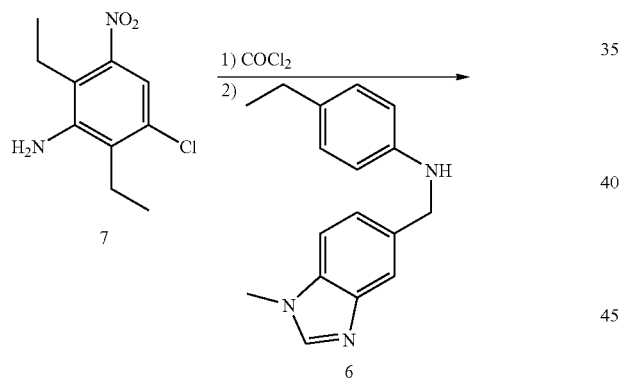

34.4 mg (0.151 mmol) 3-chloro-2,6-diethyl-5-nitro-phenylamine (7) is reacted with 40 mg (0.151 mmol; 1.0 eq.) (4-ethyl-phenyl)-(1-methyl-1H-benzoimidazol-5-ylmethyl)-amine (6) according to GP-2A. The crude product 8 is used without further purification for subsequent reactions.

Step 6:

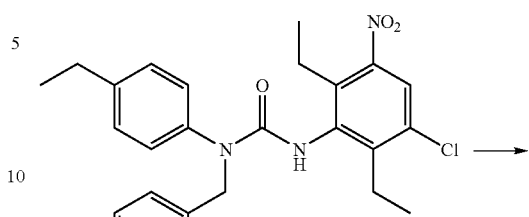

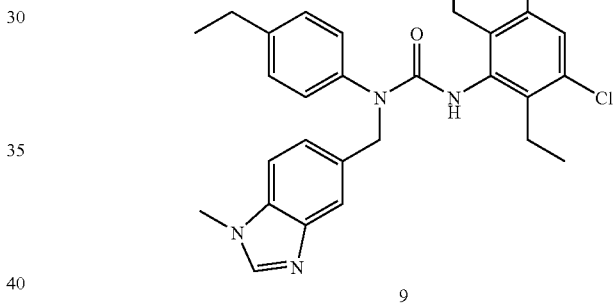

The nitro compound 8 obtained in step 5 is reduced according to GP-3B and the obtained product is purified by HPLC yielding 3.37 mg of compound 9.

Example 10

Synthesis of 131

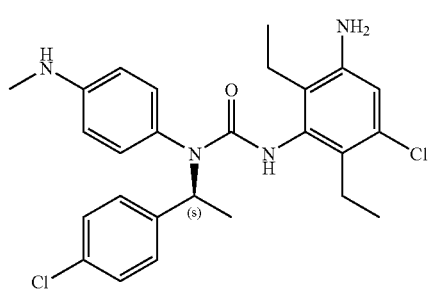

Step 1:

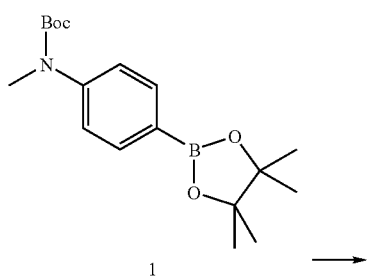

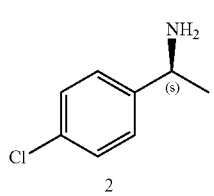

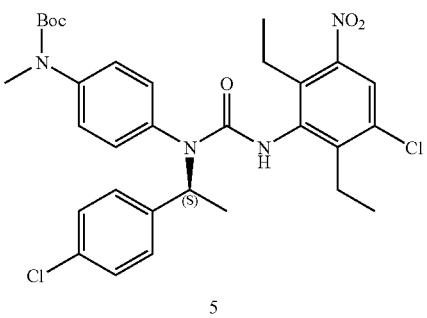

70 mg (0.307 mmol) 3-chloro-2,6-diethyl-5-nitro-phenylamine (4) and 132 mg (0.366 mmol; 1.2 eq.) {4-[1-(4-chlorophenyl)-ethyl]amino}-phenyl-methyl-carbaminic acid-tert-butyl-ester (3) are reacted according to GP-2A. The crude product is purified by HPLC yielding 105 mg (0.171 mmol; 56%) of compound 5.

Step 3:

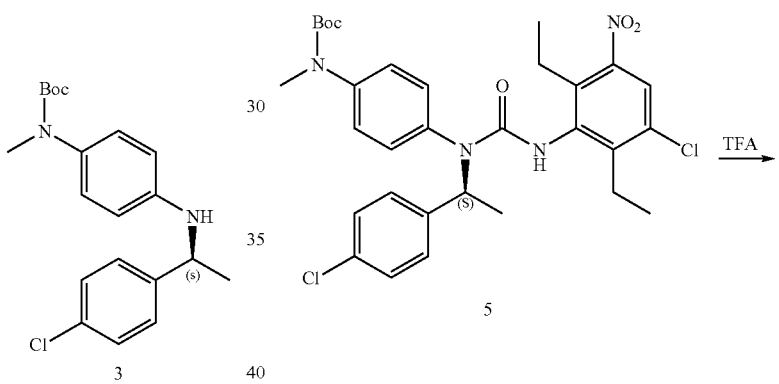

500 mg (1.50 mmol) methyl-[4-(4,4,5,5-tetramethyl-[1,3,2]dioxaborolan-2-yl)-phenyl]-carbaminic acid-tert-butyl-ester (1) 252 µl (1.80 mmol; 1.2 eq.) (S)-1-(4-chlorophenyl)-ethylamine (2) and 418 µl (3.0 mmol; 2.0 eq.) triethylamine are reacted according to GP-1B. After purification by flash chromatography (hexane/EE) 133 mg (0.37 mmol; 25%) of amine 3 is obtained.

Step 2:

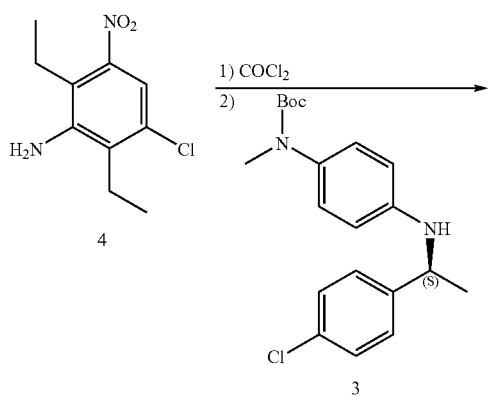

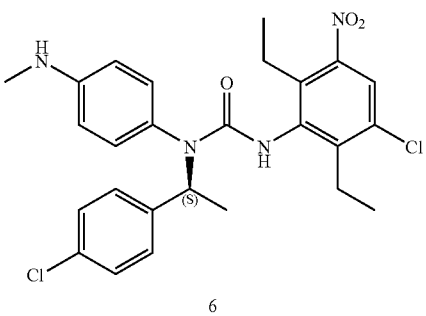

80 mg (0.130 mmol) of the Boc-protected compound 5 from step 2 is dissolved in ca. 5 ml DCM/TFA/H$_2$O 50:50:0.05 and stirred for 10 min at room temperature. The solvent is removed under reduced pressure and 73 mg (0.142 mmol; 109%) of amine 6, is obtained which is used without further purification for subsequent reactions.

Step 4:

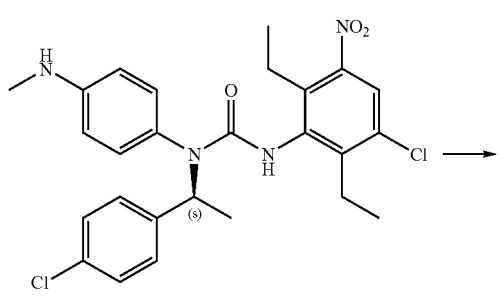

50 mg (0.097 mmol) of the nitro compound 6 from step 3 is reduced within 3 min according to GP-3A. Purification by HPLC of the crude product afforded 12.5 mg (0.026 mmol; 27%) of desired compound 7 and 2.7 mg (0.006 mmol; 6%) of the dechlorinated compound 8.

Example 11

Synthesis of 141

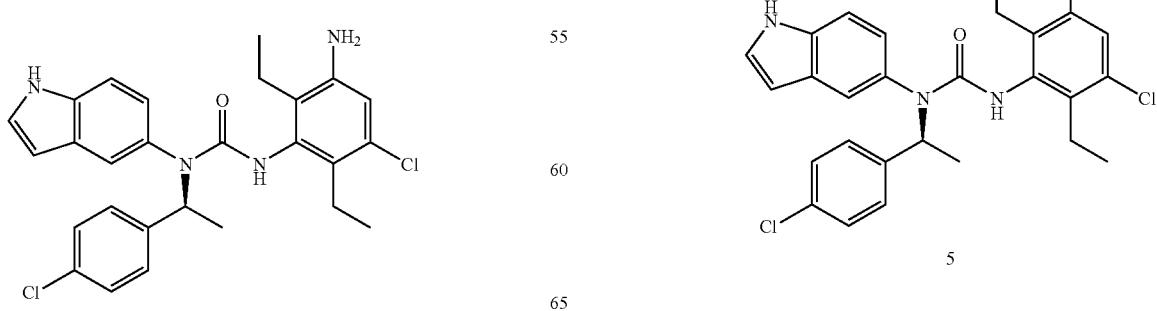

Step 1:

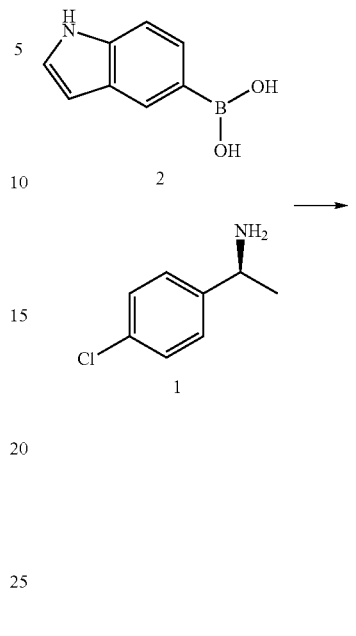

140.2 μl (1.0 mmol) of compound 1 and 210 mg (1.3 eq.) 5-indolylboronic acid (2) are reacted according to GP-1B in the presence of 151 μl (1.3 eq.) lutidine and 236 mg (1.3 eq.) copper acetate. The 240 mg of obtained crude product is purified yielding by flash chromatography 26 mg (0.10 mmol; 10%) of amine 3.

Step 2:

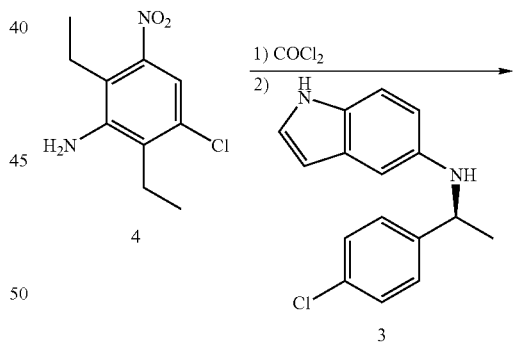

26 mg (0.116 mmol, 1.2 eq.) 3-chloro-2,6-diethyl-5-nitro-phenylamine (4) and 26 mg (0.096 mmol; 1.0 eq.) [1-(4- chloro-phenyl)-ethyl]-(1H-indol-5-yl)-amine (3) are reacted at 40° C. according to GP-2A. The obtained product is purified by HPLC yielding 6 mg (0.011 mmol; 10%) of 5.

Step 3:

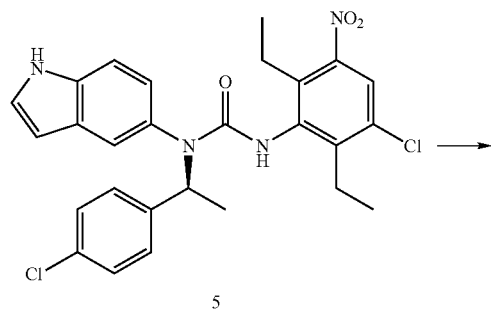

The nitro compound 5 from step 2 is reduced according to GP-3A. Purification by HPLC of the crude product afforded 2.70 mg (0.0054 mmol; 50%) of desired compound 6.

Example 12

Synthesis of 27

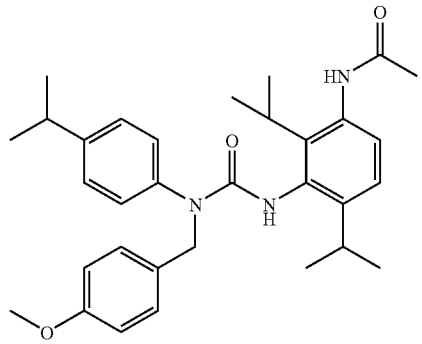

Step 1:

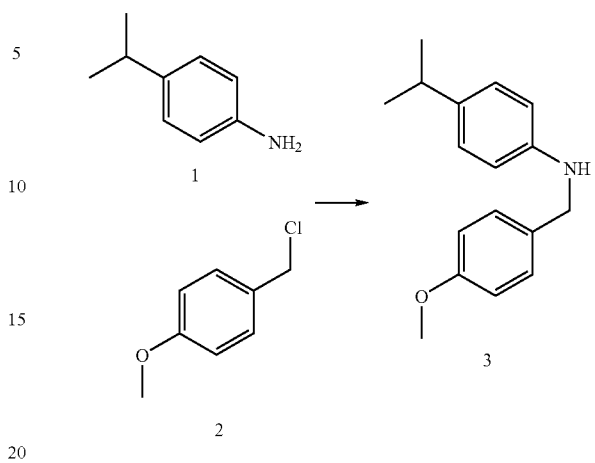

1.46 ml (18 mmol) 4-isopropylaniline (1) is reacted with 4-methoxy-benzylchloroide (2) according to GP-1C. After purification by HPLC 1.1 g (4.3 mmol; 72%) of compound 3 is obtained.

Step 2:

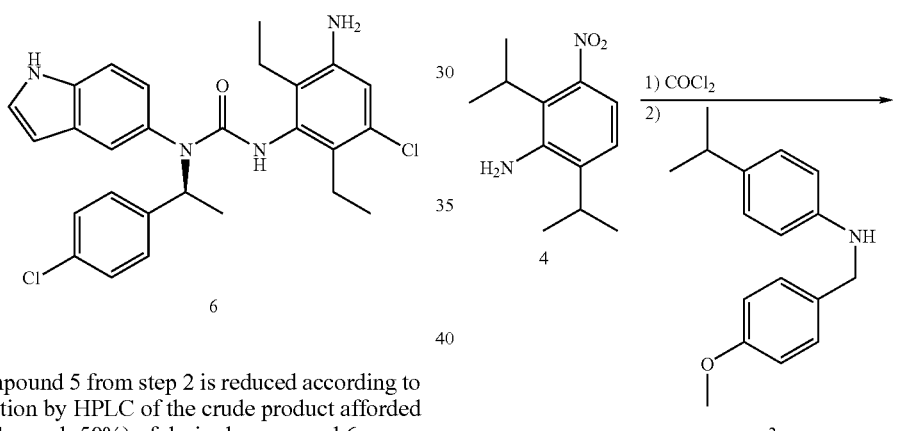

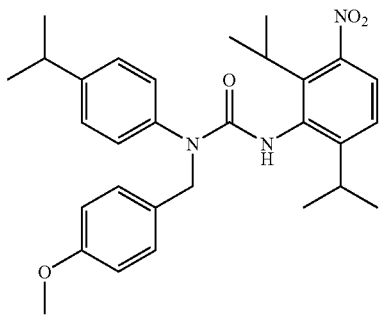

90 mg of the nitro compound 4 is reacted with 134 mg (0.525 mmol; 1.5 eq.) of amine 3 according to GP-2A. The crude product 5 is used without further purification for subsequent reactions.

Step 3:

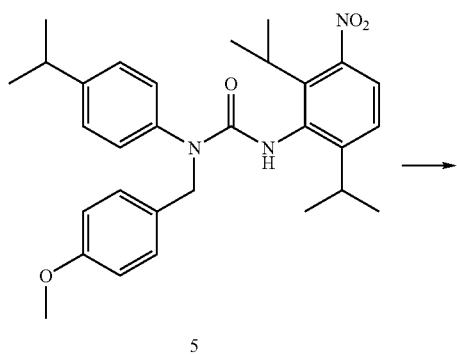

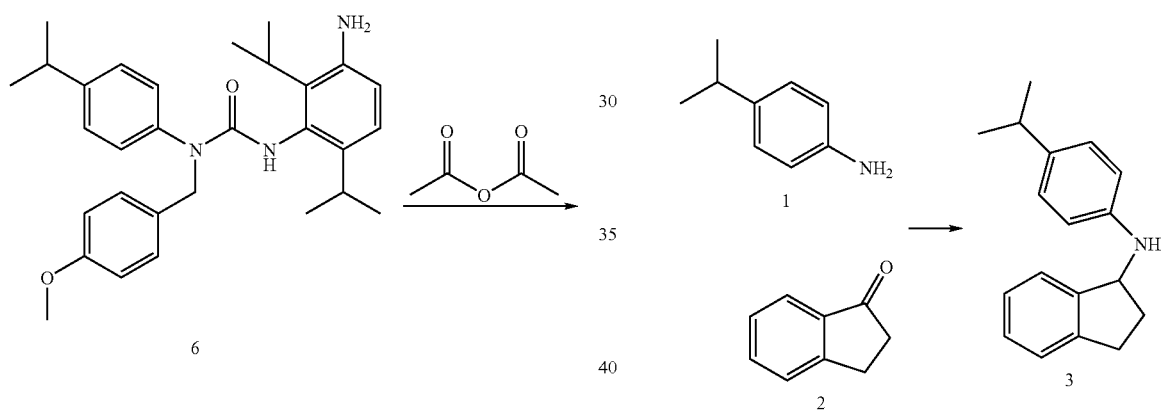

The nitro compound 5 from step 2 is reduced according to GP-3B and purified by HPLC yielding 18 mg of compound 6. 10.0 mg 6 are dissolved in acetonitrile (20 ml), 10 eq. acetic anhydride and 2 eq. TEA were added. The reaction mixture is stirred for 30 min at room temperature. Purification by HPLC yielded 9 mg of compound 7.

Example 13

Synthesis of 84

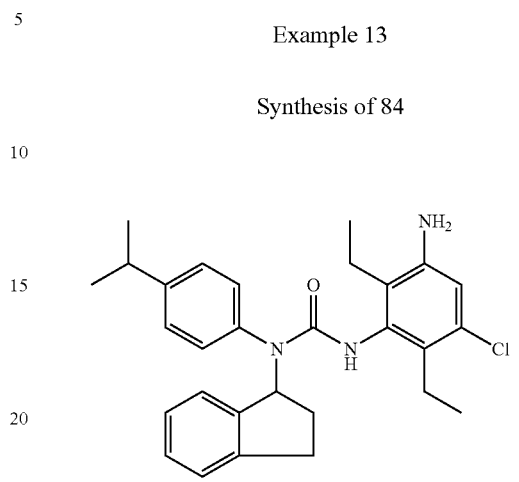

Step 1:

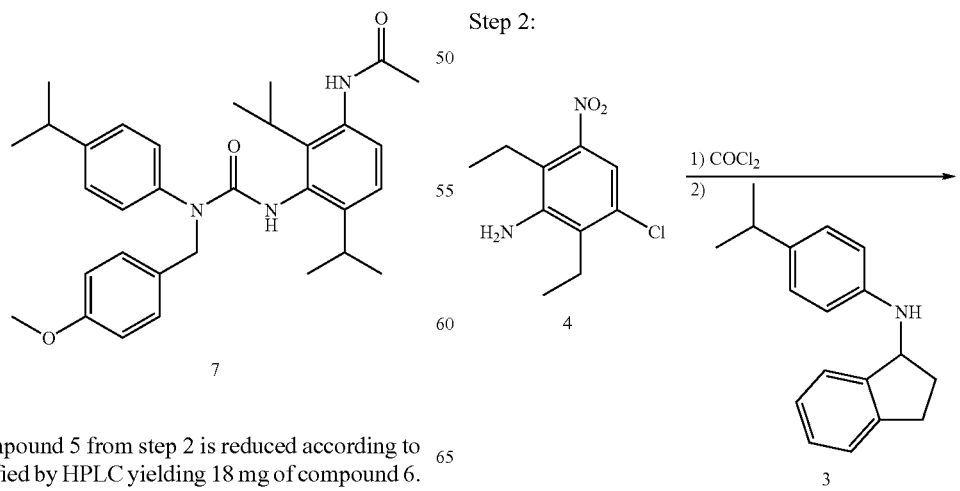

1.46 ml (18 mmol) 4-isopropylaniline (1) is reacted with 1-indanone (2) according to GP-1A. Purification of the crude product by HPLC yielded 1.1 g (4.3 mmol; 72%) of compound 3.

Step 2:

-continued

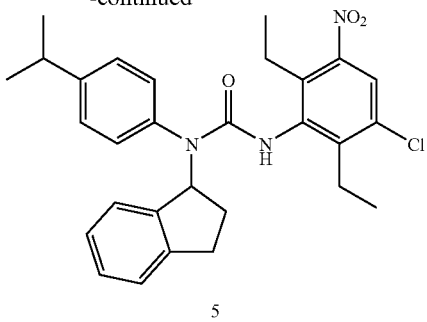

5

180 mg of the nitro compound 4 is reacted with 180 mg (0.76 mmol; 1 eq.) amine 3 according to GP-2A. The crude product 5 is used without further purification for subsequent reactions.

Step 3:

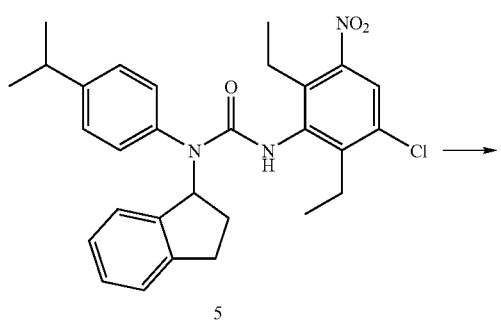

5

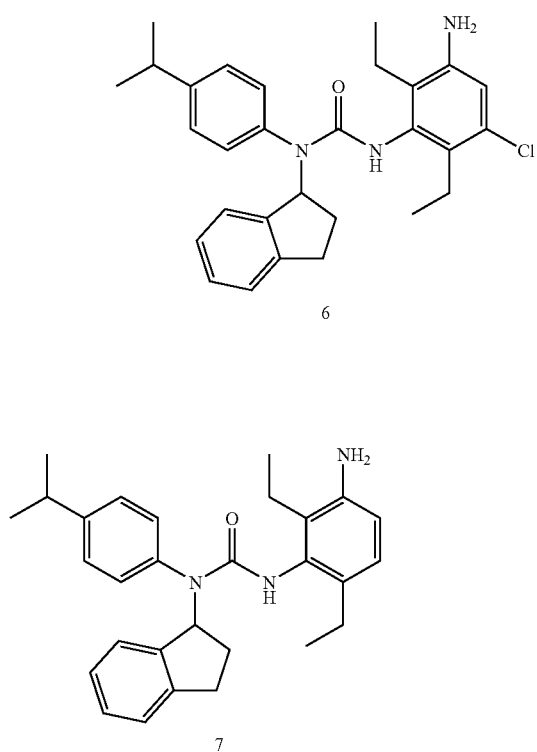

The nitro compound 5 obtained in step 2 is reduced according to GP-3B and the obtained product is purified by HPLC yielding 19 mg of compound 6 and 5.0 mg of the dechlorinated compound 7.

Example 14

Synthesis of 110

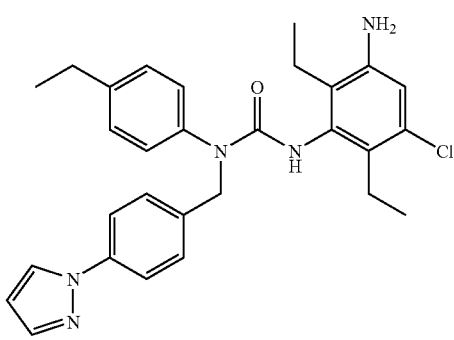

Step 1:

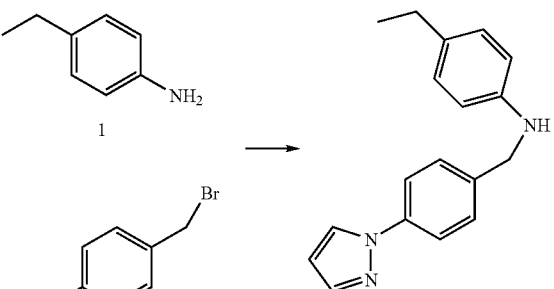

150 µl (1.2 mmol) 4-isopropylaniline (1) is reacted with 1-(4-bromomethyl-phenyl)-1H-pyrazole (2) according to GP-1C yielding 180 mg (0.78 mmol; 64%) of 3 as crude product which is used without further purifications.

Step 2:

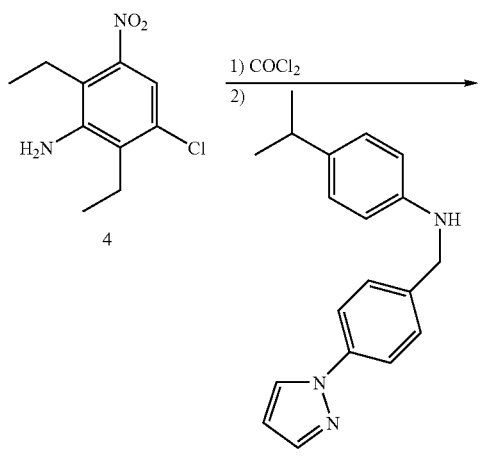

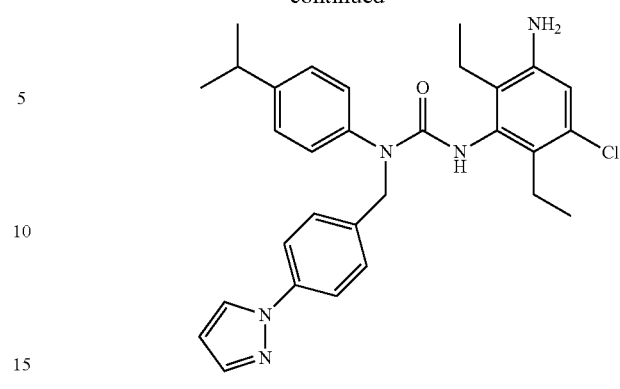

60 mg of the nitro compound 4 is reacted with 75 mg (0.26 mmol; 1 eq.) amine 3 according to GP-2A. The obtained crude product is used without further purification for subsequent reactions.

Step 3:

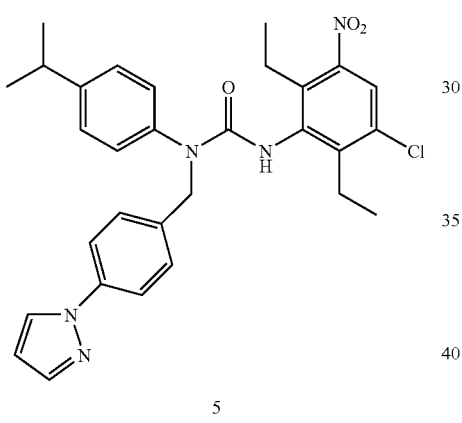

The nitro compound 5 obtained in step 2 is reduced according to GP-3B. Purification by HPLC of the crude product yielded 12 mg of compound 6.

Example 15

Synthesis of 116

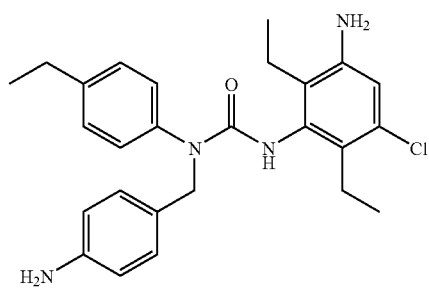

Step 1:

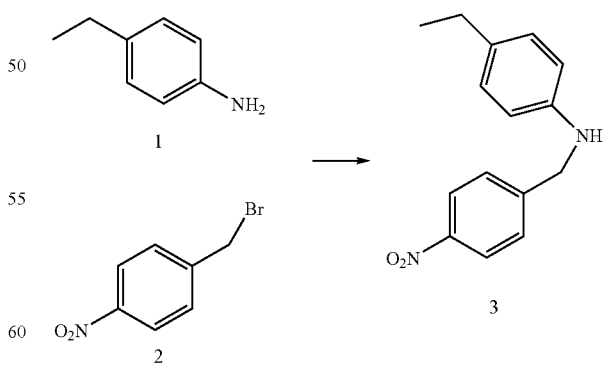

150 µl (1.2 mmol) 4-isopropylaniline (1) is reacted with 4-nitrobenzylbromide (2) according to GP-1C. The obtained compound 3 (260 mg; 1.02 mmol; 85%) is used without purification for further reactions.

Step 2:

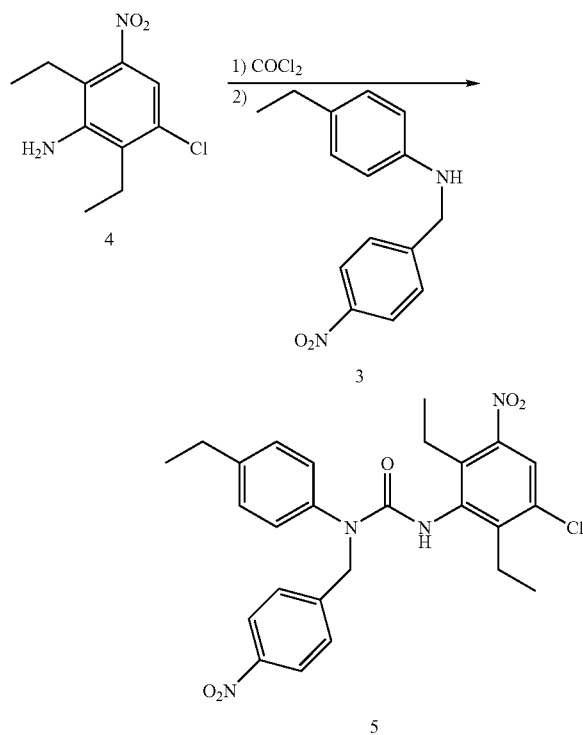

60 mg of the nitro aniline 4 is reacted with 70 mg (0.26 mmol; 1 eq.) amine 3 according to GP-2A. The obtained crude product is used without purification for further reactions.

Step 3:

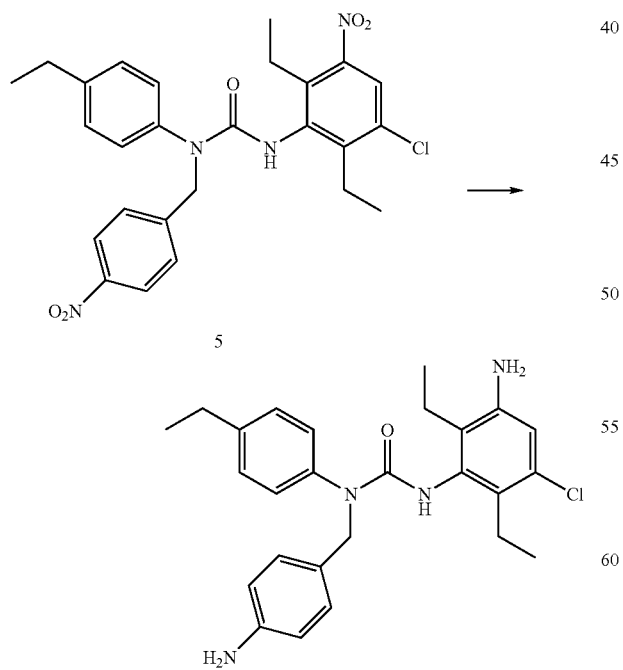

The nitro compound 5 obtained in step 2 is reduced according to GP-3A. The product is purified by HPLC yielding 6 mg of compound 6.

Example 16

Synthesis of 120

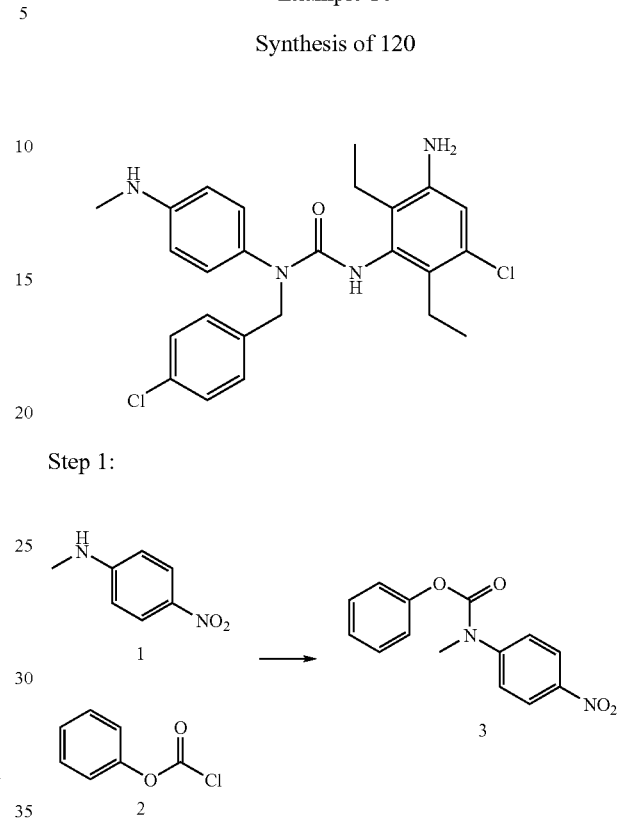

Step 1:

107 mg N-methyl-4-nitroaniline (1) are dissolved in 10 ml THF and 186 mg (1.1 eq.) phenyl chloroformate (2) are added in the presence of 187 mg (1 eq.) potassium carbonate. The reaction mixture is stirred for 16 h at room temperature. The solvent is removed under reduced pressure and the residue is redissolved in EE and extracted twice with water. Removal of the solvent yielded 250 mg of crude product which is used without further purification for subsequent reactions.

Step 2:

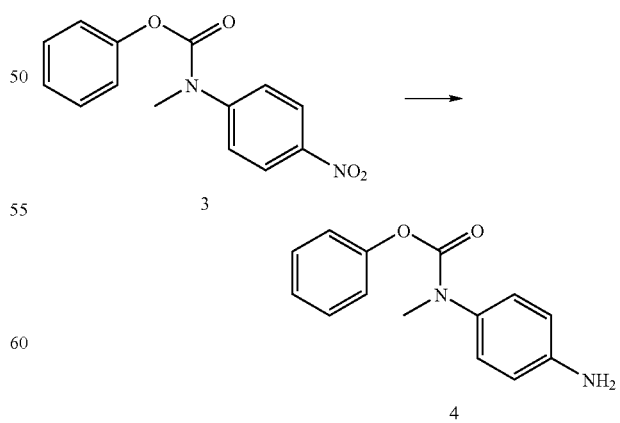

The nitro compound 3 obtained in step 1 is reduced according to GP-3B yielding 180 mg of crude 4 which is used without further purification for subsequent reactions.

Step 3:

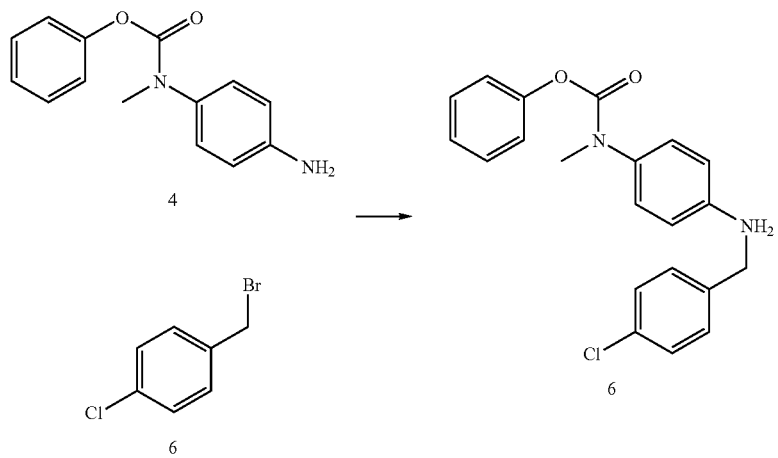

180 mg (0.744 mmol) of amine 4 is reacted with 4-chlorobenzylbromide (5) according to GP-1C. The obtained crude 6 (300 mg) is used without further purification for subsequent reactions.

Step 4:

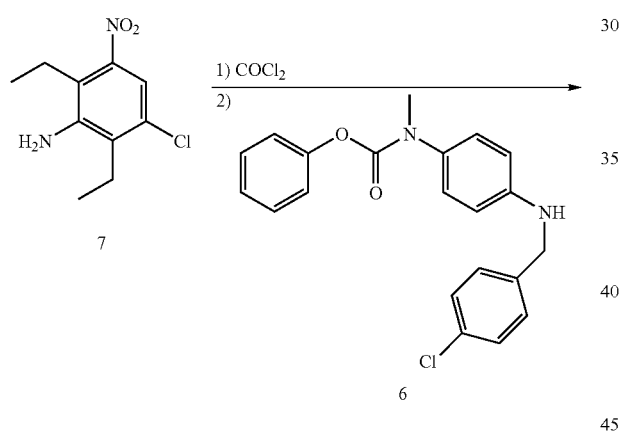

63 mg of the nitro aniline 7 is reacted with 120 mg (0.33 mmol; 1.1 eq.) of amine 6 according to GP-2A. The obtained crude product 8 is used without further purification for subsequent reactions.

Step 5:

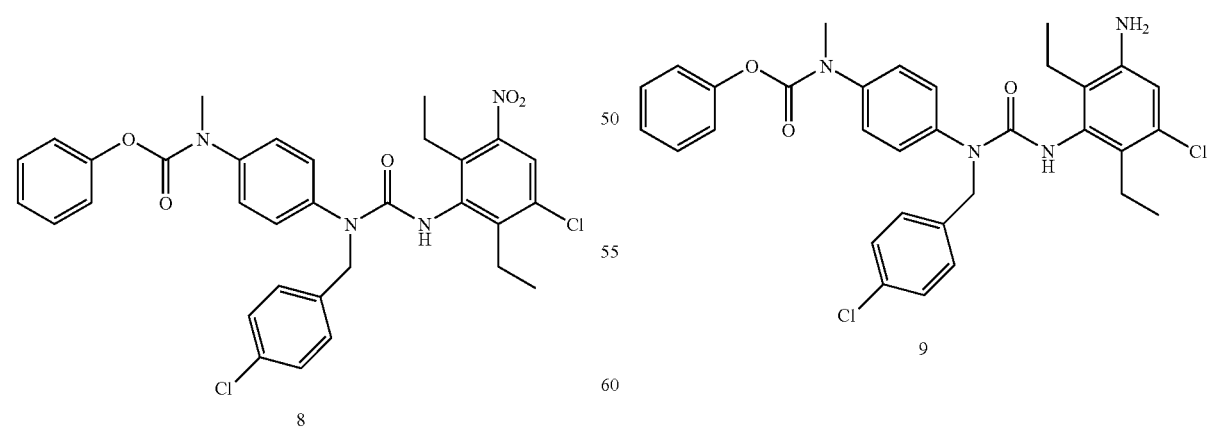

The nitro compound 8 obtained in step 2 is reduced according to GP-3A yielding crude 9 which is used without further purification for subsequent reactions.

Step 6:

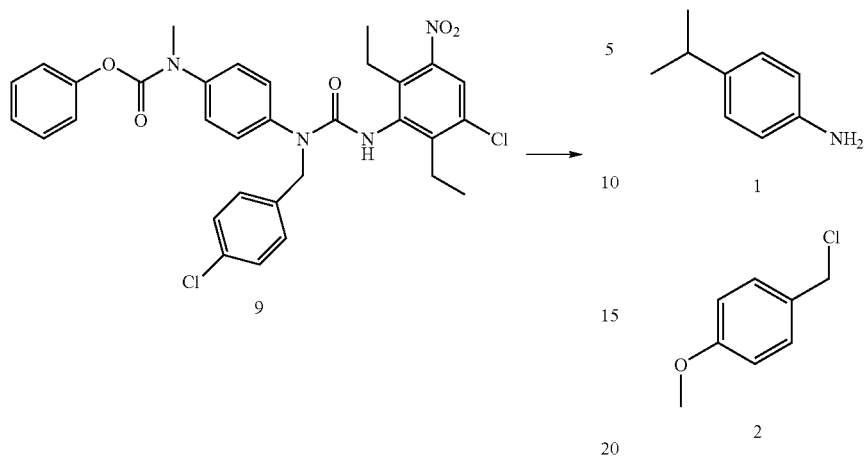

Step 1:

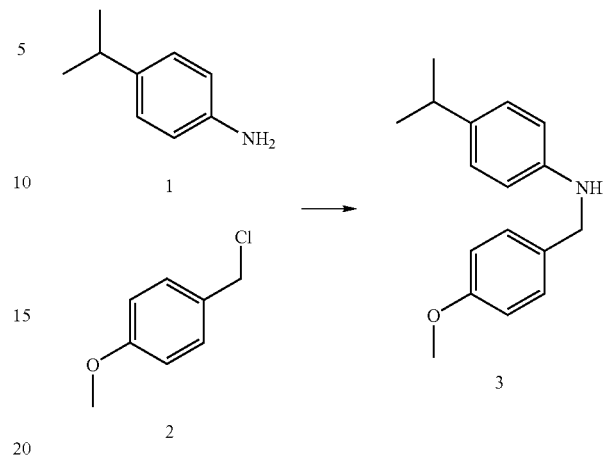

1.46 ml (18 mmol) 4-isopropylaniline (1) is reacted with 4-methoxybenzylchloroide (2) according to GP-1C. Purification of the crude product by HPLC yielded 1.1 g (4.3 mmol; 72%) of compound 3.

Step 2:

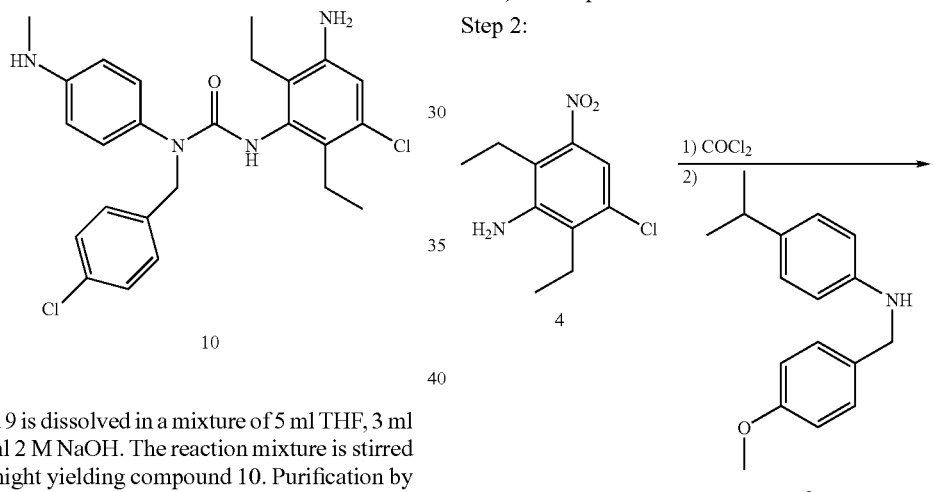

The crude urea 9 is dissolved in a mixture of 5 ml THF, 3 ml DMSO and 2.5 ml 2 M NaOH. The reaction mixture is stirred vigorously over night yielding compound 10. Purification by HPLC afforded 3 mg of compound 10.

Example 17

Synthesis of 31

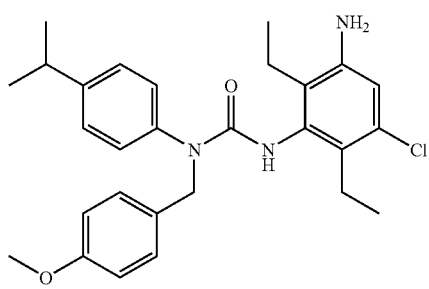

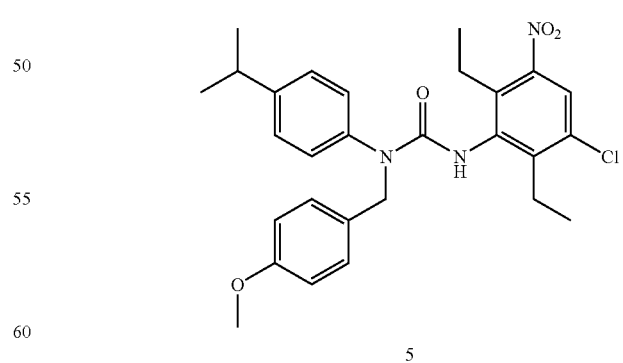

53 mg of the nitro aniline 4 is reacted with 67 mg (0.26 mmol; 1.5 eq.) amine 3 according to GP-2A. The obtained crude product 5 is used without further purification for subsequent reactions.

Step 3:

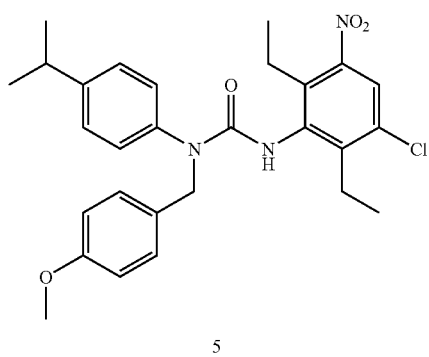

5

The nitro compound 5 obtained in step 2 is reduced according to GP-3A. Purification of the crude product by HPLC yielded 13 mg of compound 6.

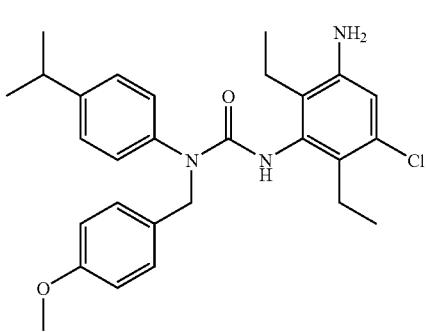

6

Example 18

Synthesis of 80

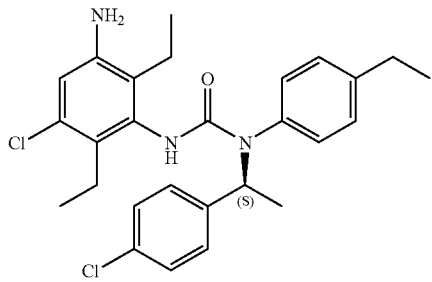

Step 1:

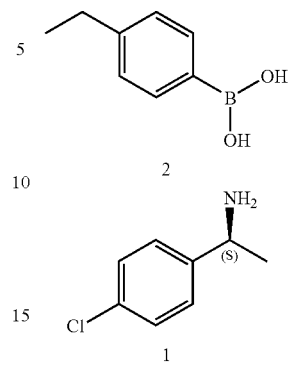

841 µl (6.0 mmol) (S)-4-chloro-alpha-methylbenzylamine (1) react according to GP-1B with 1.35 g (9.0 mmol; 1.5 eq.) 4-ethylphenylboronic acid (2). After flash chromatographic purification (hexane/ethylacetate 12:1) 450 mg (1.73 mmol; 29%) of the desired amine 3 is yielded.

Step 2:

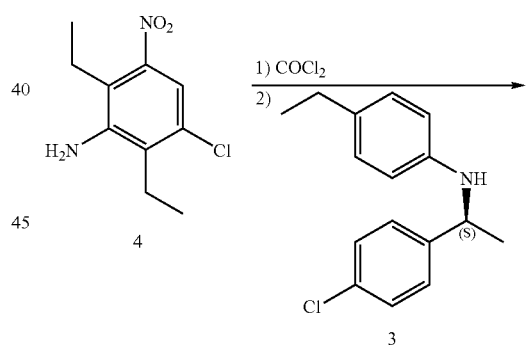

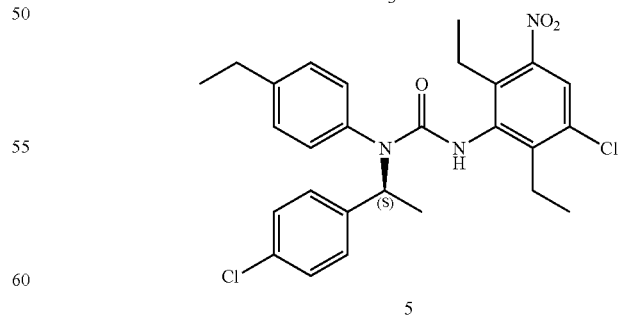

131.7 mg (0.576 mmol) of 3-chloro-2,6-diethyl-5-nitro-phenylamine (4) react according to GP-2A with 485 µl (0.922 mmol; 1.6 eq.) of a 20% solution of phosgene in toluol and with 224.4 mg (0.864 mmol; 1.5 eq.) (S)-[1-(4-chlorophenyl)-ethyl]-(4-ethyl-phenyl)-amine (3). The raw product is purified via HPLC which yields 276 mg (0.537 mmol; 93%) of 5.

Step 3:

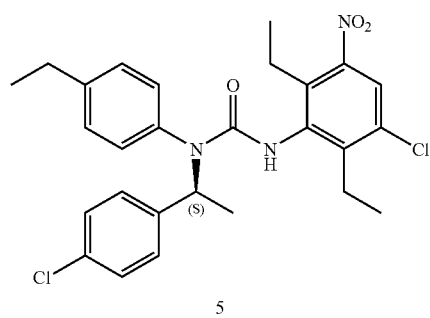

5

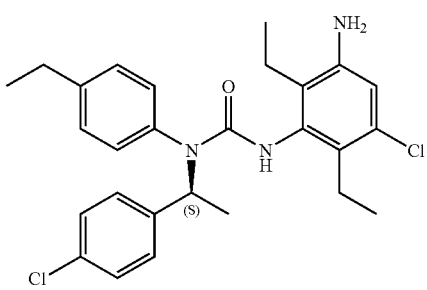

6

The nitro compound 5 obtained in step 2 is reduced with 9 equivalents of tindichloride-dihydrate according to GP-3B. The raw product is purified via HPLC. This yields 190 mg of the desired compound 6.

Example 19

Synthesis of 102

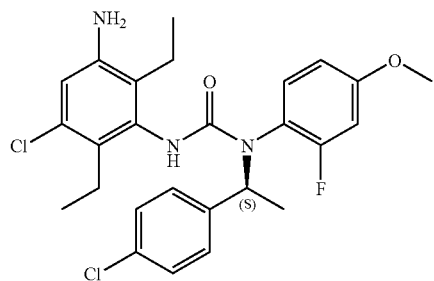

Step 1:

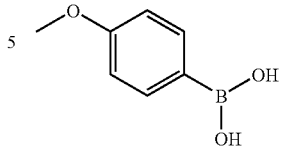

2

1

3

701 µl (5.0 mmol) (S)-4-chloro-alpha-methylbenzylamine (1) react according to GP-1B with 757 µl (6.5 mmol; 1.3 eq.) Lutidin, 1.18 g (6.5 mmol; 1.3 eq.) copper-II-acetate and 1.7 g (10.0 mmol; 2.0 eq.) 2-fluoro-4-methoxybenzyl-boronic acid (2). After flash chromatographical purification (hexane/ ethylacetate 10:1) 23.9 mg (0.086 mmol) of the desired amine 3 is yielded.

Step 2:

4

3

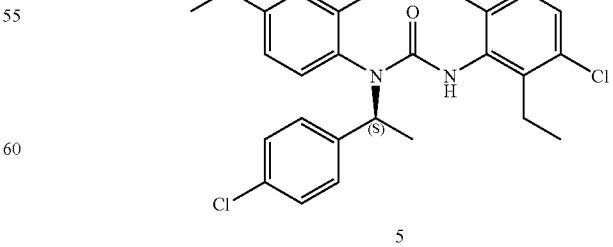

5

42.5 mg (0.186 mmol; 2 eq.) 3-chloro-2,6-diethyl-5-nitro-phenylamine (4) react according to GP-2A with 24.6 mg (0.232 mmol; 2.5 eq.) sodium carbonate, 122 μl (0.232 mmol; 2.5 eq.) of a 20% solution of phosgen in toluol and 26.0 mg (0.093 mmol; 1.0 eq.)

(S)-[1-(4-chlorophenyl)-ethyl]-(2-fluoro-4-methoxy-phenyl)-amine (3). The raw product is purified via HPLC. This yields 12 mg (0.023 mmol; 26%) of compound 5.

Step 3:

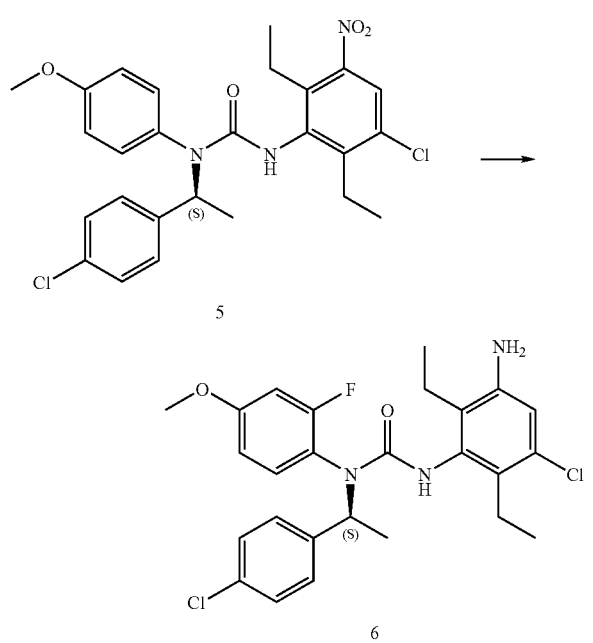

The nitro compound 5 obtained in step 2 is reduced with 9 eq. of tindichloride dihydrate according to GP-3B. Purification of the raw product via HPLC yields 8 mg of the desired compound 6.

Example 20

Synthesis of 36

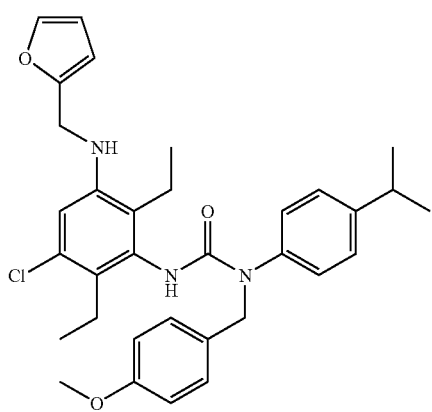

Step 1:

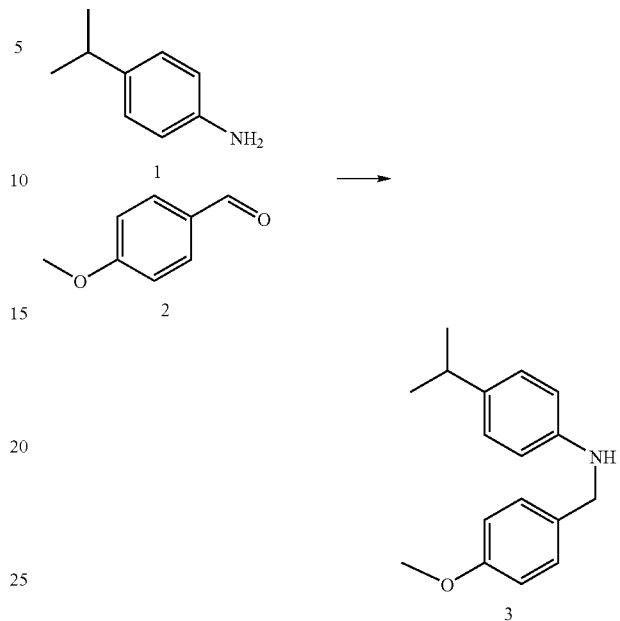

2.02 ml (14.8 mmol) 4-isopropylaniline (1) react according to GP-1A with 4-methoxy-benzaldehyde (2). As raw product 3.44 g (13.5 mmol; 91%) of compound 3 is yielded, which is used without purification for the next reaction step.

Step 2:

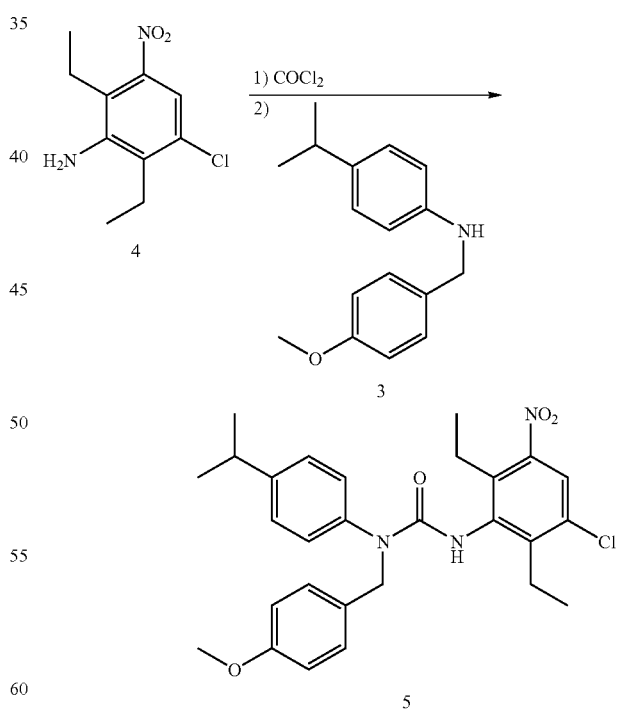

724 mg (3.17 mmol) 3-chloro-2,6-diethyl-5-nitro-phenylanine (4) react according to GP-2A with 1.05 g (4.12 mmol; 1.3 eq.) (4-isopropyl-phenyl)-(4-methoxy-benzyl)-amine (3). Flash chromatographical purification (hexane/ethylacetate 12:1) yields 78 mg (0.15 mmol) of compound 5.

Step 3:

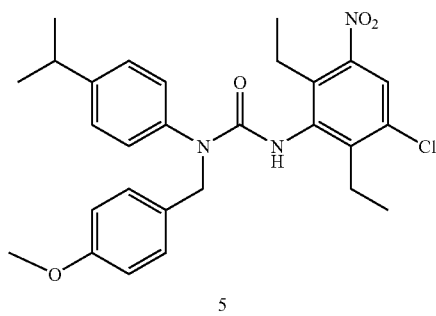

5

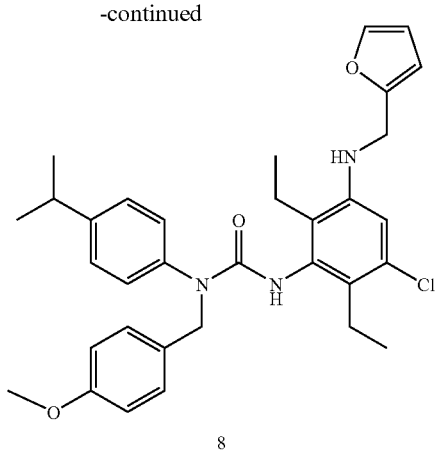

8

34.4 mg (0.072 mmol) 3-(3-amino-5-chloro-2,6-diethyl-phenyl)-1-(4-isopropyl-phenyl)-1-(4-methoxy-benzyl)-urea (6) react according to GP-1A with 9.0 μl (0.108 mmol, 1.5 eq.) 2-furaldehyd (7), 32.1 μl (0.108 mmol; 1.5 eq.) titanium-tetraisopropylate and 4.1 mg (0.108 mmol; 1.5 eq.) sodium borhydride. The obtained raw product is purified via HPLC, which yields 14 mg of the desired compound 8.

Example 21

Synthesis of 37

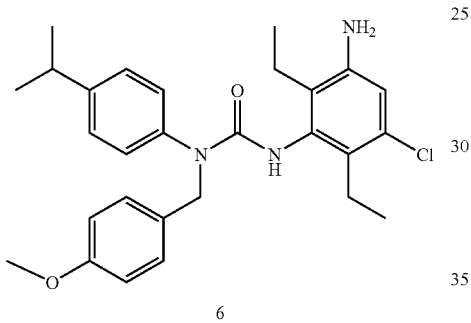

6

The nitro compound 5 obtained in step 2 is reduced according to GP-3A. This yields 34.4 mg (0.072 mmol; 47%) of compound 6 as raw product, which is used without purification in the next reaction step.

Step 4:

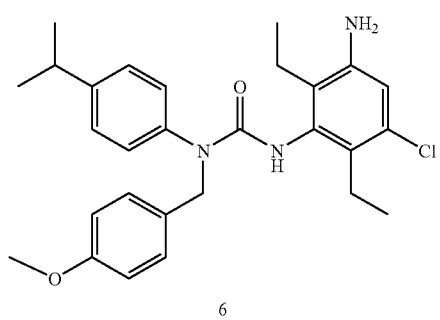

6

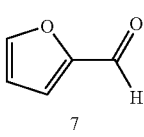

7

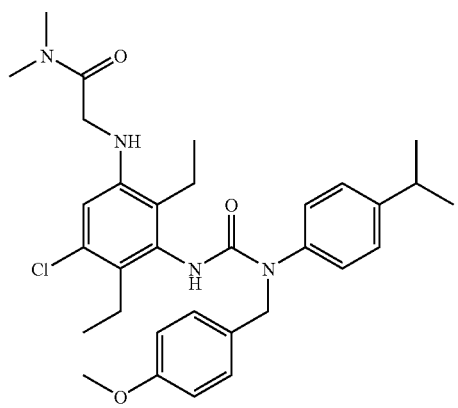

Step 1: as in example 19, step 1
Step 2: as in example 19, step 2
4: 1.06 g (4.63 mmol)
3: 1.54 g (6.02 mmol; 1.3 eq.)
  Yield: 410 mg (0.8 mmol; 17%)
Step 3: as in example 19, step 3
  Yield: 220 mg (0.46 mmol; 57%)

Step 4:

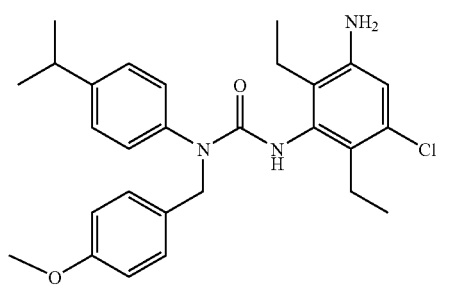

6

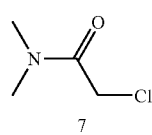

7

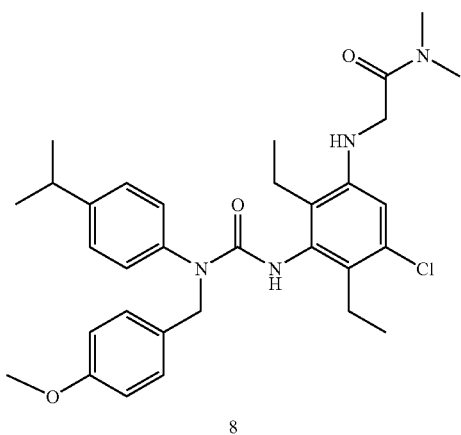

8

10.0 mg (0.021 mmol) 3-(3-amino-5-chloro-2,6-diethyl-phenyl)-1-(4-isopropyl-phenyl)-1-(4-methoxy-benzyl)-urea (6) is desolved in DMF. 11.1 mg (0.105 mmol, 5.0 eq.) sodium carbonate is added. To the obtained solution 10.8 µl (0.105 mmol, 5.0 eq.) 2-chloro-N,N-dimethyl-acetamide (7) is added. The solution is heated to 40° C. and stirred for 4 days. The obtained raw product is purified via HPLC, which yields 5 mg of the desired compound 8.

Example 22

Synthesis of 2,6-diethyl-3-nitro-phenylamine (2)

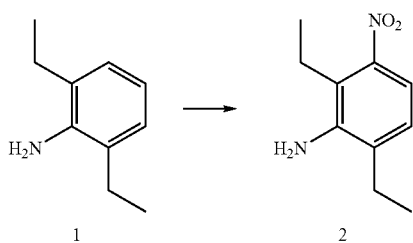

4.42 ml (26.8 mmol) 2,6-diethyl-phenylamine (1) react according to example 3. Flash chromatographical separation yields 4.41 g (22.7 mmol; 85%) of compound 2.

Example 23

Synthesis of 142

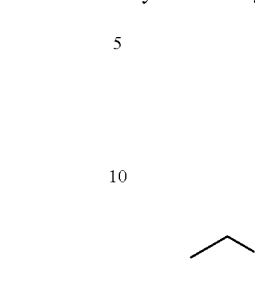

Step 1: as in example 19, step 1
1: 2.02 ml (14.8 mmol)
2: 1.79 ml (14.8 mmol)
Yield: 3.39 g (13.3 mmol; 90%)
Step 2:

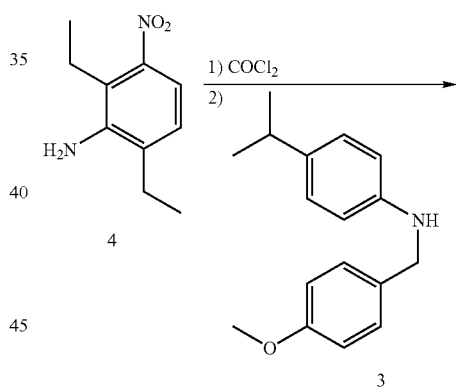

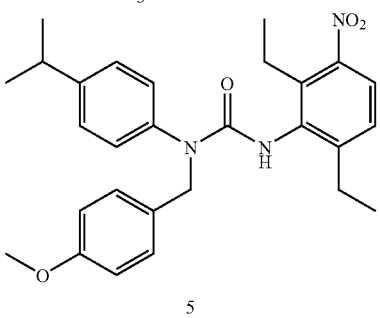

587 mg (3.02 mmol) 2,6-diethyl-5-nitro-phenylamine (4) react according GP-2A with 2.54 ml (4.83 mmol; 1.6 eq.) of a 20% solution of phosgen in toluol and 1.0 g (3.92 mmol; 1.3 eq.) of (4-isopropyl-phenyl)-(4-methoxy-benzyl)-amine (3). Flash chromatographical purification (hexane/ethyl acetate 12:1) yields 1.16 g (2.43 mmol; 80.5%) of compound 5.

Step 3:

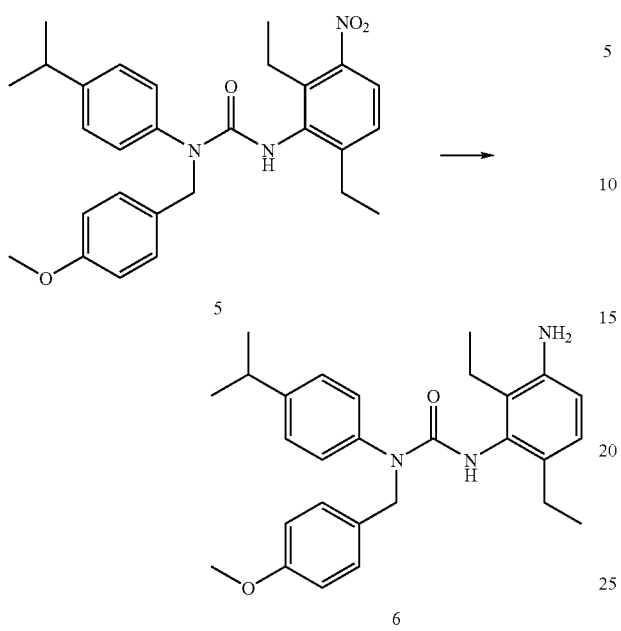

The nitrocompound 5 obtained in step 2 is reduced according to GP-3A. The raw product is purified via HPLC yielding 800 mg of the desired amin 6.

Step 4:

44.6 mg (0.1 mmol) 3-(3-amino-2,6-diethyl-phenyl)-1-(4-isopropyl-phenyl)-1-(4-methoxy-benzyl)-urea (6) react according to GP-1A with 2.8 µl (0.05 mmol, 0.5 eq.) of acetaldehyde (7) but without titanium tetraisopropylat. The obtained raw product is purified via HPLC, which yields 21 mg (mmol) of the desired compound 8.

Example 24

Synthesis of 109

Step 1:

50 mg (0.278 mmol) 4-methoxy-2-formylphenylboronic acid (1) is desolved in methanol. 32 mg (0.834 mmol; 3 eq.) sodium borhydride are carefully added. After 2 hours of stirring at room temperature the solvent is removed in the evaporator. After adding 50 ml of saturated sodium chloride solution and 50 ml ethylacetate the aqueous phase is extracted three times with ethylacetate. The combined organic phases are dried over magnesium sulphate and the solvent is removed in vacuum. The raw product is used without purification in the next reaction step.

Step 2:

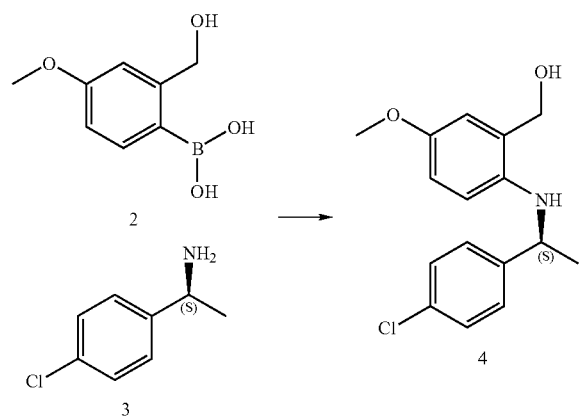

292 µl (2.085 mmol; 5 eq.) of (S)-4-chloro-alpha-methyl-benzylamine (3) react according to GP-1B with 76 mg (0.417 mmol; 1.0 eq.) of 2-hydroxymethyl-4-methoxybenzyl-boronic acid (2). Flash chromatographical purification (hexane/ethylacetate 10:1) yields 58.6 mg (0.2 mmol; 48%) of the desired amine 4.

Step 3:

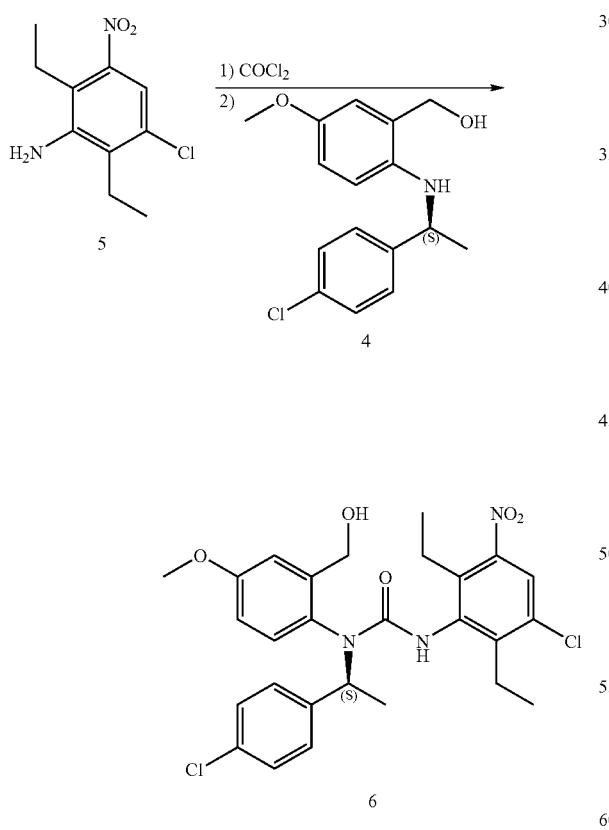

According to GP-2A 55.1 mg (0.24 mmol; 1.2 eq.) of 3-chloro-2,6-diethyl-5-nitro-phenylamine (5) react with 58.6 mg (0.2 mmol; 1.0 eq.) of (S)-[1-(4-chlorphenyl)-ethyl]-(2-hydroxymethyl-4-methoxy-phenyl)-amine (4). The obtained raw product is purified via HPLC, yielding 82.8 mg (0.152 mmol; 76%) of compound 6.

Step 4:

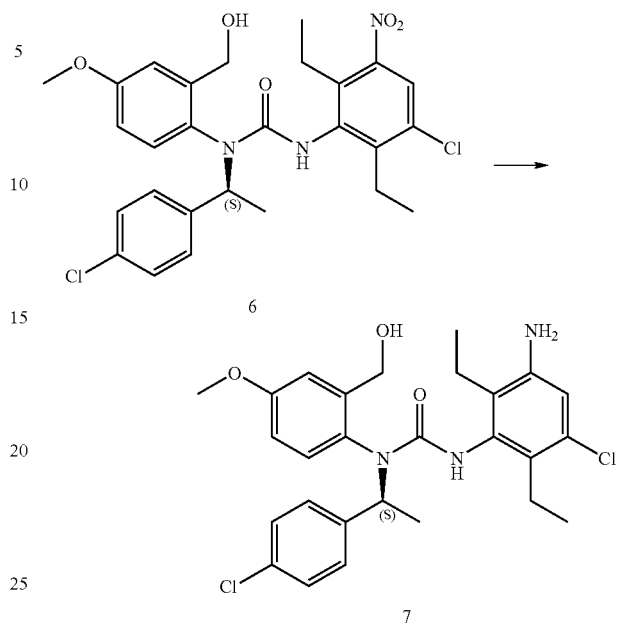

The nitro compound 6 obtained in step 3 is reduced according to GP-3C and the raw product is purified via HPLC. The procedure yields 65 mg of the desired compound 7.

Example 25

Stability (Shelf Life) of Various Compounds

Compounds 11 and 13 were synthesized and purified via HPLC (eluent MeCN/H$_2$O with varying volume proportions, 0.05% TFA).

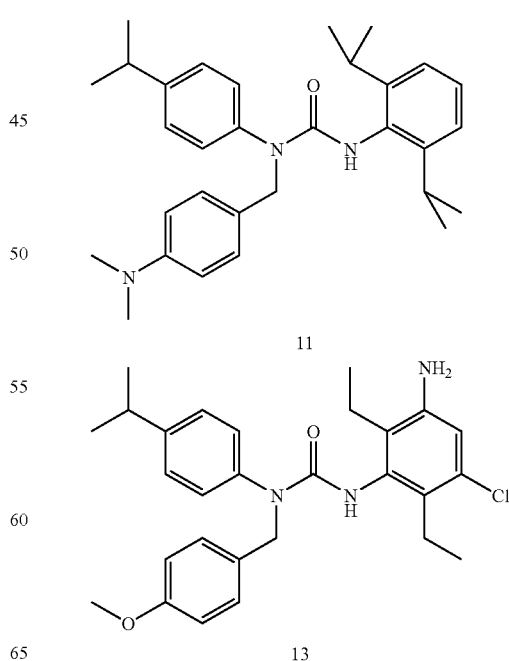

The synthesis of compound 13 is described in the examples.

Compound 11 is synthesized as follows: 50 mg (0.186 mmol) of (4-isopropylphenyl)-(4-dimethylaminobenzyl) amine is desolved in 2 ml of acetonitrile. 60 µl (0.280 mmol; 1.5 eq.) 2,6-diisopropylphenylisocyanate and 51 mg (0.373 mmol; 2.0 eq.) potassium carbonate are added and the solution is stirred for 24 hours at room temperature. As work up the reaction solution is concentrated in vacuum and after addition of 20 ml water extracted two times with EE. The combined organic phases are dried over magnesium sulphate and the solvent is removed in vacuum. Purification via HPLC yields 38 mg (0.081 mmol; 44%) of the desired compound 11.

The fractions containing the desired compound are lyophilized. In this way 1-40 mg of the compounds 11 and 13 are isolated as solid. Due to the basic amino groups the compounds are obtained as TFA salts. 0.5-10 mg of the solid are stored under the influence of light at room temperature to determine their stability over time.

FIG. 1 shows analytical RP-HPLC chromatograms of 11 and 13 obtained under various conditions of storage as well as a possible mechanism of the decomposition of compound 11. The upper section of FIG. 1 shows the UV detection, the middle section the MS detection and the lower section the MS detection of the respective target mass. The conditions were as follows:

FIG. 1 A): after purification via HPLC (solution in MeCN/H₂O/TFA),

FIG. 1 B) after lyophilization (0 days of storage as solid)

FIG. 1 C) after 7 days of storage as solid

It turns out that under the conditions described, according to the state of the art, compound 11 (described to show a binding affinity to the C5a receptor of 100 nM, EP1308438) is not stable. Decomposition into 2 compounds with masses of 338 and 604 occurs, possibly via benzyl transfer (see reaction equation below). Thus the compound is not suited to be used as a drug, at least not as TFA salt.

In contrast, compound 13 of the invention described herein does not show such instabilities, which is a clear advantage compared to current state of the art compounds.

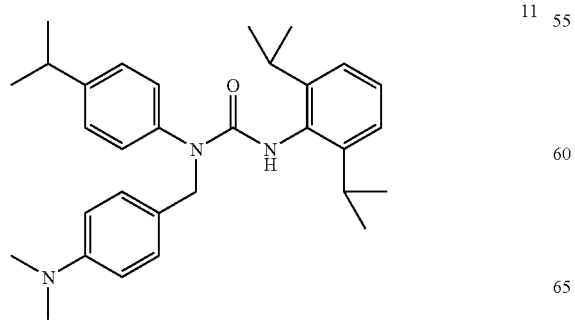

11

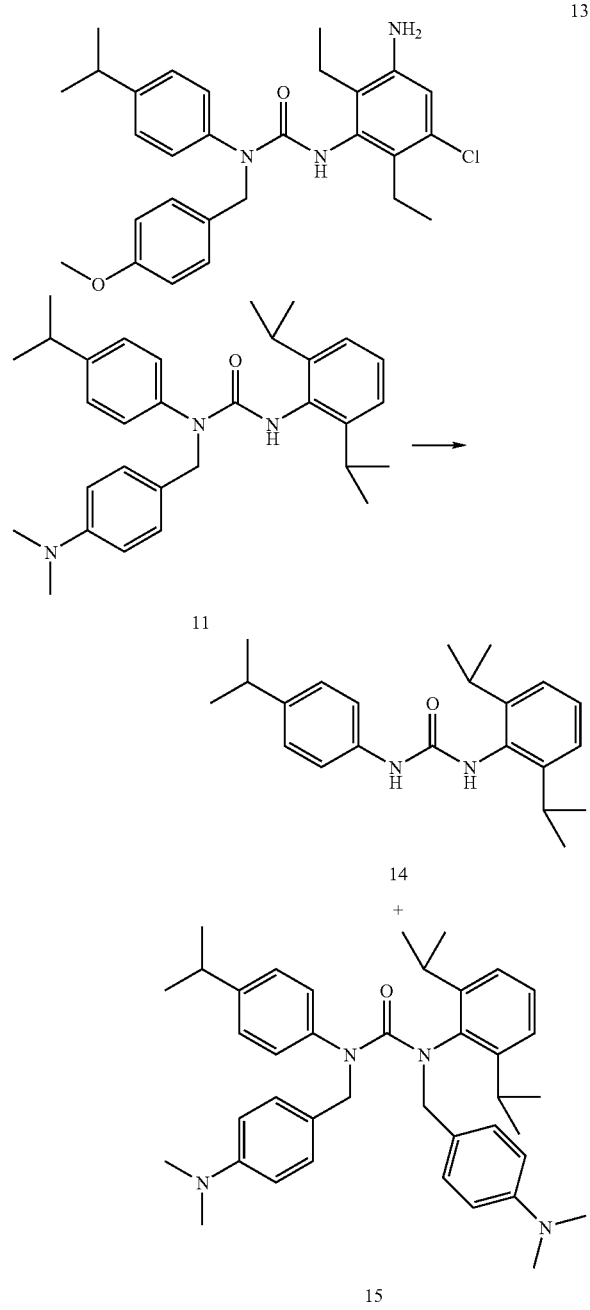

Example 26

Determination of the IC$_{50}$ Value in Human Whole Blood

The whole blood assay is carried out according to the instructions from the Phagoburst-Kit (Orpegen Pharma). 50 µg/ml of Refludan is used to inhibit blood clotting (Mollnes et al. 2002 Blood 100: 1869).

Freshly drawn, anticoagulated blood is cooled over ice and 100 µl thereof are added to 10 µl of the compound solution containing at most 1.3% of DMSO. The mixture is incubated for 10 minutes at 37° C. After this the samples are put on ice again and 20 µl of opsonisated E. coli suspension (10⁹ cells/ml) is added followed by 10 minutes of incubation at 37° C. 20 µl of the substrate are added to the cells followed by another 10 minutes of incubation at 37° C. After this 2 ml of lysis buffer are added to the cells, which are then kept at room temperature for 20 minutes. The cellular components are separated by centrifugation at 250×g for 5 minutes. The supernatant is discarded and 3 ml of washing solution are added to the pellet. The cells are centrifuged again and the resulting pellet is taken up in 200 µl DNA staining solution. The neutrophiles are analysed by means of a FACS device (FACSCalibur, Becton-Dickinson) according to the parameters given in the manual. Table 5 shows the $IC_{50}$ values determined from human whole blood. It can be seen that, due to the determined activity, the compounds of this invention are suited to be used as therapeutics in human.

TABLE 5

$IC_{50}$ values for the inhibition of the E. coli induced oxidative burst in human whole blood

| Molecule | $IC_{50}$ [µM] |
| --- | --- |
| 20 | 3.84 |
| 102 | 3.2 |
| 103 | 0.8 |
| 106 | 1.6 |
| 120 | 1.9 |
| 122 | 3.5 |
| 132 | 0.62 |

Example 27

Determination of $IC_{50}$ Values for the Binding of the Compounds to the C5a Receptor The binding studies are done as determination of $IC_{50}$ values with radioactively labeled C5a (125I) as tracer. For this purpose, human C5aR transfected HEK293 cells are adjusted to a concentration of 5×106 l/ml. 30 µl of the cell suspension are added into a microtiter plate. Then the C5a receptor antagonists are added followed by 10 minutes pre-incubation at room temperature. After that, 10 µl of labelled C5a are added (15.000 cpm). The mixture is now incubated over ice for 30 minutes. After this the cells are isolated by means of a filter plate (Millipore MHVB 4510) and washed two times with 100 µl HAG-CM each (see example 32). The cells are dried and, after transferring the filter plate onto the adapter plate (Canberra 6005178), 50 µl/well Microscint 0 are added and the plate is measured in the scintillation counter.

Table 6 shows the $IC_{50}$ values for the binding to the C5a receptor. As can be seen, the compounds of this invention are inhibitors of the binding of C5a to the C5a receptor.

TABLE 6

$IC_{50}$ values for the inhibition of the bindung of C5a to the C5a receptor

| Molecule | $IC_{50}$ [nM] |
| --- | --- |
| C5a | 4.7 |
| 20 | 118 |
| 88 | 44 |
| 103 | 58.6 |

TABLE 6-continued $IC_{50}$ values for the inhibition of the bindung of C5a to the C5a receptor

| Molecule | $IC_{50}$ [nM] |
| --- | --- |
| 120 | 86.5 |
| 132 | 43.4 |

Example 28

Determination of $IC_{50}$ Values in an Enzyme Release Assay

The assay has been described by Köhl (Köhl 1997 The Anaphylatoxins. In: Dodds, A. W., Sim, R. B. (Eds.), Complement: A Practical Approach. Oxford: 135). Basophile leukemia cells from rats (RBL), which express the human C5a receptor (CD88), are cultivated in DMEM with 10% fetal calf serum, 100 U/ml penicillin, 100 µg/ml streptomycin and 2 mM glutamin (all constituents are from Biochrome, Berlin) at 37° C. and with 10% $CO_2$ until a confluent layer is obtained. All following details refer to a tissue culture flask with 75 cm² surface. The used up medium is removed. The cells are washed with 10 ml PBS (Dulbecco's PBS, Biochrome) and then covered with 3 ml cell dissociation solution (CDS, Sigma). The cells are incubated for 1 minute at room temperature. Then the CDS is removed and the cells are incubated for further 10-15 minutes at 37° C. to detach the cells completely from the flask. 20 µl solution of the compound to be testet are used in the assay. The assay solution must not contain more than 2.8% DMSO. The dilution series are prepared in ⅓ or ½ steps. To the 20 µl of the compound solutions 75 µl RBL cells are added which are prepared as follows: After the detachment of the cells from the flask surface they are taken up with 10 ml HAG-CM (20 mM HEPES; 125 mM NaCl, 5 mM KCl, 1 mM $CaCl_2$, 1 mM $MgCl_2$, 0.5 mM glucose, 0.25% BSA. HEPES preparation: 2.3 g/l HEPES salt+2.66 g/l HEPES acid) thermostated at 37° C. The cells are counted and centrifuged (200 g, 10 min). The cell pellet is taken up with pre-heated HAG-CM, and the cell density is adjusted to 2×10⁶ Zellen/ml. The cells are incubated for 5 minutes at 37° C. 2.7 µl of a cytochalasin B solution (1000 µg/ml in DMSO, Sigma) are added per ml cell suspension. The Zellen are incubated for another 3 min at 37° C. Then, 75 µl of the cell suspension are added to the 20 µl solution containing the compounds to be tested. Thus a volume of 95111 per well is obtained. The cells are again incubated for 10 minutes at 37° C. Then 10 µl hrC5a (10.5 nM in HAG-CM, Sigma) are added per well, which is followed by 5 minutes incubation at 37° C. After this the plates are put on ice and centrifuged for 3 minutes at 1200×g and 4° C. 75 µl of the supernatant are added to 100 µl substrate solution (2.7 mg/ml p-nitrophenyl-N-acetyl-b-D-glucosaminide (Sigma) in 42.5 mM sodium acetate, pH 4.5). The plate is incubated for 1 hour at 37° C. Per well 75 µl 0.4 M glycine (pH 10.4) are added. After this the plate can be measured at a wave length of 405 nm. The $IC_{50}$ value is determined by solving the four parameter equation $y=((A-D)/(1+(x/C)^B))+D$.

The results of the tests to determine the $IC_{50}$ values are shown in Table 1.

TABLE 1

Antagonistic activity of representative compounds of the invention

| Structure | No. | [M + H]+ calculated | [M + H]+ measured | Activity-range | Chemical name |
|---|---|---|---|---|---|
| 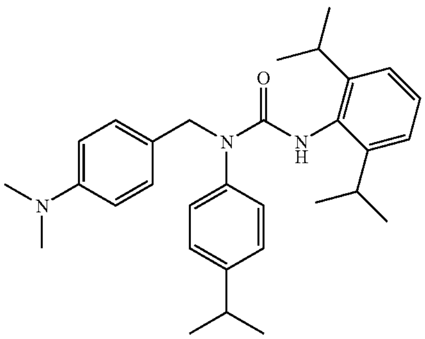 | 11 | 472.3 | 472.7 | C | 3-(2,6-diisopropyl-phenyl)-1-(4-dimethylamino-benzyl)-1-(4-isopropyl-phenyl)-urea |
| 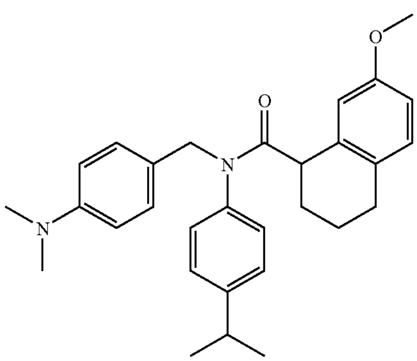 | 12 | 457.3 | 457.4 | B, 89 nM | 7-methoxy-1,2,3,4-tetrahydro-naphthalin-1-carbonsäure (4-dimethylamino-benzyl)-(4-isopropyl-phenyl)-amide |
| 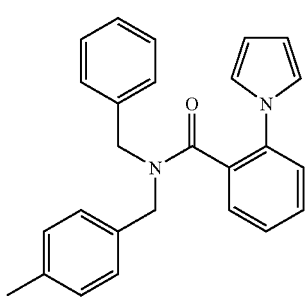 | 8 | 381.2 | 381.1 | C, 1917 nM | N-Benzyl-N-(4-methyl-benzyl)-2-pyrrol-1-yl-benzamide |
| 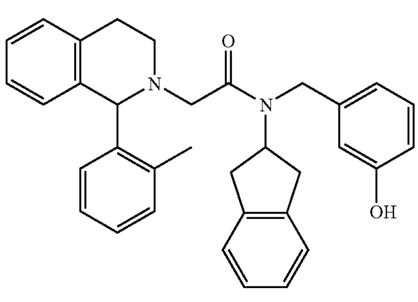 | 9 | 503.3 | 503.5 | D, 7142 nM | N-(3-Hydroxy-benzyl)-N-indane-2-yl-2-(1-o-tolyl-3,4-dihydro-1H-isochinolin-2-yl)-acetamide |

TABLE 1-continued

Antagonistic activity of representative compounds of the invention

| Structure | No. | [M + H]+ calculated | [M + H]+ measured | Activity-range | Chemical name |
|---|---|---|---|---|---|
| 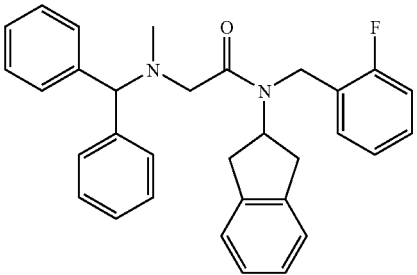 | 10 | 479.2 | 479.1 | D, >4760 nM | 2-(Benzhydryl-methyl-amino)-N-(2-fluoro-benzyl)-N-indane-2-yl-acetamide |
| 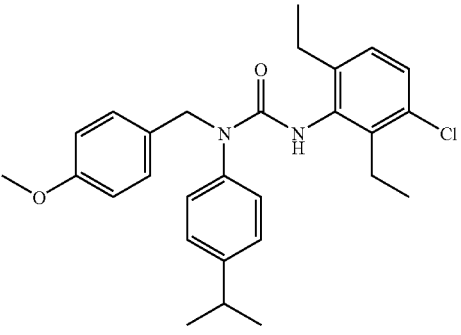 | 24 | 465.2 | 465.9 | C, 1051 nM | 3-(3-Chlor-2,6-diethyl-phenyl)-1-(4-isopropyl-phenyl)-1-(4-methoxy-benzyl)-urea |
| 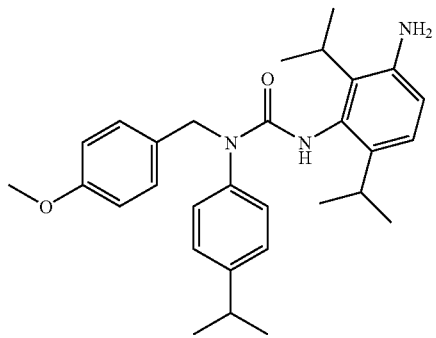 | 25 | 474.3 | 474.8 | C | 3-(3-Amino-2,6-diisopropyl-phenyl)-1-(4-isopropyl-phenyl)-1-(4-methoxy-benzyl)-urea |
| 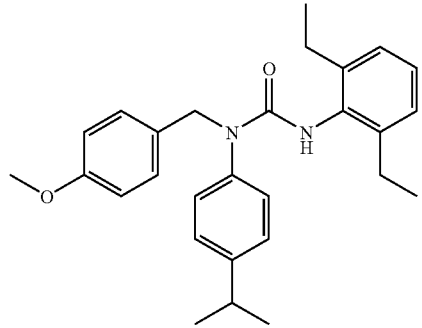 | 26 | 431.3 | 431.8 | C, 524 nM | 3-(2,6-diethyl-phenyl)-1-(4-isopropyl-phenyl)-1-(4-methoxy-benzyl)-urea |

TABLE 1-continued

Antagonistic activity of representative compounds of the invention

| Structure | No. | [M + H]+ calculated | [M + H]+ measured | Activity-range | Chemical name |
|---|---|---|---|---|---|
| 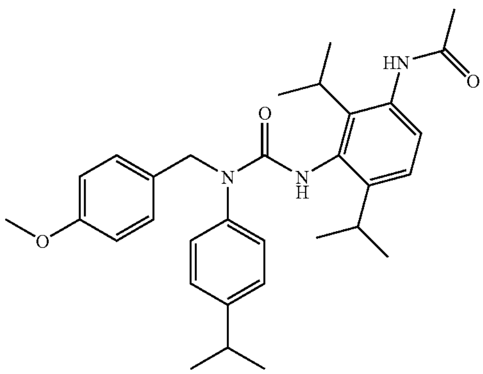 | 27 | 516.3 | 516.3 | D | N-{2,4-diisopropyl-3-[3-(4-isopropyl-phenyl)-3-(4-methoxy-benzyl)-ureido]-phenyl}-acetamide |
| 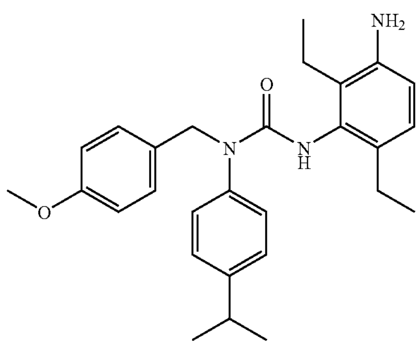 | 28 | 446.3 | 446.3 | C | 3-(3-amino-2,6-diethyl-phenyl)-1-(4-isopropyl-phenyl)-1-(4-methoxy-benzyl)-urea |
| 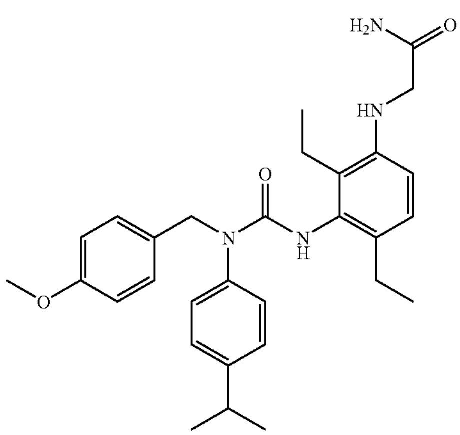 | 29 | 503.3 | 504.2 | C | 2-{2,4-diethyl-3-[3-(4-isopropyl-phenyl)-3-(4-methoxy-benzyl)-ureido]-phenylamino}-acetamide |

TABLE 1-continued

Antagonistic activity of representative compounds of the invention

| Structure | No. | [M + H]+ calculated | [M + H]+ measured | Activity-range | Chemical name |
|---|---|---|---|---|---|
| 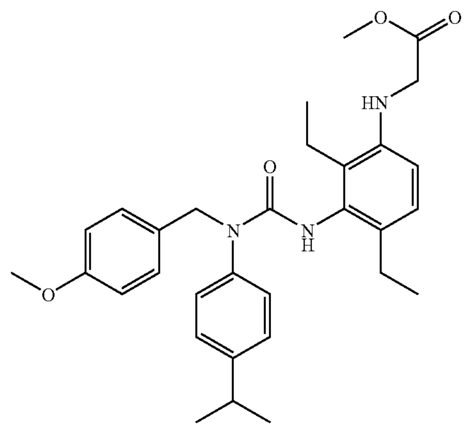 | 30 | 518.3 | 518.2 | C | {2,4-diethyl-3-[3-(4-isopropyl-phenyl)-3-(4-methoxy-benzyl)-ureido]-phenylamino}-acetic acid methyl ester |
| 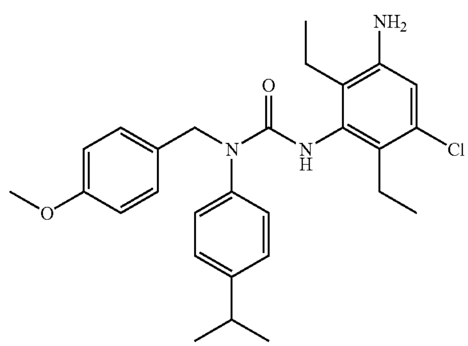 | 31 | 480.2 | 480.1 | B, 164 nM | 3-(3-amino-5-chloro-2,6-diethyl-phenyl)-1-(4-isopropyl-phenyl)-1-(4-methoxy-benzyl)-urea |
| 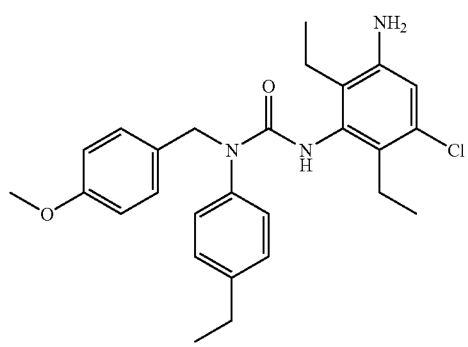 | 32 | 466.2 | 466.1 | C | 3-(3-amino-5-chloro-2,6-diethyl-phenyl)-1-(4-ethyl-phenyl)-1-(4-methoxy-benzyl)-urea |
| 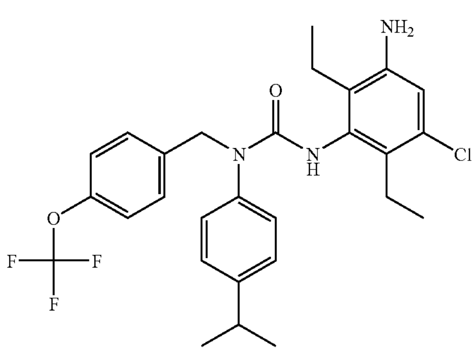 | 33 | 534.2 | 534.1 | C | 3-(3-amino-5-chloro-2,6-diethyl-phenyl)-1-(4-isopropyl-phenyl)-1-(4-trifluoromethoxy-benzyl)-urea |

TABLE 1-continued

Antagonistic activity of representative compounds of the invention

| Structure | No. | [M + H]+ calculated | [M + H]+ measured | Activity-range | Chemical name |
|---|---|---|---|---|---|
| 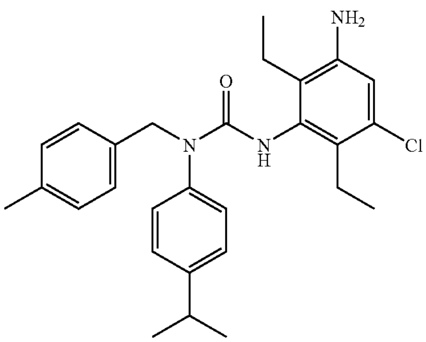 | 34 | 464.2 | 464.2 | B | 3-(3-amino-5-chloro-2,6-diethyl-phenyl)-1-(4-isopropyl-phenyl)-1-(4-methyl-benzyl)-urea |
| 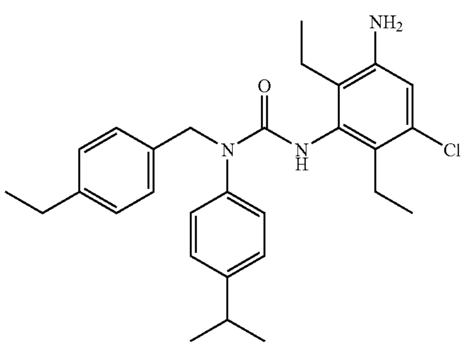 | 35 | 478.3 | 478.2 | C | 3-(3-amino-5-chloro-2,6-diethyl-phenyl)-1-(4-ethyl-benzyl)-1-(4-isopropyl-phenyl)-urea |
| 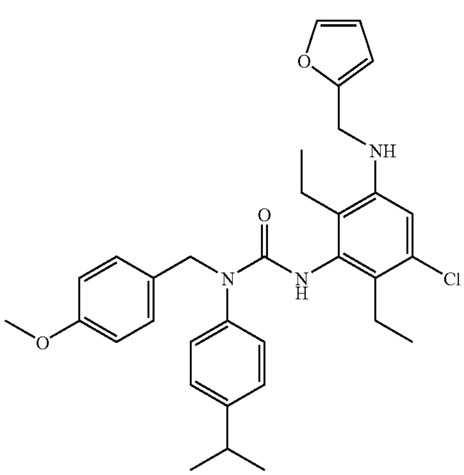 | 36 | 560.3 | 560.9 | C | 3-{3-Chloro-2,6-diethyl-5-[(furan-2-ylmethyl)-amino]-phenyl}-1-(4-isopropyl-phenyl)-1-(4-methoxy-benzyl)-urea |

TABLE 1-continued

Antagonistic activity of representative compounds of the invention

| Structure | No. | [M + H]+ calculated | [M + H]+ measured | Activity-range | Chemical name |
|---|---|---|---|---|---|
| 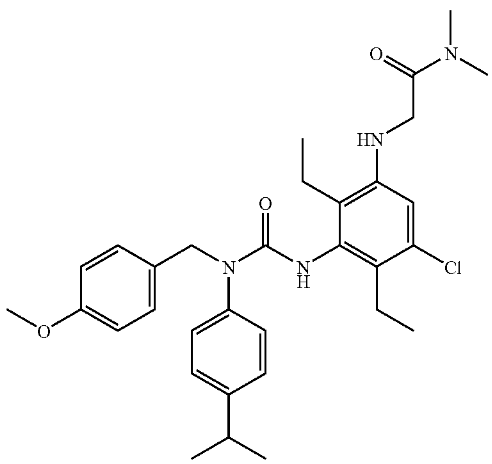 | 37 | 565.3 | 566.0 | C | 2-{5-chloro-2,4-diethyl-3-[3-(4-isopropyl-phenyl)-3-(4-methoxy-benzyl)-ureido]-phenylamino}-N,N-dimethyl-acetamide |
| 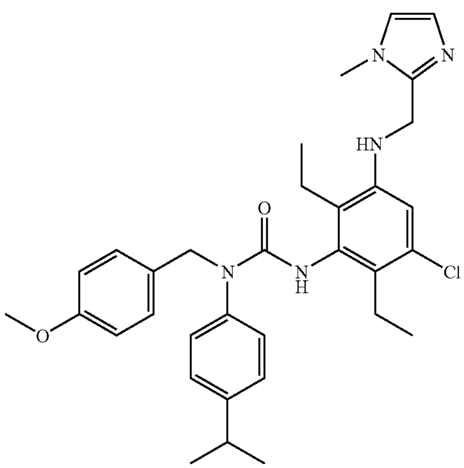 | 38 | 574.3 | 574.2 | C | 3-{3-chloro-2,6-diethyl-5-[(1-methyl-1H-imidazol-2-ylmethyl)-amino]-phenyl}-1-(4-isopropyl-phenyl)-1-(4-methoxy-benzyl)-urea |
| 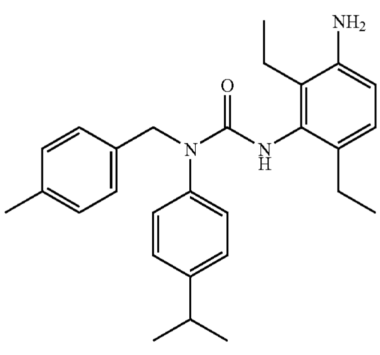 | 39 | 430.3 | 430.2 | C | 3-(3-amino-2,6-diethyl-phenyl)-1-(4-isopropyl-phenyl)-1-(4-methyl-benzyl)-urea |
| 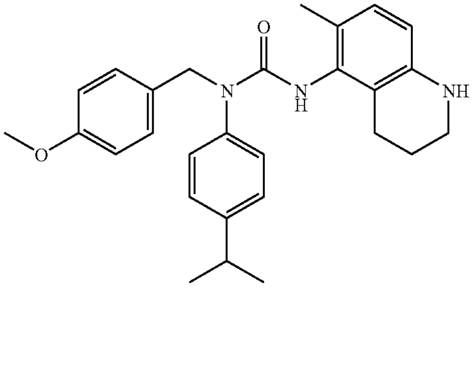 | 40 | 444.3 | 444.2 | D | 1-(4-isopropyl-phenyl)-1-(4-methoxy-benzyl)-3-(6-methyl-1,2,3,4-tetrahydro-chinolin-5-yl)-urea |

TABLE 1-continued

Antagonistic activity of representative compounds of the invention

| Structure | No. | [M + H]+ calculated | [M + H]+ measured | Activity-range | Chemical name |
| --- | --- | --- | --- | --- | --- |
| 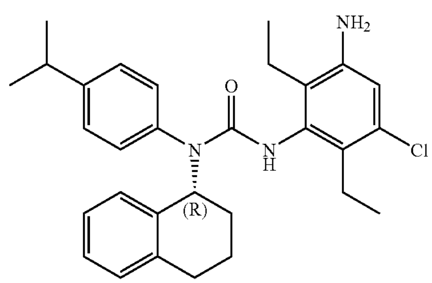 | 41 | 490.3 | 490.1 | C | (R)-3-(3-amino-5-chloro-2,6-diethyl-phenyl)-1-(4-isopropyl-phenyl)-1-(1,2,3,4-tetrahydro-naphthaline-1-yl)-urea |
| 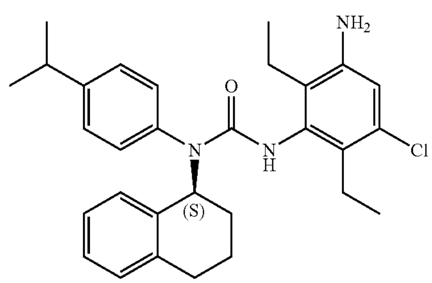 | 42 | 490.3 | 490.1 | B | (S)-3-(3-amino-5-chloro-2,6-diethyl-phenyl)-1-(4-isopropyl-phenyl)-1-(1,2,3,4-tetrahydro-naphthaline-1-yl)-urea |
| 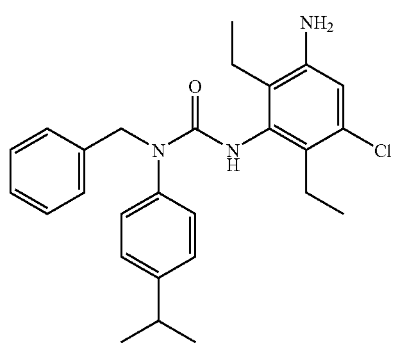 | 43 | 450.2 | 450.2 | C | 3-(3-amino-5-chloro-2,6-diethyl-phenyl)-1-benzyl-1-(4-isopropyl-phenyl)-urea |
| 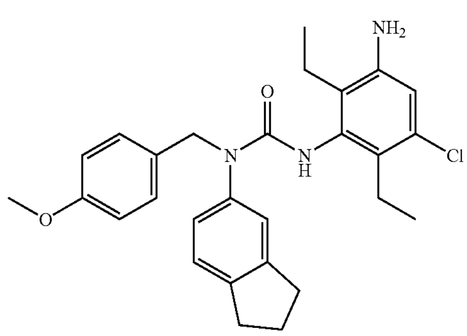 | 44 | 478.2 | 478.1 | C | 3-(3-amino-5-chloro-2,6-diethyl-phenyl)-1-indane-5-yl-1-(4-methoxy-benzyl)-urea |

TABLE 1-continued

Antagonistic activity of representative compounds of the invention

| Structure | No. | [M + H]+ calculated | [M + H]+ measured | Activity-range | Chemical name |
|---|---|---|---|---|---|
| 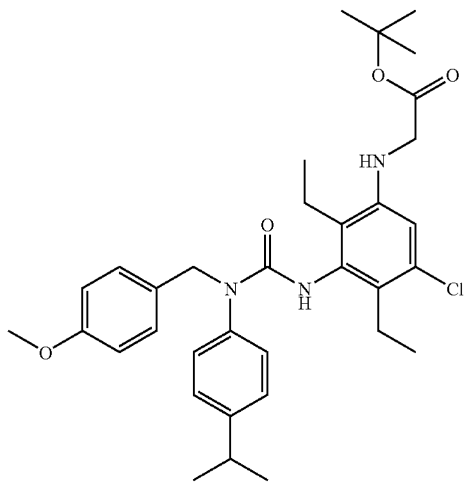 | 45 | 594.3 | 594.1 | B | {5-chloro-2,4-diethyl-3-[3-(4-isopropyl-phenyl)-3-(4-methoxy-benzyl)-ureido]-phenylamino} acetic acid tert-butyl ester |
| 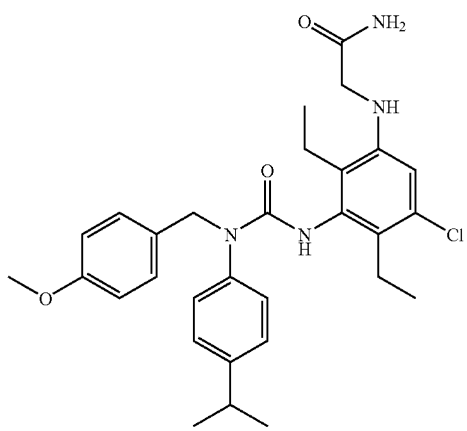 | 46 | 537.3 | 537.9 | C | 2-{5-chloro-2,4-diethyl-3-[3-(4-isopropyl-phenyl)-3-(4-methoxy-benzyl)-ureido]-phenylamino}-acetamide |
| 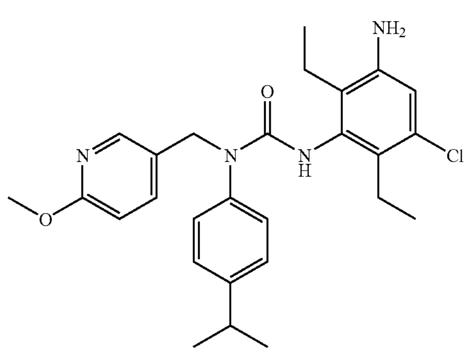 | 47 | 481.2 | 481.2 | C | 3-(3-amino-5-chloro-2,6-diethyl-phenyl)-1-(4-isopropyl-phenyl)-1-(6-methoxy-pyridin-3-ylmethyl)-urea |

TABLE 1-continued

Antagonistic activity of representative compounds of the invention

| Structure | No. | [M + H]+ calculated | [M + H]+ measured | Activity-range | Chemical name |
|---|---|---|---|---|---|
| 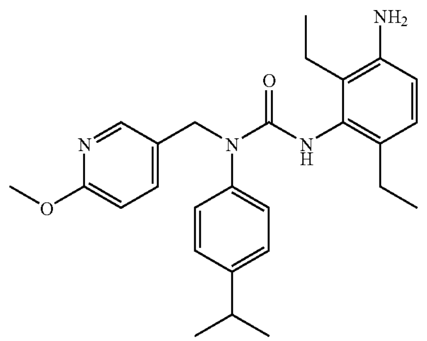 | 48 | 447.3 | 447.3 | C | 3-(3-amino-2,6-diethyl-phenyl)-1-(4-isopropyl-phenyl)-1-(6-methoxy-pyridin-3-ylmethyl)-urea |
| 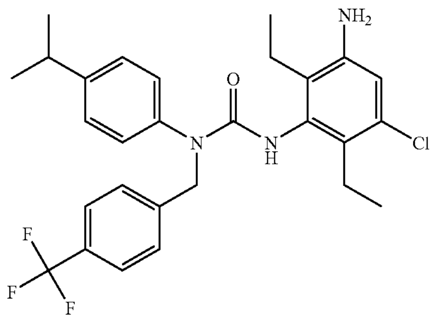 | 49 | 518.2 | 518.1 | C | 3-(3-amino-5-chloro-2,6-diethyl-phenyl)-1-(4-isopropyl-phenyl)-1-(4-trifluormethyl-benzyl)-urea |
| 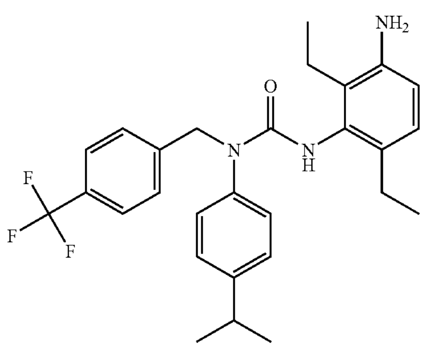 | 50 | 484.3 | 484.2 | C | 3-(3-amino-2,6-diethyl-phenyl)-1-(4-isopropyl-phenyl)-1-(4-trifluoromethyl-benzyl)-urea |
| 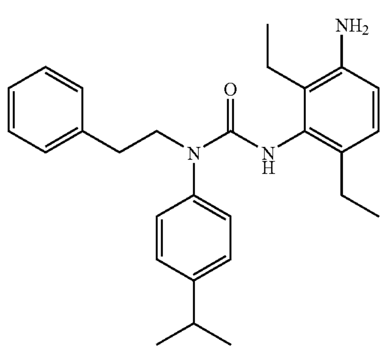 | 51 | 430.3 | 430.8 | C | 3-(3-amino-2,6-diethyl-phenyl)-1-(4-isopropyl-phenyl)-1-phenethyl-urea |

TABLE 1-continued

Antagonistic activity of representative compounds of the invention

| Structure | No. | [M + H]+ calculated | [M + H]+ measured | Activity-range | Chemical name |
|---|---|---|---|---|---|
| 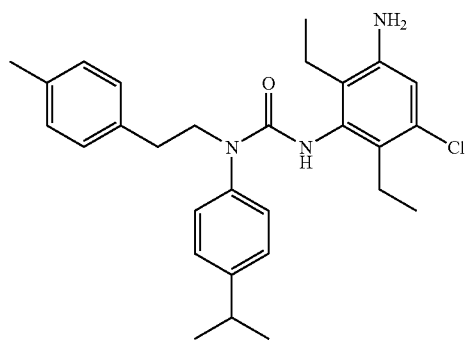 | 52 | 478.3 | 478.4 | C | 3-(3-amino-5-chloro-2,6-diethyl-phenyl)-1-(4-isopropyl-phenyl)-1-(2-p-tolyl-ethyl)-urea |
| 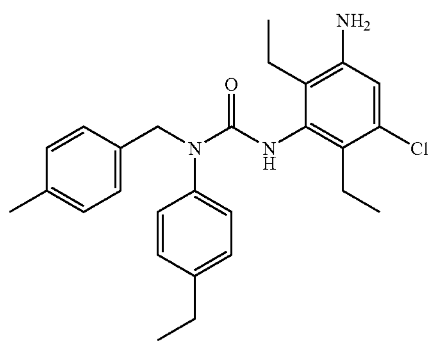 | 53 | 450.2 | 450.2 | B | 3-(3-amino-5-chloro-2,6-diethyl-phenyl)-1-(4-ethyl-phenyl)-1-(4-methyl-benzyl)-urea |
| 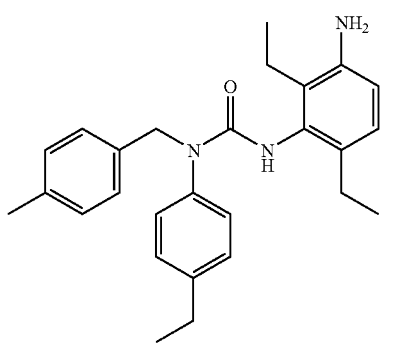 | 54 | 416.3 | 416.2 | C | 3-(3-amino-2,6-diethyl-phenyl)-1-(4-ethyl-phenyl)-1-(4-methyl-benzyl)-urea |
| 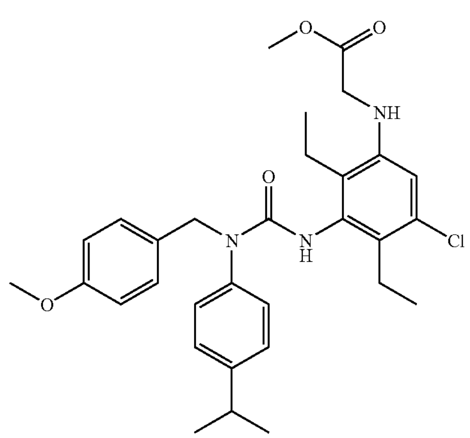 | 55 | 552.3 | 553.5 | C | {5-chloro-2,4-diethyl-3-[3-(4-isopropyl-phenyl)-3-(4-methoxy-benzyl)-ureido]-phenylamino} acetic acid methyl-ester |

TABLE 1-continued

Antagonistic activity of representative compounds of the invention

| Structure | No. | [M + H]+ calculated | [M + H]+ measured | Activity-range | Chemical name |
|---|---|---|---|---|---|
| 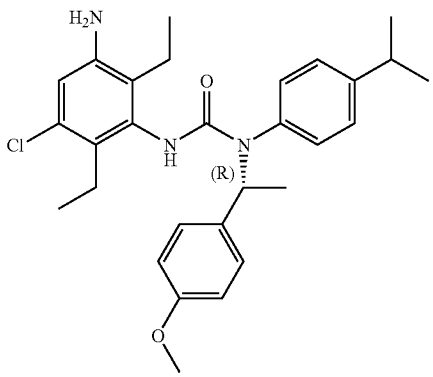 | 56 | 494.3 | 494.9 | C, 619 nM | (R)-3-(3-amino-5-chloro-2,6-diethyl-phenyl)-1-(4-isopropyl-phenyl)-1-[1-(4-methoxy-phenyl)ethyl]-urea |
| 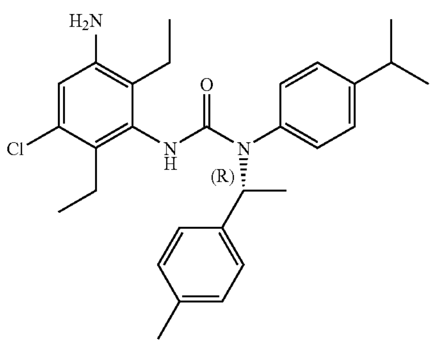 | 57 | 478.3 | 479.0 | C | (R)-3-(3-Amino-5-chloro-2,6-diethyl-phenyl)-1-(4-isopropyl-phenyl)-1-(1-p-tolyl-ethyl)-urea |
| 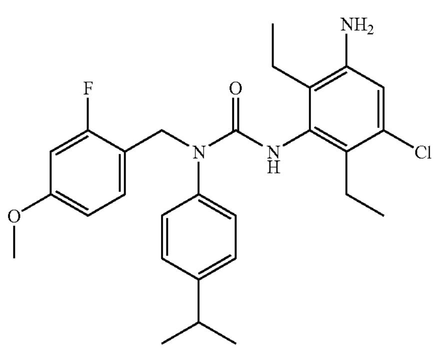 | 58 | 498.2 | 498.1 | C | 3-(3-amino-5-chloro-2,6-diethyl-phenyl)-1-(2-fluoro-4-methoxy-benzyl)-1-(4-isopropyl-phenyl)-urea |
| 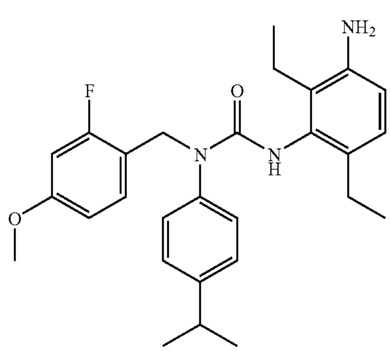 | 59 | 464.3 | 464.2 | C | 3-(3-amino-2,6-diethyl-phenyl)-1-(2-fluoro-4-methoxy-benzyl)-1-(4-isopropyl-phenyl)-urea |

TABLE 1-continued

Antagonistic activity of representative compounds of the invention

| Structure | No. | [M + H]+ calculated | [M + H]+ measured | Activity-range | Chemical name |
|---|---|---|---|---|---|
| 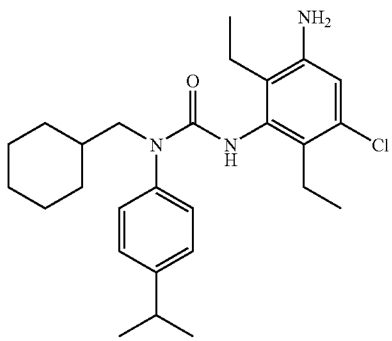 | 60 | 456.3 | 456.2 | C | 3-(3-amino-5-chloro-2,6-diethyl-phenyl)-1-cyclohexylmethyl-1-(4-isopropyl-phenyl)-urea |
| 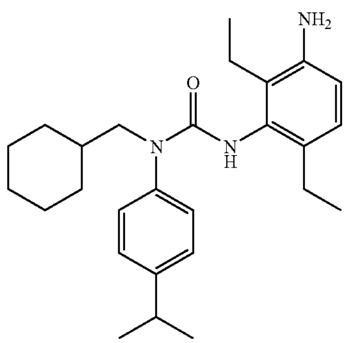 | 61 | 422.3 | 422.3 | C | 3-(3-amino-2,6-diethyl-phenyl)-1-cyclohexylmethyl-1-(4-isopropyl-phenyl)-urea |
| 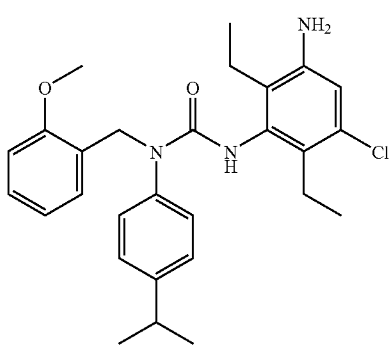 | 62 | 480.2 | 480.2 | C | 3-(3-amino-5-chloro-2,6-diethyl-phenyl)-1-(4-isopropyl-phenyl)-1-(2-methoxy-benzyl)-urea |
| 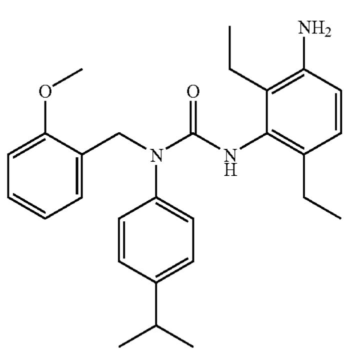 | 63 | 446.3 | 446.7 | C | 3-(3-amino-2,6-diethyl-phenyl)-1-(4-isopropyl-phenyl)-1-(2-methoxy-benzyl)-urea |

TABLE 1-continued

Antagonistic activity of representative compounds of the invention

| Structure | No. | [M + H]+ calculated | [M + H]+ measured | Activity-range | Chemical name |
|---|---|---|---|---|---|
| 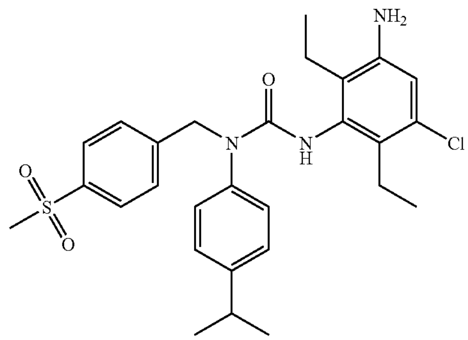 | 64 | 528.2 | 528.1 | C | 3-(3-amino-5-chloro-2,6-diethyl-phenyl)-1-(4-isopropyl-phenyl)-1-(4-methansulfonyl-benzyl)-urea |
| 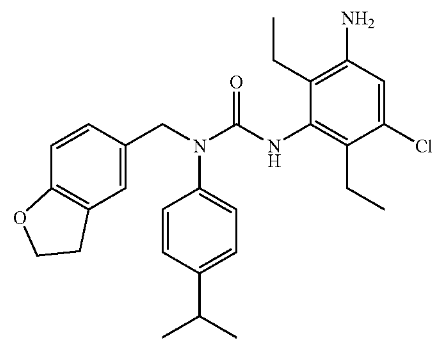 | 65 | 492.2 | 492.1 | B | 3-(3-amino-5-chloro-2,6-diethyl-phenyl)-1-(2,3-dihydro-benzofuran-5-ylmethyl)-1-(4-isopropyl-phenyl)-urea |
| 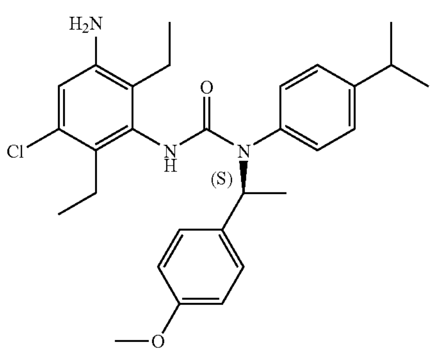 | 66 | 494.3 | 494.1 | A, 55 nM | (S)-3-(3-amino-5-chloro-2,6-diethyl-phenyl)-1-(4-isopropyl-phenyl)-1-[1-(4-methoxy-phenyl)-ethyl]-urea |
| 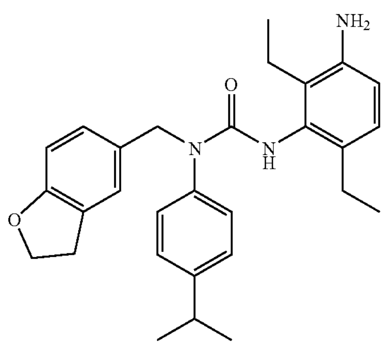 | 67 | 458.3 | 458.2 | C | 3-(3-amino-2,6-diethyl-phenyl)-1-(2,3-dihydro-benzofuran-5-ylmethyl)-1-(4-isopropyl-phenyl)-urea |

TABLE 1-continued

Antagonistic activity of representative compounds of the invention

| Structure | No. | [M + H]+ calculated | [M + H]+ measured | Activity-range | Chemical name |
|---|---|---|---|---|---|
| 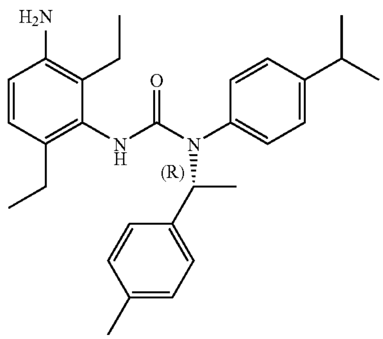 | 68 | 444.3 | 444.9 | C | (R)-3-(3-amino-2,6-diethyl-phenyl)-1-(4-isopropyl-phenyl)-1-(1-p-tolyl-ethyl)-urea |
| 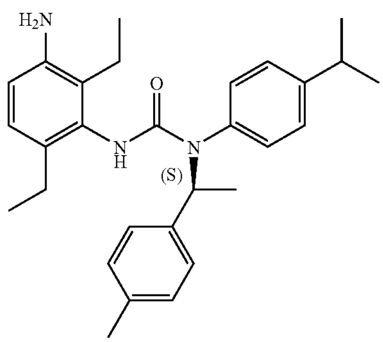 | 69 | 444.3 | 444.8 | B | (S)-3-(3-amino-2,6-diethyl-phenyl)-1-(4-isopropyl-phenyl)-1-(1-p-tolyl-ethyl)-urea |
| 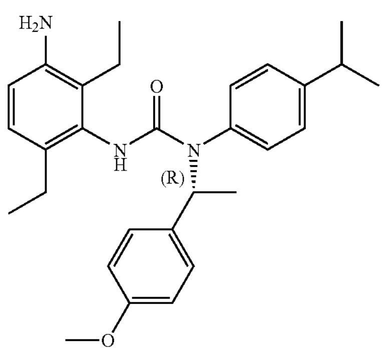 | 70 | 460.3 | 461.0 | C | (R)-3-(3-amino-2,6-diethyl-phenyl)-1-(4-isopropyl-phenyl)-1-[1-(4-methoxy-phenyl)-ethyl]-urea |
| 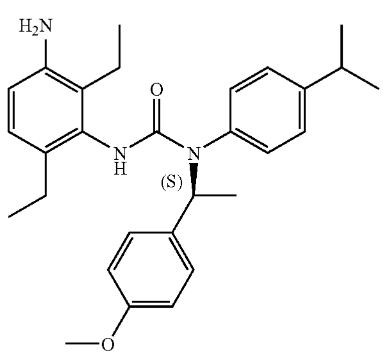 | 71 | 460.3 | 462.3 | B | (S)-3-(3-amino-2,6-diethyl-phenyl)-1-(4-isopropyl-phenyl)-1-[1-(4-methoxy-phenyl)-ethyl]-urea |

TABLE 1-continued

Antagonistic activity of representative compounds of the invention

| Structure | No. | [M + H]+ calculated | [M + H]+ measured | Activity-range | Chemical name |
|---|---|---|---|---|---|
| 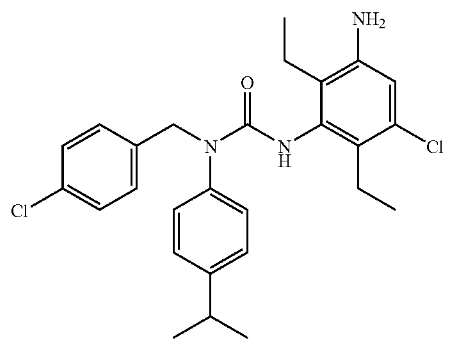 | 72 | 484.2 | 484.1 | B | 3-(3-amino-5-chloro-2,6-diethyl-phenyl)-1-(4-chlor-benzyl)-1-(4-isopropyl-phenyl)-urea |
| 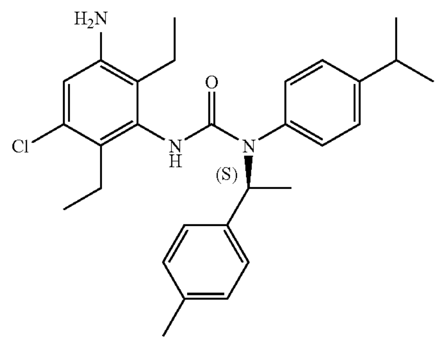 | 73 | 478.3 | 478.9 | A, 32 nM | (S)-3-(3-amino-5-chloro-2,6-diethyl-phenyl)-1-(4-isopropyl-phenyl)-1-(1-p-tolyl-ethyl)-urea |
| 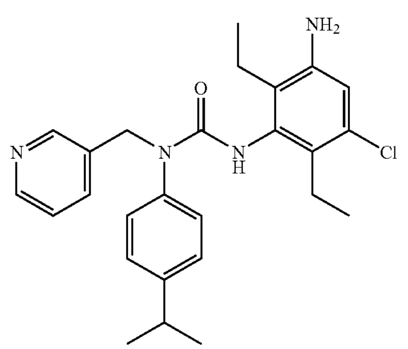 | 74 | 451.2 | 451.3 | C | 3-(3-amino-5-chloro-2,6-diethyl-phenyl)-1-(4-isopropyl-phenyl)-1-pyridin-3-ylmethyl-urea |
| 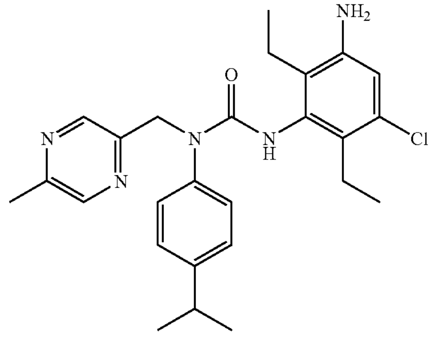 | 75 | 466.2 | 466.1 | B | 3-(3-amino-5-chloro-2,6-diethyl-phenyl)-1-(4-isopropyl-phenyl)-1-(5-methyl-pyrazin-2-ylmethyl)-urea |

TABLE 1-continued

Antagonistic activity of representative compounds of the invention

| Structure | No. | [M + H]+ calculated | [M + H]+ measured | Activity-range | Chemical name |
|---|---|---|---|---|---|
| 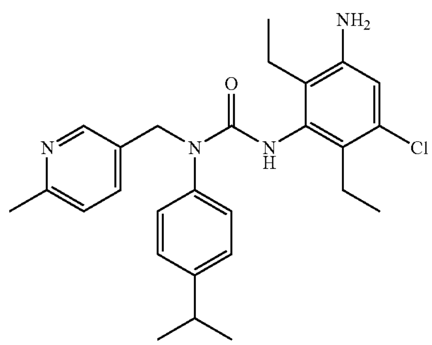 | 76 | 465.2 | 465.2 | B | 3-(3-amino-5-chloro-2,6-diethyl-phenyl)-1-(4-isopropyl-phenyl)-1-(6-methyl-pyridin-3-ylmethyl)-urea |
| 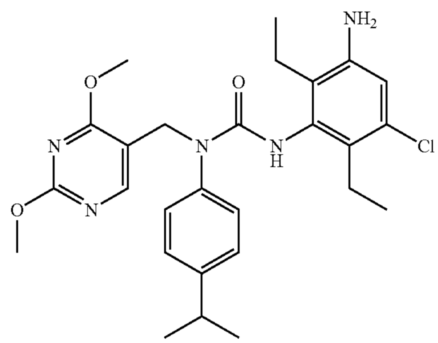 | 77 | 512.2 | 512.3 | C | 3-(3-amino-5-chloro-2,6-diethyl-phenyl)-1-(2,4-dimethoxy-pyrimidin-5-ylmethyl)-1-(4-isopropyl-phenyl)-urea |
| 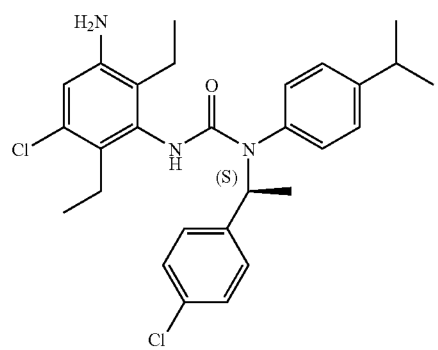 | 78 | 498.2 | 498.9 | A | (S)-3-(3-amino-5-chloro-2,6-diethyl-phenyl)-1-[1-(4-chlor-phenyl)-ethyl]-1-(4-isopropyl-phenyl)-urea |
| 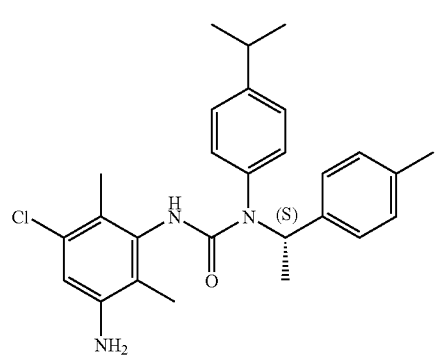 | 79 | 450.2 | 450.8 | C | (S)-3-(3-amino-5-chloro-2,6-dimethyl-phenyl)-1-(4-isopropyl-phenyl)-1-(1-p-tolyl-ethyl)-urea |

TABLE 1-continued

Antagonistic activity of representative compounds of the invention

| Structure | No. | [M + H]+ calculated | [M + H]+ measured | Activity-range | Chemical name |
|---|---|---|---|---|---|
| 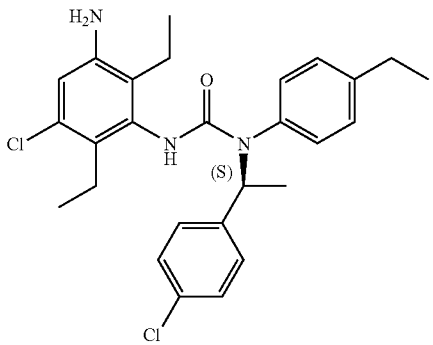 | 80 | 484.2 | 484.9 | A | (S)-3-(3-amino-5-chloro-2,6-diethyl-phenyl)-1-[1-(4-chlor-phenyl)-ethyl]-1-(4-ethyl-phenyl)-urea |
| 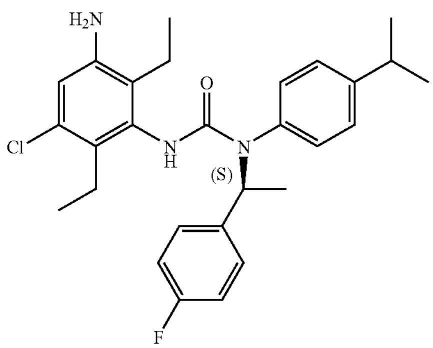 | 81 | 482.2 | 483.0 | A, 38 nM | (S)-3-(3-amino-5-chloro-2,6-diethyl-phenyl)-1-[1-(4-fluor-phenyl)-ethyl]-1-(4-isopropyl-phenyl)-urea |
| 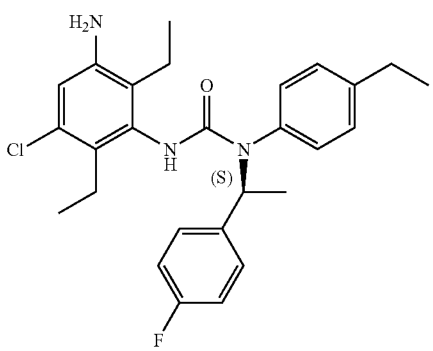 | 82 | 468.2 | 468.9 | B | (S)-3-(3-amino-5-chloro-2,6-diethyl-phenyl)-1-(4-ethyl-phenyl)-1-[1-(4-fluoro-phenyl)-ethyl]-urea |
| 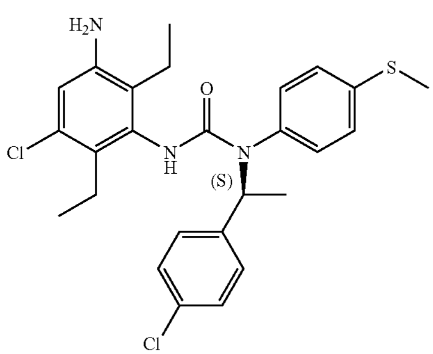 | 83 | 502.1 | 503.1 | B | (S)-3-(3-amino-5-chloro-2,6-diethyl-phenyl)-1-[1-(4-chloro-phenyl)-ethyl]-1-(4-methylsulfanyl-phenyl)-urea |

TABLE 1-continued

Antagonistic activity of representative compounds of the invention

| Structure | No. | [M + H]+ calculated | [M + H]+ measured | Activity-range | Chemical name |
|---|---|---|---|---|---|
| 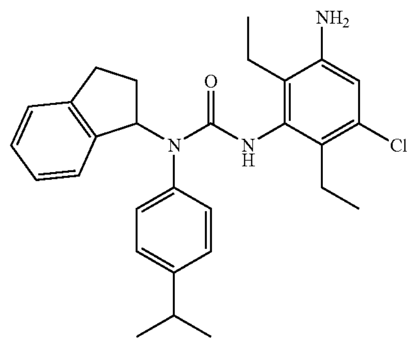 | 84 | 476.2 | 476.8 | C | 3-(3-amino-5-chloro-2,6-diethyl-phenyl)-1-indane-1-yl-1-(4-isopropyl-phenyl)-urea |
| 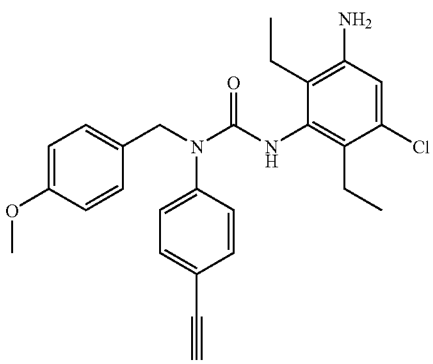 | 85 | 462.2 | 462.5 | C | 3-(3-amino-5-chloro-2,6-diethyl-phenyl)-1-(4-ethynyl-phenyl)-1-(4-methoxy-benzyl)-urea |
| 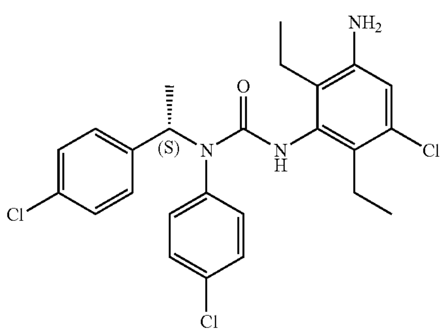 | 86 | 490.1 | 490.9 | C | (S)-3-(3-amino-5-chloro-2,6-diethyl-phenyl)-1-(4-chlor-phenyl)-1-[1-(4-chloro-phenyl)-ethyl]-urea |
| 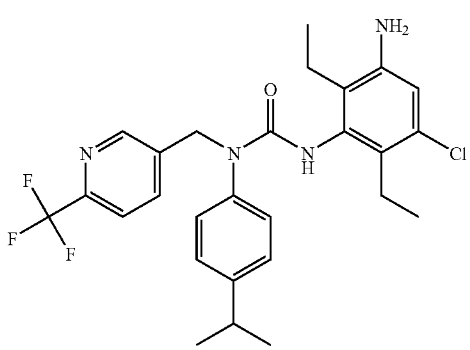 | 87 | 519.2 | 519.2 | C | 3-(3-amino-5-chloro-2,6-diethyl-phenyl)-1-(4-isopropyl-phenyl)-1-(6-trifluoromethyl-pyridin-3-ylmethyl)-urea |

TABLE 1-continued

Antagonistic activity of representative compounds of the invention

| Structure | No. | [M + H]+ calculated | [M + H]+ measured | Activity-range | Chemical name |
|---|---|---|---|---|---|
| 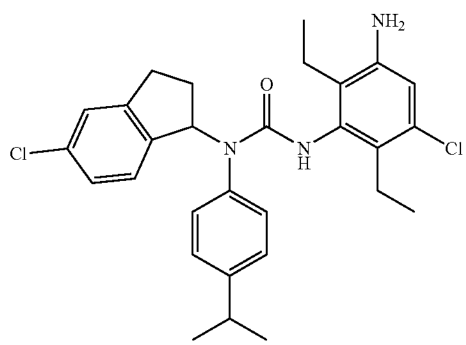 | 88 | 510.2 | 510.0 | B | 3-(3-amino-5-chloro-2,6-diethyl-phenyl)-1-(5-chloro-indane-1-yl)-1-(4-isopropyl-phenyl)-urea |
| 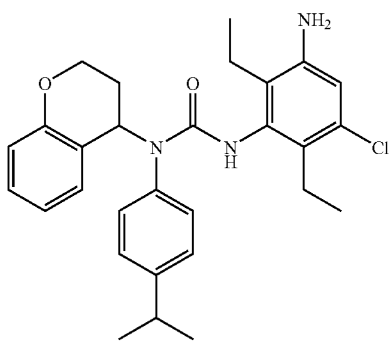 | 89 | 492.2 | 492.1 | C | 3-(3-amino-5-chloro-2,6-diethyl-phenyl)-1-chroman-4-yl-1-(4-isopropyl-phenyl)-urea |
| 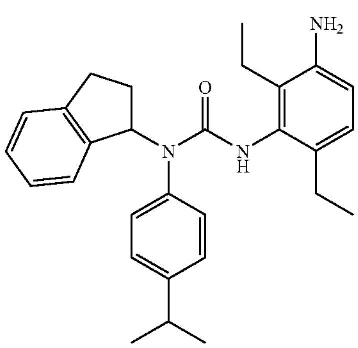 | 90 | 442.3 | 442.1 | C | 3-(3-amino-2,6-diethyl-phenyl)-1-indane-1-yl-1-(4-isopropyl-phenyl)-urea |
| 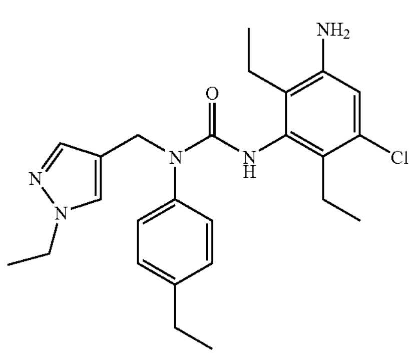 | 91 | 454.2 | 454.9 | C | 3-(3-amino-5-chloro-2,6-diethyl-phenyl)-1-(4-ethyl-phenyl)-1-(1-ethyl-1H-pyrazol-4-ylmethyl)-urea |

TABLE 1-continued

Antagonistic activity of representative compounds of the invention

| Structure | No. | [M + H]+ calculated | [M + H]+ measured | Activity-range | Chemical name |
|---|---|---|---|---|---|
| 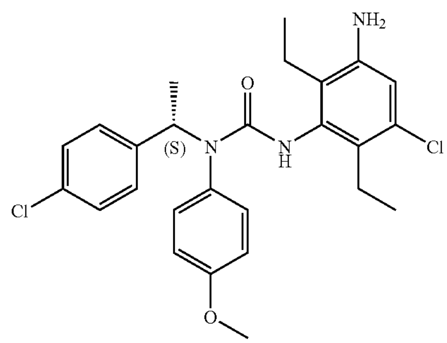 | 92 | 486.2 | 486.9 | B | (S)-3-(3-amino-5-chloro-2,6-diethyl-phenyl)-1-[1-(4-chloro-phenyl)-ethyl]-1-(4-methoxy-phenyl)-urea |
| 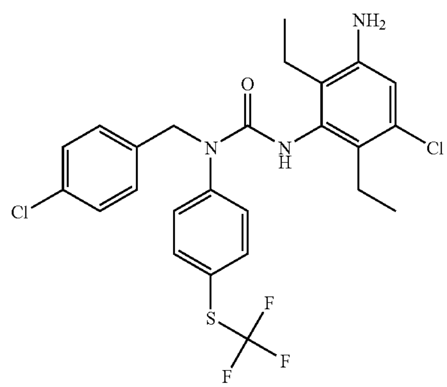 | 93 | 542.1 | 543.1 | C | 3-(3-amino-5-chloro-2,6-diethyl-phenyl)-1-(4-chloro-benzyl)-1-(4-trifluoromethylsulfanyl-phenyl)-urea |
| 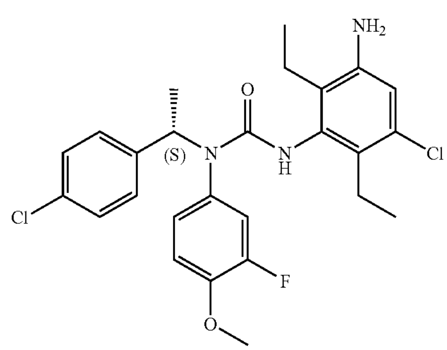 | 94 | 504.2 | 505.0 | A | (S)-3-(3-amino-5-chloro-2,6-diethyl-phenyl)-1-[1-(4-chloro-phenyl)-ethyl]-1-(3-fluoro-4-methoxy-phenyl)-urea |
| 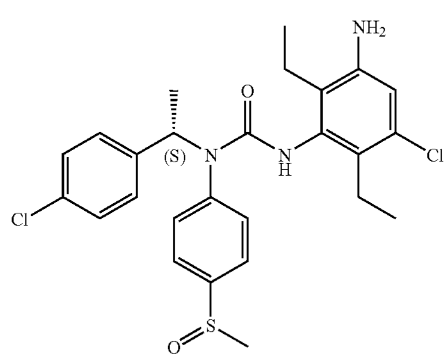 | 95 | 518.1 | 518.5 | C | (S)-3-(3-amino-5-chloro-2,6-diethyl-phenyl)-1-[1-(4-chloro-phenyl)-ethyl]-1-(4-methanesulfinyl-phenyl)-urea |

TABLE 1-continued

Antagonistic activity of representative compounds of the invention

| Structure | No. | [M + H]+ calculated | [M + H]+ measured | Activity-range | Chemical name |
|---|---|---|---|---|---|
| 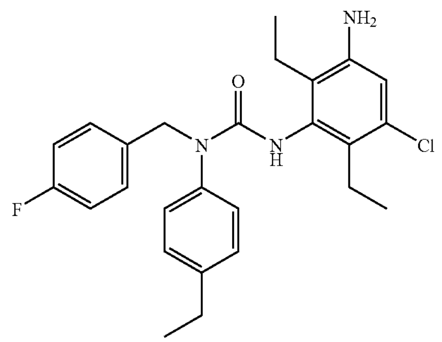 | 96 | 454.2 | 454.1 | B | 3-(3-amino-5-chloro-2,6-diethyl-phenyl)-1-(4-ethyl-phenyl)-1-(4-fluoro-benzyl)-urea |
| 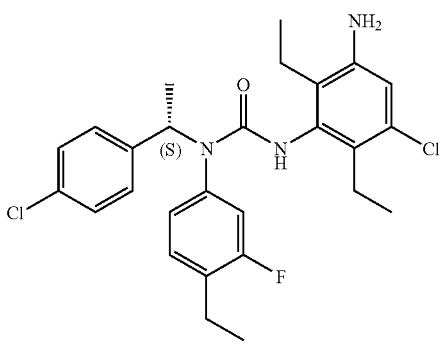 | 97 | 502.2 | 502.5 | A, 35 nM | (S)-3-(3-amino-5-chloro-2,6-diethyl-phenyl)-1-[1-(4-chlor-phenyl)-ethyl]-1-(4-ethyl-3-fluor-phenyl)-urea |
| 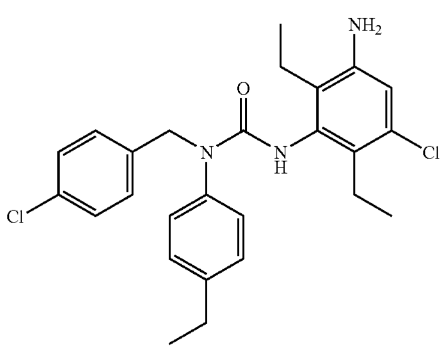 | 98 | 470.2 | 470.2 | B, 86 nM | 3-(3-amino-5-chloro-2,6-diethyl-phenyl)-1-(4-chloro-benzyl)-1-(4-ethyl-phenyl)-urea |
| 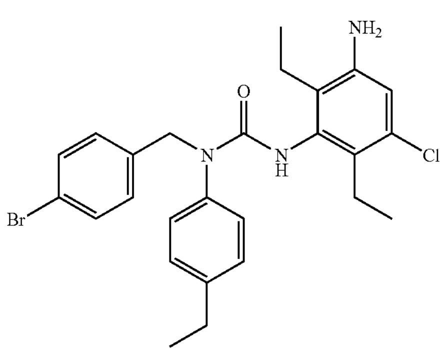 | 99 | 514.1 | 514.1 | A | 3-(3-amino-5-chloro-2,6-diethyl-phenyl)-1-(4-bromo-benzyl)-1-(4-ethyl-phenyl)-urea |

TABLE 1-continued

Antagonistic activity of representative compounds of the invention

| Structure | No. | [M + H]+ calculated | [M + H]+ measured | Activity-range | Chemical name |
|---|---|---|---|---|---|
| 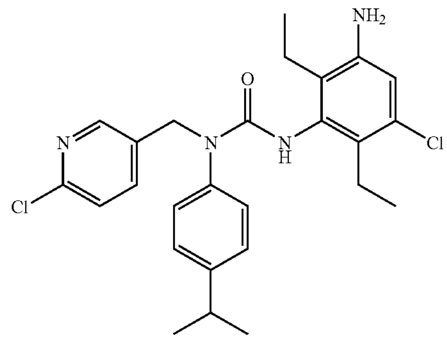 | 100 | 485.2 | 485.2 | B, 62 nM | 3-(3-amino-5-chloro-2,6-diethyl-phenyl)-1-(6-chloro-pyridin-3-ylmethyl)-1-(4-isopropyl-phenyl)-urea |
| 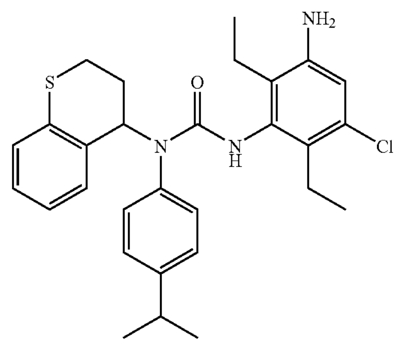 | 101 | 508.2 | 508.7 | C | 3-(3-amino-5-chloro-2,6-diethyl-phenyl)-1-(4-isopropyl-phenyl)-1-thiochroman-4-yl-urea |
| 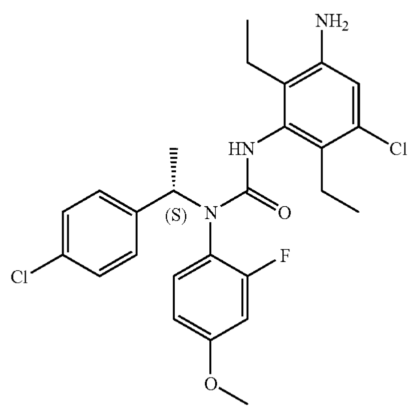 | 102 | 504.2 | 504.9 | A, 31 nM | (S)-3-(3-amino-5-chloro-2,6-diethyl-phenyl)-1-[1-(4-chloro-phenyl)-ethyl]-1-(2-fluoro-4-methoxy-phenyl)-urea |
| 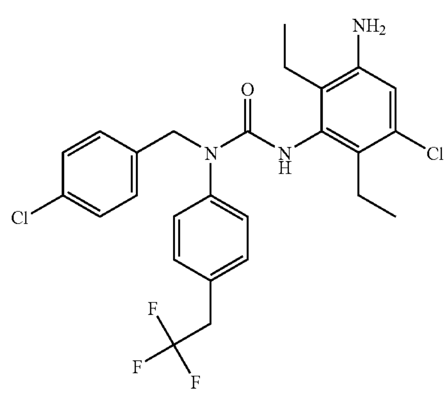 | 103 | 524.1 | 524.1 | B | 3-(3-amino-5-chloro-2,6-diethyl-phenyl)-1-(4-chloro-benzyl)-1-[4-(2,2,2-trifluoro-ethyl)-phenyl]-urea |

TABLE 1-continued

Antagonistic activity of representative compounds of the invention

| Structure | No. | [M + H]+ calculated | [M + H]+ measured | Activity- range | Chemical name |
|---|---|---|---|---|---|
| 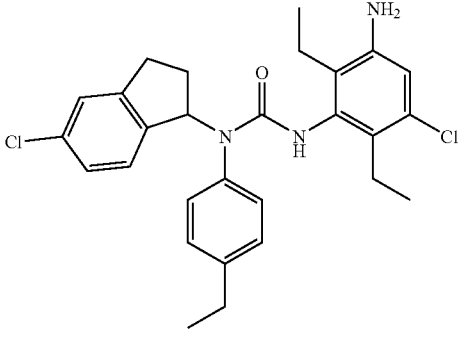 | 104 | 496.2 | 496.1 | B | 3-(3-amino-5-chloro-2,6-diethyl-phenyl)-1-(5-chloro-indane-1-yl)-1-(4-ethyl-phenyl)-urea |
| 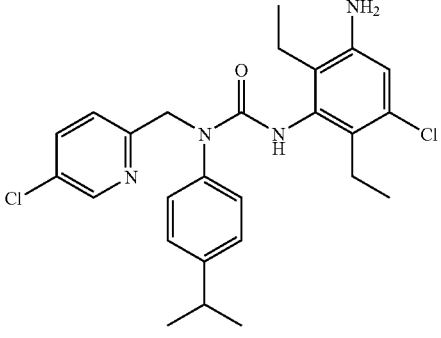 | 105 | 485.2 | 485.1 | C | 3-(3-amino-5-chloro-2,6-diethyl-phenyl)-1-(5-chloro-pyridin-2-ylmethyl)-1-(4-isopropyl-phenyl)-urea |
| 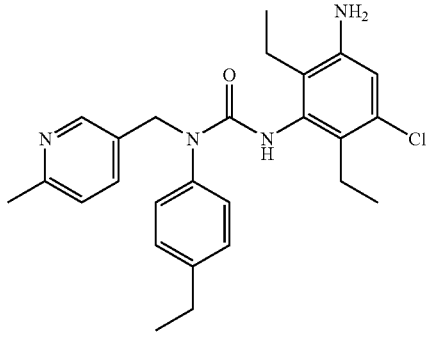 | 106 | 451.2 | 451.8 | B | 3-(3-amino-5-chloro-2,6-diethyl-phenyl)-1-(4-ethyl-phenyl)-1-(6-methyl-pyridin-3-ylmethyl)-urea |
| 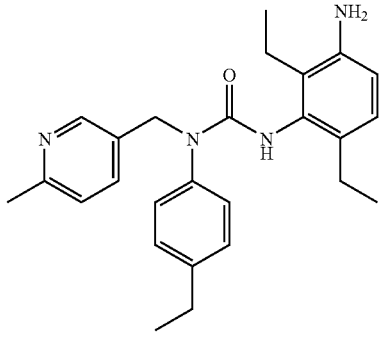 | 107 | 417.3 | 417.3 | C | 3-(3-amino-2,6-diethyl-phenyl)-1-(4-ethyl-phenyl)-1-(6-methyl-pyridin-3-ylmethyl)-urea |

TABLE 1-continued

Antagonistic activity of representative compounds of the invention

| Structure | No. | [M + H]+ calculated | [M + H]+ measured | Activity-range | Chemical name |
|---|---|---|---|---|---|
| 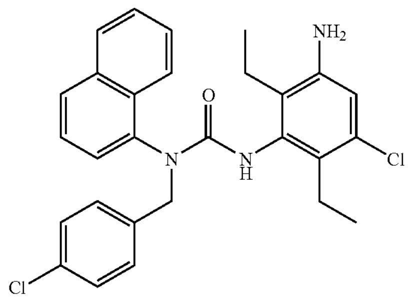 | 108 | 492.2 | 492.1 | C | 3-(3-amino-5-chloro-2,6-diethyl-phenyl)-1-(4-chloro-benzyl)-1-naphthaline-1-yl-urea |
| 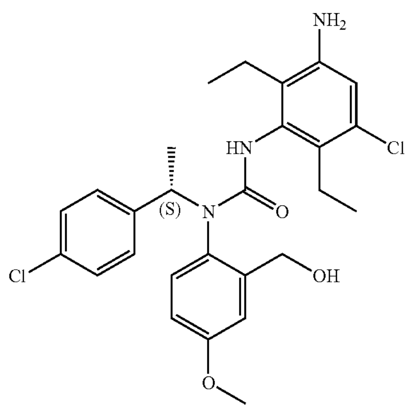 | 109 | 516.2 | 516.7 | C | (S)-3-(3-amino-5-chloro-2,6-diethyl-phenyl)-1-[1-(4-chloro-phenyl)-ethyl]-1-(2-hydroxymethyl-4-methoxy-phenyl)-urea |
| 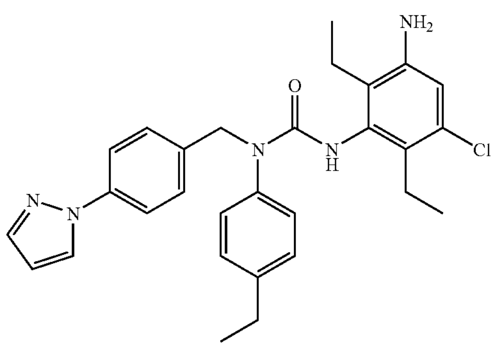 | 110 | 502.2 | 502.1 | C | 3-(3-amino-5-chloro-2,6-diethyl-phenyl)-1-(4-ethyl-phenyl)-1-(4-pyrazol-1-yl-benzyl)-urea |
| 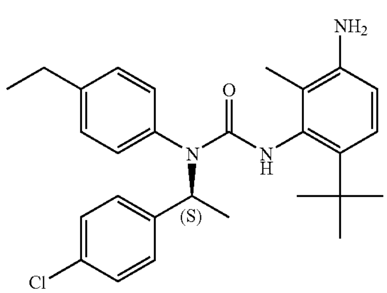 | 111 | 464.2 | 464.0 | C | (S)-3-(3-amino-6-tert-butyl-2-methyl-phenyl)-1-[1-(4-chloro-phenyl)-ethyl]-1-(4-ethyl-phenyl)-urea |

TABLE 1-continued

Antagonistic activity of representative compounds of the invention

| Structure | No. | [M + H]+ calculated | [M + H]+ measured | Activity- range | Chemical name |
|---|---|---|---|---|---|
| 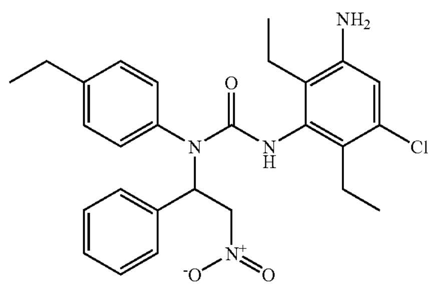 | 112 | 495.2 | 495.6 | C | 3-(3-amino-5-chloro-2,6-diethyl-phenyl)-1-(4-ethyl-phenyl)-1-(2-nitro-1-phenyl-ethyl)-urea |
| 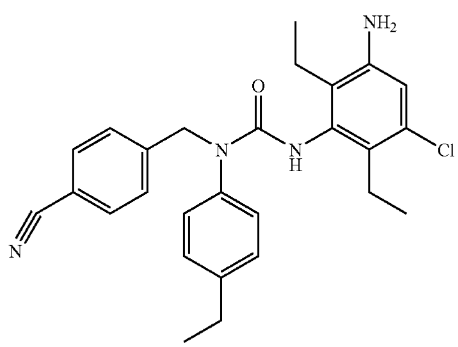 | 113 | 461.2 | 461.1 | C | 3-(3-amino-5-chloro-2,6-diethyl-phenyl)-1-(4-cyano-benzyl)-1-(4-ethyl-phenyl)-urea |
| 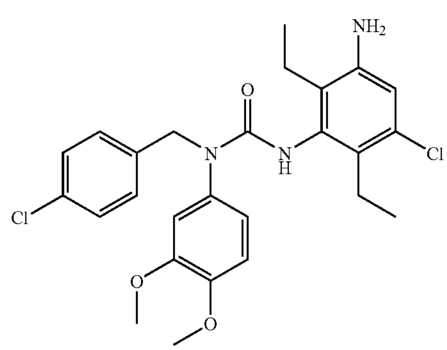 | 114 | 502.2 | 502.1 | C | 3-(3-amino-5-chloro-2,6-diethyl-phenyl)-1-(4-chloro-benzyl)-1-(3,4-dimethoxy-phenyl)-urea |
| 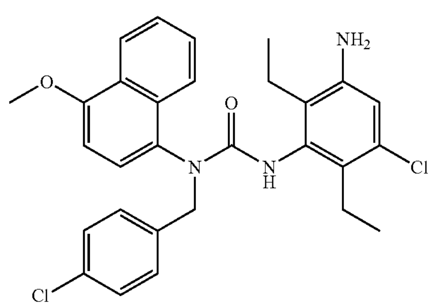 | 115 | 522.2 | 522.5 | B | 3-(3-amino-5-chloro-2,6-diethyl-phenyl)-1-(4-chloro-benzyl)-1-(4-methoxy-naphthaline-1-yl)-urea |

TABLE 1-continued

Antagonistic activity of representative compounds of the invention

| Structure | No. | [M + H]+ calculated | [M + H]+ measured | Activity-range | Chemical name |
|---|---|---|---|---|---|
| 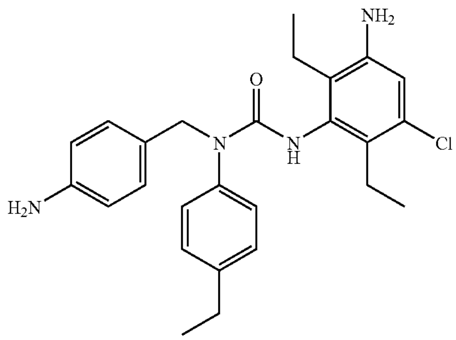 | 116 | 451.2 | 451.8 | C | 1-(4-amino-benzyl)-3-(3-amino-5-chloro-2,6-diethyl-phenyl)-1-(4-ethyl-phenyl)-urea |
| 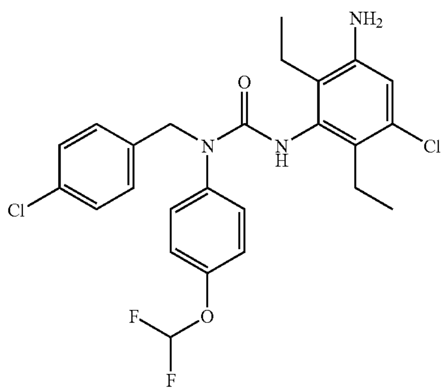 | 117 | 508.1 | 508.9 | C | 3-(3-amino-5-chloro-2,6-diethyl-phenyl)-1-(4-chloro-benzyl)-1-(4-difluoromethoxy-phenyl)-urea |
| 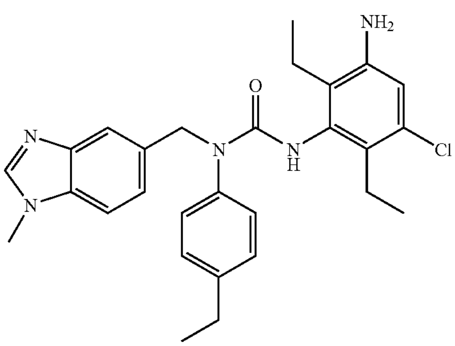 | 118 | 490.2 | 490.2 | C | 3-(3-amino-5-chloro-2,6-diethyl-phenyl)-1-(4-ethyl-phenyl)-1-(1-methyl-1H-benzoimidazol-5-ylmethyl)-urea |
| 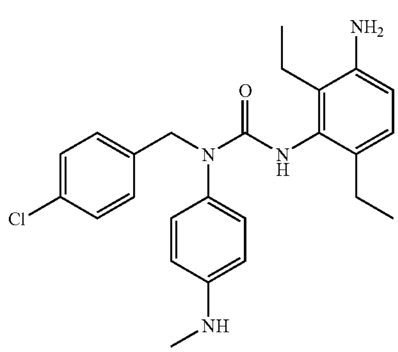 | 119 | 437.2 | 437.1 | B | 3-(3-amino-2,6-diethyl-phenyl)-1-(4-chloro-benzyl)-1-(4-methylamino-phenyl)-urea |

TABLE 1-continued

Antagonistic activity of representative compounds of the invention

| Structure | No. | [M + H]+ calculated | [M + H]+ measured | Activity-range | Chemical name |
|---|---|---|---|---|---|
| 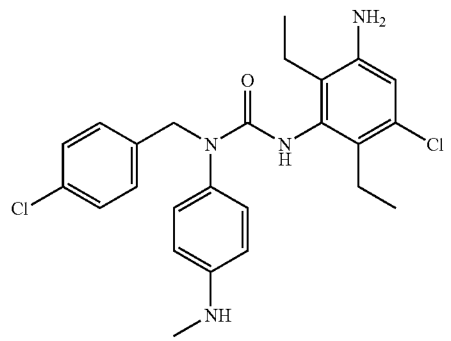 | 120 | 471.2 | 471.1 | A, 19 nM | 3-(3-amino-5-chloro-2,6-diethyl-phenyl)-1-(4-chloro-benzyl)-1-(4-methylamino-phenyl)-urea |
| 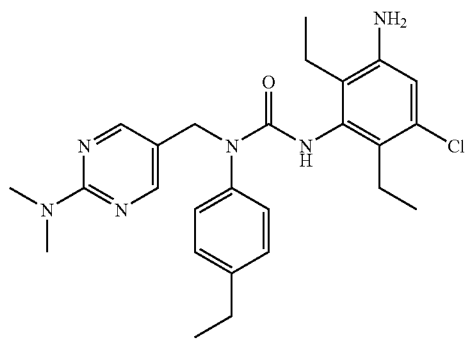 | 121 | 481.2 | 481.3 | C | 3-(3-amino-5-chloro-2,6-diethyl-phenyl)-1-(2-dimethylamino-pyrimidin-e5-ylmethyl)-1-(4-ethyl-phenyl)-urea |
| 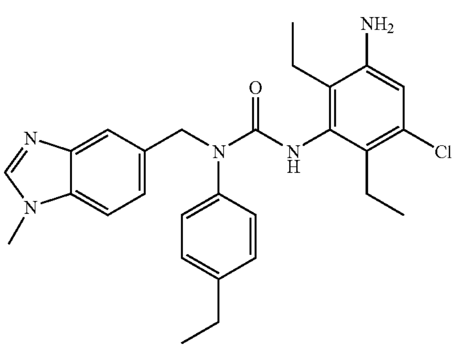 | 122 | 504.3 | 504.3 | B | 3-(3-amino-5-chloro-2,6-diethyl-phenyl)-1-(4-ethyl-phenyl)-1-[1-(1-methyl-1H-benzoimidazol-5-yl)-ethyl]-urea |
| 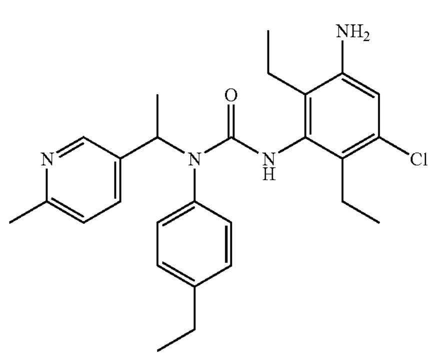 | 123 | 465.2 | 465.3 | B | 3-(3-amino-5-chloro-2,6-diethyl-phenyl)-1-(4-ethyl-phenyl)-1-[1-(6-methyl-pyridin-3-yl)-ethyl]-urea |

TABLE 1-continued

Antagonistic activity of representative compounds of the invention

| Structure | No. | [M + H]+ calculated | [M + H]+ measured | Activity-range | Chemical name |
|---|---|---|---|---|---|
| 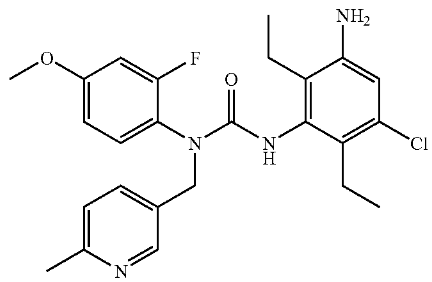 | 124 | 471.2 | 471.4 | C | 3-(3-amino-5-chloro-2,6-diethyl-phenyl)-1-(2-fluoro-4-methoxy-phenyl)-1-(6-methyl-pyridin-3-ylmethyl)-urea |
| 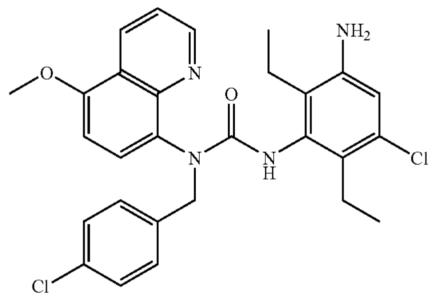 | 125 | 523.2 | 523.0 | B | 3-(3-amino-5-chloro-2,6-diethyl-phenyl)-1-(4-chloro-benzyl)-1-(5-methoxy-chinolin-8-yl)-urea |
| 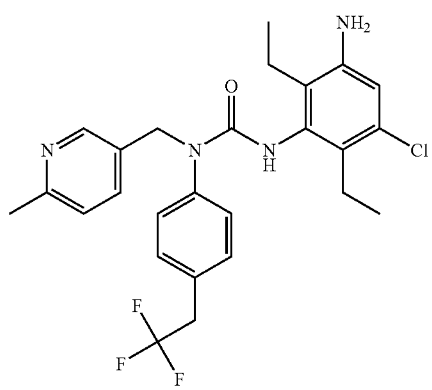 | 126 | 505.2 | 505.3 | B | 3-(3-amino-5-chloro-2,6-diethyl-phenyl)-1-(6-methyl-pyridin-3-ylmethyl)-1-[4-(2,2,2-trifluoro-ethyl)-phenyl]-urea |
| 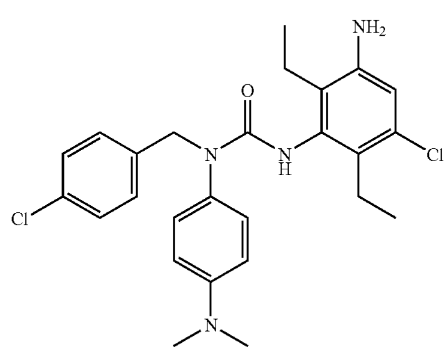 | 127 | 485.2 | 485.6 | C | 3-(3-amino-5-chloro-2,6-diethyl-phenyl)-1-(4-chloro-benzyl)-1-(4-dimethylamino-phenyl)-urea |

TABLE 1-continued

Antagonistic activity of representative compounds of the invention

| Structure | No. | [M + H]+ calculated | [M + H]+ measured | Activity-range | Chemical name |
|---|---|---|---|---|---|
| 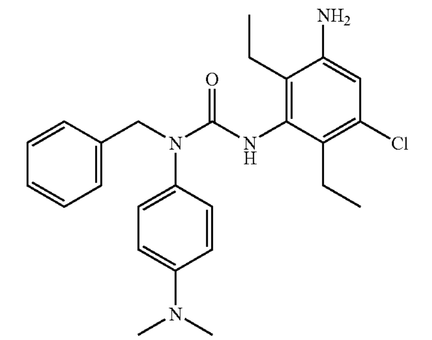 | 128 | 451.2 | 452.0 | C | 3-(3-amino-5-chloro-2,6-diethyl-phenyl)-1-benzyl-1-(4-dimethylamino-phenyl)-urea |
| 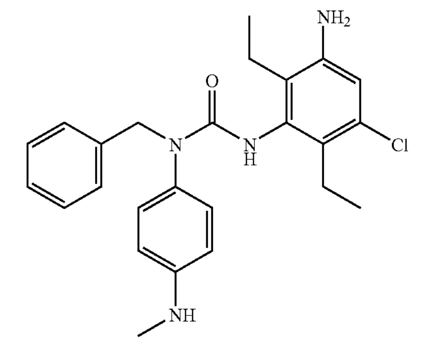 | 129 | 437.2 | 437.1 | B | 3-(3-amino-5-chloro-2,6-diethyl-phenyl)-1-benzyl-1-(4-methylamino-phenyl)-urea |
| 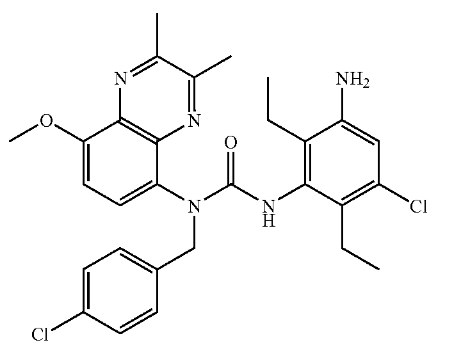 | 130 | 552.2 | 552.1 | C | 3-(3-amino-5-chloro-2,6-diethyl-phenyl)-1-(4-chloro-benzyl)-1-(8-methoxy-2,3-dimethyl-chinoxalin-5-yl)-urea |
| 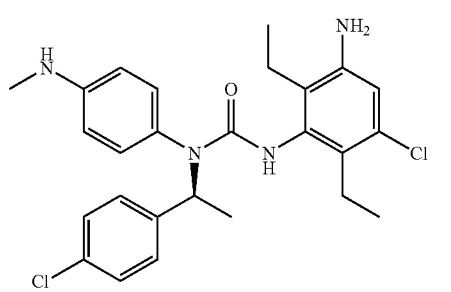 | 131 | 485.2 | 485.8 | A, 3 nM | (S)-3-(3-amino-5-chloro-2,6-diethyl-phenyl)-1-[1-(4-chloro-phenyl)-ethyl]-1-(4-methylamino-phenyl)-urea |

// TABLE 1-continued
// Antagonistic activity of representative compounds of the invention

| Structure | No. | [M + H]+ calculated | [M + H]+ measured | Activity-range | Chemical name |
|---|---|---|---|---|---|
| 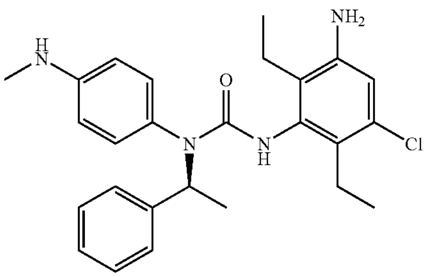 | 132 | 451.2 | 451.7 | A | (S)-3-(3-amino-5-chloro-2,6-diethyl-phenyl)-1-(4-methylamino-phenyl)-1-(1-phenyl-ethyl)-urea |
| 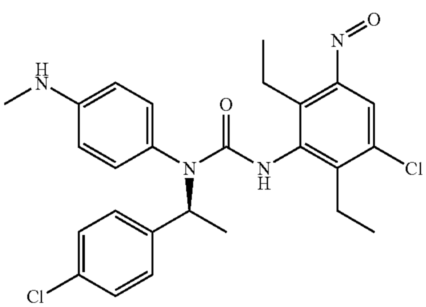 | 133 | 499.2 | 499.7 | A | (S)-3-(3-chloro-2,6-diethyl-5-nitroso-phenyl)-1-[1-(4-chloro-phenyl)-ethyl]-1-(4-methylamino-phenyl)-urea |
| 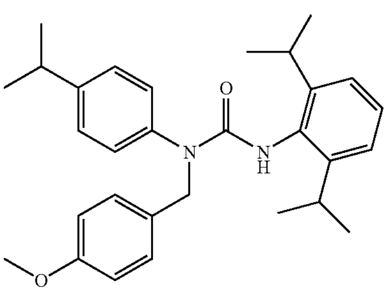 | 134 | 459.3 | 459.2 | C | 3-(2,6-diisopropyl-phenyl)-1-(4-isopropyl-phenyl)-1-(4-methoxy-benzyl)-urea |
| 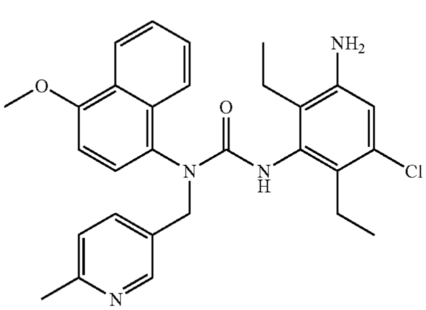 | 135 | 503.2 | 503.2 | A, 55 nM | 3-(3-amino-5-chloro-2,6-diethyl-phenyl)-1-(4-methoxy-naphthaline-1-yl)-1-(6-methyl-pyridin-3-ylmethyl)-urea |

TABLE 1-continued

Antagonistic activity of representative compounds of the invention

| Structure | No. | [M + H]+ calculated | [M + H]+ measured | Activity-range | Chemical name |
|---|---|---|---|---|---|
| 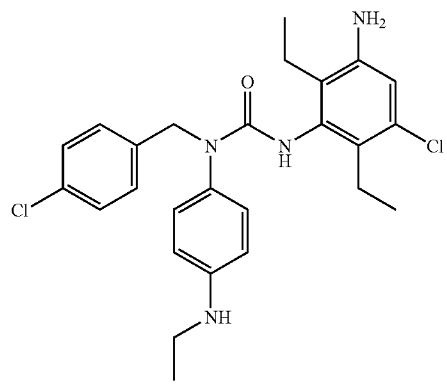 | 136 | 485.2 | 485.8 | A | 3-(3-amino-5-chloro-2,6-diethyl-phenyl)-1-(4-chloro-benzyl)-1-(4-ethylamino-phenyl)-urea |
| 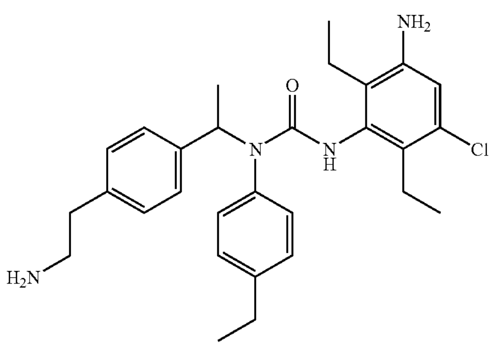 | 137 | 493.3 | 493.2 | C | 3-(3-amino-5-chloro-2,6-diethyl-phenyl)-1-[4-(2-amino-ethyl)-benzyl]-1-(4-ethyl-phenyl)-urea |
| 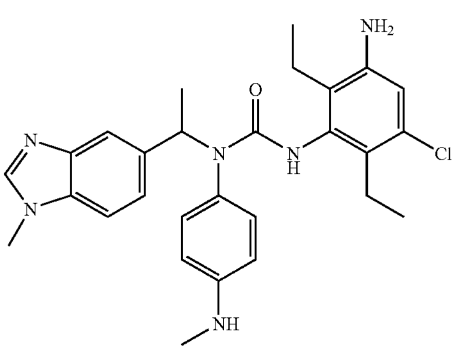 | 138 | 505.2 | 505.8 | B | 3-(3-amino-5-chloro-2,6-diethyl-phenyl)-1-(4-methylamino-phenyl)-1-[1-(1-methyl-1H-benzoimidazol-5-yl)-ethyl]-urea |
| 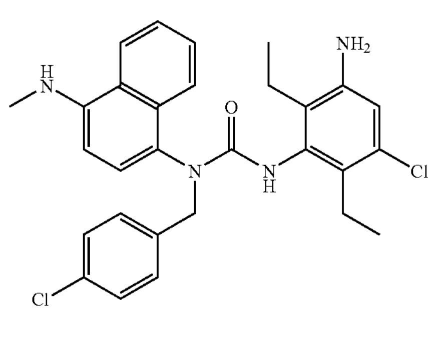 | 139 | 521.2 | 521.9 | C | 3-(3-amino-5-chloro-2,6-diethyl-phenyl)-1-(4-chloro-benzyl)-1-(4-methylamino-naphthalin-1-yl)-urea |

TABLE 1-continued

Antagonistic activity of representative compounds of the invention

| Structure | No. | [M + H]+ calculated | [M + H]+ measured | Activity-range | Chemical name |
|---|---|---|---|---|---|
| 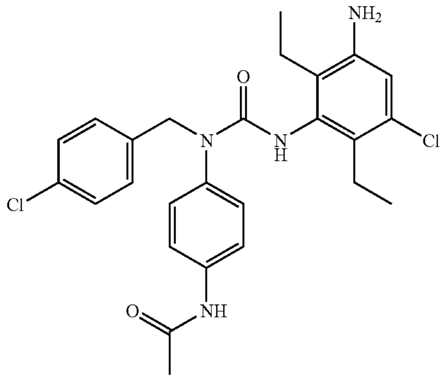 | 140 | 499.2 | 500.1 | C | N-{4-[3-(3-amino-5-chloro-2,6-diethyl-phenyl)-1-(4-chloro-benzyl)-ureido]-phenyl}-acetamide |
| 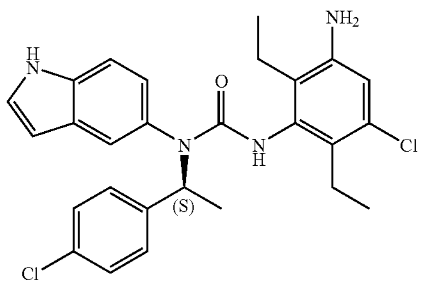 | 141 | 495.2 | 495.6 | A | (S)-3-(3-amino-5-chloro-2,6-diethyl-phenyl)-1-[1-(4-chloro-phenyl)-ethyl]-1-(1H-indol-5-yl)-urea |
| 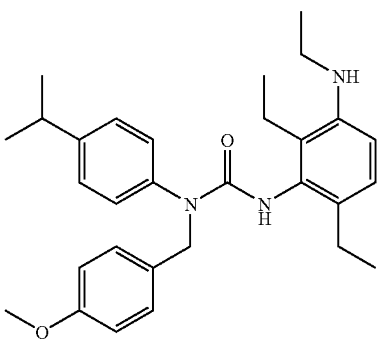 | 142 | 474.3 | 474.3 | D | 3-(2,6-diethyl-3-ethylamino-phenyl)-1-(4-isopropyl-phenyl)-1-(4-methoxy-benzyl)-urea |

Activity ranges:
IC$_{50}$ ≦ 60 nM: A
60 nM < IC$_{50}$ ≦ 200 nM: B
200 nM < IC$_{50}$ ≦ 5000 nM: C
5000 nM < IC$_{50}$: D Example 29

Increase of antagonistic activity by introduction of a NH$_2$ group

A comparison of compounds 24 and 31 shows that a NR21R22 group can result in an increased antagonistic activity. By introducing a NH$_2$ group in 24 an increase of the activity by a factor of 6.4 is observed (given are the IC$_{50}$ values for the inhibition C5a triggered enzyme release according to example 28).

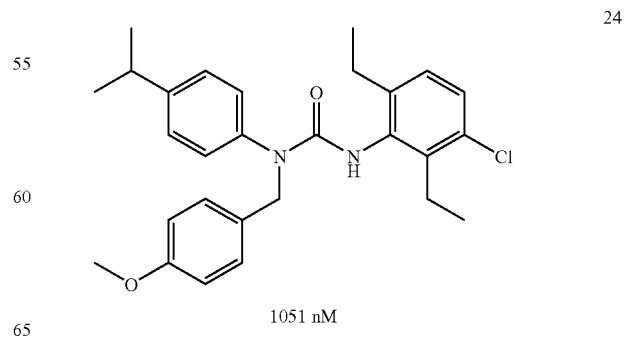

1051 nM

Example 30

Improvement of the Antagonistic Activity by Introduction of a Stereo Center

Introduction of a chiral center at a suitable position can have a positive effect on the antagonistic activity. This is observed, for example, in the case of compounds 66, 31 and 56, in which the S configuration (66) shows 11 times higher antagonistic activity as the (R) configuration (56) (given are the $IC_{50}$ values for the inhibition C5a triggered enzyme release according to example 32).

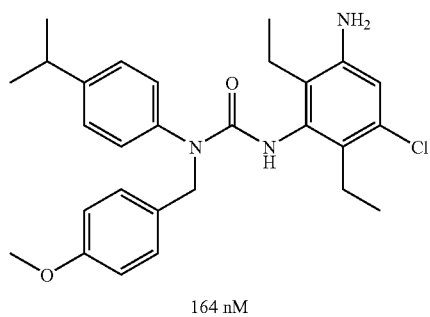

31

164 nM

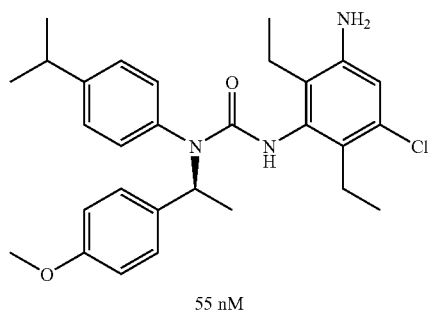

66

55 nM

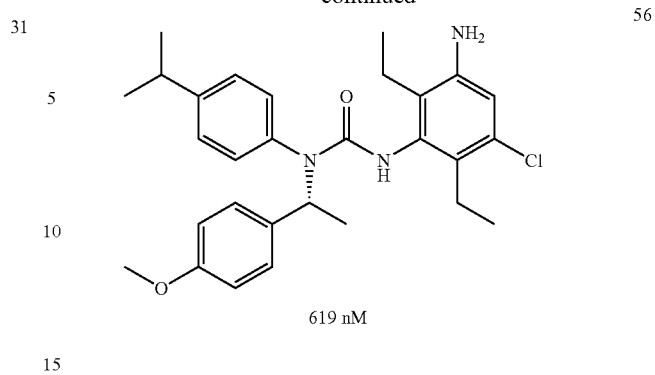

56

619 nM

Example 31

Improvement of the Antagonistic Activity by Introduction of a H-Bond Donor

Surprisingly the present inventors have found that the introduction of a hydrogen bond donor at the R3 position in structure (IV) leads to an increased antagonistic activity.

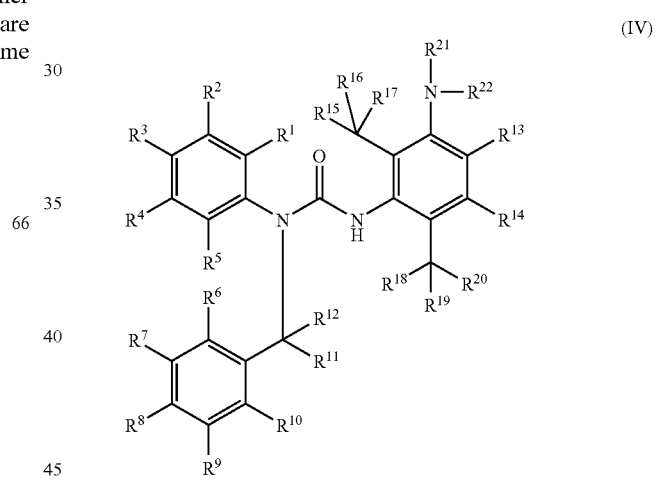

(IV)

This has been shown for example for compounds 98 and 120. Here, the exchange of a $CH_2$ group by a NH group results in an improvement of the antagonistic activity by a factor of 4.5 (given are the $IC_{50}$ values for the inhibition C5a triggered enzyme release according to example 32).

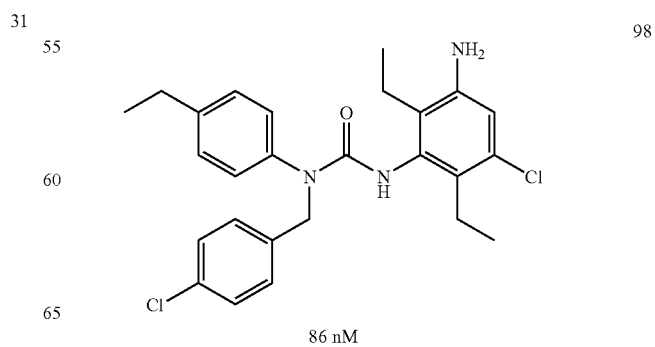

98

86 nM

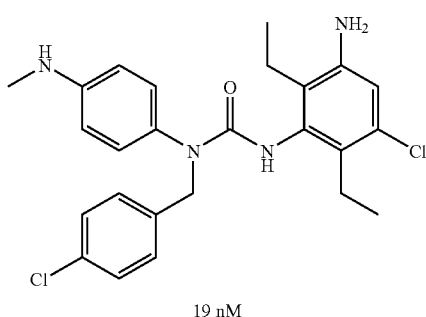

19 nM

Example 32

Determination of the $EC_{50}$ Value in an Enzyme Release Assay

The determination of the $EC_{50}$ value is comparable to the procedure described in example 32. The only difference is the fact that 30 µl of the substance to be tested are mixed with 75 µl of the cell suspension described in example 28. The cells are not pre-incubated and no C5a is added to stimulate enzyme release. The results for the compounds tested are given in Table 2. Apparently, none of the tested compounds shows significant agonistic activity.

TABLE 2

Agonism of selected compounds

| Molecule | Concentration applied | Agonism (% of the maximum enzyme release induced by C5a) |
|---|---|---|
| 20 | 7.1 µM | 0.06 |
| 31 | 7.1 µM | 0.12 |
| 102 | 7.1 µM | 0.00 |
| 103 | 7.1 µM | 0.00 |
| 106 | 7.1 µM | 0.00 |
| 122 | 7.1 µM | 0.00 |
| 125 | 7.1 µM | 0.00 |
| C5a | 228 nM | 100 |

Example 33

Determination of the Solubility of Selected C5a Receptor Antagonists

To determine the solubility the compound to be measured is dissolved (e.g, 2 µM of a 5 mM solution in DMSO) in organic solvent (e.g. 198 µl DMSO) as well as in aqueous buffer solution (e.g. 198 µl HEPES buffer). Both solutions are analyzed via analytical HPLC and the areas under the peaks are compared. The value for the organic solution is taken as 100%. The presented compounds (Table 3) are significantly better soluble in aqueous HEPES buffer than compound 20.

TABLE 3

Solubility of selected compounds in aqeous HEPES buffer

| Molecule | Solubility [µM] |
|---|---|
| 20 | 1 |
| 31 | 2 |
| 80 | 4 |
| 103 | 7 |
| 106 | 83 |
| 122 | 29 |
| 125 | 4 |

Example 34

Determination of the AB Permeability in a TC-7 Based Assay-System

Compounds to be tested are prepared at a concentration of 50 µM in HBSS-MES (5 mM, pH 6.5) (from a 10 mM stock solution in 100% DMSO). $^{14}C$-mannitol (about 4 µM) is added and the solution is mixed and centrifuged. The supernatant is added to the apical side of a TC-7 cell culture (passage 15, in 24 well transwell plate) to obtain a DMSO concentration of 1%. At the basolateral side HBSS-HEPES (5 mM, pH 7.4) is placed. Subsequently, the cells are incubated for 120 minutes at 37° C. The integrity of the TC-7 cell layer is checked by means of the added mannitol ($P_{app}$ <2.5 $10^{-6}$ cm/s). The Permeabilität $P_{app}$ [cm/s] is equal to $(V_R \times C_{R120})/(\Delta t \times A \times (C_{D,mid} - C_{R,mid}))$. $V_R$ is the volume of the receiver chamber, $C_{R120}$ the concentration the test compound in the receiver chamber after 120 minutes, $\Delta t$ the incubation time, A the area of the TC-7 cell layer, $C_{D,mid}$ the midpoint concentration of the test substance in the donor chamber and $C_{R,mid}$ the concentration of the test compound in the receiver chamber.

The presented compounds (Table 4) are permeable, which might be an indicator that the compounds are orally available.

TABLE 4

AB permeability of selected compounds

| Molecule name | AB-permeability ($10^{-6}$ cm/s) |
|---|---|
| 102 | 1.1 |
| 106 | 22.3 |
| 122 | 3.5 |
| 125 | 2.9 |

Example 35

Efficacy of Compounds 131 and 80 in a Model of C5a Induced Neutropenia

C5a induced neutropenia is a model for shock induced diseases (e.g. septic shock), where amongst others the systemic role of C5a (blood pressure decrease, neutropenia) plays an important role. The reason for the decrease of the neutrophils in the circulation is their binding to the vessel walls due to the C5a stimulus. These processes of neutrophil recruitment are playing an important role in many other diseases like reperfusion injury. This model was also described by Short et al. (1999 British Journal of Pharmacology 125: 551-554).

Male gerbils (*Meriones unguiculatus*) are anaesthesized i.p. with ketamine (80 mg/kg) and xylazine (12 mg/kg). The animals are intubated and a catheter is inserted in the jugular vene and the animals are subjected to the following procedure:

1. The gerbils are pre-treated with vehicle or the compounds of the present invention 80 (3 mg/kg) or 131 (1 mg/kg) via i.v. infusion.

One minute before compound treatment a blood sample is taken.

2. 10 minutes after the infusion of the compounds the gerbils are treated i.v. with 100 μg/kg hrC5a.

Blood samples are taken shortly before and at several time intervals after the hrC5a administration.

3. Blood samples (about 0.2 ml) are taken into lithium-heparin vials from the jugular vene and are used for the differential blood count.

White Blood Cells:

White blood cell counts are measured with a haematology-cell-counter.

Differential Hemogram:

Blood smears are prepared from the heparinized blood samples. Each sample is dehydrated with methanol prior to the staining. After fixation, each sample is incubated for 5 minutes with May Grünwald staining. After this the samples are washed with aqua dest. Subsequently a Giemsa staining is done for 2 minutes and the samples are washed again.

The differential cell count is determined as the sum of neutrophils, eosinophile, easophile, lymphocytes and monocytes from 100 cells. Then, the percentage of neutrophils in relation to all white blood cells is determined.

Figure 2:
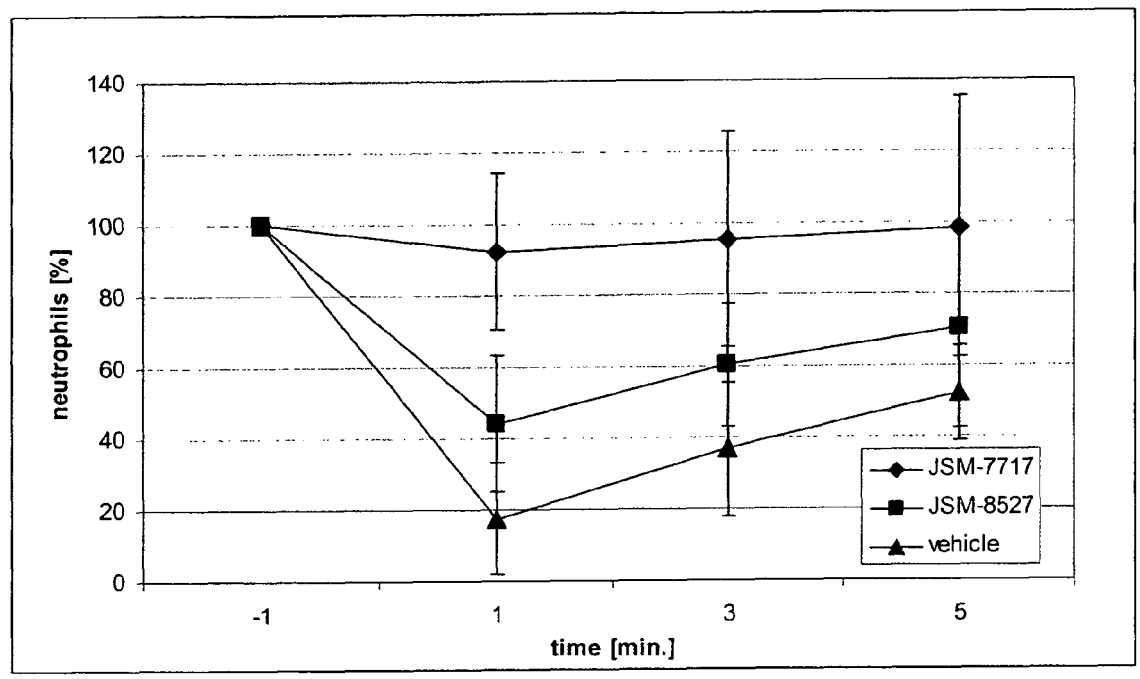
FIG. 2) shows in vivo efficacy of an exemplary compound according to the present invention in a model of C5a induced neutropenia. X-axis: time. Y-axis: portion of neutrophils (in percent) in the blood.

The result is presented in FIG. 2, in which the course of the neutropenia in gerbil after administration of C5a and vehicle or compound is shown. It can be seen that treatment with compounds 131 and 80 significantly reduces C5a induced neutropenia. Thus, in this inflammation model, the compounds show the desired anti-inflammatory effect.

The properties disclosed in the above descriptions, claims or drawings of the invention can be separately or in arbitrary combination relevant for the fulfilment of the invention in different execute modes.

The invention claimed is:

1. A compound, preferably a C5a receptor antagonist, having the following structure (IV):

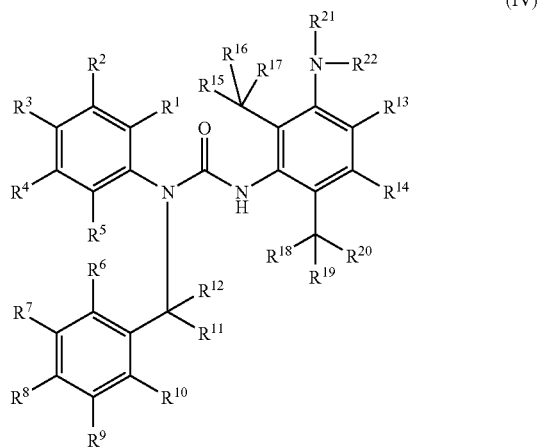

(IV)

whereby R1, R2, R4, R5, R6, R7, R9, R10, R11, R13, R15, R17, R18, R20, R21 and R22 are each H,
R16 and R19 are each methyl; and R3, R8, R12, and R14 are individually and independently selected from the group consisting of H, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl, arylalkyl, substituted arylalkyl, heteroarylalkyl, substituted heteroarylalkyl, alkoxyl, substituted alkoxyl, aryloxy, substituted aryloxy, arylalkyloxy, substituted arylalkyloxy, acyloxy, substituted acyloxy, halogen, hydroxyl, nitro, cyano, acyl, substituted acyl, mercapto, alkylthio, substituted alkylthio, amino, substituted amino, alkylamino, substituted alkylamino, bisalkyl amino, substituted bisalkyl amino, cyclic amino, substituted cyclic amino, carbamoyl (—$CONH_2$), substituted carbamoyl, carboxyl, carbamate, alkoxycarbonyl, substituted alkoxycarbonyl, acylamino, substituted acylamino, sulfamoyl (—$SO_2NH_2$), substituted sulfamoyl, haloalkyl, haloalkyloxy, —C(O)H, trialkylsilyl and azido.

2. The compound according to claim 1, wherein R3 is selected from the group consisting of H, alkyl, substituted alkyl, alkynyl, cycloalkyl, alkoxyl, substituted alkoxyl, acyloxy, halogen, nitro, cyano, acyl, alkylthio, substituted alkylthio, amino, substituted amino, alkylamino, substituted alkylamino, bisalkyl amino, cyclic amino, carbamoyl (—$CONH_2$), acylamino, and substituted acylamino.

3. The compound according to claim 1, whereby
R1, R2, R4 and R5 are each H, and
R3 is selected from the group consisting of H, alkyl, substituted alkyl, alkynyl, cycloalkyl, alkoxyl, acyl, alkylthio, substituted alkylthio, alkylamino and substituted alkylamino.

4. The compound according to claim 1, whereby
R1, R2, R4 and R5 are each H, and
R3 is selected from the group consisting of Et-, iPr—, $CF_3CH_2$—, cyclopropyl, HCC—, MeO—, MeS—, $CF_3S$—, MeNH—, and $CF_3NH$—.

5. The compound according to claim 1, wherein $R^8$ is selected from the group consisting of H, alkyl, substituted alkyl, heterocyclyl, substituted heterocyclyl, aryl, substituted aryl, heteroaryl, substituted heteroaryl, alkoxyl, substituted alkoxyl, acyloxy, halogen, nitro, cyano, acyl, alkylthio, substituted alkylthio, amino, substituted amino, alkylamino, substituted alkylamino, bisalkyl amino, substituted bisalkyl amino, cyclic amino, carbamoyl (—$CONH_2$) and acylamino.

6. The compound according to claim 5, whereby
R6, R7, R9 and R10 are each H, and
R8 is selected from the group consisting of H, alkyl, substituted alkyl, heterocyclyl, substituted heterocyclyl, aryl, heteroaryl, substituted heteroaryl, alkoxyl, substituted alkoxyl, halogen, alkylthio, substituted alkylthio, amino, substituted amino, alkylamino, substituted alkylamino, bisalkyl amino, substituted bisalkyl amino and cyclic amino.

7. The compound according to claim 5, whereby
R6, R7, R9 and R10 are each H, and
R8 is selected from the group consisting of H—, Me—, —$CF_3$, —OMe, —F, —Cl, —Br, —SMe, —$NMe_2$ and —NHMe.

8. The compound according to claim 1, whereby
R11 is H, and R12 is selected from the group consisting of H, alkyl, substituted alkyl and halogen.

9. The compound according to claim 8, whereby
R11 is H and $R^{12}$ is selected from the group consisting of —H, —Me, -Et, —$CF_3$, and —F.

10. The compound according to claim 1, whereby this moiety

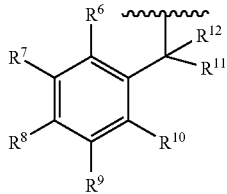

is substituted by the following moiety

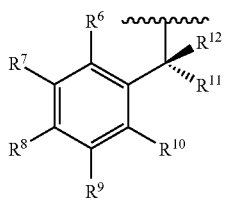

(XVII)

whereby R11 is H,
whereby R12 is selected from the group comprising H, alkyl, substituted alkyl and halogen.

11. The compound according to claim 10,
whereby R11 is H, and
whereby R12 is selected from the group comprising —H, —Me, -Et, —CF$_3$ and —F.

12. The compound according to claim 1, wherein
R13 is H and R14 is selected from the group consisting of H, alkyl, substituted alkyl, alkoxyl, substituted alkoxyl, halogen, cyano, alkylthio, amino and substituted amino.

13. The compound according to claim 12, whereby R13 is H and R14 is selected from the group consisting of —H, —Me, —CF$_3$, —OMe, —F, —Cl and —Br.

14. A compound, whereby the compound has the following structure
and wherein
R3 is selected from the group consisting of Et-, iPr—, CF$_3$CH$_2$—, cyclopropyl, HCC—, MeO—, MeS—, CF$_3$S—, MeNH— and CF$_3$NH—,
R8 is selected from the group consisting of H—, Me-, —CF$_3$, —OMe, —F, —Cl, —Br, —SMe, —NMe$_2$ and —NHMe,
R2 is selected from the group consisting of H— and Me—, and
R14 is selected from the group consisting of H— and —Cl.

15. The compound according to claim 1, whereby the compound has the following structure

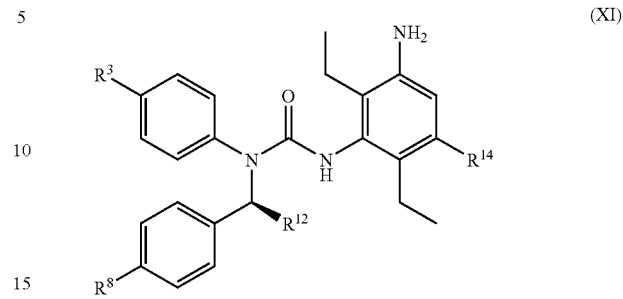

(XI)

and whereby
R3 is selected from the group comprising Et-, iPr—, CF$_3$CH$_2$—, cyclopropyl, HCC—, MeO—, MeS—, CF$_3$S—, MeNH— and CF$_3$NH—,
R8 is selected from the group comprising H—, Me—, —CF$_3$, —OMe, —F, —Cl, —Br, —SMe, —NMe$_2$, and —NHMe,
R12 is selected from the group comprising H— and Me—, and
R14 is selected from the group comprising H— and —Cl.

16. The compound according to claim 1, whereby the compound is selected from the group consisting of
3-(3-Amino-2,6-diethyl-phenyl)-1-(4-isopropyl-phenyl)-1-(4-methoxy-benzyl)-urea
3-(3-Amino-5-chloro-2,6-diethyl-phenyl)-1-(4-isopropyl-phenyl)-1-(4-methoxy-benzyl)-urea
3-(3-Amino-5-chloro-2,6-diethyl-phenyl)-1-(4-ethyl-phenyl)-1-(4-methoxy-benzyl)-urea
3-(3-Amino-5-chloro-2,6-diethyl-phenyl)-1-(4-isopropyl-phenyl)-1-(4-trifluoromethoxy-benzyl)-urea
3-(3-Amino-5-chloro-2,6-diethyl-phenyl)-1-(4-isopropyl-phenyl)-1-(4-methyl-benzyl)-urea
3-(3-Amino-5-chloro-2,6-diethyl-phenyl)-1-(4-ethyl-benzyl)-1-(4-isopropyl-phenyl)-urea
3-(3-Amino-2,6-diethyl-phenyl)-1-(4-isopropyl-phenyl)-1-(4-methyl-benzyl)-urea
3-(3-Amino-5-chloro-2,6-diethyl-phenyl)-1-benzyl-1-(4-isopropyl-phenyl)-urea
3-(3-Amino-5-chloro-2,6-diethyl-phenyl)-1-(4-isopropyl-phenyl)-1-(4-trifluoromethyl-benzyl)-urea
3-(3-Amino-2,6-diethyl-phenyl)-1-(4-isopropyl-phenyl)-1-(4-trifluoromethyl-benzyl)-urea
3-(3-Amino-5-chloro-2,6-diethyl-phenyl)-1-(4-ethyl-phenyl)-1-(4-methyl-benzyl)-urea
3-(3-Amino-2,6-diethyl-phenyl)-1-(4-ethyl-phenyl)-1-(4-methyl-benzyl)-urea
(R)-3-(3-Amino-5-chloro-2,6-diethyl-phenyl)-1-(4-isopropyl-phenyl)-1-[1-(4-methoxy-phenyl)-ethyl]-urea
(R)-3-(3-Amino-5-chloro-2,6-diethyl-phenyl)-1-(4-isopropyl-phenyl)-1-(1-p-tolyl-ethyl)-urea
3-(3-Amino-5-chloro-2,6-diethyl-phenyl)-1-cyclohexylmethyl-1-(4-isopropyl-phenyl)-urea
3-(3-Amino-2,6-diethyl-phenyl)-1-cyclohexylmethyl-1-(4-isopropyl-phenyl)-urea
3-(3-Amino-5-chloro-2,6-diethyl-phenyl)-1-(4-isopropyl-phenyl)-1-(4-methanesulfonyl-benzyl)-urea
(S)-3-(3-Amino-5-chloro-2,6-diethyl-phenyl)-1-(4-isopropyl-phenyl)-1-[1-(4-methoxy-phenyl)-ethyl]-urea
(R)-3-(3-Amino-2,6-diethyl-phenyl)-1-(4-isopropyl-phenyl)-1-(1-p-tolyl-ethyl)-urea (S)-3-(3-Amino-2,6-diethyl-phenyl)-1-(4-isopropyl-phenyl)-1-(1-p-tolyl-ethyl)-urea
(R)-3-(3-Amino-2,6-diethyl-phenyl)-1-(4-isopropyl-phenyl)-1-[1-(4-methoxy-phenyl)-ethyl]-urea
(S)-3-(3-Amino-2,6-diethyl-phenyl)-1-(4-isopropyl-phenyl)-1-[1-(4-methoxy-phenyl)-ethyl]-urea
3-(3-Amino-5-chloro-2,6-diethyl-phenyl)-1-(4-chloro-benzyl)-1-(4-isopropyl-phenyl)-urea
(S)-3-(3-Amino-5-chloro-2,6-diethyl-phenyl)-1-(4-isopropyl-phenyl)-1-(1-p-tolyl-ethyl)-urea
(S)-3-(3-Amino-5-chloro-2,6-diethyl-phenyl)-1-[1-(4-chloro-phenyl)-ethyl]-1-(4-isopropyl-phenyl)-urea
(S)-3-(3-Amino-5-chloro-2,6-diethyl-phenyl)-1-[1-(4-chloro-phenyl)-ethyl]-1-(4-ethyl-phenyl)-urea
(S)-3-(3-Amino-5-chloro-2,6-diethyl-phenyl)-1-[1-(4-fluoro-phenyl)-ethyl]-1-(4-isopropyl-phenyl)-urea
(S)-3-(3-Amino-5-chloro-2,6-diethyl-phenyl)-1-(4-ethyl-phenyl)-1-[1-(4-fluoro-phenyl)-ethyl]-urea
(S)-3-(3-Amino-5-chloro-2,6-diethyl-phenyl)-1-[1-(4-chloro-phenyl)-ethyl]-1-(4-methylsulfanyl-phenyl)-urea
3-(3-Amino-5-chloro-2,6-diethyl-phenyl)-1-(4-ethynyl-phenyl)-1-(4-methoxy-benzyl)-urea
(S)-3-(3-Amino-5-chloro-2,6-diethyl-phenyl)-1-(4-chloro-phenyl)-1-[1-(4-chloro-phenyl)-ethyl]-urea
(S)-3-(3-Amino-5-chloro-2,6-diethyl-phenyl)-1-[1-(4-chloro-phenyl)-ethyl]-1-(4-methoxy-phenyl)-urea
3-(3-Amino-5-chloro-2,6-diethyl-phenyl)-1-(4-chloro-benzyl)-1-(4-trifluoromethylsulfanyl-phenyl)-urea
(S)-3-(3-Amino-5-chloro-2,6-diethyl-phenyl)-1-[1-(4-chloro-phenyl)-ethyl]-1-(4-methanesulfinyl-phenyl)-urea
3-(3-Amino-5-chloro-2,6-diethyl-phenyl)-1-(4-ethyl-phenyl)-1-(4-fluoro-benzyl)-urea
3-(3-Amino-5-chloro-2,6-diethyl-phenyl)-1-(4-chloro-benzyl)-1-(4-ethyl-phenyl)-urea
3-(3-Amino-5-chloro-2,6-diethyl-phenyl)-1-(4-chloro-benzyl)-1-[4-(2,2,2-trifluoro-ethyl)-phenyl]-urea
3-(3-Amino-5-chloro-2,6-diethyl-phenyl)-1-(4-ethyl-phenyl)-1-(4-pyrazol-1-yl-benzyl)-urea
3-(3-Amino-5-chloro-2,6-diethyl-phenyl)-1-(4-ethyl-phenyl)-1-(2-nitro-1-phenyl-ethyl)-urea
3-(3-Amino-5-chloro-2,6-diethyl-phenyl)-1-(4-cyano-benzyl)-1-(4-ethyl-phenyl)-urea
1-(4-Amino-benzyl)-3-(3-amino-5-chloro-2,6-diethyl-phenyl)-1-(4-ethyl-phenyl)-urea
3-(3-Amino-5-chloro-2,6-diethyl-phenyl)-1-(4-chloro-benzyl)-1-(4-difluoromethoxy-phenyl)-urea
3-(3-Amino-2,6-diethyl-phenyl)-1-(4-chloro-benzyl)-1-(4-methylamino-phenyl)-urea
3-(3-Amino-5-chloro-2,6-diethyl-phenyl)-1-(4-chloro-benzyl)-1-(4-methylamino-phenyl)-urea
3-(3-Amino-5-chloro-2,6-diethyl-phenyl)-1-(4-chloro-benzyl)-1-(4-dimethylamino-phenyl)-urea
3-(3-Amino-5-chloro-2,6-diethyl-phenyl)-1-benzyl-1-(4-dimethylamino-phenyl)-urea
3-(3-Amino-5-chloro-2,6-diethyl-phenyl)-1-benzyl-1-(4-methylamino-phenyl)-urea
(S)-3-(3-Amino-5-chloro-2,6-diethyl-phenyl)-1-[1-(4-chloro-phenyl)-ethyl]-1-(4-methylamino-phenyl)-urea
3-(3-Amino-5-chloro-2,6-diethyl-phenyl)-1-(4-methylamino-phenyl)-1-(1-phenyl-ethyl)-urea
3-(3-Amino-5-chloro-2,6-diethyl-phenyl)-1-(4-chloro-benzyl)-1-(4-ethylamino-phenyl)-urea
3-(3-Amino-5-chloro-2,6-diethyl-phenyl)-1-[4-(2-amino-ethyl)-benzyl]-1-(4-ethyl-phenyl)-urea
N-{4-[3-(3-Amino-5-chloro-2,6-diethyl-phenyl)-1-(4-chloro-benzyl)-ureido]-phenyl}-acetamide
3-(3-Amino-5-chloro-2,6-diethyl-phenyl)-1-[1-(4-chloro-phenyl)-ethyl]-1-[4-(2,2,2-trifluoro-ethyl)-phenyl]-urea 17. The compound according to claim 16, whereby the compound is selected from the group consisting of
3-(3-Amino-2,6-diethyl-phenyl)-1-(4-isopropyl-phenyl)-1-(4-methoxy-benzyl)-urea
3-(3-Amino-5-chloro-2,6-diethyl-phenyl)-1-(4-isopropyl-phenyl)-1-(4-methoxy-benzyl)-urea
3-(3-Amino-5-chloro-2,6-diethyl-phenyl)-1-(4-ethyl-phenyl)-1-(4-methoxy-benzyl)-urea
3-(3-Amino-5-chloro-2,6-diethyl-phenyl)-1-(4-isopropyl-phenyl)-1-(4-methyl-benzyl)-urea
3-(3-Amino-5-chloro-2,6-diethyl-phenyl)-1-(4-ethyl-benzyl)-1-(4-isopropyl-phenyl)-urea
3-(3-Amino-2,6-diethyl-phenyl)-1-(4-isopropyl-phenyl)-1-(4-methyl-benzyl)-urea
3-(3-Amino-5-chloro-2,6-diethyl-phenyl)-1-benzyl-1-(4-isopropyl-phenyl)-urea
3-(3-Amino-5-chloro-2,6-diethyl-phenyl)-1-(4-isopropyl-phenyl)-1-(4-trifluoromethyl-benzyl)-urea
3-(3-Amino-2,6-diethyl-phenyl)-1-(4-isopropyl-phenyl)-1-(4-trifluoromethyl-benzyl)-urea
3-(3-Amino-5-chloro-2,6-diethyl-phenyl)-1-(4-ethyl-phenyl)-1-(4-methyl-benzyl)-urea
3-(3-Amino-2,6-diethyl-phenyl)-1-(4-ethyl-phenyl)-1-(4-methyl-benzyl)-urea
(R)-3-(3-Amino-5-chloro-2,6-diethyl-phenyl)-1-(4-isopropyl-phenyl)-1-[1-(4-methoxy-phenyl)-ethyl]-urea
(R)-3-(3-Amino-5-chloro-2,6-diethyl-phenyl)-1-(4-isopropyl-phenyl)-1-(1-p-tolyl-ethyl)-urea
3-(3-Amino-2,6-diethyl-phenyl)-1-cyclohexylmethyl-1-(4-isopropyl-phenyl)-urea
(S)-3-(3-Amino-5-chloro-2,6-diethyl-phenyl)-1-(4-isopropyl-phenyl)-1-[1-(4-methoxy-phenyl)-ethyl]-urea
(S)-3-(3-Amino-2,6-diethyl-phenyl)-1-(4-isopropyl-phenyl)-1-(1-p-tolyl-ethyl)-urea
(S)-3-(3-Amino-2,6-diethyl-phenyl)-1-(4-isopropyl-phenyl)-1-[1-(4-methoxy-phenyl)-ethyl]-urea
3-(3-Amino-5-chloro-2,6-diethyl-phenyl)-1-(4-chloro-benzyl)-1-(4-isopropyl-phenyl)-urea
(S)-3-(3-Amino-5-chloro-2,6-diethyl-phenyl)-1-(4-isopropyl-phenyl)-1-(1-p-tolyl-ethyl)-urea
(S)-3-(3-Amino-5-chloro-2,6-diethyl-phenyl)-1-[1-(4-chloro-phenyl)-ethyl]-1-(4-isopropyl-phenyl)-urea
(S)-3-(3-Amino-5-chloro-2,6-diethyl-phenyl)-1-[1-(4-chloro-phenyl)-ethyl]-1-(4-ethyl-phenyl)-urea
(S)-3-(3-Amino-5-chloro-2,6-diethyl-phenyl)-1-[1-(4-fluoro-phenyl)-ethyl]-1-(4-isopropyl-phenyl)-urea
(S)-3-(3-Amino-5-chloro-2,6-diethyl-phenyl)-1-(4-ethyl-phenyl)-1-[1-(4-fluoro-phenyl)-ethyl]-urea
(S)-3-(3-Amino-5-chloro-2,6-diethyl-phenyl)-1-[1-(4-chloro-phenyl)-ethyl]-1-(4-methylsulfanyl-phenyl)-urea
3-(3-Amino-5-chloro-2,6-diethyl-phenyl)-1-(4-ethynyl-phenyl)-1-(4-methoxy-benzyl)-urea
(S)-3-(3-Amino-5-chloro-2,6-diethyl-phenyl)-1-(4-chloro-phenyl)-1-[1-(4-chloro-phenyl)-ethyl]-urea
(S)-3-(3-Amino-5-chloro-2,6-diethyl-phenyl)-1-[1-(4-chloro-phenyl)-ethyl]-1-(4-methoxy-phenyl)-urea
3-(3-Amino-5-chloro-2,6-diethyl-phenyl)-1-(4-chloro-benzyl)-1-(4-trifluoromethylsulfanyl-phenyl)-urea
(S)-3-(3-Amino-5-chloro-2,6-diethyl-phenyl)-1-[1-(4-chloro-phenyl)-ethyl]-1-(4-methanesulfinyl-phenyl)-urea 3-(3-Amino-5-chloro-2,6-diethyl-phenyl)-1-(4-ethyl-phenyl)-1-(4-fluoro-benzyl)-urea
3-(3-Amino-5-chloro-2,6-diethyl-phenyl)-1-(4-chloro-benzyl)-1-(4-ethyl-phenyl)-urea
3-(3-Amino-5-chloro-2,6-diethyl-phenyl)-1-(4-bromo-benzyl)-1-(4-ethyl-phenyl)-urea
3-(3-Amino-5-chloro-2,6-diethyl-phenyl)-1-(4-chloro-benzyl)-1-[4-(2,2,2-trifluoro-ethyl)-phenyl]-urea
3-(3-Amino-5-chloro-2,6-diethyl-phenyl)-1-(4-cyano-benzyl)-1-(4-ethyl-phenyl)-urea
3-(3-Amino-5-chloro-2,6-diethyl-phenyl)-1-(4-chloro-benzyl)-1-(4-difluoromethoxy-phenyl)-urea
3-(3-Amino-2,6-diethyl-phenyl)-1-(4-chloro-benzyl)-1-(4-methylamino-phenyl)-urea
3-(3-Amino-5-chloro-2,6-diethyl-phenyl)-1-(4-chloro-benzyl)-1-(4-methylamino-phenyl)-urea
3-(3-Amino-5-chloro-2,6-diethyl-phenyl)-1-(4-chloro-benzyl)-1-(4-dimethylamino-phenyl)-urea
3-(3-Amino-5-chloro-2,6-diethyl-phenyl)-1-benzyl-1-(4-methylamino-phenyl)-urea
(S)-3-(3-Amino-5-chloro-2,6-diethyl-phenyl)-1-[1-(4-chloro-phenyl)-ethyl]-1-(4-methylamino-phenyl)-urea
3-(3-Amino-5-chloro-2,6-diethyl-phenyl)-1-(4-methylamino-phenyl)-1-(1-phenyl-ethyl)-urea
3-(3-Amino-5-chloro-2,6-diethyl-phenyl)-1-(4-chloro-benzyl)-1-(4-ethylamino-phenyl)-urea
3-(3-Amino-5-chloro-2,6-diethyl-phenyl)-1-[4-(2-amino-ethyl)-benzyl]-1-(4-ethyl-phenyl)-urea
N-{4-[3-(3-Amino-5-chloro-2,6-diethyl-phenyl)-1-(4-chloro-benzyl)-ureido]-phenyl}-acetamide 3-(3-Amino-5-chloro-2,6-diethyl-phenyl)-1-[1-(4-chloro-phenyl)-ethyl]-1-[4-(2,2,2-trifluoro-ethyl)-phenyl]-urea.

18. A pharmaceutical composition comprising at least one compound according to claim 1 and a pharmaceutically acceptable carrier.

* * * * *

UNITED STATES PATENT AND TRADEMARK OFFICE
CERTIFICATE OF CORRECTION

PATENT NO. : 8,071,810 B2
APPLICATION NO. : 11/915892
DATED : December 6, 2011
INVENTOR(S) : Karsten Schnatbaum et al.

It is certified that error appears in the above-identified patent and that said Letters Patent is hereby corrected as shown below:

In the Claims:

In claim 14, line 55, the structure

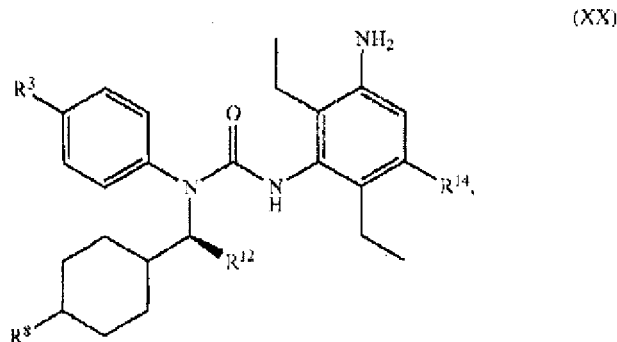

should be added after "structure";

In claim 14, line 64, the word --R2-- should be replaced with "R12"; and

In claim 16, line 38, the compound name "3-(3-Amino-5-chloro-2,6-diethyl-phenyl)-1-(4-bromoo-benzyl)-1-(4-ethyl-phenyl)-urea" should be added before "3-(3-Amino-5-chloro-2,6-diethyl-phenyl)-1-(4-chloro-benzyl)-1-[4-(2,2,2-trifluoro-ethyl)-phenyl]-urea".

Signed and Sealed this
Ninth Day of July, 2013

Teresa Stanek Rea
*Acting Director of the United States Patent and Trademark Office*

UNITED STATES PATENT AND TRADEMARK OFFICE
CERTIFICATE OF CORRECTION

PATENT NO. : 8,071,810 B2
APPLICATION NO. : 11/915892
DATED : December 6, 2011
INVENTOR(S) : Karsten Schnatbaum et al.

It is certified that error appears in the above-identified patent and that said Letters Patent is hereby corrected as shown below:

In the Claims:

In claim 14, Column 201, line 55, the structure

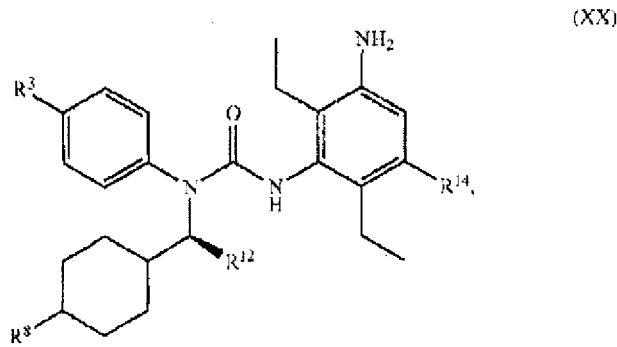

should be added after "structure";

In claim 14, Column 201, line 64, the word --R2-- should be replaced with "R12"; and In claim 16, Column 203, line 38, the compound name "3-(3-Amino-5-chloro-2,6-diethyl-phenyl)-1-(4-bromoo-benzyl)-1-(4-ethyl-phenyl)-urea" should be added before "3-(3-Amino-5-chloro-2,6-diethyl-phenyl)-1-(4-chloro-benzyl)-1-[4-(2,2,2-trifluoro-ethyl)-phenyl]-urea".

This certificate supersedes the Certificate of Correction issued July 9, 2013.

Signed and Sealed this
Thirteenth Day of August, 2013

Teresa Stanek Rea
*Acting Director of the United States Patent and Trademark Office*